US011999778B2

(12) United States Patent
Monson

(10) Patent No.: US 11,999,778 B2
(45) Date of Patent: Jun. 4, 2024

(54) VH4 ANTIBODIES AND COMPOSITIONS COMPRISING THE SAME

(71) Applicant: The Board of Regents of the University of Texas System, Austin, TX (US)

(72) Inventor: Nancy Monson, Ovilla, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 447 days.

(21) Appl. No.: 16/301,187

(22) PCT Filed: May 12, 2017

(86) PCT No.: PCT/US2017/032411

§ 371 (c)(1),
(2) Date: Nov. 13, 2018

(87) PCT Pub. No.: WO2017/197265

PCT Pub. Date: Nov. 16, 2017

(65) Prior Publication Data

US 2022/0281961 A1 Sep. 8, 2022

Related U.S. Application Data

(60) Provisional application No. 62/336,409, filed on May 13, 2016.

(51) Int. Cl.
*C07K 16/18* (2006.01)
*A61P 25/28* (2006.01)
*C12N 15/113* (2010.01)

(52) U.S. Cl.
CPC .............. *C07K 16/18* (2013.01); *A61P 25/28* (2018.01); *C12N 15/113* (2013.01); *C07K 2317/21* (2013.01); *C07K 2317/56* (2013.01); *C12N 2310/11* (2013.01); *C12N 2310/14* (2013.01)

(58) Field of Classification Search
CPC .............. C07K 16/18; C07K 2317/565; C07K 2317/567; C07K 2317/56
See application file for complete search history.

(56) References Cited

U.S. PATENT DOCUMENTS

| | | | |
|---|---|---|---|
| 5,591,629 | A | 1/1997 | Rodriguez et al. |
| 8,394,583 | B2 | 3/2013 | Monson |
| 8,968,735 | B2 | 3/2015 | Gruskin et al. |
| 2014/0371103 | A1 | 12/2014 | Eastman et al. |
| 2014/0371132 | A1 | 12/2014 | Monson |

FOREIGN PATENT DOCUMENTS

| | | |
|---|---|---|
| WO | WO 2015-070009 | 5/2015 |

OTHER PUBLICATIONS

Rudikoff et al. (1982). PNAS. 79:1979-1983.*
Bennett et al., "CSF IgG heavy-chain bias in patients at the time of a clinically isolated syndrome." *Journal of Neuroimmunology* 199. 1-2 (2008): 126-132.
Bö et al., "Lack of correlation between cortical demyelination and white matter pathologic changes in multiple sclerosis." *Archives of Neurology* 64.1 (2007): 76-80.
Cameron et al., "Potential of a unique antibody gene signature to predict conversion to clinically definite multiple sclerosis." *Journal of Neuroimmunology* 213.1-2 (2009): 123-130.
Cepok et al., "Short-lived plasma blasts are the main B cell effector subset during the course of multiple sclerosis." *Brain* 128.7 (2005): 1667-1676.
Fisniku et al., "Gray matter atrophy is related to long-term disability in multiple sclerosis." *Ann Neuorl.*, 64(3):247-254, 2008.
Lassman et al., "The immunopathology of multiple sclerosis: and overview." *Brain Pathol.* 17.2 (2007): 210-8.
Ligocki et al., "A unique antibody gene signature is prevalent in the central nervous system of patients with multiple sclerosis." *Journal of Neuroimmunology* 226.1-2 (2010): 192-193.
Ligocki et al., "Expansion of CD27 high plasmablasts in transverse myelitis patients that utilize VH4 and JH6 genes and undergo extensive somatic hypermutation." *Genes and Immunity* 14.5 (2013): 291.
Lovato et al., "Related B cell clones populate the meninges and parenchyma of patients with multiple sclerosis." *Brain* 134.2 (2011): 534-541.
Obermeier et al., "Related B cell clones that populate the CSF and CNS of patients with multiple sclerosis produce CSF immunoglobulin." *Journal of Neuroimmunology* 233.1-2 (2011): 245-248.
Owens et al., "VH4 gene segments dominate the intrathecal humoral immune response in multiple sclerosis," *J Immunol*, 179(9):6343-6351, 2007.
Parratt et al., "Neuromyelitis optica: a demyelinating disease characterized by acute destruction and regeneration of perivascular astrocytes." *Mult. Scler.* 16.10 (2010): 1156-1172.
PCT International Preliminary Report on Patentability issued in International Application No. PCT/US2017/032411, mailed Nov. 22, 2018.
PCT International Search Report and Written Opinion issued in International Application No. PCT/US2017/032411, mailed on Oct. 6, 2017.
Rivas et al., "Peripheral VH4+ plasmablasts demonstrate autoreactive B cell expansion toward brain antigens in early multiple sclerosis patients." *Acta Neuropathologica* 133.1 (2017): 43-60.
Vercellino et al., "Grey matter pathology in multiple sclerosis." *Journal of Neuropathology & Experimental Neurology* 64.12 (2005): 1101-1107.

* cited by examiner

*Primary Examiner* — Christine J Saoud
*Assistant Examiner* — Jon M Lockard
(74) *Attorney, Agent, or Firm* — Parker Highlander PLLC

(57) ABSTRACT

The present disclosure in various aspects provides methods for making pharmaceutical compositions for treating neurodegenerative diseases (e.g., demyelinating diseases), such as but not limited to multiple sclerosis, neuromyelitis optica, and transverse myelitis. The pharmaceutical compositions impact specific antibody-mediated processes involved in the biology of neurodegenerative disease. In certain aspects, the disclosure provides pharmaceutical compositions for treating neurodegenerative disease, which are based on inhibiting the action of pathologic antibodies, or alternatively providing antibodies to stimulate neuroprotection or repair processes.

5 Claims, 148 Drawing Sheets

Specification includes a Sequence Listing.

B1: SLE-neg

G11: SLE-pos

MOUSE

HUMAN

MOUSE

HUMAN

MOUSE

HUMAN

NeuN AJL02: CDMS1

NeuN AJL07: $ON_{cis}3$

GFAP WR10: $TM_{cis}4$

NeuN AJL19: $TM_{cis}6$

AJL01 IgG VH insert: *VH4-34; JH3* (SEQ ID NO: 1)

TGVHSQVQLQQWGAGLLKPSETLSLTCAVYGGSFNEFYWSWIRQPARKGLEWIGEISHSGRANYNPSLKSRVTLSVDRSKNQFSLNLSPVAAADTAVYYCARREIVVTVRGRRAFDIWGQGTMVTVSSAS

AJL01 IgK VK insert: *VK3-20; JK5* (SEQ ID NO: 2)

TGVHSEIVLTQSPGTLSLSPGERAALSCRASQSLIGSFLAWYQQKPGQAPRLLIYHTSNRASGIPDRFSGGGFGTDFTLTISRLEPEDFAVYYCQQYDSSPITFGQGTRLEIKRT

AJL02 IgG VH insert: *VH4-31; JH4* (SEQ ID NO: 3)

TGVHSQVQLQESGPGLVKPSQTLSLTCTVSGGSISSGGHYWSWIRQSPGKGLEWIGNVYYSGSTYYTPSLDSRLTISLDTSKNQFSLRLSNVTVADTAVYYCARGRNWEGEFDPWGQGTLVTVSSAS

AJL02 IgK VK insert: *VK1-39; JK2* (SEQ ID NO: 4)

TGVHSDIQMTQSPSSLSASLGDRVTITCRASQGISSSVNWFQQKPGKAPELLIYAASTLQSGVPSRFSGSGSGTDFTLTVSSLQPEDFATYYCQQSYSPPRTFGQGTKLEIKRT

FIG. 11

AJL03 IgG VH insert: *VH4-39; JH1* (SEQ ID NO: 5)

TGVHSQLQLQESGPGLVKPSETLSLTCTVSGASISSSRSYWGWIRQPPGKGLEWIGSMYQSGSTYYSPSLKSRVTISMDTSKNQFSLNLTSVTAADTAVYFCARHSNPGTANKLRLGEFSPWGQGTLVTVSSAS

AJL03 IgK VK insert: *VK1-33; JK2* (SEQ ID NO: 6)

TGVHSDIQMTQSPSSLSASVGDRVTITCQASQDINNYLNWFQQQPGKAPKLLIYDASKLQMGVPSRFSGSASGTDFTFTISSLQPEDIGTYYCQQYYNLPYTFGQGTKLEIKRT

AJL04 IgG VH insert: *VH4-59; JH5* (SEQ ID NO: 7)

TGVHSQVQLQESGPGLVKPSETLSLTCTVSGDSIRSNFWTWIRQSPGRGLEWIGYFSYSGGINYSPSLKSRVTISVDTSKNQFSLKLTSVTAADAAVYYCARDPNGDYEVNWWGQGTLVTVSSAS

AJL04 IgK VK insert: *VK1-16; JK5* (SEQ ID NO: 8)

TGVHSDIQMTQSPSSLSASVGDRVTITCRASQDIIIYLAWFQQRPGKAPRSLIYSASTLQSGVPSKFSGSGSGTYFTLTISSLQPEDSATYYCQQYKSYPITFGQGTRLEIKRT

FIG. 11 (cont.)

AJL05 IgG VH insert: *VH4-39; JH5* (SEQ ID NO: 9)

TGVHSQLQLQESGPGLVKPSETLSLTCTVSGGSIRNSNYYWDWIRQPPGKGLEWIGSGYYSGSAYYHSSLKSRVSISVDTSKNQFSLNLTSVTAADTAFYY
CARRSYYYASGSHDYWGQGTLVTVSSAS

AJL05 IgK VK insert: *VK1-16; JK5* (SEQ ID NO: 10)

TGVHSDIQMTQSPSSLSASVGDRVTITCRASQDISSYLAWFQQKPGKAPKSLIYGASSLQSGVPSKFSGSGSGTDFTLTISGLQPEDFATYHCQQYRSFPITF
GQGTRLEIKRT

AJL06 IgG VH insert: *VH4-30; JH4* (SEQ ID NO: 11)

TGVHSQLQLQESGSGLVKPSQTLSLTCAVSGGSINTGNYFWSWIRQPPGKGLEWIGYMFRSTSTYYNPSLKGRVTISGGTSLSQFSLRLDSVTAADTAIYY
CARGRYYCGVNCHPFDSWGQGTLVTVSSAS

AJL06 IgK VK insert: *VK1-33; JK2* (SEQ ID NO: 12)

TGVHSDIQMTQSPSSLSASVGDRVIITCQASQDISIYLNWYQVKPGKAPKLLIYDASNLQAGVPSRFSGSGSGTDFSFTISSLQPEDVAAYYCHQYDSLPSF
GQGTKLEIKRT

FIG. 11 (cont.)

AJL07 IgG VH insert: *VH4-59; JH4* (SEQ ID NO: 13)

TGVHSQVQLQESGPGLVKPSETLSLTCNVSGGSINNYYWSWIRQPPGKGLEWIGYIYYNGNINYNPSLKSRVTISRDMSKNQFSLNLRSVTAADTAVYYC
GIGYSAVAAGTVDYWGHGTLVTVSSAS

AJL07 IgK VK insert: *VK1-13; JK2* (SEQ ID NO: 14)

TGVHSAIQLTQSPSSLSASVGDRVTITCRASQGISSGLAWYQQEPGKAPKLLIYDASTLESGVPSRFSGSGSAIDFTLTISSLQPEDFATYYCQQFNTFPYTF
GQGTKLEIKRT

AJL08 IgG VH insert: *VH4b; JH4* (SEQ ID NO: 15)

TGVHSQVQLQESGPGLVKPSETLSLTCAVSGFSITSGYYWGWIRQPPGKGLEWIGSIYHTGTTYYNPSLKSRVTISVDTSKNQFSLNLNSVTAADTAFYYC
ARDPLFPGRNLLSVFDNWGQGTLVTVSSAS

AJL08 IgK VK insert: *VK1-5; JK2* (SEQ ID NO: 16)

TGVHSDIQMTQSPSTLSASVGDRVTITCRASQSISTWLAWYQQKPGKAPRLLIYKASSLESGVPSRFSGSGSGTEFTLTISGLQPDDFANYSCQQYNIYPFT
FGQGTKLEIKRT

FIG. 11 (cont.)

AJL09 IgG VH insert: *VH4-59; JH5* (SEQ ID NO: 17)

TGVHSQVQLQESGPGLVKPSETLSLTCSVSGGSISSYYWGWIRQSPGKGLECIGYIYFSGSTSYNPSLKSRVTISVDTAKNQISLNLTSVTAADTAVYFCARV
WGSSWYANWFDPWGQGTLVTVSSAS

AJL09 IgK VK insert: *VK1-13; JK5* (SEQ ID NO: 18)

TGVHSAIQLTQSPSSLSASVGDRVTITCRASQGISSALAWYQHKPGKAPKLLIFDASTLAAGVPSRFSGSGSGTDFTLTISSLQPEDFATYYCQQYNTYVLT
FGQGTRLEIKRT

AJL10 IgG VH insert: *VH4-4; JH6* (SEQ ID NO: 19)

TGVHSQVQLQESGPGLVKPSETLSLTCSVSGGAVSNYYWSWIRQSAGKGLEWLGRIYINGTTYYNPSLRSRVSMSVDTSKGQFSLRLTSVTAADTAIYYC
ARWGALLGDYYYGLDVWGQGTTVTVSSAS

AJL10 IgK VK insert: *VK2-28; JK5* (SEQ ID NO: 20)

TGVHGDIVMTQSPLSLPVTPGEPASISCRSTQSLLHSNEYIYLDWYVQKPGQSPQLLIFLASNRASGVPDRFSGSASGTDFTLKISRVEAEDVGVYYCMQA
LEAPWTFGQGTRLEIKRT

FIG. 11 (cont.)

AJL11 IgG VH insert: *VH4-39; JH5* (SEQ ID NO: 21)

TGVHSQLQLQESGPGLVKPSETLSLTCSVSGGSITSTSYYWGWIRQSPGKGLEWIGSVYYSGNTFYNASLKSRVTISIDTSKYQFSLMLRSVTAADTAVYYCARRHDWFWFDPWGQGTLVTVSSAS

AJL11 IgK VK insert: *VK3-20; JK2* (SEQ ID NO: 22)

TGVHSEIVLTQSPGTLSLSPGERVTLSCRASQSVSSSYLAWYQQKPGQAPRLLIYDSSSRATGIPDRFSGSGSGTDFTLTISRLDPEDFAVYYCQQYGSSPSTFGQGTKLEIKRT

AJL12 IgG VH insert: *VH4-39; JH5* (SEQ ID NO: 23)

TGVHSQLQLQESGPGLVKPSETLSLTCTVSGGSVTSSDYYWAWIRQPPGKGPEWIGSISNSGNTYYSPSLKSRVSISGDTSKKQFSLNLSSVTDADTAVYYCTRHGHYVSGGLGPWGQGTLVTVSSAS

AJL12 IgK VK insert: *VK3-20; JK1* (SEQ ID NO: 24)

TGVHSEIVLTQSPGTLSLSPGERATLSCRASQSVGSYYLAWYQQKPGQAPRLLIHGASSRATGTPDRFSGSGSGTDFTLTISKLEPEDFALYYCQQYGPSPWTFGQGTKVEIKRT

FIG. 11 (cont.)

AJL13 IgG VH insert: *VH4-59; JH4* (SEQ ID NO: 25)

TGVHSQVQLQESGPGLVKPSETLSLTCNVSGGSINNYYWSWIRQPPGKGLEWIGYIYYNGNINYNPSLKSRVTISRDMSKNQFSLNLRSVTAADTAVYYC
GIGYSAVAAGTVDYWGQGTLVTVSSAS

AJL13 IgK VK insert: *VK2-30; JK5* (SEQ ID NO: 26)

TGVHGDVVMTQSPLSLPVTLGQPASISCRSSQSLVHRNGNTYLNWFQQRPGQSPRRLIYTVSKRGSGVPDRFSGSGSGTDFTLKISRVEAEDVGDYYCMQ
GTHWPWTSGQGTRLEIKRT

AJL14 IgG VH insert: *VH4-61; JH6* (SEQ ID NO: 27)

TGVHSQVQLQESGPGLVKPSQTLSLTCTVSGGSLSSVNYYWNWIRQPAGKGLEWMGRIYASGYTTYNPSFQSRVTISLDPSKNQISLKVTSLTAADTAIY
YCARHDLGHCSSTSCYLSWFDAWGQGTTVTVSSAS

AJL14 IgK VK insert: *VK4-1; JK2* (SEQ ID NO: 28)

TGVHSDIVMTQSPDSLAVSLGERATINCRSSQTIFFSPNNNNHLAWYQQKPGQPPRLLIYWASTRESGVPDRFSGSGSGTDFTLTISGLQAEDVAVYYCQ
QYYSLPYTFGQGTKLEIKRT

FIG. 11 (cont.)

AJL15 IgG VH insert: *VH4-39; JH5* (SEQ ID NO: 29)

TGVHSQLQLQESGPGLVKPSETLSLTCTVSGGSITSRNNYWGWIRQSPGKGLEWIGSLYYTGSDYYNPSLKSRVTISVDTSKNQFSLRLSSVTAADTAVYY
CVRVNVDDFWSGLGGAWFDPWGQGTLVTVSSAS

AJL15 IgK VK insert: *VK2D-29; JK2* (SEQ ID NO: 30)

TGVHGDIVMTQTPLSLSVTPGQPASISCKSSQSLLDSDGKTHLYWYLQKPGQSPQSLIYEVSKRFSGVPDRFTGSGSGTDFTLKISRVEAEDVGLYYCMQS
AQLPYTFGQGTKLEIKRT

AJL16 IgG VH insert: *VH4-39; JH5* (SEQ ID NO: 31)

TGVHSQLQLQESGPGLVKPSETLSLTCTVSGGSISSSPYYWGWIRQPPGKGLEWIGSIYYSGHTYYNPSLKSRVTISVDTSKNQFSLRLTSVTAADTSVYYC
AKQTDDYGDYASRGWFDPWGQGTLVTVSSAS

AJL16 IgK VK insert: *VK1-33; JK5* (SEQ ID NO: 32)

TGVHSDIQMTQSPSSLSASVGDRVTFTCQASHDISNYLNWYQQKPGKVPELLIYDASNLKTGVPSRFSGSGSGTDFTFTISSLQPEDIATYYCQQYDNLPI
TFGQGTRLEIKRT

FIG. 11 (cont.)

AJL18 IgG VH insert: *VH4-31; JH5* (SEQ ID NO: 33)

TGVHSQVQLQESGPGLVKPSQTLSLTCTVSGDSISSDKYYWTWIRQLPGKGLEWIGYISYSGTTYYNPSLKSRVSISVDTSGNQFSLRLSSVTAADTARYY
CARVYYDVLSAYYNMGSWVDPWGQGTLVTVSSAS

AJL18 IgK VK insert: *VK1-39; JK1* (SEQ ID NO: 34)

TGVHSDIQMTQSPSSLPASVGDRVTITCRASQSISSYLNWYQQKPGRAPKLLIYAASSLQSGVSSRFSGSGSGTDFTLTISSLQPEDSATYYCQQSYSTPWT
FGQGTKVEIKRT

AJL19 IgG VH insert: *VH4-34; JH3* (SEQ ID NO: 35)

TGVHSQVQLQQWGAGLLKPPETLSLTCAVFGGSLSGYYWSWIRQPPGKGPEWIAEINHSGDANYNPSLKSRVTISVDTSKNQFSLKMSSVTVADTALYY
CATQGSRLTTFAFDVWGQGTMVTVSSAS

AJL19 IgK VK insert: *VK3-20; JK2* (SEQ ID NO: 36)

TGVHSEIVLTQSPGTLSLSPGERVTLSCRTSQSVSSDSLAWYQQKPGQTPRLLIYHTSTRAAGIPDRFSGTGSGTDFTLTIARLEPEDFAVYYCQHYGRSSL
FTFGQGTKLEIKRT

FIG. 11 (cont.)

AJL20 IgG VH insert: *VH4-39; JH4* (SEQ ID NO: 37)

TGVHSQLQLQESGPGLVKPSETLSLTCTVSGGSISGSSFYWGWVRQPPGRGLEWIGTIYYRGTTYYTPSLKSRVTISVDTSKNQFSLRLNSVTAADTAIYY
CASLPHYDFWSGSVFFDYWGQGTLVTVSSAS

AJL20 IgK VK insert: *VK1-27; JK4* (SEQ ID NO: 38)

TGVHSDIQMTQSPSSLSASVGDRVTITCRASQGIANYLAWYQQKPGNIPKLLIYAASTLQSGVPSRFSGSGSGTDFALTISCLQPEDVATYYCQKYNSAPLT
FGGGTKVEIKRT

WR01 IgG VH insert: *VH4-59; JH6* (SEQ ID NO: 39)

TGVHSQVQLQESGPGLVKPSETLSLTCTVSGGSIDTYYWTWIRQPPGKGLEWIGYIYSTGSPKYKPSLKSRVVMSVDTSTNEFALRLSSVTAADTAVYYC
ARSSGFYVEHLEKWGQGTTVTVSSAS

WR01 IgK VK insert: *VK3-20; JK2* (SEQ ID NO: 40)

TGVHSEIVLTQSPATLSLSPGERATLSCRASQTVSSSYLDWFQQKPGQAPRLLIYGASSRATGIPDRFSGSGSGTDFTLTISRLEPEDFAVYYCQQFATSPY
TFGQGTKLEIKRT

FIG. 11 (cont.)

WR02 IgG VH insert: *VH4-30; JH6* (SEQ ID NO: 41)

TGVHSQVQLQESGPGLVKPSQTLSLTCTVSGGSISSGDYHWSWIRQPPGKGLEWIGNINYNGGAYHNPSLTNRVIMSVDTSKNHFSLKLTSVTAADTAV
YYCARESQWLRYGAFGMDVWGQGTTVTVSSAS

WR02 IgK VK insert: *VK3-20; JK2* (SEQ ID NO: 42)

TGVHSEIVLTQSPGTLSLSPGERATLSCRASQSVSSSHLVWYQQKAGQAPRLVIYGANRRASGTPDRFSGSGSGTDFTLTISRLEPEDFAVYYCQQYGSSPY
TFGQGTKLEIKRT

WR03 IgG VH insert: *VH4-4; JH3* (SEQ ID NO: 43)

TGVHSQVQLQESGPGLVKPSGTLSLTCAVSGGSISSSYWWSWVRQPPGKGLEWVGEIYHSGGANYSPSLKSRVTISVDKSKNQFSLNLISVTAADTAVYF
CARSRMLVGADGGGAFDIWGQGTMVTVSSAS

WR03 IgK VK insert: *VK3-20; JK1* (SEQ ID NO: 44)

TGVHSEIVLTQSPGTLSLSPGERATLSCGASQSVSSSYLAWYQQKPGLAPRLLIYDASSRATGIPDRFSGSGSGTDFTLTISRLEPEDFAVYYCQQYGSSPQT
FGQGTKVEIKRT

FIG. 11 (cont.)

WR04 IgG VH insert: *VH4-39; JH4* (SEQ ID NO: 45)

TGVHSQLQLQQSGPGLVKPSETLSLTCTVSGGSISSGGSYWGWIRQAPGKGLEWIGSMYYSGSTFYNPSVKSRVTISVDRSKEQFSLNLNAVTAADTAVY
YCVRHRRSEPSDSWGQGTLVTVSSAS

WR04 IgK VK insert: *VK3-15; JK2* (SEQ ID NO: 46)

TGVHSEIVMTQSPATLSVSPGERATLSCRASQSVSSNLAWYQQKPGQAPRLLIYGTSTRATGIPARFSGSGSGTEFTLTISSLQSEDSAVYFCQQYNNWPL
YTFGQGTKVEIKRT

WR05 IgG VH insert: *VH4-61; JH1* (SEQ ID NO: 47)

TGVHSQVQLQESGPGLVKPSETLSLTCSVSGGSVSSNGHFWSWIRLPPGKGLEWIGYVYNTGTSGYSPSLKSRVTISVDTSKNQFSLTLRSVTAADTAIYY
CARGLTGNYPSHWGQGTLVTVSSAS

WR05 IgK VK insert: *VK1-5; JK4* (SEQ ID NO: 48)

TGVHSDIQMTQSPSSVSASVGDRVTITCRASRGVSTWLAWYQQKPGEAPKLLIYASSRLEGGVPARFSGSGSGTDFTLTISSLQPEDFATYYCQQGNSFPL
TFGGGTKVEIKRT

FIG. 11 (cont.)

WR06 IgG VH insert: *VH4-39; JH3* (SEQ ID NO: 49)

TGVHSQLQLQESGPGLVKPSETLSLTCTVSGGSVSSSAYWWAWIRQPPGGGLEWIGHIYYFGNKYYKSSLESRVTISLDASQNQFSLKLTSVTAADTALY
YCARVDTALAFDFWGQGTMVTVSSAS

WR06 IgK VK insert: *VK1-5; JK3* (SEQ ID NO: 50)

TGVHSDIQMTQSPSSLSASVGDRVTITCRASQYVSSSLNWYQQKPGKAPTLLIYLASNLRSGVPSRFSGSESGTDFTLTINSLQPEDVATYFCQQSYSLPRT
FGPGTKVDIKRT

WR07 IgG VH insert: *VH4-39; JH4* (SEQ ID NO: 51)

TGVHSQLQLQESGPGLVKPSETLSLTCSVSGGSVSSTTYYWGWIRQSPGKGLEWIGSIYHSGKTYYNPSLKSRVTISVDTSKNQFSLNLSSVTAADTAVYY
CARENSHHYDSSGYYLGGFDYWGQGTLVTVSSAS

WR07 IgK VK insert: *VK3-20; JK1* (SEQ ID NO: 52)

TGVHSEIVLTQSPGTLSLSPGERATLSCRASQSVSSSYLAWYQQKPGQAPRLLIYGASSRATGIPDRFSGSGSGTDFTLTISRLEPEDFAVYFCQHYGSPSTF
GQGTKVEIKRT

FIG. 11 (cont.)

WR08 IgG VH insert: *VH4-31; JH4* (SEQ ID NO: 53)

TGVHSQVQLQESGPGLVKPSQTLSLTCTVSGGSISSGYYWSWIRQHPGKGLDCIGYIHYTGTTYYNPSLKSRLTISVDTSKNQFSLNLTSVTAADTAVYYC
AREEYTTSSVDYWGRGTLVTVSSAS

WR08 IgK VK insert: *VK2-30; JK5* (SEQ ID NO: 54)

TGVHGDVVMTQSPLSLPVTLGQPASISCRSSESLVSVDGNTYLNWFHQRPGQSPRRLIYKVSNRDSGVPDRFSGSGSGTDFTLKISRVEAEDVGIYYCMQ
ATHWLRTFGQGTRLEIKRT

WR09 IgG VH insert: *VH4-31; JH4* (SEQ ID NO: 55)

TGVHSQVQLQESGPGLVKPSQTLSLTCTVSGGSISSGYYWSWIRQHPGKGLEWIGYIHYTGTTYYNPSLKSRVTISVDTSKNQFSLNLTSVTAADTAVYYC
AREEYTTSSVDYWGRGTLVTVSSAS

WR09 IgK VK insert: *VK3-20; JK2* (SEQ ID NO: 56)

TGVHSEIVLTQSPGTLSLSPGERATLSCRASQRVSSGFLAWYQQKPGQAPRLLIYGASSRATGIPDRFSGSGSGTDFTLTISRLEPEDFAVYYCQQYESSPSP
YNFGQGTKLEIKRT

FIG. 11 (cont.)

WR10 IgG VH insert: *VH4-4; JH6* (SEQ ID NO: 57)

TGVHSQVQLQESGPGLVKPSGTLSLTCAVSGGSISNNKWWNWVRQSPGKGLEWIGEIYHSGGTNYNPSLKSRVTISVDKSKNLFSLKLSSVTAADTAVY
YCASATTMVRGLSLYYYGLDVWGPGTTVTVSSAS

WR10 IgK VK insert: *VK3-20; JK5* (SEQ ID NO: 58)

TGVHSEIVLTQSPGTLSLSPGERAALSCRASQSLIGSFLAWYQQKPGQAPRLLIYHTSNRASGIPDRFSGGGFGTDFTLTISRLEPEDFAVYYCQQYDSSPIT
FGQGTRLEIKRT

WR11 IgG VH insert: *VH4-4; JH6* (SEQ ID NO: 59)

TGVHSQVQLQESGPGLVKPSGTLSLTCAVSGGSISNNKWWNWVRQSPGKGLEWIGEIYHSGGTNYNPSLKSRVTISVDKSKNLFSLKLSSVTAADTAVY
YCASATTMVRGLSLYYYGLDVWGQGTTVTVSSAS

WR11 IgK VK insert: *VK3-11; JK4* (SEQ ID NO: 60)

TGVHSEIVLTQSPGTLSLSPGERATLSCRASQSVSSFLAWYQQKPGQAPRLLIYDASNRATGIPARFSGSGSGTDFTLTISSLEPEDFAVYYCQQRTNWPPS
LTFGGGTKVEIKRT

FIG. 11 (cont.)

WR12 IgG VH insert: *VH4-30; JH4* (SEQ ID NO: 61)

TGVHSQVQLQESGPGLVKPSQTLSLTCTVSGDSVSSNDHYWSWIRQPPGQGLEWIGYISHGGTTYYNPSLKSRVTMSIDTSTNQFSLRVTSVRAADMAVYFCARAPAPITTFGMVTPVPYFHSWGQGTLVTVSSAS

WR12 IgK VK insert: *VK2-28; JK4* (SEQ ID NO: 62)

TGVHGDIVMTQSPLSLPVSPGEPASISCRSSQSLLHSNGYNYLSWYLQKPGQSPQLLIFSSSIRASGVPDRFSGSGSGTDFTLTINRVEAEDVGVYYCMQALQTPLTFGGGTKLEIKRT

WR13 IgG VH insert: *VH4-30; JH4* (SEQ ID NO: 63)

TGVHSQVQLQESGPGLVKPSQTLSLTCTVSGDSVSSNDHYWSWIRQPPGQGLEWIGYISHGGTTYYNPSLKSRVTMSIDTSTNQFSLRVTSVRAADMAVYFCARAPAPITTFGMVTPVPYFHSWGQGTLVTVSSAS

WR13 IgK VK insert: *VK2-28; JK2* (SEQ ID NO: 64)

TGVHGDIVMTQSPLSLPVSPGESASISCRSSQSLLHSNGYNYLSWYLQKPGQSPQLLIFSSSIRASGVPDRFSGSGSGTDFTLTINRVEAEDVGVYYCMQALQTPLTFGQGTKLEIKRT

FIG. 11 (cont.)

AJL01 IgG VH insert: *VH4-34; JH3* (SEQ ID NO: 65)

ACCGGTGTACATTCCCAGGTGCAGCTACAGCAGTGGGGCGCAGGACTGTTGAAGCCTTCGGAGACCCTGTCCCTCACCTGCGCTGTCTATGGTGGGTCCTTCAAT
GAATTCTACTGGAGCTGGATCCGTCAGCCCGCACGGAAGGGCCTGGAGTGGATTGGAGAAATCAGTCATAGCGGAAGAGCCAACTACAACCCGTCCCTCAAGA
GTCGCGTCACCCTGTCTGTAGACAGGTCCAAGAACCAGTTCTCCCTGAACCTGAGCCCTGTGGCCGCCGCGGACACAGCTGTCTATTACTGTGCGCGACGGGAGA
TAGTCGTAACTGTTCGGGGGCGTCGTGCTTTTGATATCTGGGGCCAAGGGACAATGGTCACCGTCTCTTCAGCGTCGAC

AJL01 IgK VK insert: *VK3-20; JK5* (SEQ ID NO: 66)

ACCGGTGTACATTCAGAAATTGTGTTGACGCAGTCTCCAGGCACCCTGTCTTTGTCTCCAGGGGAAAGAGCCGCCCTCTCCTGCAGGGCCAGTCAGAGTCTTATC
GGCAGCTTCTTAGCCTGGTACCAGCAGAAACCTGGCCAGGCTCCCAGGCTCCTCATCTATCATACATCCAACAGGGCCTCTGGCATCCCAGACAGGTTCAGTGGC
GGTGGGTTTGGGACAGACTTCACTCTCACCATCAGCAGACTGGAGCCTGAAGATTTTGCAGTTTATTACTGTCAACAGTATGATAGCTCACCGATCACCTTCGGCC
AAGGGACACGACTGGAGATTAAACGTACG

AJL02 IgG VH insert: *VH4-31; JH4* (SEQ ID NO: 67)

ACCGGTGTACATTCCCAGGTGCAGCTGCAGGAGTCGGGCCCAGGACTGGTGAAGCCTTCACAGACCCTGTCCCTCACCTGTACTGTCTCTGGTGGCTCCATCAGC
AGTGGTGGTCACTACTGGAGCTGGATCCGCCAGTCCCCAGGGAAGGGCCTGGAGTGGATTGGGAACGTCTATTATAGTGGAAGCACCTACTACACCCCGTCCCT
CGACAGCCGACTTACCATATCATTAGACACGTCTAAGAACCAGTTCTCCCTGAGGCTGAGTAATGTGACTGTCGCGGACACGGCCGTCTATTACTGTGCGAGAGG
TAGAAATTGGGAGGGCGAATTCGACCCCTGGGGCCAAGGAACCCTGGTCACCGTCTCCTCAGCGTCGAC

AJL02 IgK VK insert: *VK1-39; JK2* (SEQ ID NO: 68)

ACCGGTGTACATTCTGACATCCAGATGACCCAGTCTCCGTCCTCCCTGTCTGCGTCTTTAGGAGACAGAGTCACCATCACTTGCCGGGCAAGTCAGGGCATTAGCA
GCTCTGTAAATTGGTTTCAGCAGAAACCAGGGAAAGCCCCTGAACTCCTGATCTATGCTGCATCCACTTTGCAAAGTGGGGTCCCATCAAGATTCAGTGGCAGTG
GATCTGGGACAGATTTCACTCTCACCGTCAGCAGTCTGCAACCTGAAGATTTTGCAACTTACTACTGTCAGCAGAGTTACAGTCCCCCTCGAACTTTTGGCCAGGG
GACCAAGCTGGAAATCAAACGTACG

FIG. 12

AJL03 IgG VH insert: *VH4-39; JH1* (SEQ ID NO: 69)

ACCGGTGTACATTCCCAGCTGCAGCTGCAGGAGTCGGGCCCAGGACTGGTGAAGCCTTCGGAGACCCTGTCCCTCACGTGCACTGTCTCTGGTGCCTCCATCAGC
AGTAGTCGTTCCTACTGGGGCTGGATCCGCCAGCCCCCAGGGAAGGGGCTGGAGTGGATTGGGAGTATGTATCAAAGTGGGAGCACTTACTACAGTCCGTCCCT
CAAGAGTCGAGTCACCATATCCATGGACACGTCCAAGAACCAGTTCTCCCTAAACCTGACGTCTGTGACCGCCGCGGACACGGCTGTGTATTTCTGTGCGAGACA
TTCGAACCCCGGAACGGCGAACAAATTGCGTTTGGGGGAGTTTTCGCCCTGGGGCCAGGGAACCCTGGTCACCGTCTCCTCAGCGTCGAC

AJL03 IgK VK insert: *VK1-33; JK2* (SEQ ID NO: 70)

ACCGGTGTACATTCTGACATCCAGATGACCCAGTCTCCATCCTCCCTGTCTGCATCTGTAGGAGACAGAGTCACCATCACTTGCCAGGCGAGTCAGGACATTAACA
ACTATTTAAATTGGTTTCAGCAGCAACCAGGGAAAGCCCCTAAGCTGCTGATCTACGATGCATCCAAATTGCAAATGGGGGTCCCATCAAGGTTCAGTGGAAGTG
CATCTGGGACAGATTTTACTTTTACCATCAGCAGCCTGCAGCCTGAAGATATTGGCACATATTACTGTCAACAGTATTATAATCTCCCGTACACTTTTGGCCAGGGG
ACCAAGCTGGAGATCAAACGTACG

AJL04 IgG VH insert: *VH4-59; JH5* (SEQ ID NO: 71)

ACCGGTGTACATTCCCAGGTGCAGCTGCAGGAGTCGGGCCCAGGACTGGTGAAGCCTTCGGAGACCCTGTCCCTCACCTGCACTGTCTCTGGTGACTCCATCAGA
AGTAACTTCTGGACCTGGATCCGGCAGTCCCCAGGGAGGGGACTGGAGTGGATTGGGTATTTCTCTTACAGTGGGGGCATCAACTACAGCCCCTCCCTCAAGAG
TCGCGTCACCATTTCAGTGGACACATCCAAGAACCAGTTCTCCCTAAAACTGACCTCTGTGACCGCGGCGGACGCGGCCGTATATTACTGTGCGAGAGATCCCAA
CGGTGACTACGAAGTTAACTGGTGGGGCCAAGGAACCCTGGTCACCGTCTCCTCAGCGTCGAC

AJL04 IgK VK insert: *VK1-16; JK5* (SEQ ID NO: 72)

ACCGGTGTACATTCTGACATCCAGATGACCCAGTCTCCATCTTCACTGTCTGCATCTGTAGGAGACAGAGTCACCATCACTTGTCGGGCGAGTCAGGACATTATTA
TTTATTTAGCCTGGTTTCAGCAGAGACCAGGGAAAGCCCCTAGGTCCCTGATCTATTCTGCATCCACTTTGCAGAGTGGGGTCCCATCAAAATTCAGCGGCAGTG
GATCTGGGACATATTTCACTCTCACCATCAGCAGCCTGCAGCCTGAAGATTCTGCAACTTATTACTGCCAACAATATAAAAGTTATCCCATCACCTTCGGCCAAGG
GACACGACTGGAGATTAAACGTACG

FIG. 12 (cont.)

AJL05 IgG VH insert: *VH4-39; JH5* (SEQ ID NO: 73)

ACCGGTGTACATTCCCAGCTGCAGCTGCAGGAGTCGGGCCCAGGACTGGTGAAGCCTTCGGAGACCCTGTCCCTCACCTGCACTGTCTCTGGTGGCTCCATCAGA
AATAGTAATTACTACTGGGACTGGATCCGCCAGCCCCCAGGAAAGGGGCTGGAGTGGATTGGGAGTGGCTATTATAGTGGGAGCGCCTACTACCATTCGTCCCT
CAAGAGTCGAGTCAGCATATCCGTAGACACGTCCAAGAACCAGTTTTCCCTTAATCTGACCTCTGTGACCGCCGCAGACACGGCTTTTTATTACTGTGCGAGACGT
TCCTATTATTATGCTTCGGGGAGCCACGACTACTGGGGCCAGGGAACCCTGGTCACCGTCTCCTCAGCGTCGAC

AJL05 IgK VK insert: *VK1-16; JK5* (SEQ ID NO: 74)

ACCGGTGTACATTCTGACATCCAGATGACCCAGTCTCCATCCTCACTGTCTGCATCTGTAGGAGACAGAGTCACCATCACTTGTCGGGCGAGTCAGGACATTAGCA
GTTACTTAGCCTGGTTTCAGCAGAAACCAGGGAAAGCCCCTAAGTCCCTGATCTATGGTGCTTCCAGTTTGCAGAGTGGGGTCCCATCAAAATTCAGCGGCAGTG
GATCTGGGACAGATTTCACTCTCACCATCAGCGGCCTGCAGCCTGAAGATTTTGCAACTTATCACTGCCAACAATACAGGAGTTTCCCTATCACTTTCGGCCAAGG
GACACGACTGGAGATTAAACGTACG

AJL06 IgG VH insert: *VH4-30; JH4* (SEQ ID NO: 75)

ACCGGTGTACATTCCCAGCTGCAGCTGCAGGAGTCCGGCTCAGGACTGGTGAAGCCTTCACAGACCCTGTCCCTCACCTGCGCTGTCTCTGGTGGCTCCATCAAC
ACTGGCAATTACTTCTGGAGCTGGATCCGGCAGCCACCAGGGAAGGGCCTGGAGTGGATTGGGTACATGTTTCGAAGTACGAGTACCTACTACAACCCGTCCCT
CAAGGGTCGAGTCACCATTTCAGGAGGCACGTCCCTGAGCCAGTTCTCCCTGAGACTGGACTCTGTGACTGCCGCGGACACGGCCATCTACTACTGTGCGAGAG
GACGTTATTATTGTGGTGTTAATTGCCATCCCTTTGACTCCTGGGGCCAAGGAACCCTGGTCACCGTCTCCTCAGCGTCGAC

AJL06 IgK VK insert: *VK1-33; JK2* (SEQ ID NO: 76)

ACCGGTGTACATTCTGACATCCAGATGACCCAGTCTCCATCCTCCCTGTCTGCATCTGTAGGAGACAGAGTCATCATCACTTGCCAGGCGAGCCAAGACATTAGCA
TCTATTTAAATTGGTATCAGGTGAAACCAGGGAAAGCCCCTAAACTCCTGATCTACGATGCCTCCAATTTGCAAGCAGGGGTCCCATCAAGGTTCAGTGGAAGTG
GATCAGGGACAGATTTTAGTTTCACCATCAGCAGCCTGCAGCCTGAAGATGTGGCAGCATATTACTGTCATCAGTATGATTCTTTACCGAGTTTTGGCCAGGGGA
CCAAGCTGGAAATCAAACGTACG

FIG. 12 (cont.)

AJL07 IgG VH insert: *VH4-59; JH4* (SEQ ID NO: 77)

ACCGGTGTACATTCCCAGGTGCAGCTGCAGGAGTCGGGCCCAGGACTGGTGAAGCCTTCGGAGACCCTGTCCCTCACCTGCAATGTCTCTGGTGGCTCCATCAAC
AACTATTACTGGAGTTGGATCCGGCAGCCCCCAGGGAAGGGACTGGAGTGGATTGGTTATATCTATTACAATGGGAATATTAATTACAACCCTTCCCTCAAGAGT
CGAGTCACCATATCAAGAGACATGTCCAAGAACCAGTTCTCCCTGAACCTGCGGTCTGTGACCGCTGCGGACACGGCCGTGTATTACTGTGGAATTGGATATAGT
GCGGTGGCAGCTGGTACAGTTGACTACTGGGGCCATGGCACCCTGGTCACCGTCTCCTCAGCGTCGAC

AJL07 IgK VK insert: *VK1-13; JK2* (SEQ ID NO: 78)

ACCGGTGTACATTCAGCCATCCAGTTGACCCAGTCTCCATCCTCCCTGTCTGCATCTGTGGGAGACAGAGTCACCATCACTTGCCGGGCAAGTCAGGGCATTAGCA
GTGGTTTAGCCTGGTATCAGCAGGAACCAGGGAAAGCTCCTAAACTCCTGATCTATGATGCCTCCACTTTGGAAAGTGGGGTCCCATCAAGATTCAGCGGCAGTG
GATCTGCAATAGATTTCACTCTCACCATCAGCAGTCTGCAGCCTGAAGATTTTGCAACTTATTACTGTCAACAGTTTAATACTTTCCCGTACACTTTTGGCCAGGGG
ACCAAGCTGGAGATCAAACGTACG

AJL08 IgG VH insert: *VH4b; JH4* (SEQ ID NO: 79)

ACCGGTGTACATTCCCAGGTGCAGCTGCAGGAGTCGGGCCCAGGACTGGTGAAGCCTTCGGAGACCCTGTCCCTCACCTGCGCTGTCTCTGGTTTCTCCATCACC
AGTGGTTACTACTGGGGCTGGATCCGGCAGCCCCCCGGGAAGGGGCTGGAGTGGATAGGGAGTATCTATCATACTGGGACTACCTACTACAACCCGTCCCTCAA
GAGTCGAGTCACCATATCAGTAGACACGTCCAAGAACCAGTTCTCCCTGAACCTAAACTCTGTGACCGCCGCAGACACGGCCTTTTATTACTGTGCGAGAGATCCT
CTATTCCCGGGGCGGAACCTACTCTCCGTTTTTGACAACTGGGGCCAGGGCACCCTGGTCACCGTCTCCTCAGCGTCGAC

AJL08 IgK VK insert: *VK1-5; JK2* (SEQ ID NO: 80)

ACCGGTGTACATTCTGACATCCAGATGACCCAGTCTCCTTCCACCCTGTCTGCATCTGTAGGAGACAGAGTCACCATCACTTGCCGGGCCAGTCAGAGTATTAGTA
CCTGGTTGGCCTGGTATCAGCAGAAACCAGGGAAAGCCCCTAGGCTCCTGATCTATAAGGCATCTAGTTTAGAAAGTGGGGTCCCATCACGTTTCAGCGGCAGT
GGATCTGGGACAGAATTCACTCTCACCATCAGCGGCCTGCAGCCTGATGACTTTGCAAATTATTCCTGCCAACAATATAATATTTACCCGTTCACTTTTGGCCAGG
GGACCAAGCTGGAGATCAAACGTACG

FIG. 12 (cont.)

AJL09 IgG VH insert: *VH4-59; JH5* (SEQ ID NO: 81)

ACCGGTGTACATTCCCAGGTGCAGCTGCAGGAGTCGGGCCCAGGACTGGTGAAGCCTTCGGAGACCCTGTCCCTCACCTGCAGTGTCTCTGGTGGCTCCATCAGT
AGTTACTACTGGGGCTGGATCCGGCAGTCCCCAGGGAAAGGACTGGAGTGCATTGGATACATCTATTTCAGTGGGAGCACCAGCTACAACCCCTCCCTCAAGAG
TCGAGTCACCATATCAGTAGACACGGCCAAGAACCAGATCTCCCTGAACCTGACCTCTGTGACCGCTGCGGACACGGCCGTGTATTTTTGTGCGAGAGTTTGGGG
CAGCAGCTGGTACGCTAACTGGTTCGACCCCTGGGGCCAGGGCACCCTGGTCACCGTCTCCTCAGCGTCGAC

AJL09 IgK VK insert: *VK1-13; JK5* (SEQ ID NO: 82)

ACCGGTGTACATTCAGCCATCCAGTTGACCCAGTCTCCATCCTCCCTGTCTGCGTCTGTTGGAGACAGAGTCACCATCACTTGCCGGGCAAGTCAGGGCATTAGCA
GTGCCTTAGCCTGGTATCAGCACAAACCAGGGAAGGCTCCTAAACTCCTGATCTTTGATGCCTCCACTTTGGCAGCTGGGGTCCCATCCAGGTTCAGCGGCAGTG
GATCTGGGACAGATTTCACTCTCACCATCAGCAGTCTGCAGCCTGAAGATTTTGCTACTTATTACTGTCAGCAGTATAATACTTACGTTCTCACTTTCGGCCAAGGG
ACACGACTGGAGATTAAACGTACG

AJL10 IgG VH insert: *VH4-4; JH6* (SEQ ID NO: 83)

ACCGGTGTACATTCCCAGGTGCAGCTGCAGGAGTCGGGCCCAGGACTGGTGAAGCCTTCGGAGACCCTGTCCCTCACCTGCAGTGTCTCTGGTGGCGCCGTCAG
TAATTACTACTGGAGTTGGATCCGGCAGTCCGCCGGGAAGGGACTGGAGTGGCTTGGGCGGATCTATATCAATGGAACTACTTACTACAACCCCTCCCTCAGGA
GCCGGGTCTCCATGTCAGTTGACACGTCCAAGGGCCAGTTCTCCCTGAGGTTGACCTCTGTGACCGCCGCGGACACGGCCATATATTATTGTGCGAGATGGGGTG
CCCTATTGGGCGACTACTATTACGGTTTGGACGTCTGGGGCCAAGGGACCACGGTCACCGTCTCCTCAGCGTCGAC

AJL10 IgK VK insert: *VK2-28; JK5* (SEQ ID NO: 84)

ACCGGTGTACATGGGGATATTGTGATGACTCAGTCTCCACTCTCCCTGCCCGTCACCCCTGGAGAGCCGGCCTCCATCTCCTGCAGGTCTACTCAGAGCCTCCTAC
ACAGTAATGAATACATTTATTTGGATTGGTACGTGCAGAAGCCAGGGCAGTCTCCACAACTCCTGATCTTTTTGGCTTCTAATCGGGCCTCCGGGGTCCCTGACAG
GTTCAGTGGCAGTGCATCAGGCACAGATTTTACACTGAAAATCAGCAGAGTGGAGGCTGAGGATGTTGGGGTTTATTACTGCATGCAAGCTCTAGAAGCTCCGT
GGACGTTCGGCCAAGGGACACGACTGGAGATTAAACGTACG

FIG. 12 (cont.)

AJL11 IgG VH insert: *VH4-39; JH5* (SEQ ID NO: 85)

ACCGGTGTACATTCCCAGCTGCAGCTGCAGGAGTCGGGCCCAGGACTGGTGAAGCCTTCGGAGACCCTGTCCCTCACCTGCTCTGTCTCTGGTGGCTCCATCACC
AGTACTTCTTATTACTGGGGGTGGATCCGCCAGTCCCCAGGGAAGGGACTGGAGTGGATTGGCAGTGTCTATTACAGTGGGAACACCTTCTACAACGCGTCCCTC
AAGAGTCGAGTCACCATATCCATAGACACGTCCAAGTACCAGTTCTCCCTGATGCTGAGGTCTGTGACCGCCGCAGACACGGCTGTGTATTACTGTGCGAGACGA
CATGATTGGTTCTGGTTCGACCCCTGGGGCCAAGGAACCCTGGTCACCGTCTCCTCAGCGTCGAC

AJL11 IgK VK insert: *VK3-20; JK2* (SEQ ID NO: 86)

ACCGGTGTACATTCAGAAATTGTGTTGACGCAGTCTCCAGGCACCCTGTCTTTGTCTCCAGGGGAAAGAGTCACCCTCTCCTGCAGGGCCAGTCAGAGTGTTAGC
AGCAGCTACTTAGCCTGGTACCAGCAGAAACCTGGCCAGGCTCCCAGGCTCCTCATCTATGATTCATCCAGCAGGGCCACTGGCATCCCAGACAGGTTCAGTGGC
AGTGGGTCTGGGACAGACTTCACTCTCACCATCAGCAGACTGGACCCTGAAGATTTTGCCGTGTATTACTGTCAGCAGTATGGTAGCTCACCAAGCACTTTTGGCC
AGGGGACCAAGCTGGAGATCAAACGTACG

AJL12 IgG VH insert: *VH4-39; JH5* (SEQ ID NO: 87)

ACCGGTGTACATTCCCAGCTGCAGCTGCAGGAGTCGGGCCCAGGACTGGTGAAGCCTTCGGAGACCCTGTCCCTCACCTGCACTGTCTCTGGTGGCTCCGTCACC
AGTAGTGATTACTACTGGGCCTGGATCCGCCAGCCCCCAGGGAAGGGGCCGGAGTGGATTGGGAGTATCTCTAATAGTGGGAACACGTATTACAGTCCGTCCCT
CAAGAGTCGAGTCTCCATATCGGGAGACACGTCCAAGAAGCAGTTCTCCCTGAACCTGAGCTCTGTGACCGACGCAGACACGGCTGTGTATTACTGTACGAGAC
ACGGTCACTACGTTTCAGGGGGGCTGGGCCCCTGGGGCCAAGGAACCCTGGTCACCGTCTCCTCAGCGTCGAC

AJL12 IgK VK insert: *VK3-20; JK1* (SEQ ID NO: 88)

ACCGGTGTACATTCAGAAATTGTGTTGACGCAGTCTCCAGGCACCCTGTCTTTGTCTCCAGGGGAAAGAGCCACCCTCTCCTGCAGGGCCAGTCAGAGTGTTGGC
AGTTACTACTTAGCCTGGTACCAGCAGAAACCTGGCCAGGCTCCCAGGCTCCTCATCCACGGTGCATCCAGCAGGGCCACTGGCACCCCAGACAGGTTCAGTGGC
AGTGGGTCTGGGACAGACTTCACTCTCACCATCAGCAAACTGGAGCCTGAAGATTTTGCACTGTATTACTGTCAGCAGTATGGTCCCTCACCTTGGACGTTCGGCC
AAGGGACCAAGGTGGAAATCAAACGTACG

FIG. 12 (cont.)

AJL13 IgG VH insert: *VH4-59; JH4* (SEQ ID NO: 89)

ACCGGTGTACATTCCCAGGTGCAGCTGCAGGAGTCGGGCCCAGGACTGGTGAAGCCTTCGGAGACCCTGTCCCTCACCTGCAATGTCTCTGGTGGCTCCATCAAC
AACTATTACTGGAGTTGGATCCGGCAGCCCCCAGGGAAGGGACTGGAGTGGATTGGTTATATCTATTACAATGGGAATATTAATTACAACCCTTCCCTCAAGAGT
CGAGTCACCATATCAAGAGACATGTCCAAGAACCAGTTCTCCCTGAACCTGCGGTCTGTGACCGCTGCGGACACGGCCGTGTATTACTGTGGAATTGGATATAGT
GCGGTGGCAGCTGGTACAGTTGACTACTGGGGCCAGGGAACCCTGGTCACCGTCTCCTCAGCGTCGAC

AJL13 IgK VK insert: *VK2-30; JK5* (SEQ ID NO: 90)

ACCGGTGTACATGGGGATGTTGTGATGACTCAGTCTCCACTCTCCCTGCCCGTCACCCTTGGACAACCGGCCTCCATCTCCTGCAGGTCTAGTCAAAGCCTCGTAC
ACAGGAATGGAAACACCTACTTGAATTGGTTTCAGCAGAGGCCAGGCCAATCGCCAAGGCGCCTAATTTATACAGTTTCTAAGCGGGGCTCTGGGGTCCCAGAC
AGATTCAGCGGCAGTGGGTCAGGCACTGATTTCACACTGAAAATCAGCAGGGTGGAGGCTGAAGATGTTGGGGACTATTACTGCATGCAAGGTACACACTGGC
CTTGGACGTCCGGCCAAGGGACACGACTGGAGATTAAACGTACG

AJL14 IgG VH insert: *VH4-61; JH6* (SEQ ID NO: 91)

ACCGGTGTACATTCCCAGGTGCAGCTGCAGGAGTCGGGCCCAGGACTGGTGAAGCCTTCACAGACCCTGTCCCTCACCTGCACTGTCTCTGGTGGCTCCCTCAGT
AGTGTTAATTACTACTGGAACTGGATCCGGCAGCCCGCCGGGAAGGGACTGGAGTGGATGGGGCGTATCTATGCCAGCGGGTACACCACCTACAACCCGTCCTT
CCAGAGTCGAGTCACCATATCACTGGACCCGTCCAAGAACCAGATCTCCCTGAAGGTGACTTCTCTGACCGCCGCAGACACGGCCATCTATTACTGTGCGAGACA
CGACCTTGGGCATTGTAGTAGTACGAGCTGTTACCTCAGTTGGTTCGACGCCTGGGGCCAAGGGACCACGGTCACCGTCTCCTCAGCGTCGAC

AJL14 IgK VK insert: *VK4-1; JK2* (SEQ ID NO: 92)

ACCGGTGTACATTCGGACATCGTGATGACCCAGTCTCCCGACTCCCTGGCTGTGTCTCTGGGCGAGAGGGCCACCATCAACTGCAGGTCCAGCCAGACTATTTTC
TTCAGCCCCAACAATAACAACCACTTAGCTTGGTACCAGCAAAAACCAGGGCAGCCTCCTAGGCTGCTCATTTACTGGGCATCTACCCGGGAATCCGGGGTCCCT
GACCGATTCAGTGGCAGCGGGTCTGGGACAGATTTCACTCTCACCATCAGCGGCCTGCAGGCTGAAGATGTGGCAGTTTATTACTGTCAGCAATATTATAGTCTT
CCCTACACTTTTGGCCAGGGGACCAAGCTGGAGATCAAACGTACG

FIG. 12 (cont.)

AJL15 IgG VH insert: *VH4-39; JH5* (SEQ ID NO: 93)

ACCGGTGTACATTCCCAGCTGCAGCTGCAGGAGTCGGGCCCAGGACTGGTGAAGCCTTCGGAGACCCTGTCCCTCACCTGCACTGTCTCTGGTGGCTCCATCACC
AGTAGGAATAACTACTGGGGCTGGATCCGCCAGTCCCCAGGGAAGGGGCTGGAGTGGATTGGGAGTCTCTATTATACTGGGAGCGACTACTACAACCCGTCCCT
CAAGAGTCGAGTCACCATATCGGTAGACACATCGAAGAACCAATTCTCCCTGAGGCTGAGTTCTGTGACCGCCGCGGACACGGCCGTGTATTATTGTGTCAGAGT
TAACGTAGACGACTTTTGGAGTGGTTTAGGGGGGGCCTGGTTCGACCCCTGGGGCCAAGGAACCCTGGTCACCGTCTCCTCAGCGTCGAC

AJL15 IgK VK insert: *VK2D-29; JK2* (SEQ ID NO: 94)

ACCGGTGTACATGGGGATATTGTGATGACCCAGACTCCACTCTCTTTGTCCGTCACCCCTGGACAGCCGGCCTCCATCTCCTGCAAATCTAGTCAGAGCCTCCTGG
ATAGTGATGGAAAGACCCATTTGTACTGGTACCTGCAGAAGCCAGGCCAGTCTCCACAGTCCCTGATCTATGAAGTTTCTAAACGGTTCTCTGGAGTGCCAGATA
GGTTCACTGGCAGCGGGTCAGGGACAGATTTCACACTGAAAATCAGCCGGGTGGAGGCTGAGGATGTTGGGCTTTATTACTGCATGCAAAGTGCACAGCTTCCG
TACACTTTTGGCCAGGGGACCAAGCTGGAAATCAAACGTACG

AJL16 IgG VH insert: *VH4-39; JH5* (SEQ ID NO: 95)

ACCGGTGTACATTCCCAGCTGCAGCTGCAGGAGTCGGGCCCAGGACTGGTGAAGCCTTCGGAGACCCTGTCCCTCACCTGCACTGTCTCTGGTGGCTCCATCAGC
AGTAGTCCTTACTACTGGGGCTGGATCCGCCAGCCCCCAGGGAAGGGGCTGGAGTGGATTGGGAGTATCTATTATAGTGGGCACACCTATTATAACCCCTCCCTC
AAGAGTCGAGTCACCATATCCGTTGACACGTCCAAGAACCAGTTCTCCCTGCGGCTGACCTCTGTGACCGCCGCAGACACGTCTGTGTATTACTGTGCGAAACAG
ACCGATGACTACGGTGACTACGCGTCCAGGGGCTGGTTCGACCCCTGGGGCCAAGGAACCCTGGTCACCGTCTCCTCAGCGTCGAC

AJL16 IgK VK insert: *VK1-33; JK5* (SEQ ID NO: 96)

ACCGGTGTACATTCTGACATCCAGATGACCCAGTCTCCATCCTCCCTGTCTGCATCTGTAGGAGACAGAGTCACCTTCACTTGCCAGGCGAGTCACGACATTAGCA
ACTATTTAAATTGGTATCAGCAGAAACCAGGGAAAGTCCCTGAGCTCCTGATCTACGATGCATCCAATTTGAAAACAGGGGTCCCATCAAGGTTCAGTGGAAGTG
GATCTGGGACAGATTTTACTTTCACCATCAGCAGCCTGCAGCCTGAAGATATTGCAACATATTACTGTCAACAGTATGATAATCTCCCTATCACCTTCGGCCAAGG
GACACGACTGGAGATTAAACGTACG

FIG. 12 (cont.)

AJL18 IgG VH insert: *VH4-31; JH5* (SEQ ID NO: 97)

ACCGGTGTACATTCCCAGGTGCAGCTGCAGGAGTCGGGCCCAGGACTGGTGAAGCCTTCACAGACCCTGTCCCTCACCTGCACTGTCTCTGGTGACTCCATCAGC
AGTGATAAATACTACTGGACCTGGATCCGCCAGCTCCCAGGGAAGGGCCTGGAGTGGATTGGCTACATCTCTTACAGTGGGACCACCTACTACAATCCGTCCCTC
AAGAGTCGAGTTTCCATTTCAGTTGACACGTCTGGGAACCAGTTCTCCCTGAGGCTGAGCTCTGTGACTGCCGCGGACACGGCCCGCTATTACTGTGCGCGAGTA
TATTACGATGTTTTGTCTGCTTATTATAATATGGGGTCCTGGGTAGACCCCTGGGGCCAAGGAACCCTGGTCACCGTCTCCTCAGCGTCGAC

AJL18 IgK VK insert: *VK1-39; JK1* (SEQ ID NO: 98)

ACCGGTGTACATTCTGACATCCAGATGACCCAGTCTCCATCCTCCCTGCCTGCATCTGTAGGAGACAGAGTCACCATCACTTGCCGGGCAAGTCAGAGCATTAGCA
GCTATTTAAATTGGTATCAGCAGAAACCAGGGAGAGCCCCTAAGCTCCTGATCTATGCTGCATCCAGTTTACAAAGTGGGGTCTCATCAAGGTTCAGTGGCAGTG
GATCTGGGACAGATTTCACTCTCACCATCAGCAGTCTGCAACCTGAAGATTCTGCAACTTACTACTGTCAACAGAGTTACAGTACCCCGTGGACGTTCGGCCAAGG
GACCAAGGTGGAGATCAAACGTACG

AJL19 IgG VH insert: *VH4-34; JH3* (SEQ ID NO: 99)

ACCGGTGTACATTCCCAGGTGCAGCTACAGCAGTGGGGCGCAGGACTGTTGAAGCCTCCGGAGACCCTGTCCCTCACCTGCGCTGTCTTTGGTGGGTCCCTCAGT
GGTTACTACTGGAGTTGGATCCGCCAGCCCCCAGGGAAGGGGCCGGAGTGGATTGCGGAAATCAATCATAGTGGAGATGCCAACTACAACCCGTCCCTCAAGA
GTCGAGTCACTATCTCAGTAGACACGTCCAAGAACCAGTTTTCCCTGAAGATGAGTTCTGTGACCGTCGCAGACACGGCTTTATATTACTGTGCGACTCAAGGCTC
TAGGTTGACTACATTCGCTTTTGATGTGTGGGGCCAAGGGACAATGGTCACCGTCTCTTCAGCGTCGAC

AJL19 IgK VK insert: *VK3-20; JK2* (SEQ ID NO: 100)

ACCGGTGTACATTCAGAAATTGTGTTGACGCAGTCTCCAGGCACCCTGTCTTTGTCTCCAGGGGAAAGAGTCACCCTCTCCTGCAGGACCAGTCAGAGTGTTAGC
AGCGACTCCTTAGCCTGGTACCAGCAGAAACCTGGCCAGACTCCCAGGCTCCTCATTTATCATACATCCACCAGGGCCGCTGGCATCCCAGACAGGTTCAGTGGC
ACTGGGTCTGGGACAGACTTCACTCTCACCATCGCCAGACTGGAGCCTGAAGATTTTGCAGTCTATTACTGTCAGCACTATGGTCGGTCATCCCTATTCACCTTTG
GCCAGGGGACCAAGCTGGAAATCAAACGTACG

FIG. 12 (cont.)

AJL20 IgG VH insert: *VH4-39; JH4* (SEQ ID NO: 101)

ACCGGTGTACATTCCCAGCTGCAGCTGCAGGAGTCGGGCCCAGGACTGGTGAAGCCTTCGGAGACCCTGTCCCTCACCTGCACTGTCTCTGGTGGCTCCATCAGC
GGTAGTTCTTTCTACTGGGGCTGGGTCCGCCAGCCCCCAGGGAGGGGCTGGAGTGGATTGGCACTATCTATTATCGTGGGACCACCTATTACACCCCGTCTCTC
AAGAGTCGAGTCACCATATCCGTGGACACCTCCAAGAACCAGTTCTCCCTGAGGTTGAACTCTGTGACCGCCGCAGACACGGCTATATATTACTGTGCGAGCCTT
CCCCACTACGATTTTTGGAGTGGTTCTGTTTTCTTTGACTACTGGGGCCAAGGAACCCTGGTCACCGTCTCCTCAGCGTCGAC

AJL20 IgK VK insert: *VK1-27; JK4* (SEQ ID NO: 102)

ACCGGTGTACATTCTGACATCCAGATGACCCAGTCTCCATCCTCCCTGTCTGCATCTGTAGGAGACAGAGTCACCATCACTTGCCGGGCGAGTCAGGGCATTGCCA
ATTATTTAGCCTGGTATCAGCAGAAACCAGGGAACATTCCTAAGCTCCTGATCTATGCTGCATCCACTTTGCAATCAGGGGTCCCATCTCGGTTCAGTGGCAGTGG
ATCTGGAACAGATTTCGCTCTCACCATCAGCTGCCTACAGCCTGAGGATGTTGCAACTTATTACTGTCAAAAGTATAACAGTGCCCCTCTCACTTTCGGCGGAGGG
ACCAAGGTGGAGATCAAACGTACG

WR01 IgG VH insert: *VH4-59; JH6* (SEQ ID NO: 103)

ACCGGTGTACATTCCCAGGTGCAGCTGCAGGAGTCGGGCCCAGGACTGGTGAAGCCTTCGGAGACCCTGTCCCTCACGTGCACTGTTTCTGGTGGCTCCATCGAT
ACTTACTACTGGACCTGGATCCGGCAGCCCCCGGGGAAGGGACTGGAGTGGATTGGGTATATTTATTCCACTGGGAGCCCCAAGTACAAGCCCTCCCTCAAGAG
TCGGGTCGTCATGTCAGTGGACACGTCCACGAACGAGTTCGCCCTGAGGCTGAGCTCTGTGACCGCTGCGGACACGGCCGTGTATTACTGTGCGAGAAGTTCGG
GATTTTACGTTGAACACCTGGAAAAGTGGGGCCAAGGGACCACGGTCACCGTCTCCTCAGCGTCGAC

WR01 IgK VK insert: *VK3-20; JK2* (SEQ ID NO: 104)

ACCGGTGTACATTCAGAAATTGTGTTGACGCAGTCTCCAGCCACCCTGTCTTTGTCTCCAGGGGAAAGAGCCACTCTCTCCTGCAGGGCCAGTCAGACTGTGAGC
AGCAGCTACTTAGACTGGTTCCAGCAGAAACCTGGCCAGGCTCCCAGGCTCCTCATCTATGGTGCATCCAGCAGGGCCACTGGCATCCCAGACAGGTTCAGTGGC
AGTGGGTCTGGGACAGACTTCACTCTAACTATCAGCAGACTGGAGCCTGAAGATTTTGCAGTGTATTATTGTCAGCAGTTTGCTACCTCACCGTACACTTTTGGCC
AGGGGACCAAGCTGGAGATCAAACGTACG

FIG. 12 (cont.)

WR02 IgG VH insert: *VH4-30; JH6* (SEQ ID NO: 105)

ACCGGTGTACATTCCCAGGTGCAGCTGCAGGAGTCGGGCCCAGGACTGGTGAAGCCTTCACAGACCCTGTCCCTCACCTGCACTGTCTCTGGTGGCTCCATCAGC
AGTGGTGATTACCACTGGAGTTGGATCCGCCAGCCCCCAGGGAAGGGCCTGGAGTGGATTGGGAACATCAATTATAATGGGGGCGCGTACCACAATCCGTCCCT
CACGAATCGAGTTATCATGTCAGTAGACACGTCCAAGAATCACTTCTCCCTGAAACTGACCTCTGTGACTGCCGCAGACACGGCCGTGTATTACTGTGCCAGAGA
GTCTCAGTGGCTGCGATACGGCGCGTTCGGTATGGACGTCTGGGGCCAAGGGACCACGGTCACCGTCTCCTCAGCGTCGAC

WR02 IgK VK insert: *VK3-20; JK2* (SEQ ID NO: 106)

ACCGGTGTACATTCAGAAATTGTGTTGACGCAGTCTCCAGGCACCCTGTCTTTGTCTCCAGGGGAAAGAGCCACCCTCTCCTGCAGGGCCAGTCAGAGCGTTAGC
AGCAGCCACTTAGTCTGGTACCAGCAGAAAGCTGGCCAGGCTCCCAGGCTCGTCATCTATGGTGCAAACAGGAGGGCCTCTGGCACCCCAGACAGGTTCAGTGG
CAGTGGGTCTGGGACAGACTTCACTCTCACCATCAGCAGACTGGAGCCTGAAGACTTTGCAGTCTATTACTGTCAGCAGTATGGTAGCTCGCCGTACACTTTTGG
CCAGGGGACCAAGCTGGAGATCAAACGTACG

WR03 IgG VH insert: *VH4-4; JH3* (SEQ ID NO: 107)

ACCGGTGTACATTCCCAGGTGCAGCTGCAGGAGTCGGGCCCAGGACTGGTGAAGCCTTCGGGGACCCTGTCCCTCACCTGCGCTGTCTCTGGTGGCTCCATCAGC
AGTAGTTACTGGTGGAGTTGGGTCCGCCAGCCCCCCGGGAAGGGGCTGGAGTGGGTTGGAGAAATCTATCATAGTGGGGGCGCCAACTACAGCCCGTCCCTCA
AGAGTCGAGTCACCATATCAGTGGACAAGTCCAAGAACCAGTTCTCCCTGAACCTGATCTCTGTGACCGCCGCGGACACGGCCGTGTATTTCTGTGCGAGATCAC
GGATGCTAGTGGGTGCTGATGGTGGAGGTGCTTTTGATATCTGGGGCCAAGGGACAATGGTCACCGTCTCTTCAGCGTCGAC

WR03 IgK VK insert: *VK3-20; JK1* (SEQ ID NO: 108)

ACCGGTGTACATTCAGAAATTGTGTTGACGCAGTCTCCAGGCACCCTGTCTTTGTCTCCAGGGGAAAGAGCCACCCTCTCCTGCGGGGCCAGTCAGAGTGTTAGC
AGCAGCTACTTAGCCTGGTACCAGCAGAAACCTGGCCTGGCGCCCAGGCTCCTCATCTATGATGCATCCAGCAGGGCCACTGGCATCCCAGACAGGTTCAGTGGC
AGTGGGTCTGGGACAGACTTCACTCTCACCATCAGCAGACTGGAGCCTGAAGATTTTGCAGTGTATTACTGTCAGCAGTATGGTAGCTCACCTCAAACGTTCGGC
CAAGGGACCAAGGTGGAAATCAAACGTACG

FIG. 12 (cont.)

WR04 IgG VH insert: *VH4-39; JH4* (SEQ ID NO: 109)

ACCGGTGTACATTCCCAGCTGCAGCTGCAGCAGTCGGGCCCAGGACTGGTGAAGCCTTCGGAGACCCTGTCCCTCACCTGCACTGTCTCTGGTGGCTCCATCAGC
AGTGGTGGCTCATACTGGGGCTGGATCCGCCAGGCCCCCGGGAAGGGCCTGGAGTGGATTGGGAGTATGTATTATAGTGGGAGCACCTTCTACAACCCGTCCGT
CAAGAGTCGAGTCACCATATCCGTAGACAGGTCCAAGGAGCAGTTCTCCCTCAATCTGAACGCTGTGACCGCCGCAGACACGGCTGTGTATTACTGTGTGAGACA
TAGGAGATCGGAACCCAGCGACTCCTGGGGCCAAGGAACCCTGGTCACCGTCTCCTCAGCGTCGAC

WR04 IgK VK insert: *VK3-15; JK2* (SEQ ID NO: 110)

ACCGGTGTACATTCAGAAATAGTGATGACGCAGTCTCCAGCCACCCTGTCTGTGTCTCCAGGGGAAAGAGCCACCCTCTCCTGCAGGGCCAGTCAGAGTGTTAGC
AGCAACTTAGCCTGGTACCAGCAGAAACCTGGCCAGGCTCCCAGGCTCCTCATCTATGGTACATCCACCAGGGCCACTGGCATTCCAGCCAGGTTCAGTGGCAGT
GGGTCTGGGACAGAATTCACTCTCACCATCAGCAGCCTGCAGTCTGAAGATTCTGCAGTTTATTTCTGTCAACAGTATAATAACTGGCCGCTGTACACTTTTGGCC
AGGGGACCAAGGTGGAGATCAAACGTACG

WR05 IgG VH insert: *VH4-61; JH1* (SEQ ID NO: 111)

ACCGGTGTACATTCCCAGGTGCAGCTGCAGGAGTCGGGCCCAGGACTGGTGAAGCCTTCGGAGACCCTGTCTCTCACCTGCAGTGTCTCTGGTGGCTCCGTCAGC
AGCAATGGTCACTTCTGGAGCTGGATCCGGCTGCCCCCAGGGAAGGGACTGGAATGGATTGGCTATGTCTACAACACTGGGACCTCCGGCTACAGCCCCTCCCTC
AAGAGTCGAGTCACCATATCAGTAGACACGTCCAAGAACCAGTTCTCCCTGACACTGAGGTCTGTGACCGCTGCGGACACGGCCATTTACTACTGCGCGAGAGGT
CTCACTGGGAACTACCCGTCTCACTGGGGCCAAGGCACCCTGGTCACCGTCTCCTCAGCGTCGAC

WR05 IgK VK insert: *VK1-5; JK4* (SEQ ID NO: 112)

ACCGGTGTACATTCTGACATCCAGATGACCCAGTCTCCATCTTCCGTGTCTGCATCTGTAGGAGACAGAGTCACCATCACTTGTCGGGCGAGTCGGGGTGTTAGT
ACCTGGTTAGCCTGGTATCAGCAGAAACCAGGGGAAGCCCCTAAGCTCCTGATCTATGCTTCATCCCGTTTAGAAGGTGGGGTCCCAGCAAGGTTCAGCGGCAG
TGGATCTGGGACAGATTTCACTCTCACCATCAGCAGCCTGCAGCCTGAAGATTTTGCAACCTACTATTGTCAACAGGGTAACAGCTTCCCCCTCACTTTCGGCGGA
GGGACCAAGGTGGAGATCAAACGTACG

FIG. 12 (cont.)

WR06 IgG VH insert: *VH4-39; JH3* (SEQ ID NO: 113)

ACCGGTGTACATTCCCAGCTGCAGCTGCAGGAGTCGGGCCCAGGACTGGTGAAGCCTTCGGAGACCCTGTCCCTCACCTGCACTGTCTCTGGTGGCTCCGTCAGT
AGTAGTGCTTACTGGTGGGCCTGGATCCGCCAGCCCCCGGGGGGAGGACTGGAGTGGATCGGCCATATCTATTACTTTGGGAACAAATATTACAAGTCGTCCCT
CGAGAGTCGAGTCACCATTTCACTAGACGCGTCCCAGAACCAGTTCTCCCTGAAGCTGACCTCCGTGACCGCCGCAGACACGGCTCTGTATTACTGTGCGAGAGT
GGACACAGCTTTGGCTTTTGACTTCTGGGGCCAAGGGACAATGGTCACCGTCTCTTCAGCGTCGAC

WR06 IgK VK insert: *VK1-5; JK3* (SEQ ID NO: 114)

ACCGGTGTACATTCTGACATCCAGATGACCCAGTCTCCATCCTCCCTGTCTGCATCTGTAGGAGACAGAGTCACCATCACTTGCCGGGCAAGTCAGTATGTTAGTA
GTTCTTTGAATTGGTATCAGCAGAAACCAGGGAAAGCCCCTACACTCCTGATCTATCTTGCGTCCAATTTGCGAAGTGGGGTCCCATCAAGGTTCAGTGGCAGTG
AATCTGGGACAGATTTCACTCTCACCATCAACAGTCTGCAGCCTGAAGATGTTGCAACTTACTTCTGTCAACAGAGTTATAGTCTCCCTCGCACTTTCGGCCCTGGG
ACCAAAGTGGATATCAAACGTACG

WR07 IgG VH insert: *VH4-39; JH4* (SEQ ID NO: 115)

ACCGGTGTACATTCCCAGCTGCAGCTGCAGGAGTCGGGCCCAGGACTGGTGAAGCCCTCGGAGACCCTGTCCCTCACCTGCTCTGTCTCTGGTGGCTCCGTCAGT
AGTACAACTTACTACTGGGGGTGGATCCGCCAGTCCCCAGGGAAGGGGCTGGAGTGGATTGGGAGCATCTATCATAGTGGGAAAACCTACTACAACCCGTCCCT
CAAGAGTCGAGTCACCATATCAGTAGACACGTCCAAGAACCAGTTCTCCCTGAACCTGAGCTCTGTGACCGCCGCGGACACGGCCGTGTATTATTGTGCGAGAGA
GAATTCCCATCACTATGATAGTAGTGGTTATTACTTAGGTGGATTTGACTACTGGGGCCAGGGAACCCTGGTCACCGTCTCCTCAGCGTCGAC

WR07 IgK VK insert: *VK3-20; JK1* (SEQ ID NO: 116)

ACCGGTGTACATTCAGAAATTGTGTTGACGCAGTCTCCAGGCACCCTGTCTTTGTCTCCAGGGGAAAGAGCCACCCTCTCCTGCAGGGCCAGTCAGAGTGTTAGC
AGCAGCTACTTAGCCTGGTACCAGCAGAAACCTGGCCAGGCTCCCAGGCTCCTCATCTATGGTGCATCCAGCAGGGCCACTGGCATCCCAGACAGGTTCAGTGGC
AGTGGGTCTGGGACAGACTTCACTCTCACCATCAGCAGACTGGAGCCTGAAGATTTCGCAGTATATTTCTGCCAGCACTATGGTAGCCCCTCCACGTTTGGCCAG
GGGACCAAGGTGGAGATCAAACGTACG

FIG. 12 (cont.)

WR08 IgG VH insert: *VH4-31; JH4* (SEQ ID NO: 117)

ACCGGTGTACATTCCCAGGTGCAGCTGCAGGAGTCGGGCCCAGGACTGGTGAAGCCTTCACAGACCCTGTCCCTCACCTGCACTGTCTCTGGTGGCTCCATCAGC
AGTGGTTACTACTGGAGTTGGATCCGCCAGCACCCAGGGAAGGGCCTGGATTGTATTGGGTACATCCATTACACGGGGACCACCTACTACAACCCGTCCCTGAA
GAGTCGACTTACCATATCAGTGGACACGTCTAAGAACCAGTTCTCCCTGAACCTGACCTCTGTGACTGCCGCGGACACGGCCGTCTATTATTGTGCGAGAGAAGA
ATATACAACCTCGTCAGTTGATTACTGGGGCCGGGGCACCCTGGTCACCGTCTCCTCAGCGTCGAC

WR08 IgK VK insert: *VK2-30; JK5* (SEQ ID NO: 118)

ACCGGTGTACATGGGGATGTTGTGATGACTCAGTCTCCACTCTCCCTGCCCGTCACCCTTGGACAGCCGGCCTCTATCTCCTGCAGGTCTAGTGAAAGCCTCGTGT
CTGTTGATGGAAATACCTACTTGAATTGGTTTCACCAGAGGCCAGGCCAATCTCCAAGGCGCCTAATTTATAAGGTTTCTAACCGGGACTCTGGGGTCCCAGACA
GATTCAGCGGCAGTGGGTCAGGCACTGATTTCACACTGAAAATCAGCAGGGTGGAGGCTGAGGATGTTGGGATTTATTACTGCATGCAAGCCACACACTGGCTT
CGGACGTTCGGCCAAGGGACACGACTGGAGATTAAACGTACG

WR09 IgG VH insert: *VH4-31; JH4* (SEQ ID NO: 119)

ACCGGTGTACATTCCCAGGTGCAGCTGCAGGAGTCGGGCCCAGGACTGGTGAAGCCTTCACAGACCCTGTCCCTCACCTGCACTGTCTCTGGTGGCTCCATCAGC
AGTGGTTACTACTGGAGTTGGATCCGCCAGCACCCAGGGAAGGGCCTGGAGTGGATTGGGTACATCCATTACACGGGGACCACCTACTACAACCCGTCCCTGAA
GAGTCGAGTTACCATATCAGTGGACACGTCTAAGAACCAGTTCTCCCTGAACCTGACCTCTGTGACTGCCGCGGACACGGCCGTCTATTATTGTGCGAGAGAAGA
ATATACGACCTCGTCAGTTGATTACTGGGGCCGTGGCACCCTGGTCACCGTCTCCTCAGCGTCGAC

WR09 IgK VK insert: *VK3-20; JK2* (SEQ ID NO: 120)

ACCGGTGTACATTCAGAAATTGTGTTGACGCAGTCTCCAGGCACCCTGTCTTTGTCTCCAGGGGAAAGAGCCACCCTCTCCTGCAGGGCCAGTCAGAGGGTTAGC
AGCGGCTTTTTAGCCTGGTACCAGCAGAAACCTGGCCAGGCTCCCAGGCTCCTCATCTATGGTGCATCCAGCAGGGCCACTGGCATCCCAGACAGGTTCAGTGGC
AGTGGCTCTGGGACAGACTTCACTCTCACCATCAGCAGACTGGAGCCTGAAGATTTTGCAGTGTATTACTGTCAGCAGTATGAAAGTTCACCGTCACCGTACAACT
TTGGCCAGGGGACCAAGCTGGAGATCAAACGTACG

FIG. 12 (cont.)

WR10 IgG VH insert: *VH4-4; JH6* (SEQ ID NO: 121)

ACCGGTGTACATTCCCAGGTGCAGCTGCAGGAGTCGGGCCCAGGACTGGTGAAGCCTTCGGGGACCCTGTCCCTCACCTGCGCTGTCTCTGGTGGCTCCATCAGC
AATAATAAGTGGTGGAATTGGGTCCGCCAGTCCCCAGGGAAGGGGCTGGAGTGGATTGGGGAAATCTATCATAGTGGGGGCACCAACTACAACCCGTCCCTCA
AGAGTCGAGTCACCATATCGGTAGACAAGTCCAAGAACCTGTTCTCCCTGAAGCTGAGCTCTGTGACCGCCGCGGACACGGCCGTGTATTACTGTGCGAGTGCG
ACTACTATGGTTCGGGGACTGAGTCTTTACTACTACGGTCTGGACGTCTGGGGCCCAGGGACCACGGTCACCGTCTCCTCAGCGTCGAC

WR10 IgK VK insert: *VK3-20; JK5* (SEQ ID NO: 122)

ACCGGTGTACATTCAGAAATTGTGTTGACGCAGTCTCCAGGCACCCTGTCTTTGTCTCCAGGGGAAAGAGCCGCCCTCTCCTGCAGGGCCAGTCAGAGTCTTATC
GGCAGCTTCTTAGCCTGGTACCAGCAGAAACCTGGCCAGGCTCCCAGGCTCCTCATCTATCATACATCCAACAGGGCCTCTGGCATCCCAGACAGGTTCAGTGGC
GGTGGGTTTGGGACAGACTTCACTCTCACCATCAGCAGACTGGAGCCTGAAGATTTTGCAGTTTATTACTGTCAACAGTATGATAGCTCACCGATCACCTTCGGCC
AAGGGACACGACTGGAGATTAAACGTACG

WR11 IgG VH insert: *VH4-4; JH6* (SEQ ID NO: 123)

ACCGGTGTACATTCCCAGGTGCAGCTGCAGGAGTCGGGCCCAGGACTGGTGAAGCCTTCGGGGACCCTGTCCCTCACCTGCGCTGTCTCTGGTGGCTCCATCAGC
AATAATAAGTGGTGGAATTGGGTCCGCCAGTCCCCAGGGAAGGGGCTGGAGTGGATTGGGGAAATCTATCATAGTGGGGGCACCAACTACAACCCGTCCCTCA
AGAGTCGAGTCACCATATCGGTAGACAAGTCCAAGAACCTGTTCTCCCTGAAGCTGAGCTCTGTGACCGCCGCGGACACGGCCGTGTATTACTGTGCGAGTGCG
ACTACTATGGTTCGGGGACTGAGTCTTTACTACTACGGTCTGGACGTCTGGGGCCAAGGGACCACGGTCACCGTCTCCTCAGCGTCGAC

WR11 IgK VK insert: *VK3-11; JK4* (SEQ ID NO: 124)

ACCGGTGTACATTCAGAAATTGTGTTGACGCAGTCTCCAGGCACCCTGTCTTTGTCTCCAGGGGAAAGAGCCACCCTCTCCTGCAGGGCCAGTCAGAGTGTTAGC
AGCTTCTTAGCCTGGTACCAACAGAAACCTGGCCAGGCTCCCAGACTCCTCATCTATGATGCATCCAACAGGGCCACTGGCATCCCAGCCAGGTTCAGTGGCAGT
GGGTCTGGGACAGATTTCACTCTCACCATCAGCAGCCTAGAGCCTGAAGATTTTGCAGTTTATTACTGTCAGCAGCGTACCAACTGGCCTCCCTCGCTCACTTTCG
GCGGAGGGACCAAGGTGGAGATCAAACGTACG

FIG. 12 (cont.)

WR12 IgG VH insert: *VH4-30; JH4* (SEQ ID NO: 125)

ACCGGTGTACATTCCCAGGTGCAGCTGCAGGAGTCGGGCCCAGGACTGGTGAAGCCTTCACAGACCCTGTCCCTCACCTGCACTGTCTCTGGCGACTCCGTCAGC
AGTAATGATCACTACTGGAGTTGGATCCGCCAGCCCCCAGGGCAGGGCCTGGAGTGGATTGGGTACATCTCTCACGGTGGGACCACCTACTACAACCCGTCCCTC
AAGAGTCGAGTTACCATGTCGATCGACACGTCCACGAACCAGTTCTCCCTGAGGGTGACCTCCGTGCGAGCCGCAGACATGGCCGTCTACTTCTGTGCCAGGGCC
CCGGCCCCTATAACGACTTTTGGAATGGTGACACCAGTCCCCTACTTTCACTCCTGGGGCCAAGGCACCCTGGTCACCGTCTCCTCAGCGTCGAC

WR12 IgK VK insert: *VK2-28; JK4* (SEQ ID NO: 126)

ACCGGTGTACATGGGGATATTGTGATGACTCAGTCTCCACTGTCCCTGCCCGTCAGCCCTGGAGAGCCGGCCTCCATCTCCTGCAGGTCTAGTCAGAGCCTCCTCC
ATAGTAATGGATACAACTATTTGAGTTGGTACCTGCAGAAGCCAGGGCAGTCTCCACAACTCCTGATCTTTTCGAGTTCTATTCGGGCCTCCGGGGTCCCTGACAG
GTTCAGTGGCAGTGGATCAGGCACAGATTTTACACTGACAATCAACAGAGTGGAGGCTGAGGATGTTGGAGTTTATTACTGCATGCAGGCTCTACAAACTCCGCT
CACTTTCGGCGGAGGGACCAAGCTGGAAATCAAACGTACG

WR13 IgG VH insert: *VH4-30; JH4* (SEQ ID NO: 127)

ACCGGTGTACATTCCCAGGTGCAGCTGCAGGAGTCGGGCCCAGGACTGGTGAAGCCTTCACAGACCCTGTCCCTCACCTGCACTGTCTCTGGCGACTCCGTCAGC
AGTAATGATCACTACTGGAGTTGGATCCGCCAGCCCCCAGGGCAGGGCCTGGAGTGGATTGGGTACATCTCTCACGGTGGGACCACCTACTACAACCCGTCCCTC
AAGAGTCGAGTTACCATGTCGATCGACACGTCCACGAACCAGTTCTCCCTGAGGGTGACCTCCGTGCGAGCCGCAGACATGGCCGTCTACTTCTGTGCCAGGGCC
CCGGCCCCTATAACGACTTTTGGAATGGTGACACCAGTCCCCTACTTTCACTCCTGGGGCCAAGGCACCCTGGTCACCGTCTCCTCAGCGTCGAC

WR13 IgK VK insert: *VK2-28; JK2* (SEQ ID NO: 128)

ACCGGTGTACATGGGGATATTGTGATGACTCAGTCTCCACTGTCCCTGCCCGTCAGCCCTGGAGAGTCGGCCTCCATCTCCTGCAGGTCTAGTCAGAGCCTCCTCC
ATAGTAATGGATACAACTATTTGAGTTGGTACCTGCAGAAGCCAGGGCAGTCTCCACAACTCCTGATCTTTTCGAGTTCTATTCGGGCCTCCGGGGTCCCTGACAG
GTTCAGTGGCAGTGGATCAGGCACAGATTTTACCCTGACAATCAACAGAGTGGAGGCTGAGGATGTTGGAGTTTATTACTGCATGCAGGCTCTACAAACTCCGCT
CACTTTCGGCCAGGGGACCAAGCTGGAAATCAAACGTACG

FIG. 12 (cont.)

Comparison of VH4 and VH3 antibodies

Plasmablast rhAbs react to neurons and glial cells in mouse brain

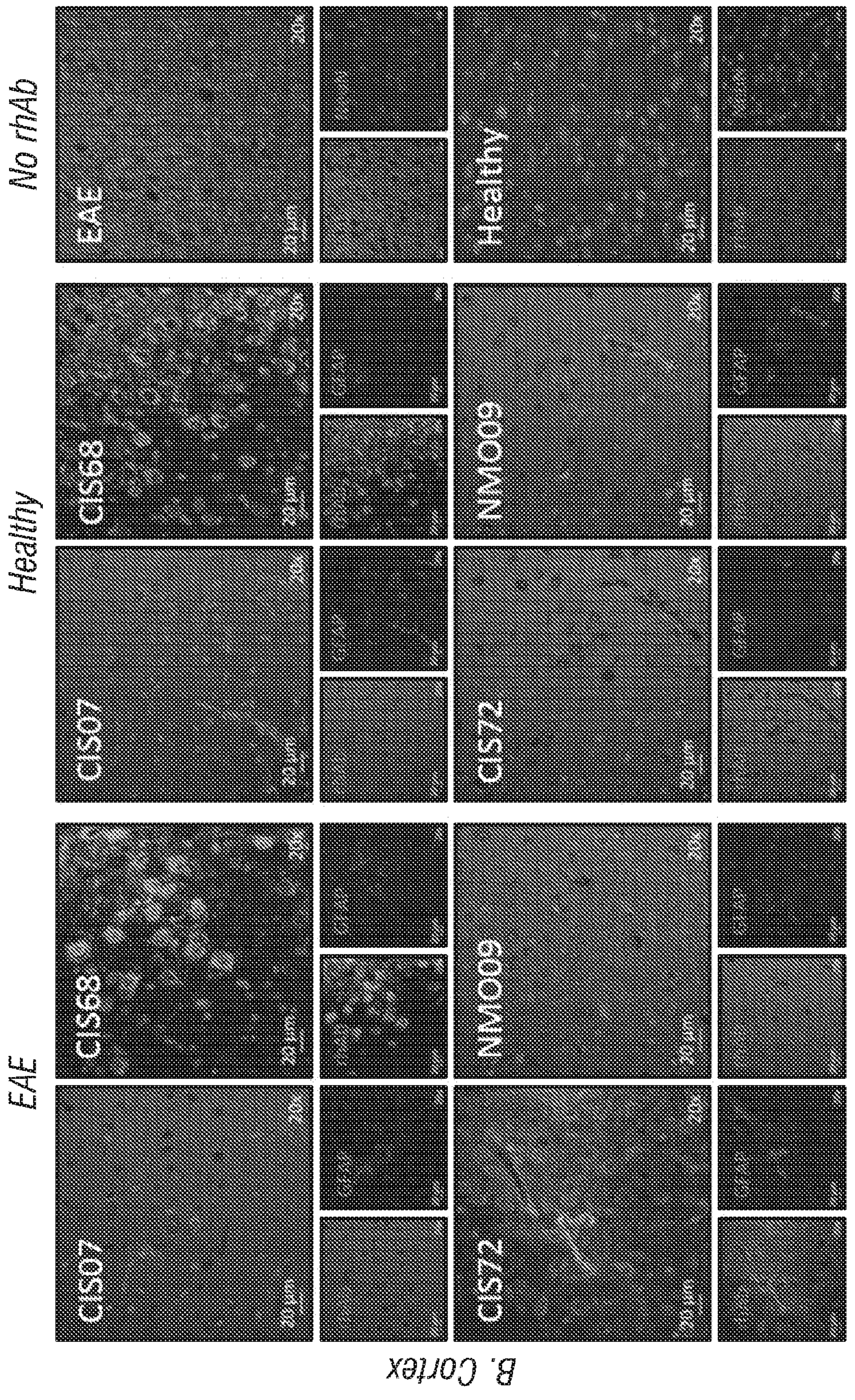
FIG. 31 (Contd.)

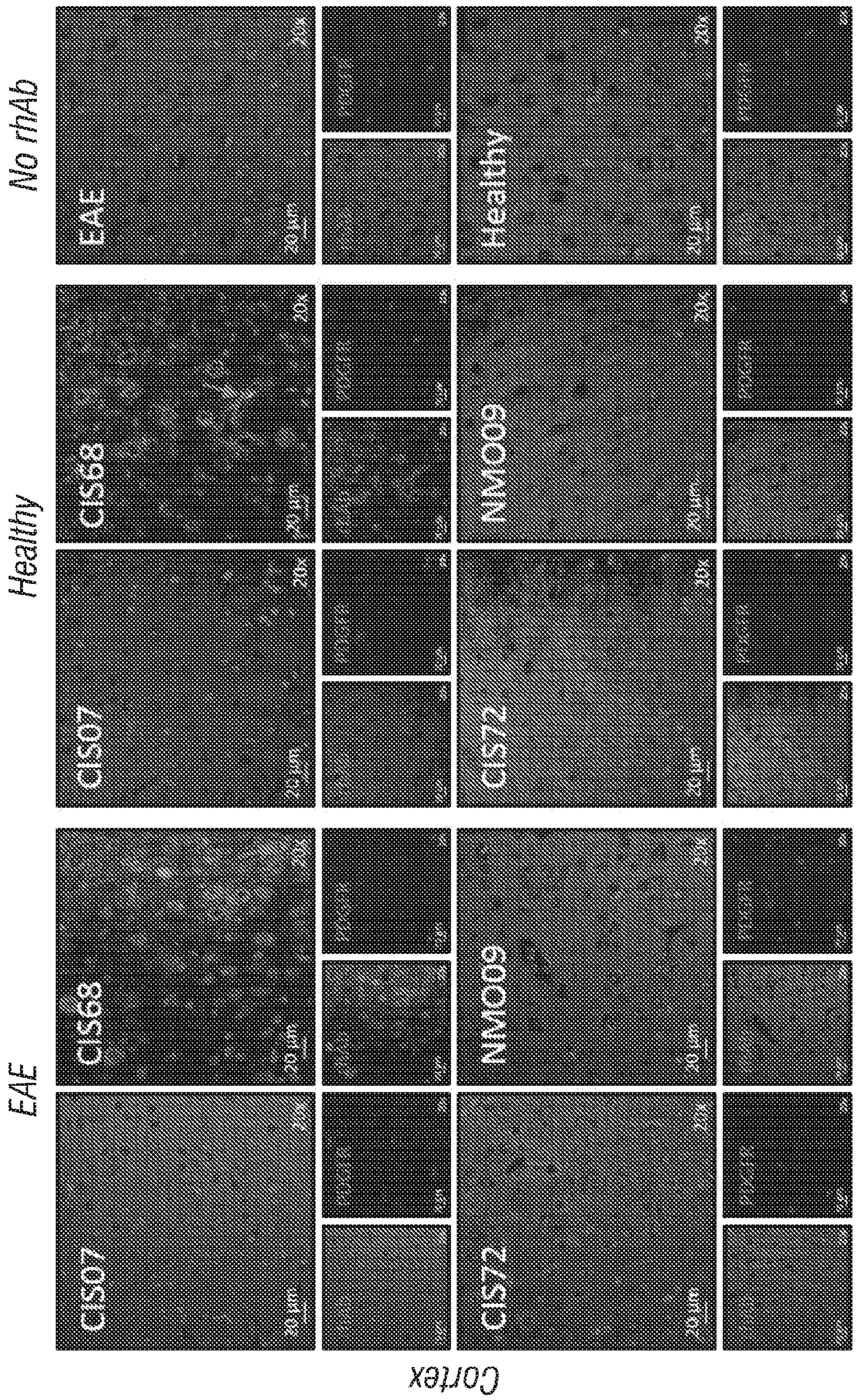
FIG. 33 (Contd.)

*Reactivity to Sy5y by ICC*

Reactivity to Sy5y by ICC

Reactivity to Hep2 by ICC

Reactivity to Neuro-2a by flow cytometry

| 4-30 Codon | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 4-30 Kabat | | 1 | 2 | 3 | 4 | 5 | 6 | 7 | 8 | 9 | 10 | 11 | 12 | 13 | 14 | 15 | 16 | 17 |
| Region | | | | | | | | | FR1 | | | | | | | | | |
| Germ. AA | Q | V | Q | L | Q | E | S | G | P | | G | L | V | K | P | S | Q | T |
| Germ. Nuc | cag | gtg | cag | ctg | cag | gag | tcg | ggc | cca | | gga | ctg | gtg | aag | cct | tca | cag | acc |
| WR12 AA | Q | V | Q | L | Q | E | S | G | P | | G | L | V | K | P | S | Q | T |
| WR12 Nuc | cag | gtg | cag | ctg | cag | gag | tcg | ggc | cca | | gga | ctg | gtg | aag | cct | tca | cag | acc |
| WR13 AA | Q | V | Q | L | Q | E | S | G | P | | G | L | V | K | P | S | Q | T |
| WR13 Nuc | cag | gtg | cag | ctg | cag | gag | tcg | ggc | cca | | gga | ctg | gtg | aag | cct | tca | cag | acc |

| 4-30 Codon | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| 4-30 Kabat | 18 | 19 | 20 | 21 | 22 | 23 | 24 | 25 | 26 | 27 | 28 | 29 | 30 | | | 31 | 31a | 31b |
| Region | | | | FR1 | | | | | | | | | | CDR1 | | | | |
| Germ. AA | L | S | L | T | C | T | V | S | G | G | S | I | S | | | S | G | D |
| Germ. Nuc | ctg | tcc | ctc | acc | tgc | act | gtc | tct | ggt | ggc | tcc | atc | agc | | | agt | ggt | gat |
| WR12 AA | L | S | L | T | C | T | V | S | G | D | S | V | S | | | S | N | D |
| WR12 Nuc | ctg | tcc | ctc | acc | tgc | act | gtc | tct | ggc | gac | tcc | gtc | agc | | | agt | aat | gat |
| WR13 AA | L | S | L | T | C | T | V | S | G | D | S | V | S | | | S | N | D |
| WR13 Nuc | ctg | tcc | ctc | acc | tgc | act | gtc | tct | ggc | gac | tcc | gtc | agc | | | agt | aat | gat |

| 4-30 Codon | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|
| 4-30 Kabat | 32 | 33 | 34 | 35 | 36 | 37 | 38 | 39 | 40 | 41 | 42 | 43 | 44 | 45 | 46 | 47 | 48 | 49 |
| Region | CDR1 | | | | | | | | | FR2 | | | | | | | | |
| Germ. AA | Y | Y | W | S | W | I | R | Q | P | P | G | K | G | L | E | W | I | G |
| Germ. Nuc | tac | tac | tgg | agt | tgg | atc | cgc | cag | ccc | cca | ggg | aag | ggc | ctg | gag | tgg | att | ggg |
| WR12 AA | II | Y | W | S | W | I | R | Q | P | P | G | Q | G | L | E | W | I | G |
| WR12 Nuc | cac | tac | tgg | agt | tgg | atc | cgc | cag | ccc | cca | ggg | cag | ggc | ctg | gag | tgg | att | ggg |
| WR13 AA | H | Y | W | S | W | I | R | Q | P | P | G | Q | G | L | E | W | I | G |
| WR13 Nuc | cac | tac | tgg | agt | tgg | atc | cgc | cag | ccc | cca | ggg | cag | ggc | ctg | gag | tgg | att | ggg |

| 4-30 Codon | 55 | 56 | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|---|---|
| 4-30 Kabat | 50 | 51 | 52 | 53 | 54 | | | | 55 | 56 | 57 | 58 | 59 | 60 | 61 | 62 | 63 | 64 |
| Region | FR2 | | | | | | CDR2 | | | | | | | | FR3 | | | |
| Germ. AA | Y | I | Y | Y | S | | | | G | S | T | Y | Y | N | P | S | L | K |
| Germ. Nuc | tac | atc | tat | tac | agt | | | | ggg | agc | acc | tac | tac | aac | ccg | tcc | ctc | aag |
| WR12 AA | Y | I | S | H | G | | | | G | T | T | Y | Y | N | P | S | L | K |
| WR12 Nuc | tac | atc | tct | cac | ggt | | | | ggg | acc | acc | tac | tac | aac | ccg | tcc | ctc | aag |
| WR13 AA | Y | I | S | H | G | | | | G | T | T | Y | Y | N | P | S | L | K |
| WR13 Nuc | tac | atc | tct | cac | ggt | | | | ggg | acc | acc | tac | tac | aac | ccg | tcc | ctc | aag |

| 4-30 Codon | 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|---|
| 4-30 Kabat | | 65 | 66 | 67 | 68 | 69 | 70 | 71 | 72 | 73 | 74 | 75 | 76 | 77 | 78 | 79 | 80 | 81 |
| Region | | | | | | | | | FR3 | | | | | | | | | |
| Germ. AA | | S | R | V | T | I | S | V | D | T | S | K | N | Q | F | S | L | K |
| Germ. Nuc | | agt | cga | gtt | acc | ata | tca | gta | gac | acg | tcc | aag | aac | cag | ttc | tcc | ctg | aag |
| WR12 AA | | S | R | V | T | M | S | I | D | T | S | T | N | Q | F | S | L | R |
| WR12 Nuc | | agt | cga | gtt | acc | atg | tcg | atc | gac | acg | tcc | acn | aac | cag | ttc | tcc | ctg | agg |
| WR13 AA | | S | R | V | T | M | S | I | D | T | S | T | N | Q | F | S | L | R |
| WR13 Nuc | | agt | cga | gtt | acc | atg | tcg | atc | gac | acg | tcc | acg | aac | cag | ttc | tcc | ctg | agg |

| 4-30 Codon | 91 | 92 | 93 | 94 | 95 | 96 | 97 | 98 | 99 | 100 | 101 | 102 | 103 | 104 | 105 | 106 | | |
|---|---|---|---|---|---|---|---|---|---|---|---|---|---|---|---|---|---|---|
| 4-30 Kabat | 82 | 82a | 82b | 82c | 83 | 84 | 85 | 86 | 87 | 88 | 89 | 90 | 91 | 92 | 93 | 94 | | |
| Region | | | | | | | FR3 | | | | | | | | | CDR3 | | |
| Germ. AA | L | S | S | V | T | A | A | D | T | A | V | Y | Y | C | A | R | A | |
| Germ. Nuc | ctg | agc | tct | gtg | act | gcc | gca | gac | acg | gcc | gtg | tat | tac | tgt | gcc | aga | gca | |
| WR12 AA | V | T | S | V | R | A | A | D | M | A | V | Y | F | C | A | R | A | P |
| WR12 Nuc | gtg | acc | tcc | gtg | cga | gcc | gca | gac | atg | gcc | gtc | tac | ttc | tgt | gcc | agg | gcc | ccg |
| WR13 AA | V | T | S | V | R | A | A | D | M | A | V | Y | F | C | A | R | A | P |
| WR13 Nuc | gtg | acc | tcc | gtg | cga | gcc | gca | gac | atg | gcc | gtc | tac | ttc | tgt | gcc | agg | gcc | ccg |

FIG. 43

| **4-30 Codon** | | | | | | | | | | | | | | | | | |
|---|---|---|---|---|---|---|---|---|---|---|---|---|---|---|---|---|---|
| **4-30 Kabat** | | | | | | | | | | | | | | | | | |
| **Region** | | | | | | | | | **CDR3** | | | | | | | | |
| Germ. AA | | | | | | | | | | | | | | | | | |
| Germ. Nuc | | | | | | | | | | | | | | | | | |
| WR12 AA | A | P | I | T | T | F | G | M | V | T | P | V | P | Y | F | H | S |
| WR12 Nuc | gcc | cct | ata | acg | act | ttt | gga | atg | gtg | aca | cca | gtc | ccc | tac | ttt | cac | tcc |
| WR13 AA | A | P | I | T | T | F | G | M | V | T | P | V | P | Y | F | H | S |
| WR13 Nuc | gcc | cct | ata | acg | act | ttt | gga | atg | gtg | aca | cca | gtc | ccc | tac | ttt | cac | tcc |

| **4-31 Codon** | **1** | **2** | **3** | **4** | **5** | **6** | **7** | **8** | **9** | **10** | **11** | **12** | **13** | **14** | **15** | **16** | **17** | **18** |
|---|---|---|---|---|---|---|---|---|---|---|---|---|---|---|---|---|---|---|
| **4-31 Kabat** | | **1** | **2** | **3** | **4** | **5** | **6** | **7** | **8** | **9** | **10** | **11** | **12** | **13** | **14** | **15** | **16** | **17** |
| **Region** | | | | | | | | | | **FR1** | | | | | | | | |
| Germ. AA | Q | V | Q | L | Q | E | S | G | P | | G | L | V | K | P | S | Q | T |
| Germ. Nuc | cag | gtg | cag | ctg | cag | gag | tcg | ggc | cca | | gga | ctg | gtg | aag | cct | tca | cag | acc |
| AJL02 AA | Q | V | Q | L | Q | E | S | G | P | | G | L | V | K | P | S | Q | T |
| AJL02 Nuc | cag | gtg | cag | ctg | cag | gag | tcg | ggc | cca | | gga | ctg | gtg | aag | cct | tca | cag | acc |

| **4-31 Codon** | **19** | **20** | **21** | **22** | **23** | **24** | **25** | **26** | **27** | **28** | **29** | **30** | **31** | **32** | **33** | **34** | **35** | **36** |
|---|---|---|---|---|---|---|---|---|---|---|---|---|---|---|---|---|---|---|
| **4-31 Kabat** | **18** | **19** | **20** | **21** | **22** | **23** | **24** | **25** | **26** | **27** | **28** | **29** | **30** | | | **31** | **31a** | **31b** |
| **Region** | | | | **FR1** | | | | | | | | | **CDR1** | | | | | |
| Germ. AA | L | S | L | T | C | T | V | S | G | G | S | I | S | | | S | G | G |
| Germ. Nuc | ctg | tcc | ctc | acc | tgt | act | gtc | tct | ggt | ggc | tcc | atc | agc | | | agt | ggt | ggt |
| AJL02 AA | L | S | L | T | C | T | V | S | G | G | S | I | S | | | S | G | G |
| AJL02 Nuc | ctg | tcc | ctc | acc | tgt | act | gtc | tct | ggt | ggc | tcc | atc | agc | | | agt | ggt | ggt |

| **4-31 Codon** | **37** | **38** | **39** | **40** | **41** | **42** | **43** | **44** | **45** | **46** | **47** | **48** | **49** | **50** | **51** | **52** | **53** | **54** |
|---|---|---|---|---|---|---|---|---|---|---|---|---|---|---|---|---|---|---|
| **4-31 Kabat** | **32** | **33** | **34** | **35** | **36** | **37** | **38** | **39** | **40** | **41** | **42** | **43** | **44** | **45** | **46** | **47** | **48** | **49** |
| **Region** | **CDR1** | | | | | | | | | **FR2** | | | | | | | | |
| Germ. AA | Y | Y | W | S | W | I | R | Q | H | P | G | K | G | L | E | W | I | G |
| Germ. Nuc | tac | tac | tgg | agc | tgg | atc | cgc | cag | cac | cca | ggg | aag | ggc | ctg | gag | tgg | att | ggg |
| AJL02 AA | H | Y | W | S | W | I | R | Q | S | P | G | K | G | L | E | W | I | G |
| AJL02 Nuc | cac | tac | tgg | agc | tgg | atc | cgc | cag | tcc | cca | ggg | aag | ggc | ctg | gag | tgg | att | ggg |

| **4-31 Codon** | **55** | **56** | **57** | **58** | **59** | **60** | **61** | **62** | **63** | **64** | **65** | **66** | **67** | **68** | **69** | **70** | **71** | **72** |
|---|---|---|---|---|---|---|---|---|---|---|---|---|---|---|---|---|---|---|
| **4-31 Kabat** | **50** | **51** | **52** | **53** | **54** | | | | **55** | **56** | **57** | **58** | **59** | **60** | **61** | **62** | **63** | **64** |
| **Region** | **FR2** | | | | | | **CDR2** | | | | | | | | **FR3** | | | |
| Germ. AA | Y | I | Y | Y | S | | | | G | S | T | Y | Y | N | P | S | L | K |
| Germ. Nuc | tac | atc | tat | tac | agt | | | | ggg | agc | acc | tac | tac | aac | ccg | tcc | ctc | aag |
| AJL02 AA | N | V | Y | Y | S | | | | G | S | T | Y | Y | T | P | S | L | D |
| AJL02 Nuc | aac | gtc | tat | tat | agt | | | | gga | agc | acc | tac | tac | acc | ccg | tcc | ctc | gac |

| **4-31 Codon** | **73** | **74** | **75** | **76** | **77** | **78** | **79** | **80** | **81** | **82** | **83** | **84** | **85** | **86** | **87** | **88** | **89** | **90** |
|---|---|---|---|---|---|---|---|---|---|---|---|---|---|---|---|---|---|---|
| **4-59 Kabat** | | **65** | **66** | **67** | **68** | **69** | **70** | **71** | **72** | **73** | **74** | **75** | **76** | **77** | **78** | **79** | **80** | **81** |
| **Region** | | | | | | | | | | **FR3** | | | | | | | | |
| Germ. AA | | S | R | V | T | I | S | V | D | T | S | K | N | Q | F | S | L | K |
| Germ. Nuc | | agt | cga | gtt | acc | ata | tca | gta | gac | acg | tct | aag | aac | cag | ttc | tcc | ctg | aag |
| AJL02 AA | | S | R | L | T | I | S | L | D | T | S | K | N | Q | F | S | L | R |
| AJL02 Nuc | | agc | cga | ctt | acc | ata | tca | tta | gac | acg | tct | aag | aac | cag | ttc | tcc | ctg | agg |

| **4-31 Codon** | **91** | **92** | **93** | **94** | **95** | **96** | **97** | **98** | **99** | **100** | **101** | **102** | **103** | **104** | **105** | **106** | | |
|---|---|---|---|---|---|---|---|---|---|---|---|---|---|---|---|---|---|---|
| **4-31 Kabat** | **82** | **82a** | **82b** | **82c** | **83** | **84** | **85** | **86** | **87** | **88** | **89** | **90** | **91** | **92** | **93** | **94** | | |
| **Region** | | | | | | | **FR3** | | | | | | | | | **CDR3** | | |
| Germ. AA | L | S | S | V | T | A | A | D | T | A | V | Y | Y | C | A | R | | |
| Germ. Nuc | ctg | agc | tct | gtg | act | gcc | gcg | gac | acg | gcc | gtg | tat | tac | tgt | gcg | aga | | |
| AJL02 AA | L | S | N | V | T | V | A | D | T | A | V | Y | Y | C | A | R | G | R |
| AJL02 Nuc | ctg | agt | aat | gtg | act | gtc | gcg | gac | acg | gcc | gtc | tat | tac | tgt | gcg | aga | ggt | aga |

FIG. 43 Continued

| **4-31 Codon** | | | | | | | | | | | | |
|---|---|---|---|---|---|---|---|---|---|---|---|---|
| **4-31 Kabat** | | | | | | | | | | | | |
| **Region** | | | | | | **CDR3** | | | | | | |
| Germ. AA | | | | | | | | | | | | |
| Germ. Nuc | | | | | | | | | | | | |
| AJL02 AA | N | W | E | G | E | F | D | P | W | G | Q | G |
| AJL02 Nuc | aat | tgg | gag | ggc | gaa | ttc | gac | ccc | tgg | ggc | caa | gga |

| **4-34 Codon** | **1** | **2** | **3** | **4** | **5** | **6** | **7** | **8** | **9** | **10** | **11** | **12** | **13** | **14** | **15** | **16** | **17** | **18** |
|---|---|---|---|---|---|---|---|---|---|---|---|---|---|---|---|---|---|---|
| **4-34 Kabat** | | **1** | **2** | **3** | **4** | **5** | **6** | **7** | **8** | **9** | **10** | **11** | **12** | **13** | **14** | **15** | **16** | **17** |
| **Region** | | | | | | | | | **FR1** | | | | | | | | | |
| Germ. AA | Q | V | Q | L | Q | Q | W | G | A | | G | L | L | K | P | S | E | T |
| Germ. Nuc | cag | gtg | cag | cta | cag | cag | tgg | ggc | gca | | gga | ctg | ttg | aag | cct | tcg | gag | acc |
| AJL01 AA | Q | V | Q | L | Q | Q | W | G | A | | G | L | L | K | P | S | E | T |
| AJL01 Nuc | cag | gtg | cag | cta | cag | cag | tgg | ggc | gca | | gga | ctg | ttg | aag | cct | tcg | gag | acc |
| AJL19 AA | Q | V | Q | L | Q | Q | W | G | A | | G | L | L | K | P | S | E | T |
| AJL19 Nuc | cag | gtg | cag | cta | cag | cag | tgg | ggc | gca | | gga | ctg | ttg | aag | cct | tcg | gag | acc |

| **4-34 Codon** | **19** | **20** | **21** | **22** | **23** | **24** | **25** | **26** | **27** | **28** | **29** | **30** | **31** | **32** | **33** | **34** | **35** | **36** |
|---|---|---|---|---|---|---|---|---|---|---|---|---|---|---|---|---|---|---|
| **4-34 Kabat** | **18** | **19** | **20** | **21** | **22** | **23** | **24** | **25** | **26** | **27** | **28** | **29** | | | | | **30** | **31** |
| **Region** | | | | **FR1** | | | | | | | | | | **CDR1** | | | | |
| Germ. AA | L | S | L | T | C | A | V | Y | G | G | S | F | | | | | S | G |
| Germ. Nuc | ctg | tcc | ctc | acc | tgc | gct | gtc | tat | ggt | ggg | tcc | ttc | | | | | agt | ggt |
| AJL01 AA | L | S | L | T | C | A | V | Y | G | G | S | F | | | | | N | E |
| AJL01 Nuc | ctg | tcc | ctc | acc | tgc | gct | gtc | tat | ggt | ggg | tcc | ttc | | | | | aat | gaa |
| AJL19 AA | L | S | L | T | C | A | V | F | G | G | S | L | | | | | S | G |
| AJL19 Nuc | ctg | tcc | ctc | acc | tgc | gct | gtc | ttt | ggt | ggg | tcc | ctc | | | | | agt | ggt |

| **4-34 Codon** | **37** | **38** | **39** | **40** | **41** | **42** | **43** | **44** | **45** | **46** | **47** | **48** | **49** | **50** | **51** | **52** | **53** | **54** |
|---|---|---|---|---|---|---|---|---|---|---|---|---|---|---|---|---|---|---|
| **4-34 Kabat** | **32** | **33** | **34** | **35** | **36** | **37** | **38** | **39** | **40** | **41** | **42** | **43** | **44** | **45** | **46** | **47** | **48** | **49** |
| **Region** | **CDR1** | | | | | | | | | **FR2** | | | | | | | | |
| Germ. AA | Y | Y | W | S | W | I | R | Q | P | P | G | K | G | L | E | W | I | G |
| Germ. Nuc | tac | tac | tgg | agc | tgg | atc | cgc | cag | ccc | cca | ggg | aag | ggg | ctg | gag | tgg | att | ggg |
| AJL01 AA | F | Y | W | S | W | I | R | Q | P | A | R | K | G | L | E | W | I | G |
| AJL01 Nuc | ttc | tac | tgg | agc | tgg | atc | cgt | cag | ccc | gca | cgg | aag | ggc | ctg | gag | tgg | att | gga |
| AJL19 AA | Y | Y | W | S | W | I | R | Q | P | P | G | K | G | P | E | W | I | A |
| AJL19 Nuc | tac | tac | tgg | agt | tgg | atc | cgc | cag | ccc | cca | ggg | aag | ggg | ccg | gag | tgg | att | gcg |

| **4-34 Codon** | **55** | **56** | **57** | **58** | **59** | **60** | **61** | **62** | **63** | **64** | **65** | **66** | **67** | **68** | **69** | **70** | **71** | **72** |
|---|---|---|---|---|---|---|---|---|---|---|---|---|---|---|---|---|---|---|
| **4-34 Kabat** | **50** | **51** | **52** | **53** | **54** | | | | **55** | **56** | **57** | **58** | **59** | **60** | **61** | **62** | **63** | **64** |
| **Region** | **FR2** | | | | | **CDR2** | | | | | | | | | **FR3** | | | |
| Germ. AA | E | I | N | H | S | | | | G | S | T | N | Y | N | P | S | L | K |
| Germ. Nuc | gaa | atc | aat | cat | agt | | | | gga | agc | acc | aac | tac | aac | ccg | tcc | ctc | aag |
| AJL01 AA | E | I | S | H | S | | | | G | R | A | N | Y | N | P | S | L | K |
| AJL01 Nuc | gaa | atc | agt | cat | agc | | | | gga | aga | gcc | aac | tac | aac | ccg | tcc | ctc | aag |
| AJL19 AA | E | I | N | H | S | | | | G | D | A | N | Y | N | P | S | L | K |
| AJL19 Nuc | gaa | atc | aat | cat | agt | | | | gga | gat | gcc | aac | tac | aac | ccg | tcc | ctc | aag |

| **4-34 Codon** | **73** | **74** | **75** | **76** | **77** | **78** | **79** | **80** | **81** | **82** | **83** | **84** | **85** | **86** | **87** | **88** | **89** | **90** |
|---|---|---|---|---|---|---|---|---|---|---|---|---|---|---|---|---|---|---|
| **4-34 Kabat** | | **65** | **66** | **67** | **68** | **69** | **70** | **71** | **72** | **73** | **74** | **75** | **76** | **77** | **78** | **79** | **80** | **81** |
| **Region** | | | | | | | | | **FR3** | | | | | | | | | |
| Germ. AA | | S | R | V | T | I | S | V | D | T | S | K | N | Q | F | S | L | K |
| Germ. Nuc | | agt | cga | gtc | acc | ata | tca | gta | gac | acg | tcc | aag | aac | cag | ttc | tcc | ctg | aag |
| AJL01 AA | | S | R | V | T | L | S | V | D | R | S | K | N | Q | F | S | L | N |
| AJL01 Nuc | | agt | cgc | gtc | acc | ctg | tct | gta | gac | agg | tcc | aag | aac | cag | ttc | tcc | ctg | aac |
| AJL19 AA | | S | R | V | T | I | S | V | D | T | S | K | N | Q | F | S | L | K |
| AJL19 Nuc | | agt | cga | gtc | act | atc | tca | gta | gac | acg | tcc | aag | aac | cag | ttt | tcc | ctg | aag |

FIG. 43 Continued

| 4-34 Codon | 91 | 92 | 93 | 94 | 95 | 96 | 97 | 98 | 99 | 100 | 101 | 102 | 103 | 104 | 105 | 106 | | |
|---|---|---|---|---|---|---|---|---|---|---|---|---|---|---|---|---|---|
| 4-34 Kabat | 82 | 82a | 82b | 82c | 83 | 84 | 85 | 86 | 87 | 88 | 89 | 90 | 91 | 92 | 93 | 94 | | |
| Region | | | | | | | FR3 | | | | | | | | | CDR3 | | |
| Germ. AA | L | S | S | V | T | A | A | D | T | A | V | Y | Y | C | A | R | G | |
| Germ. Nuc | ctg | agc | tct | gtg | acc | gcc | gcg | gac | acg | gct | gtg | tat | tac | tgt | gcg | aga | ggg | |
| AJL01 AA | L | S | P | V | A | A | A | D | T | A | V | Y | Y | C | A | R | R | E |
| AJL01 Nuc | ctg | agc | cct | gtg | gcc | gcc | gcg | gac | aca | gct | gtc | tat | tac | tgt | gcg | cga | cgg | gag |
| AJL19 AA | M | S | S | V | T | V | A | D | T | A | L | Y | Y | C | A | T | Q | G |
| AJL19 Nuc | atg | agt | tct | gtg | acc | gtc | gca | gac | acg | gct | tta | tat | tac | tgt | gcg | act | caa | ggc |

| 4-34 Codon | | | | | | | | | | | | | |
|---|---|---|---|---|---|---|---|---|---|---|---|---|---|
| 4-34 Kabat | | | | | | | | | | | | | |
| Region | | | | | | | CDR3 | | | | | | |
| Germ. AA | | | | | | | | | | | | | |
| Germ. Nuc | | | | | | | | | | | | | |
| AJL01 AA | I | V | V | T | V | R | G | R | R | A | F | D | I |
| AJL01 Nuc | ata | gtc | gta | act | gtt | cgg | ggg | cgt | cgt | gct | ttt | gat | atc |
| AJL19 AA | S | R | L | T | T | F | A | F | D | V | | | |
| AJL19 Nuc | tct | agg | ttg | act | aca | ttc | gct | ttt | gat | gtg | | | |

| 4-39 Codon | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 4-39 Kabat | | 1 | 2 | 3 | 4 | 5 | 6 | 7 | 8 | 9 | 10 | 11 | 12 | 13 | 14 | 15 | 16 | 17 |
| Region | | | | | | | | | FR1 | | | | | | | | | |
| Germ. AA | Q | L | Q | L | Q | E | S | G | P | | G | L | V | K | P | S | E | T |
| Germ. Nuc | cag | ctg | cag | ctg | cag | gag | tcg | ggc | cca | | gga | ctg | gtg | aag | cct | tcg | gag | acc |
| AJL03 AA | Q | L | Q | L | Q | E | S | G | P | | G | L | V | K | P | S | E | T |
| AJL03 Nuc | cag | ctg | cag | ctg | cag | gag | tcg | ggc | cca | | gga | ctg | gtg | aag | cct | tcg | gag | acc |
| AJL15 AA | Q | L | Q | L | Q | E | S | G | P | | G | L | V | K | P | S | E | T |
| AJL15 Nuc | cag | ctg | cag | ctg | cag | gag | tcg | ggc | cca | | gga | ctg | gtg | aag | cct | tcg | gag | acc |

| 4-39 Codon | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| 4-39 Kabat | 18 | 19 | 20 | 21 | 22 | 23 | 24 | 25 | 26 | 27 | 28 | 29 | 30 | | | 31 | 31a | 31b |
| Region | | | | FR1 | | | | | | | | | CDR1 | | | | | |
| Germ. AA | L | S | L | T | C | T | V | S | G | G | S | I | S | | | S | S | S |
| Germ. Nuc | ctg | tcc | ctc | acc | tgc | act | gtc | tct | ggt | ggc | tcc | atc | agc | | | agt | agt | agt |
| AJL03 AA | L | S | L | T | C | T | V | S | G | A | S | I | S | | | S | S | R |
| AJL03 Nuc | ctg | tcc | ctc | acg | tgc | act | gtc | tct | ggt | gcc | tcc | atc | agc | | | agt | agt | cgt |
| AJL15 AA | L | S | L | T | C | T | V | S | G | G | S | I | T | | | S | R | N |
| AJL15 Nuc | ctg | tcc | ctc | acc | tgc | act | gtc | tct | ggt | ggc | tcc | atc | acc | | | agt | agg | aat |

| 4-39 Codon | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|
| 4-39 Kabat | 32 | 33 | 34 | 35 | 36 | 37 | 38 | 39 | 40 | 41 | 42 | 43 | 44 | 45 | 46 | 47 | 48 | 49 |
| Region | CDR1 | | | | | | | | | FR2 | | | | | | | | |
| Germ. AA | Y | Y | W | G | W | I | R | Q | P | P | G | K | G | L | E | W | I | G |
| Germ. Nuc | tac | tac | tgg | ggc | tgg | atc | cgc | cag | ccc | cca | ggg | aag | ggg | ctg | gag | tgg | att | ggg |
| AJL03 AA | S | Y | W | G | W | I | R | Q | P | P | G | K | G | L | E | W | I | G |
| AJL03 Nuc | tcc | tac | tgg | ggc | tgg | atc | cgc | cag | ccc | cca | ggg | aag | ggg | ctg | gag | tgg | att | ggg |
| AJL15 AA | N | Y | W | G | W | I | R | Q | S | P | G | K | G | L | E | W | I | G |
| AJL15 Nuc | aac | tac | tgg | ggc | tgg | atc | cgc | cag | tcc | cca | ggg | aag | ggg | ctg | gag | tgg | att | ggg |

FIG. 43 Continued

| 4-39 Codon | 55 | 56 | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|---|---|
| 4-39 Kabat | 50 | 51 | 52 | 53 | 54 | | | | 55 | 56 | 57 | 58 | 59 | 60 | 61 | 62 | 63 | 64 |
| Region | FR2 | | | | | CDR2 | | | | | | | | | FR3 | | | |
| Germ. AA | S | I | Y | Y | S | | | | G | S | T | Y | Y | N | P | S | L | K |
| Germ. Nuc | agt | atc | tat | tat | agt | | | | ggg | agc | acc | tac | tac | aac | ccg | tcc | ctc | aag |
| AJL03 AA | S | M | Y | Q | S | | | | G | S | T | Y | Y | S | P | S | L | K |
| AJL03 Nuc | agt | atg | tat | caa | agt | | | | ggg | agc | act | tac | tac | agt | ccg | tcc | ctc | aag |
| AJL15 AA | S | L | Y | Y | T | | | | G | S | D | Y | Y | N | P | S | L | K |
| AJL15 Nuc | agt | ctc | tat | tat | act | | | | ggg | agc | gac | tac | tac | aac | ccg | tcc | ctc | aag |

| 4-39 Codon | 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|---|
| 4-39 Kabat | | 65 | 66 | 67 | 68 | 69 | 70 | 71 | 72 | 73 | 74 | 75 | 76 | 77 | 78 | 79 | 80 | 81 |
| Region | | | | | | | | | FR3 | | | | | | | | | |
| Germ. AA | | S | R | V | T | I | S | V | D | T | S | K | N | Q | F | S | L | K |
| Germ. Nuc | | agt | cga | gtc | acc | ata | tca | gta | gac | acg | tcc | aag | aac | cag | ttc | tcc | ctg | aag |
| AJL03 AA | | S | R | V | T | I | S | M | D | T | S | K | N | Q | F | S | L | N |
| AJL03 Nuc | | agt | cga | gtc | acc | ata | tcc | atg | gac | acg | tcc | aag | aac | cag | ttc | tcc | cta | aac |
| AJL15 AA | | S | R | V | T | I | S | V | D | T | S | K | N | Q | F | S | L | R |
| AJL15 Nuc | | agt | cga | gtc | acc | ata | tcg | gta | gac | aca | tcg | aag | aac | caa | ttc | tcc | ctg | agg |

| 4-39 Codon | 91 | 92 | 93 | 94 | 95 | 96 | 97 | 98 | 99 | 100 | 101 | 102 | 103 | 104 | 105 | 106 | | |
|---|---|---|---|---|---|---|---|---|---|---|---|---|---|---|---|---|---|---|
| 4-39 Kabat | 82 | 82a | 82b | 82c | 83 | 84 | 85 | 86 | 87 | 88 | 89 | 90 | 91 | 92 | 93 | 94 | | |
| Region | | | | | | | FR3 | | | | | | | | | CDR3 | | |
| Germ. AA | L | S | S | V | T | A | A | D | T | A | V | Y | Y | C | A | R | D | |
| Germ. Nuc | ctg | agc | tct | gtg | acc | gcc | gcg | gac | acg | gcc | gtg | tat | tac | tgt | gcg | aga | gat | |
| AJL03 AA | L | T | S | V | T | A | A | D | T | A | V | Y | F | C | A | R | H | S |
| AJL03 Nuc | ctg | acg | tct | gtg | acc | gcc | gcg | gac | acg | gct | gtg | tat | ttc | tgt | gcg | aga | cat | tcg |
| AJL15 AA | L | S | S | V | T | A | A | D | T | A | V | Y | Y | C | V | R | V | N |
| AJL15 Nuc | ctg | agt | tct | gtg | acc | gcc | gcg | gac | acg | gcc | gtg | tat | tat | tgt | gtc | aga | gtt | aac |

| 4-39 Codon | | | | | | | | | | | | | | | |
|---|---|---|---|---|---|---|---|---|---|---|---|---|---|---|---|
| 4-39 Kabat | | | | | | | | | | | | | | | |
| Region | | | | | | | | CDR3 | | | | | | | |
| Germ. AA | | | | | | | | | | | | | | | |
| Germ. Nuc | | | | | | | | | | | | | | | |
| AJL03 AA | N | P | G | T | A | N | K | L | R | L | G | E | F | S | P |
| AJL03 Nuc | aac | ccc | gga | acg | gcg | aac | aaa | ttg | cgt | ttg | ggg | gag | ttt | tcg | ccc |
| AJL15 AA | V | D | D | F | W | S | G | L | G | G | A | W | F | D | P |
| AJL15 Nuc | gta | gac | gac | ttt | tgg | agt | ggt | tta | ggg | ggg | gcc | tgg | ttc | gac | ccc |

| 4-4 Codon | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 4-4 Kabat | | 1 | 2 | 3 | 4 | 5 | 6 | 7 | 8 | 9 | 10 | 11 | 12 | 13 | 14 | 15 | 16 | 17 |
| Region | | | | | | | | | FR1 | | | | | | | | | |
| Germ. AA | Q | V | Q | L | Q | E | S | G | P | | G | L | V | K | P | S | E | T |
| Germ. Nuc | cag | gtg | cag | ctg | cag | gag | tcg | ggc | cca | | gga | ctg | gtg | aag | cct | tcg | gag | acc |
| AJL10 AA | Q | V | Q | L | Q | E | S | G | P | | G | L | V | K | P | S | E | T |
| AJL10 Nuc | cag | gtg | cag | ctg | cag | gag | tcg | ggc | cca | | gga | ctg | gtg | aag | cct | tcg | gag | acc |
| WR10 AA | Q | V | Q | L | Q | E | S | G | P | | G | L | V | K | P | S | G | T |
| WR10 Nuc | cag | gtg | cag | ctg | cag | gag | tcg | ggc | cca | | gga | ctg | gtg | aag | cct | tcg | ggg | acc |

| 4-4 Codon | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| 4-4 Kabat | 18 | 19 | 20 | 21 | 22 | 23 | 24 | 25 | 26 | 27 | 28 | 29 | | | | | 30 | 31 |
| Region | | | | FR1 | | | | | | | | | CDR1 | | | | | |
| Germ. AA | L | S | L | T | C | T | V | S | G | G | S | I | | | | | S | S |
| Germ. Nuc | ctg | tcc | ctc | acc | tgc | act | gtc | tct | ggt | ggc | tcc | atc | | | | | agt | agt |
| AJL10 AA | L | S | L | T | C | S | V | S | G | G | A | V | | | | | S | N |
| AJL10 Nuc | ctg | tcc | ctc | acg | tgc | agt | gtc | tct | ggt | ggc | gcc | gtc | | | | | agt | aat |
| WR10 AA | L | S | L | T | C | A | V | S | G | G | S | I | S | | | | N | N |
| WR10 Nuc | ctg | tcc | ctc | acc | tgc | gct | gtc | tct | ggt | ggc | tcc | atc | agc | | | | aat | aat |

FIG. 43 Continued

| **4-4 Codon** | **37** | **38** | **39** | **40** | **41** | **42** | **43** | **44** | **45** | **46** | **47** | **48** | **49** | **50** | **51** | **52** | **53** | **54** |
|---|---|---|---|---|---|---|---|---|---|---|---|---|---|---|---|---|---|---|
| **4-4 Kabat** | **32** | **33** | **34** | **35** | **36** | **37** | **38** | **39** | **40** | **41** | **42** | **43** | **44** | **45** | **46** | **47** | **48** | **49** |
| **Region** | **CDR1** | | | | | | | | **FR2** | | | | | | | | | |
| Germ. AA | Y | Y | W | S | W | I | R | Q | P | A | G | K | G | L | E | W | I | G |
| Germ. Nuc | tac | tac | tgg | agc | tgg | atc | cgg | cag | ccc | gcc | ggg | aag | gga | ctg | gag | tgg | att | ggg |
| AJL10 AA | Y | Y | W | S | W | I | R | Q | S | A | G | K | G | L | E | W | L | G |
| AJL10 Nuc | tac | tac | tgg | agt | tgg | atc | cgg | cag | tcc | gcc | ggg | aag | gga | ctg | gag | tgg | ctt | ggg |
| WR10 AA | K | W | W | N | W | V | R | Q | S | P | G | K | G | L | E | W | I | G |
| WR10 Nuc | aag | tgg | tgg | aat | tgg | gtc | cgc | cag | tcc | cca | ggg | aag | ggg | ctg | gag | tgg | att | ggg |

| **4-4 Codon** | **55** | **56** | **57** | **58** | **59** | **60** | **61** | **62** | **63** | **64** | **65** | **66** | **67** | **68** | **69** | **70** | **71** | **72** |
|---|---|---|---|---|---|---|---|---|---|---|---|---|---|---|---|---|---|---|
| **4-4 Kabat** | **50** | **51** | **52** | **53** | **54** | | | | **55** | **56** | **57** | **58** | **59** | **60** | **61** | **62** | **63** | **64** |
| **Region** | **FR2** | | | | | **CDR2** | | | | | | | | | **FR3** | | | |
| Germ. AA | R | I | Y | T | S | | | | G | S | T | N | Y | N | P | S | L | K |
| Germ. Nuc | cgt | atc | tat | acc | agt | | | | ggg | agc | acc | aac | tac | aac | ccc | tcc | ctc | aag |
| AJL10 AA | R | I | Y | I | N | | | | G | T | T | Y | Y | N | P | S | L | R |
| AJL10 Nuc | cgg | atc | tat | atc | aat | | | | gga | act | act | tac | tac | aac | ccc | tcc | ctc | agg |
| WR10 AA | E | I | Y | H | S | | | | G | G | T | N | Y | N | P | S | L | K |
| WR10 Nuc | gaa | atc | tat | cat | agt | | | | ggg | ggc | acc | aac | tac | aac | ccg | tcc | ctc | aag |

| **4-4 Codon** | **73** | **74** | **75** | **76** | **77** | **78** | **79** | **80** | **81** | **82** | **83** | **84** | **85** | **86** | **87** | **88** | **89** | **90** |
|---|---|---|---|---|---|---|---|---|---|---|---|---|---|---|---|---|---|---|
| **4-4 Kabat** | | **65** | **66** | **67** | **68** | **69** | **70** | **71** | **72** | **73** | **74** | **75** | **76** | **77** | **78** | **79** | **80** | **81** |
| **Region** | | | | | | | | | **FR3** | | | | | | | | | |
| Germ. AA | | S | R | V | T | M | S | V | D | T | S | K | N | Q | F | S | L | K |
| Germ. Nuc | | agt | cga | gtc | acc | atg | tca | gta | gac | acg | tcc | aag | aac | cag | ttc | tcc | ctg | aag |
| AJL10 AA | | S | R | V | S | M | S | V | D | T | S | K | G | Q | F | S | L | R |
| AJL10 Nuc | | agc | cgg | gtc | tcc | atg | tca | gtt | gac | acg | tcc | aag | ggc | cag | ttc | tcc | ctg | agg |
| WR10 AA | | S | R | V | T | I | S | V | D | K | S | K | N | L | F | S | L | K |
| WR10 Nuc | | agt | cga | gtc | acc | ata | tcg | gta | gac | aag | tcc | aag | aac | ctg | ttc | tcc | ctg | aag |

| **4-4 Codon** | **91** | **92** | **93** | **94** | **95** | **96** | **97** | **98** | **99** | **100** | **101** | **102** | **103** | **104** | **105** | **106** | | |
|---|---|---|---|---|---|---|---|---|---|---|---|---|---|---|---|---|---|---|
| **4-4 Kabat** | **82** | **82a** | **82b** | **82c** | **83** | **84** | **85** | **86** | **87** | **88** | **89** | **90** | **91** | **92** | **93** | **94** | | |
| **Region** | | | | | | | **FR3** | | | | | | | | | **CDR3** | | |
| Germ. AA | L | S | S | V | T | A | A | D | T | A | V | Y | Y | C | A | R | | |
| Germ. Nuc | ctg | agc | tct | gtg | acc | gcc | gcg | gac | acg | gcc | gtg | tat | tac | tgt | gcg | aga | | |
| AJL10 AA | L | T | S | V | T | A | A | D | T | A | I | Y | Y | C | A | R | W | G |
| AJL10 Nuc | ttg | acc | tct | gtg | acc | gcc | gcg | gac | acg | gcc | ata | tat | tat | tgt | gcg | aga | tgg | ggt |
| WR10 AA | L | S | S | V | T | A | A | D | T | A | V | Y | Y | C | A | S | A | T |
| WR10 Nuc | ctg | agc | tct | gtg | acc | gcc | gcg | gac | acg | gcc | gtg | tat | tac | tgt | gcg | agt | gcg | act |

| **4-4 Codon** | | | | | | | | | | | | | | | |
|---|---|---|---|---|---|---|---|---|---|---|---|---|---|---|---|
| **4-4 Kabat** | | | | | | | | | | | | | | | |
| **Region** | | | | | | | | **CDR3** | | | | | | | |
| Germ. AA | | | | | | | | | | | | | | | |
| Germ. Nuc | | | | | | | | | | | | | | | |
| AJL10 AA | A | L | L | G | D | Y | Y | Y | G | L | D | V | | | |
| AJL10 Nuc | gcc | cta | ttg | ggc | gac | tac | tat | tac | ggt | ttg | gac | gtc | | | |
| WR10 AA | T | M | V | R | G | L | S | L | Y | Y | Y | G | L | D | V |
| WR10 Nuc | act | atg | gtt | cgg | gga | ctg | agt | ctt | tac | tac | tac | ggt | ctg | gac | gtc |

FIG. 43 Continued

| **4-59 Codon** | **1** | **2** | **3** | **4** | **5** | **6** | **7** | **8** | **9** | **10** | **11** | **12** | **13** | **14** | **15** | **16** | **17** | **18** |
|---|---|---|---|---|---|---|---|---|---|---|---|---|---|---|---|---|---|---|
| **4-59 Kabat** | | **1** | **2** | **3** | **4** | **5** | **6** | **7** | **8** | **9** | **10** | **11** | **12** | **13** | **14** | **15** | **16** | **17** |
| **Region** | | | | | | | | | **FR1** | | | | | | | | | |
| Germ. AA | Q | V | Q | L | Q | E | S | G | P | | G | L | V | K | P | S | E | T |
| Germ. Nuc | cag | gtg | cag | ctg | cag | gag | tcg | ggc | cca | | gga | ctg | gtg | aag | cct | tcg | gag | acc |
| AJL07 AA | Q | V | Q | L | Q | E | S | G | P | | G | L | V | K | P | S | E | T |
| AJL07 Nuc | cag | gtg | cag | ctg | cag | gag | tcg | ggc | cca | | gga | ctg | gtg | aag | cct | tcg | gag | acc |

| **4-59 Codon** | **19** | **20** | **21** | **22** | **23** | **24** | **25** | **26** | **27** | **28** | **29** | **30** | **31** | **32** | **33** | **34** | **35** | **36** |
|---|---|---|---|---|---|---|---|---|---|---|---|---|---|---|---|---|---|---|
| **4-59 Kabat** | **18** | **19** | **20** | **21** | **22** | **23** | **24** | **25** | **26** | **27** | **28** | **29** | | | | | **30** | **31** |
| **Region** | | | | **FR1** | | | | | | | | | **CDR1** | | | | | |
| Germ. AA | L | S | L | T | C | T | V | S | G | G | S | I | | | | | S | S |
| Germ. Nuc | ctg | tcc | ctc | acc | tgc | act | gtc | tct | ggt | ggc | tcc | atc | | | | | agt | agt |
| AJL07 AA | L | S | L | T | C | T | V | S | G | G | S | I | | | | | N | N |
| AJL07 Nuc | ctg | tcc | ctc | acc | tgc | act | gtc | tct | ggt | ggc | tcc | atc | | | | | aac | aac |

| **4-59 Codon** | **37** | **38** | **39** | **40** | **41** | **42** | **43** | **44** | **45** | **46** | **47** | **48** | **49** | **50** | **51** | **52** | **53** | **54** |
|---|---|---|---|---|---|---|---|---|---|---|---|---|---|---|---|---|---|---|
| **4-59 Kabat** | **32** | **33** | **34** | **35** | **36** | **37** | **38** | **39** | **40** | **41** | **42** | **43** | **44** | **45** | **46** | **47** | **48** | **49** |
| **Region** | **CDR1** | | | | | | | | | **FR2** | | | | | | | | |
| Germ. AA | Y | Y | W | S | W | I | R | Q | P | P | G | K | G | L | E | W | I | G |
| Germ. Nuc | tac | tac | tgg | agc | tgg | atc | cgg | cag | ccc | cca | ggg | aag | gga | ctg | gag | tgg | att | ggg |
| AJL07 AA | Y | Y | W | S | W | I | R | Q | P | P | G | K | G | L | E | W | I | G |
| AJL07 Nuc | tat | tac | tgg | agt | tgg | atc | cgg | cag | ccc | cca | ggg | aag | gga | ctg | gag | tgg | att | ggt |

| **4-59 Codon** | **55** | **56** | **57** | **58** | **59** | **60** | **61** | **62** | **63** | **64** | **65** | **66** | **67** | **68** | **69** | **70** | **71** | **72** |
|---|---|---|---|---|---|---|---|---|---|---|---|---|---|---|---|---|---|---|
| **4-59 Kabat** | **50** | **51** | **52** | **53** | **54** | | | | **55** | **56** | **57** | **58** | **59** | **60** | **61** | **62** | **63** | **64** |
| **Region** | **FR2** | | | | | **CDR2** | | | | | | | | | **FR3** | | | |
| Germ. AA | Y | I | Y | Y | N | | | | G | S | T | N | Y | N | P | S | L | K |
| Germ. Nuc | tat | atc | tat | tac | aat | | | | ggg | agc | acc | aac | tac | aac | ccc | tcc | ctc | aag |
| AJL07 AA | Y | I | Y | Y | N | | | | G | N | I | N | Y | N | P | S | L | K |
| AJL07 Nuc | tat | atc | tat | tac | aat | | | | ggg | aat | att | aat | tac | aac | cct | tcc | ctc | aag |

| **4-59 Codon** | **73** | **74** | **75** | **76** | **77** | **78** | **79** | **80** | **81** | **82** | **83** | **84** | **85** | **86** | **87** | **88** | **89** | **90** |
|---|---|---|---|---|---|---|---|---|---|---|---|---|---|---|---|---|---|---|
| **4-59 Kabat** | | **65** | **66** | **67** | **68** | **69** | **70** | **71** | **72** | **73** | **74** | **75** | **76** | **77** | **78** | **79** | **80** | **81** |
| **Region** | | | | | | | | | **FR3** | | | | | | | | | |
| Germ. AA | | S | R | V | T | I | S | V | D | T | S | K | N | Q | F | S | L | K |
| Germ. Nuc | | agt | cga | gtc | acc | ata | tca | gta | gac | acg | tcc | aag | aac | cag | ttc | tcc | ctg | aag |
| AJL07 AA | | S | R | V | T | I | S | R | D | M | S | K | N | Q | F | S | L | N |
| AJL07 Nuc | | agt | cga | gtc | acc | ata | tca | aga | gac | atg | tcc | aag | aac | cag | ttc | tcc | ctg | aac |

| **4-59 Codon** | **91** | **92** | **93** | **94** | **95** | **96** | **97** | **98** | **99** | **100** | **101** | **102** | **103** | **104** | **105** | **106** | | |
|---|---|---|---|---|---|---|---|---|---|---|---|---|---|---|---|---|---|---|
| **4-59 Kabat** | **82** | **82a** | **82b** | **82c** | **83** | **84** | **85** | **86** | **87** | **88** | **89** | **90** | **91** | **92** | **93** | **94** | | |
| **Region** | | | | | | | **FR3** | | | | | | | | | **CDR3** | | |
| Germ. AA | L | S | S | V | T | A | A | D | T | A | V | Y | Y | C | A | R | E | |
| Germ. Nuc | ctg | agc | tct | gtg | acc | gct | gcg | gac | acg | gcc | gtg | tat | tac | tgt | gcg | aga | gaa | |
| AJL07 AA | L | R | S | V | T | A | A | D | T | A | V | Y | Y | C | G | I | G | Y |
| AJL07 Nuc | ctg | cgg | tct | gtg | acc | gct | gcg | gac | acg | gcc | gtg | tat | tac | tgt | gga | att | gga | tat |

| **4-59 Codon** | | | | | | | | | | |
|---|---|---|---|---|---|---|---|---|---|---|
| **4-59 Kabat** | | | | | | | | | | |
| **Region** | | | | | **CDR3** | | | | | |
| Germ. AA | | | | | | | | | | |
| Germ. Nuc | | | | | | | | | | |
| AJL07 AA | S | A | V | A | A | G | T | V | D | Y |
| AJL07 Nuc | agt | gcg | gtg | gca | gct | ggt | aca | gtt | gac | tac |

FIG. 43 Continued

| 1-13 Codon | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| 1-13 Kabat | 1 | 2 | 3 | 4 | 5 | 6 | 7 | 8 | 9 | 10 | 11 | 12 | 13 | 14 | 15 | 16 | 17 | 18 | 19 |
| Region | | | | | | | | | | FR1 | | | | | | | | | |
| Germ. AA | A | I | Q | L | T | Q | S | P | S | S | L | S | A | S | V | G | D | R | V |
| Germ. Nuc | gcc | atc | cag | ttg | acc | cag | tct | cca | tcc | tcc | ctg | tct | gca | tct | gta | gga | gac | aga | gtc |
| AJL07 AA | A | I | Q | L | T | Q | S | P | S | S | L | S | A | S | V | G | D | R | V |
| AJL07 Nuc | gcc | atc | cag | ttg | acc | cag | tct | cca | tcc | tcc | ctg | tct | gca | tct | gtg | gga | gac | aga | gtc |

| 1-13 Codon | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|
| 1-13 Kabat | 20 | 21 | 22 | 23 | 24 | 25 | 26 | 27 | 28 | 29 | | | | | | | 30 | 31 | 32 |
| Region | | | | FR1 | | | | | | | | | CDR1 | | | | | | |
| Germ. AA | T | I | T | C | R | A | S | Q | G | I | | | | | | | S | S | A |
| Germ. Nuc | acc | atc | act | tgc | cgg | gca | agt | cag | ggc | att | | | | | | | agc | agt | gct |
| AJL07 AA | T | I | T | C | R | A | S | Q | G | I | | | | | | | S | S | G |
| AJL07 Nuc | acc | atc | act | tgc | cgg | gca | agt | cag | ggc | att | | | | | | | agc | agt | ggt |

| 1-13 Codon | 39 | 40 | 41 | 42 | 43 | 44 | 45 | 46 | 47 | 48 | 49 | 50 | 51 | 52 | 53 | 54 | 55 | 56 | 57 |
|---|---|---|---|---|---|---|---|---|---|---|---|---|---|---|---|---|---|---|---|
| 1-13 Kabat | 33 | 34 | 35 | 36 | 37 | 38 | 39 | 40 | 41 | 42 | 43 | 44 | 45 | 46 | 47 | 48 | 49 | 50 | 51 |
| Region | | | | | | | | | FR2 | | | | | | | | | CDR2 | |
| Germ. AA | L | A | W | Y | Q | Q | K | P | G | K | A | P | K | L | L | I | Y | D | A |
| Germ. Nuc | tta | gcc | tgg | tat | cag | cag | aaa | cca | ggg | aag | gct | cct | aaa | ctc | ctg | atc | tat | gat | gcc |
| AJL07 AA | L | A | W | Y | Q | Q | E | P | G | K | A | P | K | L | L | I | Y | D | A |
| AJL07 Nuc | tta | gcc | tgg | tat | cag | cag | gaa | cca | ggg | aaa | gct | cct | aaa | ctc | ctg | atc | tat | gat | gcc |

| 1-13 Codon | 58 | 59 | 60 | 61 | 62 | 63 | 64 | 65 | 66 | 67 | 68 | 69 | 70 | 71 | 72 | 73 | 74 | 75 | 76 |
|---|---|---|---|---|---|---|---|---|---|---|---|---|---|---|---|---|---|---|---|
| 1-13 Kabat | | | | | | | | 52 | 53 | 54 | 55 | 56 | 57 | 58 | 59 | | 60 | 61 | 62 |
| Region | | | | CDR2 | | | | | | | | | | FR3 | | | | | |
| Germ. AA | | | | | | | | S | S | L | E | S | G | V | P | | S | R | F |
| Germ. Nuc | | | | | | | | tcc | agt | ttg | gaa | agt | ggg | gtc | cca | | tca | agg | ttc |
| AJL07 AA | | | | | | | | S | T | L | E | S | G | V | P | | S | R | F |
| AJL07 Nuc | | | | | | | | tcc | act | ttg | gaa | agt | ggg | gtc | cca | | tca | aga | ttc |

| 1-13 Codon | 77 | 78 | 79 | 80 | 81 | 82 | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|
| 1-13 Kabat | 63 | 64 | 65 | 66 | | | 67 | 68 | 69 | 70 | 71 | 72 | 73 | 74 | 75 | 76 | 77 | 78 | 79 |
| Region | | | | | | | | | | FR3 | | | | | | | | | |
| Germ. AA | S | G | S | G | | | S | G | T | D | F | T | L | T | I | S | S | L | Q |
| Germ. Nuc | agc | ggc | agt | gga | | | tct | ggg | aca | gat | ttc | act | ctc | acc | atc | agc | agc | ctg | cag |
| AJL07 AA | S | G | S | G | | | S | A | I | D | F | T | L | T | I | S | S | L | Q |
| AJL07 Nuc | agc | ggc | agt | gga | | | tct | gca | ata | gat | ttc | act | ctc | acc | atc | agc | agt | ctg | cag |

| 1-13 Codon | 96 | 97 | 98 | 99 | 100 | 101 | 102 | 103 | 104 | 105 | 106 | 107 | 108 | 109 | 110 | 111 | | |
|---|---|---|---|---|---|---|---|---|---|---|---|---|---|---|---|---|---|---|
| 1-13 Kabat | 80 | 81 | 82 | 83 | 84 | 85 | 86 | 87 | 88 | 89 | 90 | 91 | 92 | | | | | |
| Region | | | | | FR3 | | | | | | | | | CDR3 | | | | |
| Germ. AA | P | E | D | F | A | T | Y | Y | C | Q | Q | F | N | S | Y | P | | |
| Germ. Nuc | cct | gaa | gat | ttt | gca | act | tat | tac | tgt | caa | cag | ttt | aat | agt | tac | cct | | |
| AJL07 AA | P | E | D | F | A | T | Y | Y | C | Q | Q | F | N | T | F | P | Y | T |
| AJL07 Nuc | cct | gaa | gat | ttt | gca | act | tat | tac | tgt | caa | cag | ttt | aat | act | ttc | ccg | tat | act |

| 1-33 Codon | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| 1-33 Kabat | 1 | 2 | 3 | 4 | 5 | 6 | 7 | 8 | 9 | 10 | 11 | 12 | 13 | 14 | 15 | 16 | 17 | 18 | 19 |
| Region | | | | | | | | | | FR1 | | | | | | | | | |
| Germ. AA | D | I | Q | M | T | Q | S | P | S | S | L | S | A | S | V | G | D | R | V |
| Germ. Nuc | gac | atc | cag | atg | acc | cag | tct | cca | tcc | tcc | ctg | tct | gca | tct | gta | gga | gac | aga | gtc |
| AJL03 AA | D | I | Q | M | T | Q | S | P | S | S | L | S | A | S | V | G | D | R | V |
| AJL03 Nuc | gac | atc | cag | atg | acc | cag | tct | cca | tcc | tcc | ctg | tct | gca | tct | gta | gga | gac | aga | gtc |

FIG. 44

| 1-33 Codon | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|
| 1-33 Kabat | 20 | 21 | 22 | 23 | 24 | 25 | 26 | 27 | 28 | 29 | | | | | | | 30 | 31 | 32 |
| Region | | | | FR1 | | | | | | | | | CDR1 | | | | | | |
| Germ. AA | T | I | T | C | Q | A | S | Q | D | I | | | | | | | S | N | Y |
| Germ. Nuc | acc | atc | act | tgc | cag | gcg | agt | cag | gac | att | | | | | | | agc | aac | tat |
| AJL03 AA | T | I | T | C | Q | A | S | Q | D | I | | | | | | | N | N | Y |
| AJL03 Nuc | acc | atc | act | tgc | cag | gcg | agt | cag | gac | att | | | | | | | aac | aac | tat |

| 1-33 Codon | 39 | 40 | 41 | 42 | 43 | 44 | 45 | 46 | 47 | 48 | 49 | 50 | 51 | 52 | 53 | 54 | 55 | 56 | 57 |
|---|---|---|---|---|---|---|---|---|---|---|---|---|---|---|---|---|---|---|---|
| 1-33 Kabat | 33 | 34 | 35 | 36 | 37 | 38 | 39 | 40 | 41 | 42 | 43 | 44 | 45 | 46 | 47 | 48 | 49 | 50 | 51 |
| Region | | | | | | | | | FR2 | | | | | | | | | CDR2 | |
| Germ. AA | L | N | W | Y | Q | Q | K | P | G | K | A | P | K | L | L | I | Y | D | A |
| Germ. Nuc | tta | aat | tgg | tat | cag | cag | aaa | cca | ggg | aaa | gcc | cct | aag | ctc | ctg | atc | tac | gat | gca |
| AJL03 AA | L | N | W | F | Q | Q | Q | P | G | K | A | P | K | L | L | I | Y | D | A |
| AJL03 Nuc | tta | aat | tgg | ttt | cag | cag | caa | cca | ggg | aaa | gcc | cct | aag | ctg | ctg | atc | tac | gat | gca |

| 1-33 Codon | 58 | 59 | 60 | 61 | 62 | 63 | 64 | 65 | 66 | 67 | 68 | 69 | 70 | 71 | 72 | 73 | 74 | 75 | 76 |
|---|---|---|---|---|---|---|---|---|---|---|---|---|---|---|---|---|---|---|---|
| 1-33 Kabat | | | | | | | | 52 | 53 | 54 | 55 | 56 | 57 | 58 | 59 | | 60 | 61 | 62 |
| Region | | | | CDR2 | | | | | | | | | | FR3 | | | | | |
| Germ. AA | | | | | | | | S | N | L | E | T | G | V | P | | S | R | F |
| Germ. Nuc | | | | | | | | tcc | aat | ttg | gaa | aca | ggg | gtc | cca | | tca | agg | ttc |
| AJL03 AA | | | | | | | | S | K | L | Q | M | G | V | P | | S | R | F |
| AJL03 Nuc | | | | | | | | tcc | aaa | ttg | caa | atg | ggg | gtc | cca | | tca | agg | ttc |

| 1-33 Codon | 77 | 78 | 79 | 80 | 81 | 82 | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|
| 1-33 Kabat | 63 | 64 | 65 | 66 | | | 67 | 68 | 69 | 70 | 71 | 72 | 73 | 74 | 75 | 76 | 77 | 78 | 79 |
| Region | | | | | | | | | | FR3 | | | | | | | | | |
| Germ. AA | S | G | S | G | | | S | G | T | D | F | T | F | T | I | S | S | L | Q |
| Germ. Nuc | agt | gga | agt | gga | | | tct | ggg | aca | gat | ttt | act | ttc | acc | atc | agc | agc | ctg | cag |
| AJL03 AA | S | G | S | A | | | S | G | T | D | F | T | F | T | I | S | S | L | Q |
| AJL03 Nuc | agt | gga | agt | gca | | | tct | ggg | aca | gat | ttt | act | ttt | acc | atc | agc | agc | ctg | cag |

| 1-33 Codon | 96 | 97 | 98 | 99 | 100 | 101 | 102 | 103 | 104 | 105 | 106 | 107 | 108 | 109 | 110 | 111 | | |
|---|---|---|---|---|---|---|---|---|---|---|---|---|---|---|---|---|---|---|
| 1-33 Kabat | 80 | 81 | 82 | 83 | 84 | 85 | 86 | 87 | 88 | 89 | 90 | 91 | 92 | | | | | |
| Region | | | | | FR3 | | | | | | | | | CDR3 | | | | |
| Germ. AA | P | E | D | I | A | T | Y | Y | C | Q | Q | Y | D | N | L | P | | |
| Germ. Nuc | cct | gaa | gat | att | gca | aca | tat | tac | tgt | caa | cag | tat | gat | aat | ctc | cct | | |
| AJL03 AA | P | E | D | I | G | T | Y | Y | C | Q | Q | Y | Y | N | L | P | Y | T |
| AJL03 Nuc | cct | gaa | gat | att | ggc | aca | tat | tac | tgt | caa | cag | tat | tat | aat | ctc | ccg | tac | act |

| 1-39 Codon | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| 1-39 Kabat | 1 | 2 | 3 | 4 | 5 | 6 | 7 | 8 | 9 | 10 | 11 | 12 | 13 | 14 | 15 | 16 | 17 | 18 | 19 |
| Region | | | | | | | | | | FR1 | | | | | | | | | |
| Germ. AA | D | I | Q | M | T | Q | S | P | S | S | L | S | A | S | V | G | D | R | V |
| Germ. Nuc | gac | atc | cag | atg | acc | cag | tct | cca | tcc | tcc | ctg | tct | gca | tct | gta | gga | gac | aga | gtc |
| AJL02 AA | D | I | Q | M | T | Q | S | P | S | S | L | S | A | S | V | G | D | R | V |
| AJL02 Nuc | gac | atc | cag | atg | acc | cag | tct | cca | tcc | tcc | ctg | tct | gca | tct | gta | gga | gac | aga | gtc |

| 1-39 Codon | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|
| 1-39 Kabat | 20 | 21 | 22 | 23 | 24 | 25 | 26 | 27 | 28 | 29 | | | | | | | 30 | 31 | 32 |
| Region | | | | FR1 | | | | | | | | | CDR1 | | | | | | |
| Germ. AA | T | I | T | C | R | A | S | Q | S | I | | | | | | | S | S | Y |
| Germ. Nuc | acc | atc | act | tgc | cgg | gca | agt | cag | agc | att | | | | | | | agc | agc | tct |
| AJL02 AA | T | I | T | C | R | A | S | Q | G | I | | | | | | | S | S | S |
| AJL02 Nuc | acc | atc | act | tgc | cgg | gca | agt | cag | ggc | att | | | | | | | agc | agc | tct |

FIG. 44 Continued

| 1-39 Codon | 39 | 40 | 41 | 42 | 43 | 44 | 45 | 46 | 47 | 48 | 49 | 50 | 51 | 52 | 53 | 54 | 55 | 56 | 57 |
|---|---|---|---|---|---|---|---|---|---|---|---|---|---|---|---|---|---|---|---|
| 1-39 Kabat | 33 | 34 | 35 | 36 | 37 | 38 | 39 | 40 | 41 | 42 | 43 | 44 | 45 | 46 | 47 | 48 | 49 | 50 | 51 |
| Region | | | | | | | | | FR2 | | | | | | | | | CDR2 | |
| Germ. AA | L | N | W | Y | Q | Q | K | P | G | K | A | P | K | L | L | I | Y | A | A |
| Germ. Nuc | gta | aat | tgg | ttt | cag | cag | aaa | cca | ggg | aaa | gcc | cct | aag | ctc | ctg | atc | tat | gct | gca |
| AJL02 AA | V | N | W | F | Q | Q | K | P | G | K | A | P | E | L | L | I | Y | A | A |
| AJL02 Nuc | gta | aat | tgg | ttt | cag | cag | aaa | cca | ggg | aaa | gcc | cct | gaa | ctc | ctg | atc | tat | gct | gca |

| 1-39 Codon | 58 | 59 | 60 | 61 | 62 | 63 | 64 | 65 | 66 | 67 | 68 | 69 | 70 | 71 | 72 | 73 | 74 | 75 | 76 |
|---|---|---|---|---|---|---|---|---|---|---|---|---|---|---|---|---|---|---|---|
| 1-39 Kabat | | | | | | | | 52 | 53 | 54 | 55 | 56 | 57 | 58 | 59 | | 60 | 61 | 62 |
| Region | | | | CDR2 | | | | | | | | | | FR3 | | | | | |
| Germ. AA | | | | | | | | S | S | L | Q | S | G | V | P | | S | R | F |
| Germ. Nuc | | | | | | | | tcc | agt | ttg | caa | agt | ggg | gtc | cca | | tca | agg | ttc |
| AJL02 AA | | | | | | | | S | T | L | Q | S | G | V | P | | S | R | F |
| AJL02 Nuc | | | | | | | | tcc | act | ttg | caa | agt | ggg | gtc | cca | | tca | aga | ttc |

| 1-39 Codon | 77 | 78 | 79 | 80 | 81 | 82 | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|
| 1-39 Kabat | 63 | 64 | 65 | 66 | | | 67 | 68 | 69 | 70 | 71 | 72 | 73 | 74 | 75 | 76 | 77 | 78 | 79 |
| Region | | | | | | | | | | FR3 | | | | | | | | | |
| Germ. AA | S | G | S | G | | | S | G | T | D | F | T | L | T | I | S | S | L | Q |
| Germ. Nuc | agt | ggc | agt | gga | | | tct | ggg | aca | gat | ttc | act | ctc | acc | atc | agc | agt | ctg | caa |
| AJL02 AA | S | G | S | G | | | S | G | T | D | F | T | L | T | V | S | S | L | Q |
| AJL02 Nuc | agt | ggc | agt | gga | | | tct | ggg | aca | gat | ttc | act | ctc | acc | gtc | agc | agt | ctg | caa |

| 1-39 Codon | 96 | 97 | 98 | 99 | 100 | 101 | 102 | 103 | 104 | 105 | 106 | 107 | 108 | 109 | 110 | 111 | | |
|---|---|---|---|---|---|---|---|---|---|---|---|---|---|---|---|---|---|---|
| 1-39 Kabat | 80 | 81 | 82 | 83 | 84 | 85 | 86 | 87 | 88 | 89 | 90 | 91 | 92 | | | | | |
| Region | | | | | FR3 | | | | | | | | | CDR3 | | | | |
| Germ. AA | P | E | D | F | A | T | Y | Y | C | Q | Q | S | Y | S | T | P | | |
| Germ. Nuc | cct | gaa | gat | ttt | gca | act | tac | tac | tgt | caa | cag | agt | tac | agt | acc | cct | | |
| AJL02 AA | P | E | D | F | A | T | Y | Y | C | Q | Q | S | Y | S | P | P | R | T |
| AJL02 Nuc | cct | gaa | gat | ttt | gca | act | tac | tac | tgt | cag | cag | agt | tac | agt | ccc | cct | cga | act |

| 2-28 Codon | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| 2-28 Kabat | 1 | 2 | 3 | 4 | 5 | 6 | 7 | 8 | 9 | 10 | 11 | 12 | 13 | 14 | 15 | 16 | 17 | 18 | 19 |
| Region | | | | | | | | | | FR1 | | | | | | | | | |
| Germ. AA | D | I | V | M | T | Q | S | P | L | S | L | P | V | T | P | G | E | P | A |
| Germ. Nuc | gat | att | gtg | atg | act | cag | tct | cca | ctc | tcc | ctg | ccc | gtc | acc | cct | gga | gag | ccg | gcc |
| AJL10 AA | D | I | V | M | T | Q | S | P | L | S | L | P | V | T | P | G | E | P | A |
| AJL10 Nuc | gat | att | gtg | atg | act | cag | tct | cca | ctc | tcc | ctg | ccc | gtc | acc | cct | gga | gag | ccg | gcc |
| WR12 AA | D | I | V | M | T | Q | S | P | L | S | L | P | V | T | P | G | E | P | A |
| WR12 Nuc | gat | att | gtg | atg | act | cag | tct | cca | ctc | tcc | ctg | ccc | gtc | acc | cct | gga | gag | ccg | gcc |
| WR13 AA | D | I | V | M | T | Q | S | P | L | S | L | P | V | T | P | G | E | P | A |
| WR13 Nuc | gat | att | gtg | atg | act | cag | tct | cca | ctc | tcc | ctg | ccc | gtc | acc | cct | gga | gag | ccg | gcc |

| 2-28 Codon | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|
| 2-28 Kabat | 20 | 21 | 22 | 23 | 24 | 25 | 26 | 27 | 27a | 27b | 27c | 27d | 27e | | 28 | 29 | 30 | 31 | 32 |
| Region | | | | FR1 | | | | | | | | | CDR1 | | | | | | |
| Germ. AA | S | I | S | C | R | S | S | Q | S | L | L | H | S | | N | G | Y | N | Y |
| Germ. Nuc | tcc | atc | tcc | tgc | agg | tct | agt | cag | agc | ctc | ctg | cat | agt | | aat | gga | tac | aac | tat |
| AJL10 AA | S | I | S | C | R | S | T | Q | S | L | L | H | S | | N | E | Y | I | Y |
| AJL10 Nuc | tcc | atc | tcc | tgc | agg | tct | act | cag | agc | ctc | cta | cac | agt | | aat | gaa | tac | att | tat |
| WR12 AA | S | I | S | C | R | S | S | Q | S | L | L | H | S | | N | G | Y | N | Y |
| WR12 Nuc | tcc | atc | tcc | tgc | agg | tct | agt | cag | agc | ctc | ctc | cat | agt | | aat | gga | tac | aac | tat |
| WR13 AA | S | I | S | C | R | S | S | Q | S | L | L | H | S | | N | G | Y | N | Y |
| WR13 Nuc | tcc | atc | tcc | tgc | agg | tct | agt | cag | agc | ctc | ctc | cat | agt | | aat | gga | tac | aac | tat |

FIG. 44 Continued

| 2-28 Codon | 39 | 40 | 41 | 42 | 43 | 44 | 45 | 46 | 47 | 48 | 49 | 50 | 51 | 52 | 53 | 54 | 55 | 56 | 57 |
|---|---|---|---|---|---|---|---|---|---|---|---|---|---|---|---|---|---|---|---|
| 2-28 Kabat | 33 | 34 | 35 | 36 | 37 | 38 | 39 | 40 | 41 | 42 | 43 | 44 | 45 | 46 | 47 | 48 | 49 | 50 | 51 |
| Region | | | | | | | | | FR2 | | | | | | | | | CDR2 | |
| Germ. AA | L | D | W | Y | L | Q | K | P | G | Q | S | P | Q | L | L | I | Y | L | G |
| Germ. Nuc | ttg | gat | tgg | tac | ctg | cag | aag | cca | ggg | caa | tct | cca | caa | ctc | ctg | atc | tat | ttg | ggt |
| AJL10 AA | L | D | W | Y | V | Q | K | P | G | Q | S | P | Q | L | L | I | F | L | A |
| AJL10 Nuc | ttg | gat | tgg | tac | gtg | cag | aag | cca | ggg | cag | tct | cca | caa | ctc | ctg | atc | ttt | ttg | gct |
| WR12 AA | L | S | W | Y | L | Q | K | P | G | Q | S | P | Q | L | L | I | F | S | S |
| WR12 Nuc | ttg | agt | tgg | tac | ctg | cag | aag | cca | ggg | cag | tct | cca | caa | ctc | ctg | atc | ttt | tcg | agt |
| WR13 AA | L | S | W | Y | L | Q | K | P | G | Q | S | P | Q | L | L | I | F | S | S |
| WR13 Nuc | ttg | agt | tgg | tac | ctg | cag | aag | cca | ggg | cag | tct | cca | caa | ctc | ctg | atc | ttt | tcg | agt |

| 2-28 Codon | 58 | 59 | 60 | 61 | 62 | 63 | 64 | 65 | 66 | 67 | 68 | 69 | 70 | 71 | 72 | 73 | 74 | 75 | 76 |
|---|---|---|---|---|---|---|---|---|---|---|---|---|---|---|---|---|---|---|---|
| 2-28 Kabat | | | | | | | | 52 | 53 | 54 | 55 | 56 | 57 | 58 | 59 | | 60 | 61 | 62 |
| Region | | | | CDR2 | | | | | | | | | | FR3 | | | | | |
| Germ. AA | | | | | | | | S | N | R | A | S | G | V | P | | D | R | F |
| Germ. Nuc | | | | | | | | tct | aat | cgg | gcc | tcc | ggg | gtc | cct | | gac | agg | ttc |
| AJL10 AA | | | | | | | | S | N | R | A | S | G | V | P | | D | R | F |
| AJL10 Nuc | | | | | | | | tct | aat | cgg | gcc | tcc | ggg | gtc | cct | | gac | agg | ttc |
| WR12 AA | | | | | | | | S | I | R | A | S | G | V | P | | D | R | F |
| WR12 Nuc | | | | | | | | tct | att | cgg | gcc | tcc | ggg | gtc | cct | | gac | agg | ttc |
| WR13 AA | | | | | | | | S | I | R | A | S | G | V | P | | D | R | F |
| WR13 Nuc | | | | | | | | tct | att | cgg | gcc | tcc | ggg | gtc | cct | | gac | agg | ttc |

| 2-28 Codon | 77 | 78 | 79 | 80 | 81 | 82 | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|
| 2-28 Kabat | 63 | 64 | 65 | 66 | | | 67 | 68 | 69 | 70 | 71 | 72 | 73 | 74 | 75 | 76 | 77 | 78 | 79 |
| Region | | | | | | | | | | FR3 | | | | | | | | | |
| Germ. AA | S | G | S | G | | | S | G | T | D | F | T | L | K | I | S | R | V | E |
| Germ. Nuc | agt | ggc | agt | gga | | | tca | ggc | aca | gat | ttt | aca | ctg | aaa | atc | agc | aga | gtg | gag |
| AJL10 AA | S | G | S | A | | | S | G | T | D | F | T | L | K | I | S | R | V | E |
| AJL10 Nuc | agt | ggc | agt | gca | | | tca | ggc | aca | gat | ttt | aca | ctg | aaa | atc | agc | aga | gtg | gag |
| WR12 AA | S | G | S | G | | | S | G | T | D | F | T | L | T | I | N | R | V | E |
| WR12 Nuc | agt | ggc | agt | gga | | | tca | ggc | aca | gat | ttt | aca | ctg | aca | atc | aac | aga | gtg | gag |
| WR13 AA | S | G | S | G | | | S | G | T | D | F | T | L | T | I | N | R | V | E |
| WR13 Nuc | agt | ggc | agt | gga | | | tca | ggc | aca | gat | ttt | aca | ctg | aca | atc | aac | aga | gtg | gag |

| 2-28 Codon | 96 | 97 | 98 | 99 | 100 | 101 | 102 | 103 | 104 | 105 | 106 | 107 | 108 | 109 | 110 | 111 | | |
|---|---|---|---|---|---|---|---|---|---|---|---|---|---|---|---|---|---|---|
| 2-28 Kabat | 80 | 81 | 82 | 83 | 84 | 85 | 86 | 87 | 88 | 89 | 90 | 91 | 92 | | | | | |
| | | | | | FR3 | | | | | | | | | CDR3 | | | | |
| Germ. AA | A | E | D | V | G | V | Y | Y | C | M | Q | A | L | Q | T | P | | |
| Germ. Nuc | gct | gag | gat | gtt | ggg | gtt | tat | tac | tgc | atg | caa | gct | cta | caa | act | cct | | |
| AJL10 AA | A | E | D | V | G | V | Y | Y | C | M | Q | A | L | E | A | P | W | T |
| AJL10 Nuc | gct | gag | gat | gtt | ggg | gtt | tat | tac | tgc | atg | caa | gct | cta | gaa | gct | ccg | tgg | acg |
| WR12 AA | A | E | D | V | G | V | Y | Y | C | M | Q | A | L | Q | T | P | L | T |
| WR12 Nuc | gct | gag | gat | gtt | gga | gtt | tat | tac | tgc | atg | cag | gct | cta | caa | act | ccg | ctc | act |
| WR13 AA | A | E | D | V | G | V | Y | Y | C | M | Q | A | L | Q | T | P | L | T |
| WR13 Nuc | gct | gag | gat | gtt | gga | gtt | tat | tac | tgc | atg | cag | gct | cta | caa | act | ccg | ctc | act |

| 2D-29 Codon | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| 2D-29 Kabat | 1 | 2 | 3 | 4 | 5 | 6 | 7 | 8 | 9 | 10 | 11 | 12 | 13 | 14 | 15 | 16 | 17 | 18 | 19 |
| Region | | | | | | | | | | FR1 | | | | | | | | | |
| Germ. AA | D | I | V | M | T | Q | T | P | L | S | L | S | V | T | P | G | Q | P | A |
| Germ. Nuc | gat | att | gtg | atg | acc | cag | act | cca | ctc | tct | ctg | tcc | gtc | acc | cct | gga | cag | ccg | gcc |
| AJL15 AA | D | I | V | M | T | Q | T | P | L | S | L | S | V | T | P | G | Q | P | A |
| AJL15 Nuc | gat | att | gtg | atg | acc | cag | act | cca | ctc | tct | ttg | tcc | gtc | acc | cct | gga | cag | ccg | gcc |

FIG. 44 Continued

| 2D-29 Codon | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|
| 2D-29 Kabat | 20 | 21 | 22 | 23 | 24 | 25 | 26 | 27 | 27a | 27b | 27c | 27d | 27e | | 28 | 29 | 30 | 31 | 32 |
| Region | | | | FR1 | | | | | | | | | CDR1 | | | | | | |
| Germ. AA | S | I | S | C | K | S | S | Q | S | L | L | H | S | | D | G | K | T | Y |
| Germ. Nuc | tcc | atc | tcc | tgc | aag | tct | agt | cag | agc | ctc | ctg | cat | agt | | gat | gga | aag | acc | tat |
| AJL15 AA | S | I | S | C | K | S | S | Q | S | L | L | D | S | | D | G | K | T | H |
| AJL15 Nuc | tcc | atc | tcc | tgc | aaa | tct | agt | cag | agc | ctc | ctg | gat | agt | | gat | gga | aag | acc | cat |

| 2D-29 Codon | 39 | 40 | 41 | 42 | 43 | 44 | 45 | 46 | 47 | 48 | 49 | 50 | 51 | 52 | 53 | 54 | 55 | 56 | 57 |
|---|---|---|---|---|---|---|---|---|---|---|---|---|---|---|---|---|---|---|---|
| 2D-29 Kabat | 33 | 34 | 35 | 36 | 37 | 38 | 39 | 40 | 41 | 42 | 43 | 44 | 45 | 46 | 47 | 48 | 49 | 50 | 51 |
| Region | | | | | | | | | FR2 | | | | | | | | | CDR2 | |
| Germ. AA | L | Y | W | Y | L | Q | K | P | G | Q | S | P | Q | L | L | I | Y | E | V |
| Germ. Nuc | ttg | tat | tgg | tac | ctg | cag | aag | cca | ggc | cag | tct | cca | cag | ctc | ctg | atc | tat | gaa | gtt |
| AJL15 AA | L | Y | W | Y | L | Q | K | P | G | Q | S | P | Q | S | L | I | Y | E | V |
| AJL15 Nuc | ttg | tac | tgg | tac | ctg | cag | aag | cca | ggc | cag | tct | cca | cag | tcc | ctg | atc | tat | gaa | gtt |

| 2D-29 Codon | 58 | 59 | 60 | 61 | 62 | 63 | 64 | 65 | 66 | 67 | 68 | 69 | 70 | 71 | 72 | 73 | 74 | 75 | 76 |
|---|---|---|---|---|---|---|---|---|---|---|---|---|---|---|---|---|---|---|---|
| 2D-29 Kabat | | | | | | | | 52 | 53 | 54 | 55 | 56 | 57 | 58 | 59 | | 60 | 61 | 62 |
| Region | | | | CDR2 | | | | | | | | | | FR3 | | | | | |
| Germ. AA | | | | | | | | S | N | R | F | S | G | V | P | | D | R | F |
| Germ. Nuc | | | | | | | | tcc | aac | cgg | ttc | tct | gga | gtg | cca | | gat | agg | ttc |
| AJL15 AA | | | | | | | | S | K | R | F | S | G | V | P | | D | R | F |
| AJL15 Nuc | | | | | | | | tct | aaa | cgg | ttc | tct | gga | gtg | cca | | gat | agg | ttc |

| 2D-29 Codon | 77 | 78 | 79 | 80 | 81 | 82 | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|
| 2D-29 Kabat | 63 | 64 | 65 | 66 | | | 67 | 68 | 69 | 70 | 71 | 72 | 73 | 74 | 75 | 76 | 77 | 78 | 79 |
| Region | | | | | | | | | | FR3 | | | | | | | | | |
| Germ. AA | S | G | S | G | | | S | G | T | D | F | T | L | K | I | S | R | V | E |
| Germ. Nuc | agt | ggc | agc | ggg | | | tca | ggg | aca | gat | ttc | aca | ctg | aaa | atc | agc | cgg | gtg | gag |
| AJL15 AA | T | G | S | G | | | S | G | T | D | F | T | L | K | I | S | R | V | E |
| AJL15 Nuc | act | ggc | agc | ggg | | | tca | ggg | aca | gat | ttc | aca | ctg | aaa | atc | agc | cgg | gtg | gag |

| 2D-29 Codon | 96 | 97 | 98 | 99 | 100 | 101 | 102 | 103 | 104 | 105 | 106 | 107 | 108 | 109 | 110 | 111 | | |
|---|---|---|---|---|---|---|---|---|---|---|---|---|---|---|---|---|---|---|
| 2D-29 Kabat | 80 | 81 | 82 | 83 | 84 | 85 | 86 | 87 | 88 | 89 | 90 | 91 | 92 | | | | | |
| Region | | | | | FR3 | | | | | | | | | CDR3 | | | | |
| Germ. AA | A | E | D | V | G | V | Y | Y | C | M | Q | S | I | Q | L | P | | |
| Germ. Nuc | gct | gag | gat | gtt | ggg | gtt | tat | tac | tgc | atg | caa | agt | ata | cag | ctt | cct | | |
| AJL15 AA | A | E | D | V | G | L | Y | Y | C | M | Q | S | A | Q | L | P | Y | T |
| AJL15 Nuc | gct | gag | gat | gtt | ggg | ctt | tat | tac | tgc | atg | caa | agt | gca | cag | ctt | ccg | tac | act |

| 3-20 Codon | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| 3-20 Kabat | 1 | 2 | 3 | 4 | 5 | 6 | 7 | 8 | 9 | 10 | 11 | 12 | 13 | 14 | 15 | 16 | 17 | 18 | 19 |
| Region | | | | | | | | | | FR1 | | | | | | | | | |
| Germ. AA | E | I | V | L | T | Q | S | P | G | T | L | S | L | S | P | G | E | R | A |
| Germ. Nuc | gaa | att | gtg | ttg | acg | cag | tct | cca | ggc | acc | ctg | tct | ttg | tct | cca | ggg | gaa | aga | gcc |
| AJL01 AA | E | I | V | L | T | Q | S | P | G | T | L | S | L | S | P | G | E | R | A |
| AJL01 Nuc | gaa | att | gtg | ttg | acg | cag | tct | cca | ggc | acc | ctg | tct | ttg | tct | cca | ggg | gaa | aga | gcc |
| AJL19 AA | E | I | V | L | T | Q | S | P | G | T | L | S | L | S | P | G | E | R | A |
| AJL19 Nuc | gaa | att | gtg | ttg | acg | cag | tct | cca | ggc | acc | ctg | tct | ttg | tct | cca | ggg | gaa | aga | gcc |
| WR10 AA | E | I | V | L | T | Q | S | P | G | T | L | S | L | S | P | G | E | R | A |
| WR10 Nuc | gaa | att | gtg | ttg | acg | cag | tct | cca | ggc | acc | ctg | tct | ttg | tct | cca | ggg | gaa | aga | gcc |

FIG. 44 Continued

| 3-20 Codon | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|
| 3-20 Kabat | 20 | 21 | 22 | 23 | 24 | 25 | 26 | 27 | 27a | 28 | 29 | | | | | | 30 | 31 | 32 |
| Region | | | | FR1 | | | | | | | | | CDR1 | | | | | | |
| Germ. AA | T | L | S | C | R | A | S | Q | S | V | S | | | | | | S | S | Y |
| Germ. Nuc | acc | ctc | tcc | tgc | agg | gcc | agt | cag | agt | gtt | agc | | | | | | agc | agc | tac |
| AJL01 AA | T | L | S | C | R | A | S | Q | S | L | I | | | | | | G | S | F |
| AJL01 Nuc | acc | ctc | tcc | tgc | agg | gcc | agt | cag | agt | ctt | atc | | | | | | ggc | agc | ttc |
| AJL19 AA | T | L | S | C | R | A | S | Q | S | V | S | | | | | | S | D | S |
| AJL19 Nuc | acc | ctc | tcc | tgc | agg | gcc | agt | cag | agt | gtt | agc | | | | | | agc | gac | tcc |
| WR10 AA | T | L | S | C | R | A | S | Q | S | L | I | | | | | | G | S | F |
| WR10 Nuc | acc | ctc | tcc | tgc | agg | gcc | agt | cag | agt | ctt | atc | | | | | | ggc | agc | ttc |

| 3-20 Codon | 39 | 40 | 41 | 42 | 43 | 44 | 45 | 46 | 47 | 48 | 49 | 50 | 51 | 52 | 53 | 54 | 55 | 56 | 57 |
|---|---|---|---|---|---|---|---|---|---|---|---|---|---|---|---|---|---|---|---|
| 3-20 Kabat | 33 | 34 | 35 | 36 | 37 | 38 | 39 | 40 | 41 | 42 | 43 | 44 | 45 | 46 | 47 | 48 | 49 | 50 | 51 |
| Region | | | | | | | | | FR2 | | | | | | | | | CDR2 | |
| Germ. AA | L | A | W | Y | Q | Q | K | P | G | Q | A | P | R | L | L | I | Y | G | A |
| Germ. Nuc | tta | gcc | tgg | tac | cag | cag | aaa | cct | ggc | cag | gct | ccc | agg | ctc | ctc | atc | tat | ggt | gca |
| AJL01 AA | L | A | W | Y | Q | Q | K | P | G | Q | A | P | R | L | L | I | Y | H | T |
| AJL01 Nuc | tta | gcc | tgg | tac | cag | cag | aaa | cct | ggc | cag | gct | ccc | agg | ctc | ctc | atc | tat | cat | aca |
| AJL19 AA | L | A | W | Y | Q | Q | K | P | G | Q | T | P | R | L | L | I | Y | H | T |
| AJL19 Nuc | tta | gcc | tgg | tac | cag | cag | aaa | cct | ggc | cag | act | ccc | agg | ctc | ctc | att | tat | cat | aca |
| WR10 AA | L | A | W | Y | Q | Q | K | P | G | Q | A | P | R | L | L | I | Y | H | T |
| WR10 Nuc | tta | gcc | tgg | tac | cag | cag | aaa | cct | ggc | cag | gct | ccc | agg | ctc | ctc | atc | tat | cat | aca |

| 3-20 Codon | 58 | 59 | 60 | 61 | 62 | 63 | 64 | 65 | 66 | 67 | 68 | 69 | 70 | 71 | 72 | 73 | 74 | 75 | 76 |
|---|---|---|---|---|---|---|---|---|---|---|---|---|---|---|---|---|---|---|---|
| 3-20 Kabat | | | | | | | | 52 | 53 | 54 | 55 | 56 | 57 | 58 | 59 | | 60 | 61 | 62 |
| Region | | | | CDR2 | | | | | | | | | | FR3 | | | | | |
| Germ. AA | | | | | | | | S | S | R | A | T | G | I | P | | D | R | F |
| Germ. Nuc | | | | | | | | tcc | agc | agg | gcc | act | ggc | atc | cca | | gac | agg | ttc |
| AJL01 AA | | | | | | | | S | N | R | A | S | G | I | P | | D | R | F |
| AJL01 Nuc | | | | | | | | tcc | aac | agg | gcc | tct | ggc | atc | cca | | gac | agg | ttc |
| AJL19 AA | | | | | | | | S | T | R | A | A | G | I | P | | D | R | F |
| AJL19 Nuc | | | | | | | | tcc | acc | agg | gcc | gct | ggc | atc | cca | | gac | agg | ttc |
| WR10 AA | | | | | | | | S | N | R | A | S | G | I | P | | D | R | F |
| WR10 Nuc | | | | | | | | tcc | aac | agg | gcc | tct | ggc | atc | cca | | gac | agg | ttc |

| 3-20 Codon | 77 | 78 | 79 | 80 | 81 | 82 | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|
| 3-20 Kabat | 63 | 64 | 65 | 66 | | | 67 | 68 | 69 | 70 | 71 | 72 | 73 | 74 | 75 | 76 | 77 | 78 | 79 |
| Region | | | | | | | | | | FR3 | | | | | | | | | |
| Germ. AA | S | G | S | G | | | S | G | T | D | F | T | L | T | I | S | R | L | E |
| Germ. Nuc | agt | ggc | agt | ggg | | | tct | ggg | aca | gac | ttc | act | ctc | acc | atc | agc | aga | ctg | gag |
| AJL01 AA | S | G | G | G | | | F | G | T | D | F | T | L | T | I | S | R | L | E |
| AJL01 Nuc | agt | ggc | ggt | ggg | | | ttt | ggg | aca | gac | ttc | act | ctc | acc | atc | agc | aga | ctg | gag |
| AJL19 AA | S | G | T | G | | | S | G | T | D | F | T | L | T | I | A | R | L | E |
| AJL19 Nuc | agt | ggc | act | ggg | | | tct | ggg | aca | gac | ttc | act | ctc | acc | atc | gcc | aga | ctg | gag |
| WR10 AA | S | G | G | G | | | F | G | T | D | F | T | L | T | I | S | R | L | E |
| WR10 Nuc | agt | ggc | ggt | ggg | | | ttt | ggg | aca | gac | ttc | act | ctc | acc | atc | agc | aga | ctg | gag |

| 3-20 Codon | 96 | 97 | 98 | 99 | 100 | 101 | 102 | 103 | 104 | 105 | 106 | 107 | 108 | 109 | 110 | 111 | | | |
|---|---|---|---|---|---|---|---|---|---|---|---|---|---|---|---|---|---|---|---|
| 3-20 Kabat | 80 | 81 | 82 | 83 | 84 | 85 | 86 | 87 | 88 | 89 | 90 | 91 | 92 | | | | | | |
| Region | | | | | FR3 | | | | | | | | | | CDR3 | | | | |
| Germ. AA | P | E | D | F | A | V | Y | Y | C | Q | Q | Y | G | S | S | P | | | |
| Germ. Nuc | cct | gaa | gat | ttt | gca | gtg | tat | tac | tgt | cag | cag | tat | ggt | agc | tca | cct | | | |
| AJL01 AA | P | E | D | F | A | V | Y | Y | C | Q | Q | Y | D | S | S | P | I | T | |
| AJL01 Nuc | cct | gaa | gat | ttt | gca | gtt | tat | tac | tgt | caa | cag | tat | gat | agc | tca | ccg | atc | acc | |
| AJL19 AA | P | E | D | F | A | V | Y | Y | C | Q | H | Y | G | R | S | S | L | F | T |
| AJL19 Nuc | cct | gaa | gat | ttt | gca | gtc | tat | tac | tgt | cag | cac | tat | ggt | cgg | tca | tcc | cta | ttc | acc |
| WR10 AA | P | E | D | F | A | V | Y | Y | C | Q | Q | Y | D | S | S | P | I | T | |
| WR10 Nuc | cct | gaa | gat | ttt | gca | gtt | tat | tac | tgt | caa | cag | tat | gat | agc | tca | ccg | atc | acc | |

FIG. 44 Continued

VH4 ANTIBODIES AND COMPOSITIONS COMPRISING THE SAME

RELATED APPLICATIONS

This application is a national phase application under 35 U.S.C. § 371 of International Application No. PCT/US2017/032411, filed May 12, 2017, which claims benefit of U.S. Provisional Application No. 62/336,409, filed May 13, 2016, the entire contents of each of which are hereby incorporated by reference. The subject matter of this application is related in-part to PCT/US2014/064533, which was published as WO 2015/070009 on May 14, 2015. The subject matter of this application is also related in-part to U.S. Provisional Application Ser. No. 62/289,736, filed Feb. 1, 2016. The disclosures of PCT/US2014/064533 and U.S. Provisional Application Ser. No. 62/289,736 are hereby incorporated by reference in their entireties.

BACKGROUND

B cells are recognized to play a role in multiple sclerosis (MS) pathology in addition to the well-accepted pathological role of T cells. B cells and antibodies are present in both the cerebrospinal fluid (CSF) and the central nervous system (CNS) of patients with MS and clinically isolated syndrome (CIS) patients, who are at high risk of developing MS. Further, the most common form of MS lesion is characterized by deposition of antibodies and complement (Lucchinetti et al., 2000), and plasmapheresis treatment of patients harboring these lesions leads to symptom improvement (Keegan et al., 2005). In fact, elevated B cells in the CSF correlates with lesion activity on MRI (Cepok et al., 2005) and both increased intrathecal immunoglobulin synthesis (Sellebjerg et al., 2000) and complement activation (Sellebjerg et al., 1998) are associated with a more aggressive disease course. Collectively these findings implicate a pathological role for antibodies in the pathoetiology of MS.

A biomarker for conversion from CIS to clinically definite MS (CDMS) in the antibody genetics of $V_H4$-utilizing B cells in the CSF, termed the antibody gene signature (AGS) has been described (Cameron et al., 2009). Also see, U.S. Pat. No. 8,394,583, which is hereby incorporated by reference in its entirety. B cells isolated from CNS lesions harbor the AGS (Ligocki et al., 2010). This shared pattern of somatic hypermutation at about 6 codons along the $V_H4$ gene implicates that the B cell pools are recognizing a shared set of antigens in the MS disease state that are not recognized by B cells in healthy individuals. However, there has been no isolation, description, or characterization of antibodies that fit the AGS criteria, which would be valuable reagents for understanding the pathology of MS as well as for developing next of class therapeutics for MS and related neurodegenerative diseases.

SUMMARY

The present disclosure in various aspects provides methods for making pharmaceutical compositions for treating neurodegenerative diseases, and in particular neuroimmunological diseases (e.g., demyelinating diseases), such as but not limited to multiple sclerosis, autoimmune encephalitis, neuromyelitis optica, optic neuritis, and transverse myelitis. The pharmaceutical compositions impact specific immune-mediated processes involved in the biology of neurodegenerative disease. In certain aspects, the disclosure provides pharmaceutical compositions for treating neurodegenerative disease, which are based on inhibiting the action of pathologic antibodies, or alternatively stimulating neuroprotection or repair processes by administering therapeutic antibodies.

In one aspect, the disclosure provides a method for making a pharmaceutical composition for treating a neurodegenerative disease. The process comprises providing one or more VH4 antibodies having at least one or at least two mutations with respect to the germline sequence at codons selected from 31B, 32, 40, 56, 57, 60, 81, and 89. These antibody-encoding sequences, which are isolated from clinically diagnosed MS patients as well as patients with initial CIS presentation, encode antibodies that bind to one or more antigens in human white and gray matter. In other aspects, the antibodies are derived from peripheral plasmablasts of neurodegenerative disease patients (e.g., MS, neuromyelitis optica, or transverse myelitis), and these antibodies may also be VH4 antibodies. The antibodies from peripheral plasmablasts may or may not exhibit the VH4 mutational signature. The methods comprise selecting an active agent that reduces or inhibits the expression of the antibod(ies), or reduces or inhibits binding of the antibod(ies) to a cellular target or antigen in human gray or white matter. Active agents selected by this process are formulated as a pharmaceutical composition for human treatment.

Candidate active agents can be tested for their ability to competitively inhibit binding of the VH4 antibody or the antibody from peripheral plasmablast to its antigen or cellular target. Binding of the antibody to its target can be assessed in vitro or in vivo. Various types of candidate agents can be screened or evaluated in accordance with these aspects, and these include anti-idiotypic antibodies or antigen-binding portions thereof, an antibody or portion thereof with binding specificity for the same antigen (e.g., gray matter antigen), as well as peptide agents, aptamers, or small molecules, among others.

The effect of the active agent on neurodegenerative disease pathology can be evaluated in an animal model. For example, using a suitable animal model in which the animal expresses or is administered the target antibody in a manner that mimics a neurodegenerative disease (e.g., the animal may form CNS lesions similar to a demyelination process), the impact of the active agent on the pathology may be evaluated. In some embodiments, the active agent reduces or inhibits demyelination, inflammatory infiltrates, and/or axonal injury.

The active agent that is selected is formulated for administration to patients, for example, for administration by subcutaneous, intravenous, intramuscular, or intrathecal administration, or other route. The active agent is formulated at an amount that will effectively reduce disease activity or expression of selected antibodies in vivo. In some embodiments, the antibodies (either AGS+VH4 antibodies, or antibodies derived from plasmablasts as described) are testing in one more animal models to evaluate whether the antibody positively impacts neuroprotection or repair.

The disclosure in other aspects provides pharmaceutical compositions made through these methods, including protein, peptide, antibody, aptamer, small molecule, and oligonucleotide therapeutics.

Other aspects and embodiments will be apparent from the following detailed disclosure.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 11 shows the protein sequences for the antibody variable regions. Each consecutive pair of antibody sequences (heavy and light) constitute a single antibody. Underlined sequences are complementarity determining regions (CDRs).

FIG. 12 shows the nucleic acid sequences for the antibody variable regions. Each consecutive pair of antibody sequences (heavy and light) constitute a single antibody. Underlined sequences are restriction enzyme recognition sites.

FIGS. 13D and 13F) and 126× for the human tissue (FIGS. 13B and 13E) with the colocalization marker for NeuN (for neuronal nuclei) shown as red (Alexa Fluor 594). The primary rhAb is shown as green (Alexa Fluor 488) and nuclei are counterstained blue (DAPI). The images are shown as independent red and green channels above the overlay including DAPI. Data are representative of six coronal sections per rhAb on mouse brain tissue and three sections per rhAb on human GM brain tissue. Scale bar represents 10 μm.

FIGS. 14D and 14F) and 126× for the human tissue (FIGS. 14B and 14E) with the colocalization marker for GFAP (for astrocytes) shown as red (Alexa Fluor 594). The primary rhAb is shown as green (Alexa Fluor 488) and nuclei are counterstained blue (DAPI). The images are shown as independent red and green channels above the overlay including DAPI. Data are representative of six coronal sections per rhAb on mouse brain tissue and three sections per rhAb on human GM brain tissue. Scale bar represents 10 μm.

FIGS. 15D-E) and 126× for the human tissue (FIGS. 15C and 15F) with the colocalization marker for NeuN (neuronal nuclei) or GFAP (for astrocytes) shown as red (Alexa Fluor 594). The primary rhAb is shown as green (Alexa Fluor 488) and nuclei are counterstained blue (DAPI). The images are shown as independent red and green channels above the overlay including DAPI. Data are representative of six coronal sections per rhAb on mouse brain tissue and three sections per rhAb on human GM brain tissue. Scale bar represents 10 μm.

(FIGS. 17A and B) Binding of 10 rhAbs to common myelin proteins MOG and MBP by ELISA. A dashed line represents the threshold for background signal, as observed with the negative control antibody B1. (FIG. 17C) Binding of 8 rhAbs to myelin-derived peptides demonstrate no reactivity compared to controls (EAEA and anti-MBP). (FIG. 17D) Binding of 10 rhAbs to HEK293 cells mock transfected (left column) or transfected with MOG (right column) demonstrated no reactivity compared to control (8-18C5).

(FIG. 20A) Representative flow cytometry gating for detecting plasmablasts in peripheral blood. (FIG. 20B) Percentage of plasmablasts (CD19+ CD27high) in blood samples from patient groups as measured by flow cytometry. Levels are elevated for CIS-PTM patients as compared to healthy donors, much like that of NMO patients. (FIG. 20C) Single cell PCR of blood plasmablasts reveals an increase in usage of VH4 family genes in CIS-PTM patients, as compared to plasmablasts responding to influenza infection and total CD19+ cells from healthy donors. The increase is similar to what is seen in NMO plasmablasts and autologous memory B cells, although the latter does not reach significance. (FIG. 20D) Specific genes within the VH4 family listed as a percent of the total repertoire of genes. Only VH4-31 and VH4-34 genes are elevated in CIS-PTM patients over healthy donor total B cells or flu responding plasmablasts.

(FIG. 21A) Usage of specific heavy chain V gene segments in patient repertoires. Only VH4-31 and VH4-34 are elevated in CIS patient plasmablasts. (FIG. 21B) V gene family representation in the repertoire of each cell population. VH4 family genes are more highly represented in CIS and NMO patients, while VH6 family genes are depressed. VH1 family genes are over-represented in the flu responding plasmablasts. (FIG. 21C) J gene segment distribution in patient repertoires. Both CIS and NMO patients have a decreased usage of JH4 segments, while CIS patients have an increase in JH1 usage and NMO patients have an increase in JH6 usage. (FIG. 21D) The average heavy chain CDR3 length in each patient group. Flu responding plasmablasts have overall longer CDR3 regions. (FIG. 21E) The average charge of heavy chain CDR3s as calculated by the net number of positive and negative amino acids per sequence. No differences were observed between the groups. (FIG. 21F) The abundance of isotypes found in each patient in the plasmablast and memory B cell populations. CIS patients are represented in black and NMO patients in gray.

(FIG. 22A) Usage of specific kappa chain V gene segments in patient repertoires. No kappa chains were over represented in the CIS patients as compared to the flu responding plasmablasts. (FIG. 22B) Usage of specific lambda chain V gene segments in patient repertoires. (FIG. 22C) Kappa family representation in patient repertoires. No significant differences were observed. (FIG. 22D) Light chain J gene segment distribution in patient repertoires. CIS and NMO patients have a decrease in JK1 and JK4 usage and an increase in JK2 as compared to flu responding plasmablasts (CIS patients also displayed an increase in JK5 usage). (FIG. 22E) The average length of light chain CDR3 in patient repertoires. NMO patients have a slight decrease in length compared to flu responding plasmablasts. (FIG. 22F) The average charge of the light chain CDR3 as calculated by the net number of positive and negative amino acids. The overall charge flips from positive to negative in the CIS and NMO patients.

(FIG. 23A) Brain ELISA results grouped by patient. Most of the plasmablast antibodies did not recognize brain lysate antigens above the levels of healthy donor antibodies; however for most CIS patients two (33-50%) of the antibodies were highly reactive to brain lysate. (FIG. 23B) Results for all CIS rhAbs tested. Using healthy donor (HD) antibodies as a threshold for reactivity, 12 of the 38 CIS rhAbs and 2 of the 9 NMO rhAbs bound to brain lysate.

(FIG. 24A) Brain ELISA results grouped by V gene family of rhAb. (FIG. 24B) Summary of ELISA results grouped by V gene family. All VH3 rhAbs cloned showed little reactivity of brain lysate, but many (40%) of the VH4 family rhAbs bound strongly to brain lysate. (FIG. 24C) V gene segments utilized by rhAbs that did and did not recognize brain lysate. Only VH4 family genes recognized brain lysate above the level of healthy donor antibodies, but most VH4 family genes were represented in both the positive and negative group.

(FIG. 25B) Summary of kidney ELISA results grouped by patient. A similar proportion of CIS rhAbs were reactive to kidney lysate and many that were reactive to brain were also reactive to kidney, however the overlap was not identical. (FIG. 25C) V gene segments of rhAbs that recognized kidney lysate versus those that did not. Both VH3 and VH4 antibodies recognized the kidney lysate, indicating that the repertoire of general autoreactivity is different than that of the brain reactive repertoire.

(FIG. 27A) rhAb reactivity to stroke mouse corpus callosum brain tissue. (FIG. 27B) rhAb reactivity to stroke mouse cortex brain tissue. (FIG. 27C) 63× image of rhAb binding to stroke mouse brain. Two main patterns were observed with the rhAbs: neuronal body/cytoplasmic recognition in the cortex, and glial cell recognition in the corpus callosum.

(FIG. 28A) rhAb reactivity to stroke mouse corpus callosum. (FIG. 28B) rhAb reactivity to stroke mouse cortex.

(FIG. 34A) Summary of all the CIS and NMO rhAbs tested for binding to mouse brain tissue. One third of the CIS rhAbs and one third of the NMO rhAbs displayed affinity for only glial cells while the remaining two thirds bound both glia and neurons. (FIG. 34B) Enumeration of positively stained cells in the cortex.

(FIG. 35A) Representative images from testing rhAb binding to SH-Sy5y neurons by ICC. B1 is an isotype negative control, and G11 is an anti-NMDAR positive control. Examples of each staining pattern are represented here with the remaining images in FIG. 36. CIS07 did not bind to the SH-Sy5y cells, NMO06 displayed nuclear recognition, CIS19 showed cytoplasmic and nuclear binding, and CIS42 had strong cytoplasmic recognition with little binding to the nucleus. (FIG. 35B) Summary of ICC results. Most rhAbs derived from healthy controls did not recognize SH-Sy5y, while over half of the CIS rhAbs and a little less than a third of NMO rhAbs bound to this cell line. Cytoplasmic binding patterns were more common in the CIS rhAbs and nuclear binding patterns were more common in the NMO rhAbs.

(FIG. 37A) All images of rhAb binding to Hep2 cells by ICC. (FIG. 37B) Summary of binding to Hep2 cells. None of the healthy control rhAbs bound to Hep2 cells, but a small proportion of the CIS and NMO rhAbs did. 20% of the CIS and 10% of the NMO antibodies cross-reacted to Hep2 and SH-Sy5y, but the majority of the binding rhAbs were specific to SH-Sy5y.

(FIG. 38A) Representative histograms from testing rhAb binding to intracellular and extracellular portions of SH-Sy5y cells by flow cytometry. Examples of each binding pattern observed are presented, with the remaining plots in FIG. 39. B1 and G11 served as negative and positive controls respectively, HD10-42 and NM009 did not bind to the cell line, CIS09 and CIS35 only recognized the cell line intracellularly, and CIS48 and CIS56 recognized molecules expressed by the SH-Sy5y cell line both inside (intracellular) and outside (extracellular) the cell. (FIG. 38B) Summary of the tested rhAbs that bound to SH-Sy5y cells. 77% of the tested CIS rhAbs and 38% of tested NMO rhAbs recognized the cell line by flow cytometry. Of the positive CIS rhAbs 52% bound the cells both intra- and extracellularly while 48% only bound intracellular antigens. For the NMO rhAbs two thirds bound only intracellularly and one third bound both intracellular and extracellular targets. One third of the healthy donor rhAbs bound SH-Sy5y intracellularly, but none bound the exterior of the cells.

(FIG. 40A) Histogram data with intracellular and extracellular rhAb recognition of the astrocytic mouse cell line C8-D1A by flow cytometry. (FIG. 40B) Summary of rhAb recognition of C8-D1A astrocytes. Most healthy control rhAbs did not bind to this cell line, and none bound extracellular targets. Two thirds of the CIS rhAbs and about 40% of the NMO rhAbs recognized C8-D1A. Of the positive CIS rhAbs, about half bound only intracellularly and half bound both inside and outside the cell. Two thirds of the positive NMO rhAbs bound only intracellularly, while the remaining rhAb bound antigens only on the exterior of the cell.

(FIG. 41A) Histogram data with intracellular and extracellular rhAb recognition of the mouse neuronal cell line Neuro-2a by flow cytometry. (FIG. 41B) Summary of rhAb recognition of Neuro-2a neurons. Most healthy control rhAbs did not bind to this cell line, except one that bound both the intracellular and extracellular portion. Two thirds of the CIS rhAbs and three quarters of the NMO rhAbs recognized Neuro-2a. Of the positive CIS rhAbs, 60% bound only intracellularly and 40% both inside and outside the cell. Half of the positive NMO rhAbs bound only intracellularly, one quarter bound antigens only on the exterior of the cell, and one quarter bound antigens both inside and outside of the cells.

(FIG. 42A) Absorbance data from plasma ELISAs grouped by patient category. (FIG. 42B) Summary of brain lysate ELISAs with plasma. 1 NMO and 9 CIS patient samples were two standard devations above the mean of healthy plasma samples. The one positive NMO patient was the only NMO patient not on CellSept therapy, while all CIS patients were treatment naïve.

FIG. 43. Heavy Chain Sequences of AGS Enriched CSF Antibodies.

FIG. 44. Light Chain Sequences of AGS Enriched CSF Antibodies.

DETAILED DESCRIPTION OF THE DISCLOSURE

Figure 1A:
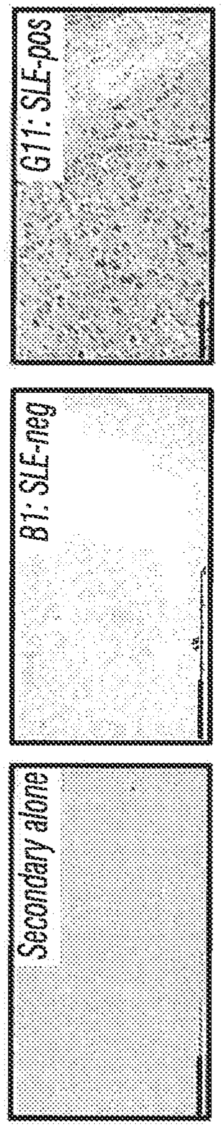
FIGS. 1A-1D show that AGS-enriched rhAbs bind to mouse brain. DAB images are shown at 20× magnification of the cortex and corpus callosum. The rhAbs in each row are grouped as follows: controls (FIG. 1A), CDMS (FIG. 1B), $ON_{CIS}$ (FIG. 1C), and $TM_{CIS}$ (FIG. 1D). The rhAb designation, patient type, and patient number are shown in the upper right corner of each image. Data are representative of three coronal sections per rhAb. Scale bar represents 100 μm.
Figure 1B:
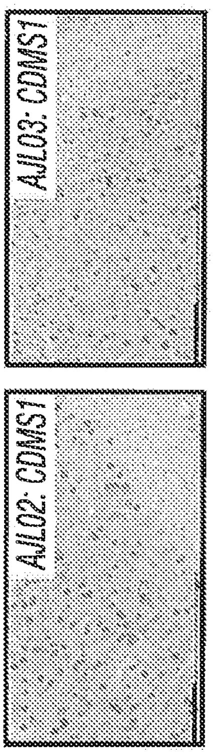
Figure 1C:
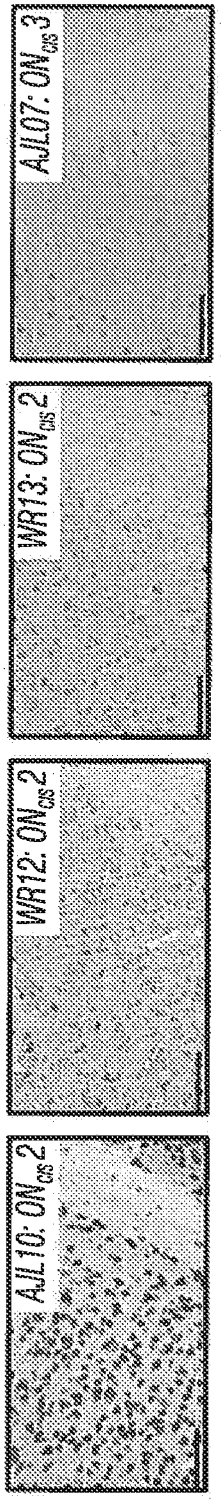
Figure 1D:
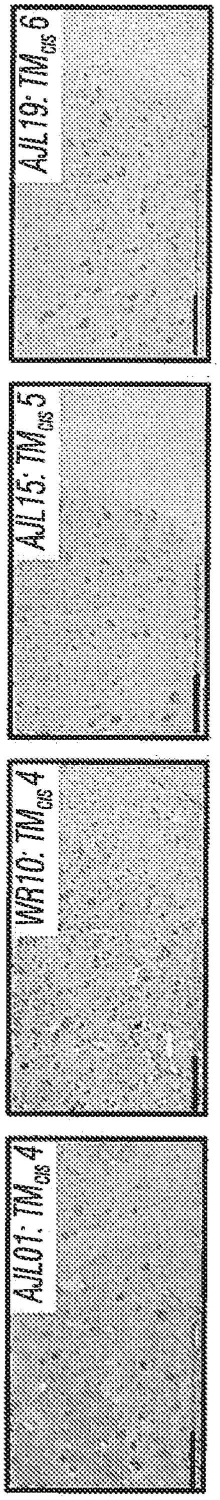

The present disclosure in various aspects provides methods for making pharmaceutical compositions for treating neurodegenerative diseases (e.g., demyelinating diseases), such as but not limited to autoimmune encephalitis, multiple sclerosis, and other related demyelinating diseases such as neuromyelitis optica, optic neuritis, and transverse myelitis. The pharmaceutical compositions impact specific immune-mediated processes involved in the biology of neurodegenerative disease. In certain aspects, the disclosure provides pharmaceutical compositions for treating neurodegenerative or neuroimmunological disease, which are based on inhibiting the action of pathologic antibodies, or alternatively providing therapeutic antibodies to stimulate neuroprotection or repair processes.

In one aspect, the disclosure provides a method for making a pharmaceutical composition for treating a neurodegenerative disease. The process comprises providing one or more VH4 antibodies having at least two mutations with respect to the germline sequence at codons selected from 31B, 32, 40, 56, 57, 60, 81, and 89. These antibodies, which are isolated from clinically diagnosed MS patients as well as patients with initial CIS presentation, bind to one or more antigens in human gray matter. In other aspects, the antibodies are derived from peripheral plasmablasts of neurodegenerative disease patients (e.g., MS, neuromyelitis optica, or transverse myelitis), and these antibodies may also be VH4 antibodies, and may or may not exhibit mutations at one or more codons selected from 31B, 32, 40, 56, 57, 60, 81, and 89 in some embodiments. The methods comprise selecting an active agent that reduces or inhibits the expression of the antibod(ies), or reduces or inhibits binding of the antibod(ies) to the antigen in human gray matter and occasionally white matter. Active agents selected by this process are formulated as a pharmaceutical composition for treatment of patients.

It is demonstrated that AGS-enriched antibodies bind to targets within the CNS. A panel of 32 full-length recombinant human antibodies (rhAbs) were prepared from single CSF B cells whose antibody genes contained AGS-targeted mutations. Surveying B cells and antibodies within the CSF is relevant to CNS disease because there are shared B cell clones between the same MS patient's CSF and CNS (Obermeier et al., 2011), between the meninges and CNS (Lovato et al., 2011), and between the CSF and peripheral blood (Palanichamy et al., 2014). This panel of 32 rhAbs came from a diverse set of patients including CDMS and two initial CIS presentations (optic neuritis ($ON_{CIS}$) and transverse myelitis ($TM_{CIS}$)). $ON_{CIS}$ patients present with optic symptoms and lesions along the optic nerve, and $TM_{CIS}$ patients exhibit sensory symptoms with lesions along short segments of the spinal cord. Regardless of either presentation of CIS, both patient types have CSF B cells pools enriched for AGS and are at high risk of converting to CDMS.

CNS targeting of the rhAb panel was determined using immunohistochemistry on both mouse and human brain tissue. Surprisingly, the AGS-enriched B cells targeted gray matter (GM) rather than the anticipated myelin-rich white matter (WM), which has been extensively studied in the MS field (Lassmann et al., 2007). GM involvement in MS disease symptoms and advancement has been understudied even though the presence of cortical lesions correlates strongly with MS disease severity and progression as opposed to the more easily detected WM lesions (Bo et al., 2007, Fisniku et al., 2008 and Vercellino et al., 2005). In fact, cortical GM demyelination is more extensive than WM (26.5% vs 6.5%) with the percentage of demyelination in the cortex increasing with disability and disease length (Bo et al., 2003). Immunofluorescence confirmed GM targeting of the rhAbs to astrocyte bodies and processes, and neuronal nuclei in both human and mouse brain tissue. This targeting pattern was observed with AGS-enriched rhAbs generated from both CIS presentations, $ON_{CIS}$ and $TM_{CIS}$, as well as established CDMS. Thus, these MS derived antibodies share a mutational pattern that targets GM, and suggest a previously unrecognized humoral immunity target for treating the pathology of multiple sclerosis and related neurodegenerative diseases.

The normal immune system has the ability to generate millions of antibodies with different antigen binding abilities. The diversity is brought about by the complexities of constructing immunoglobulin molecules. These molecules consist of paired polypeptide chains (heavy and light) each containing a constant and a variable region. The structures of the variable regions of the heavy and light chains are specified by immunoglobulin V genes. The heavy chain variable region is derived from three gene segments known as VH, D and JH. In humans there are about 100 different VH segments, over 20 D segments and six JH segments. The light chain genes have only two segments, the VL and JL segments. Antibody diversity is the result of random combinations of V(D)J segments as well as somatic mutation.

The germline VH genes can be separated into at least six families (VH1 through VH6) based on DNA nucleotide sequence identity of the first 95 to 101 amino acids. Members of the same family typically have 80% or more sequence identity, whereas members of different families have less than 70% identity. These families range in size from one VH6 gene to an estimated greater than 45 VH3 genes. In addition, many pseudogenes exist. It is estimated that the human VH repertoire is represented by approximately 50 functional VH segments with about an equal number of pseudogenes. The size of the VH locus is approximately 1100 kb. The VH4 family of genes contains 9 different members: 4-04, 4-28, 4-30, 4-31, 4-34, 4-39, 4-59, 4-61, and 4-B3.

The VH4 antibody in accordance with the various aspects of the disclosure may have 2, 3, 4, 5, or 6 mutations with respect to the germline sequence at codons selected from 31B, 32, 40, 56, 57, 60, 81, and 89. In some embodiments, the VH4 antibody has at least one mutation at residue 311B, 56 and/or 81, and one or more mutations at a position selected from 32, 40, 57, 60 and 89. Exemplary VH4 antibody amino acid sequences are shown in FIG. 11, and antibody nucleic acid sequences are shown in FIG. 12. The following table lists the VH4 antibody substitutions exemplified by the panel of 32 rhAbs:

TABLE 1

| ANTIBODIES WITH AGS SIGNATURE CHANGES | | | | | | | |
|---|---|---|---|---|---|---|---|
| rhAb | # AGS | 31B | 40 | 56 | 57 | 81 | 89 |
| AJL01 | 3 | | | S→R<br>--c; aga | T→A<br>a--; gcc | K→N<br>--g; aac | |
| AJL02 | 2 | | H→S<br>ca-; tcc | | | K→R<br>-a-; agg | |
| AJL03 | 2 | S→R<br>a--; cgt | | | | K→N<br>-g; aac | |
| AJL04 | 3 | | P→S<br>c--; tcc | S→G<br>a--; ggc | T→I<br>-c-; atc | | |
| AJL05 | 4 | S→N<br>-g-; aat | | | T→A<br>a--; gcc | K→N<br>--g; aat | V→F<br>g-g; ttt |
| AJL06 | 3 | GAN<br>gg-; aat | | | | K→R<br>--ag; aga | V→I<br>g-g; atc |
| AJL07 | 3 | | | S→N<br>-gc; aat | T→I<br>-cc; att | K→N<br>--g; aac | |
| AJL08 | 3 | | | S→T<br>-gc; act | | K→N<br>--g; aac | V→F<br>g-g; ttt |
| AJL09 | 2 | | P→S<br>c--; tcc | | | K→N<br>--g; aac | |
| AJL10 | 4 | | P→S<br>c--; tcc | S→T<br>-gc; act | | K→R<br>-a-; agg | V→I<br>g-g; ata |
| AJL11 | 3 | | P→S<br>c--; tcc | S→N<br>-g-; aac | | K→M<br>-a-; atg | |
| AJL12 | 3 | S→D<br>ag-; gat | | S→N<br>-g-; aac | | K→N<br>--g; aac | |
| AJL13 | 3 | | | S→N<br>-gc; aat | T→I<br>-cc; att | K→N<br>--g; aac | |
| AJL14 | 3 | S→N<br>-g-; aat | | S→Y<br>ag-; tac | | | V→I<br>g-g; atc |
| AJL15 | 4 | S→N<br>-g-; aat | P→S<br>c--; tcc | | T→D<br>ac-; gac | K→R<br>-a-; agg | |
| AJL16 | 3 | S→P<br>ag-; cct | | S→H<br>ag-; cac | | K→R<br>aa-; cgg | |
| AJL18 | 5 | S→K<br>-gt; aaa | H→L<br>-a-; ctc | S→T<br>-g-; acc | | K→R<br>-a-; agg | V→R<br>gtg; cgc |
| AJL19 | 3 | | | S→D<br>agc; gat | T→A<br>a--; gcc | | V→L<br>g-g; tta |
| AJL20 | 3 | | | S→T<br>-g-; acc | | K→R<br>-a-; agg | V→I<br>g-g; ata |
| WR01 | 2 | | | | T→P<br>a--; ccc | K→R<br>-a-; agg | |
| WR02 | 2 | | | S→G<br>a-; ggc | T→A<br>a-c; gcg | | |
| WR03 | 3 | | | S→G<br>a-; ggc | T→A<br>a--; gcc | K→N<br>--g; aac | |
| WR04 | 3 | S→G<br>a-t; ggc | P→A<br>c--; gcc | | | K→N<br>--g; aat | |
| WR05 | 4 | S→G<br>a--; ggt | | S→T<br>-g-; acc | T→S<br>a--; tcc | K→T<br>-ag; aca | V→I<br>g-g; att |
| WR06 | 3 | S→A<br>ag-; gct | | S→N<br>-g-; aac | T→K<br>-cc; aaa | | |
| WR07 | 4 | S→T<br>-g-; act | P→S<br>c--; tcc | S→K<br>-gc; aaa | | K→N<br>--g; aac | |
| WR08 | 2 | | | S→T<br>-g-; acc | | K→N<br>--g; aac | |

TABLE 1-continued

| ANTIBODIES WITH AGS SIGNATURE CHANGES | | | | | | | |
|---|---|---|---|---|---|---|---|
| rhAb | # AGS | 31B | 40 | 56 | 57 | 81 | 89 |
| WR09 | 2 | | | S→T<br>-g-; acc | | K→N<br>--g; aac | |
| WR10 | 2 | | P→S<br>c--; tcc | S→G<br>a--; ggc | | | |
| WR11 | 2 | | P→S<br>c--; tcc | S→G<br>a--; ggc | | | |
| WR12 | 2 | | | S→T<br>-g-; acc | | K→R<br>-a-; agg | |
| WR13 | 2 | | | S→T<br>-g-; acc | | K→R<br>-a-; agg | |

In some embodiments, the VH4 antibody has at least three mutations with respect to the germline sequence at codon positions selected from 31B, 32, 40, 56, 57, 60, 81, and 89, and may have at least four mutations with respect to the germline sequence at codon positions selected from 31B, 32, 40, 56, 57, 60, 81, and 89. In some embodiments, the VH4 antibody has one or more mutations with respect to the germline sequence at codon positions 31B, 56 and/or 81, and may further have mutations with respect to the germline sequence at one or more codon positions selected from codons 32, 40, 57, 60 and 89.

In some embodiments, the VH4 antibody has mutations at two or more of codons 56, 57, and 81 with respect to the germline sequence, or at two or more of codons 40, 56, 81, and 89 with respect to the germline sequence. In some embodiments, the VH4 antibody has mutations at one or more of codons 32, 40, 57, 60, and 89 with respect to the germline sequence. In some embodiments, the VH4 antibody has mutations at one or both of codon 40 and 81 with respect to the germline sequence.

While the identity of the amino acid substitutions are not limited, in some embodiments codon 31B may be R, N, D, P, K, G, A, or T, and in some embodiments is a charged amino acid, such as R, N, or D. In some embodiments, codon 40 may be S, L, or A. In some embodiments, codon 56 is R, G, N, T, Y, H, D, or K, and may be selected from N, T, and G. Codon 57 in various embodiments is A, I, D, S, or K, and may be selected from A and I in some embodiments. In various embodiments, codon 81 is N, R, or M. For example, codon 81 may be N or R. In some embodiments, codon 89 is F, I, R, or L. In some embodiments, codon 89 is a hydrophobic amino acid, such as F, I, or L. In various embodiments, the antibody contains a set of AGS codons shown in Table 1.

Figure 19:
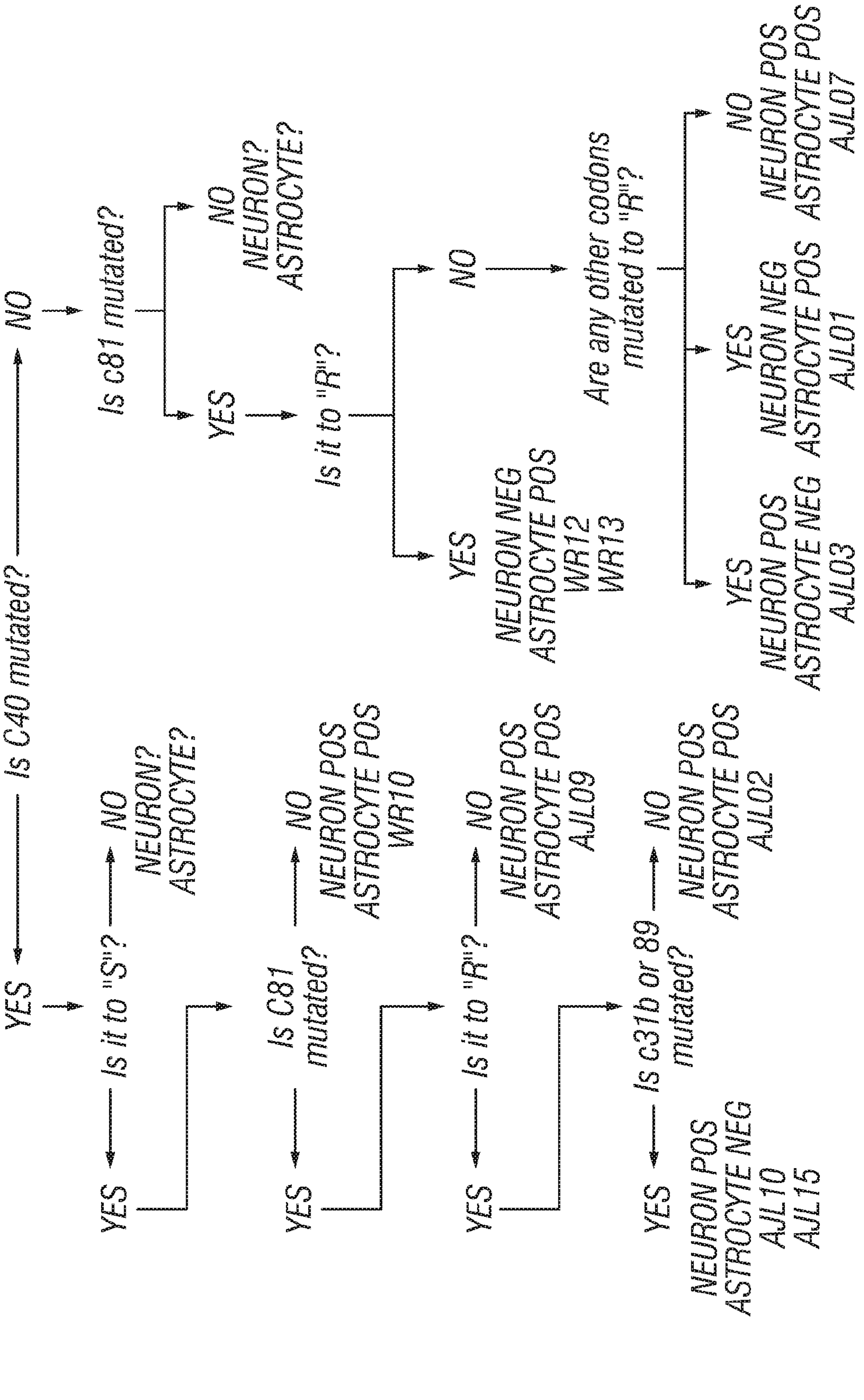
FIG. 19 illustrates a codon mutation decision tree.

In some embodiments, the VH4 antibody has a T or R replacement at codon 56, optionally with the germline amino acid at codons 31B, 40, and 89. An antibody with this mutation has the potential to bind neurons and astrocytes. Antibody binding (e.g., immunohistochemistry staining) patterns can be in part predicted from the codon signature, as illustrated in FIG. 19.

The antibody or fragment may have a heavy chain CDR or set of heavy chain CDRs selected from SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61 and 63, and light chain CDR or set of light chain CDRs selected from SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62 and 64, respectively. Alternatively, the recombinant antibody or fragment may have a heavy chain variable region sequence selected from SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61 and 63, and/or a light chain variable region sequence selected from SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62 and 64, respectively.

In some embodiments, the VH4 germline is 4-04, 4-28, 4-30, 4-31, 4-34, 4-39, 4-59, 4-61, or 4-B.

In some embodiments, the antibody has a CDR sequence as above, but with from 1 to 5 amino acid substitutions (e.g., 1, 2, 3, 4 or 5 substitutions) in the CDR sequence, while maintaining the identity at the AGS codons.

In still other embodiments, the antibody is derived from peripheral plasmablasts from MS patients, or clinically isolated syndrome patients (CIS) at high risk to develop MS. The antibodies derived from peripheral plasmablasts may or may not meet the criteria of AGS antibodies.

Plasmablasts represent a large proportion (5-40%) of the B cell pool in the CSF of untreated MS patients. The plasmablast frequency in the CSF correlates with increased inflammation as disclosed by MRI, and they are also elevated in the blood of patients experiencing their first clinical attack. When patients are left untreated, the frequency of plasmablasts continues to rise. Plasmablasts in the blood develop as a part of the antigen-stimulated memory B cell response to their cognate antigen, and after 2-3 weeks, apoptose or differentiate into long-lived plasma cells. Plasmablasts produce large amounts of antibody and their autocrine production of IL-10 positively feeds back to promote the differentiation and expansion of IgG and IgM antibody secreting plasma cells. Thus the presence of plasmablasts indicates an active B cell response and represents the fraction of memory B cells and other B cell precursors that are currently responding to stimulus.

The antibody expressed by a B cell on its surface is the primary factor in issuing their development in the bone marrow and determining their activation response in the periphery. For example, in the periphery, the lack of cognate antigen recognition results in removal from the B cell pool while engagement of cognate antigen results in activation, clonal expansion and affinity maturation. Thus, there is a critical relationship between the antibody expressed by these B cells, their cognate antigen and the B cell's potential to participate in an immune response and endure in the B cell pool.

Therefore, since patients display an expansion of plasmablasts at the time of their first attack of transverse myelitis, peripheral plasmablasts from these patients may be autoreactive. As shown herein, single peripheral plasmablasts were isolated from a patient cohort, and the antibodies they express were cloned and investigated for reactivity to brain antigens. Peripheral plasmablasts from Neuromyelitis Optica (NMO) patients were used as a comparator population since NMO patients also present with transverse myelitis and possess pathogenic autoantibodies, but do not classically exhibit brain inflammation as indicated by MRI.

These studies show that antibodies expressed by plasmablasts from these early MS patients displayed high levels of reactivity for cellular and protein targets in the brain using a panel of methodology to verify binding. Remarkably, only those antibodies that utilized variable heavy chain family 4 (VH4) genes bound to brain antigens. In addition, CNS reactive antibodies were detected in blood plasma samples of all patients from whom single peripheral plasmablasts were isolated. This is the first evidence that peripheral plasmablasts from CIS patients displaying transverse myelitis symptoms express antibodies that bind to brain antigens, demonstrating their autoreactive nature.

The antibody in various embodiments is a human recombinant antibody. Antibodies may be produced by standard methods well known in the art (see, e.g., Antibodies: A Laboratory Manual, Cold Spring Harbor Laboratory, 1988; U.S. Pat. No. 4,196,265). For example, the VH4 antibodies can be prepared by co-transfection of cells with paired cloning vectors harboring IgK and IgH genes of the desired VH4 antibody. Recombinant antibodies can be harvested from transfected cell supernatants.

In some embodiments, the antibody further binds to mouse brain tissue, in addition to human gray matter. In some embodiments the VH4 antibody binds to astrocytes and neuronal nuclei in human gray matter, and optionally mouse gray matter.

In accordance with some aspects, the VH4 antibodies are used as a target for therapeutic agents that are useful for treating neurodegenerative disease (e.g., a demyelinating disease), such as MS, NMO or TM. Candidate active agents can be tested for their ability to competitively inhibit binding of the VH4 antibody to its antigen. Binding of the VH4 antibody to its target can be assessed in vitro or in vivo, e.g., using an animal model. For example, in vitro assays can make use of human or mouse brain tissue (e.g., including by immunohistochemistry), fractionated portions of brain or CNS tissue, cell lines, or purified, semi-purified, or isolated gray matter antigen. Further, animal models can be created by administering the antibodies to an animal model, to create one or more symptoms relating to neurodegenerative disease (e.g., a demyelinating disease). Reduction or inhibition of these symptoms can be determined upon administration of candidate agents to the model.

Various types of candidate agents can be screened in accordance with these aspects, and these include anti-idiotypic antibodies or antigen-binding portions thereof, an antibody or portion thereof with binding specificity for the same antigen (e.g., GM antigen), as well as peptide agents, aptamers, or small molecules.

In some embodiments, the candidate agent is an anti-idiotypic antibody. The anti-idiotypic antibody binds to the idiotope of the VH4 antibody. The idiotype is the unique antigen binding site of the VH4 antibody. The combination of epitopes within the idiotype (i.e. the idiotopes) is unique for each antibody. Anti-idiotypic antibodies can be generated to bind specifically to the hypervariable region of the selected antibody target.

In some embodiments, the candidate agent is an antibody or portion thereof with binding specificity for the same antigen (e.g., gray matter antigen). For example, monoclonal antibody fragments can be prepared that compete for binding by the VH4 antibody, but lack immune effector functions (e.g., Fc) that may be responsible for disease pathology. Immune effector functions can be altered by deletion of immunoglobulin domains or by mutation of one or more amino acids in the Fc region.

Fc receptors (FcRs) are key immune regulatory receptors connecting the antibody mediated (humoral) immune response to cellular effector functions. There are receptors for all classes of immunoglobulins. For example, there are three classes of receptors for human IgG found on leukocytes: CD64 (FcγRI), CD32 (FcγRIIa, FcγRIIb and FcγRIIc) and CD16 (FcγRIIIa and FcγRIIIb). In antibody dependent cellular cytotoxicity (ADCC), FcRs on the surface of effector cells (natural killer cells, macrophages, monocytes and eosinophils) bind to the Fc region of an IgG which itself is bound to a target cell. Upon binding, a signalling pathway is triggered which results in the secretion of various substances, such as lytic enzymes, perforin, granzymes and tumour necrosis factor, which mediate in the destruction of the target cell. The level of ADCC effector function varies for human IgG subtypes. Although this is dependent on the allotype and specific FcR, in simple terms, ADCC effector function is high for human IgG1 and IgG3, and low for IgG2 and IgG4. Knowledge of the binding site has resulted in engineering efforts to modulate IgG effector functions.

Thus, the active agent can be an antibody fragment lacking an Fc. The antibody may be a F(ab')2 or Fab, a single chain antibody, or single chain variable fragment (scFv). Other antibody or antigen-binding formats that can be employed include: a single-domain antibody, a recombinant heavy-chain-only antibody (VHH), a single-chain antibody (scFv), a shark heavy-chain-only antibody (VNAR), a microprotein (cysteine knot protein, knottin), a DARPin, a Tetranectin, an Affibody; a Transbody, an Anticalin, an AdNectin, an Affilin, a Microbody, a phylomer, a stradobody, a maxibody, an evibody, a fynomer, an armadillo repeat protein, a Kunitz domain, an avimer, an atrimer, a probody, an immunobody, a triomab, a troybody, a pepbody, a vaccibody, a UniBody, a DuoBody. These other formats are described in US Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In some embodiments, the candidate agent is a peptide agent. The peptide agent in these embodiments may mimic the natural ligand by binding to the complementarity determining region (CDR), and may be identified by homology modeling and/or physical screening through use of antibody-antigen binding assays. Antibody variable regions may be modeled for docking studies using known processes, including homology models. Sircar et al., "Rosetta Antibody: antibody variable region homology modeling server," *Nucleic Acid Res.* 2009 Jul. 1; 37(Web Server issue): W474-W479. Antibody-antigen binding can be qualitatively or quantitatively assessed using any direct or competitive immunoassay. A peptide can be selected from a peptide library based on antibody-antigen binding, and then optimized for its binding affinity to the antibody target (e.g., based on homology modeling and/or quantitative binding assay).

In some embodiments, the candidate agent is an aptamer. Aptamers are oligonucleotide or peptide molecules that bind to a specific target molecule. Aptamers can be identified by selecting them from a large random sequence pool. Aptamers can be classified as DNA, RNA, or XNA aptamers. They often consist of short strands of oligonucleotides. Nucleic acid aptamers can be engineered through repeated rounds of in vitro selection (e.g., SELEX, systematic evolution of ligands by exponential enrichment) to bind to the antibody target.

In some embodiments, the candidate agent is a small molecule. Small molecule drugs can mimic the natural antigen of the target antibody by binding to the complementarity determining region (CDR), and may be identified by homology modeling and/or physical screening through use of antibody-antigen binding assays. Antibody variable regions may be modeled for dockeing studies using known processes, including homology models. Sircar et al., "Rosetta Antibody: antibody variable region homology modeling server," *Nucleic Acid Res.* 2009 Jul. 1; 37(Web Server issue): W474-W479. Antibody-antigen binding can be qualitatively or quantitatively assessed using any direct or competitive immunoassay. A small molecule hit or core can be selected from a small molecule library based on antibody binding, and then optimized for its binding affinity to the antibody target (e.g., based on homology modeling and/or quantitative binding assay).

The effect of the active agent on neurodegenerative disease pathology can be evaluated in an animal model. For example, using a suitable animal model in which the animal expresses or is administered the target antibody in a manner that mimics a neurodegenerative disease (e.g., the animal may form CNS lesions similar to a demyelination process), the impact of the active agent on the pathology may be evaluated. In some embodiments, the active agent reduces or inhibits demyelination, inflammatory infiltrates, axonal injury or cell target function (e.g. metabolism).

In still other embodiments, an oligonucleotide is designed to inhibit the expression of the antibody target. For example, the active agent can be an antisense oligonucleotide or siRNA. Generally, these molecules can be designed against the CDR region of the target antibody, to specifically silence only this pathological immunity. For example, antisense oligonucleotides may be designed to hybridize to the CDR region of the antibody including at least two of the AGS codons, or alternatively, to any VH4-specific sequence (e.g., of any VH4-specific germline sequence). Without limitation, exemplary VH4-specific regions and sequences are disclosed in US 2014/0371103, which is hereby incorporated by reference. Antisense oligonucleotides are typically in the range of 8 to 30 nucleotides in length, and may contain one or more chemical modifications to impart stability and/or increase affinity for the target sequence. Exemplary chemical modifications include backbone modifications (e.g., phosphorothioate or phosphorodiamidate morpholino), as well as 2' modifications (e.g., 2' O-methyl) and bridging modifications (e.g., locked nucleic acid, or other 2' to 4' bridge), base modifications, and/or cap structures. Exemplary modifications are described in U.S. Pat. Nos. 9,163,235 and 8,642,751, which are hereby incorporated by reference in their entireties. Candidate sequences can be tested in various in vitro systems (e.g., cell culture), in which cells are transfected with sequences to express the target antibody, and effects on expression of the antibody are evaluated upon delivery of the oligonucleotide to the cells. Candidate agents can also be tested in vivo, e.g., in rodent models, where the rodents express antibodies comprising the target sequence.

The active agent is selected and formulated for administration to patients, for example, by subcutaneous, intravenous, intramuscular, oral, or intrathecal administration, or other route. In some embodiments, the active agent is delivered in an encapsulated form, either in micelles, liposomes, or nanoparticles, and which may be targeted to desired cells (e.g., antibody expressing B cells). The active agent is formulated at an amount effective reduce activity or expression of target antibodies in vivo. In some embodiments, the pharmaceutical composition may be administered by intrathecal, intravenous, or subcutaneous injection at a frequency of at least once per week, or once per month. The pharmaceutical composition may be administered from 2 to 20 times per year in various embodiments.

In some embodiments, the antibodies (either AGS VH4 antibodies, or antibodies derived from plasmablasts as described) are tested in one more animal models to evaluate whether the antibody positively impacts neuroprotection or repair. Antibodies have been observed to positively impact MS lesions. See U.S. Pat. Nos. 5,591,629 and 8,968,735, which are hereby incorporated by reference in their entirety.

Exemplary animal models include EAE (Experimental Autoimmune Encephalomyelitis) models that are reminiscent of monophasic, relapsing, progressive or relapsing to progressive forms of MS and toxicity models such as the cuprizone and lysolecithine models of demelination that are not initiated by inflammatory components. A mild EAE model, in which sub-optimal doses of recombinant human MOG35-55 peptide are used to induce EAE resulting in scores within the 1-2 range on the EAE scale indicating mild CNS damage. Subsequent introduction of an anti-MOG antibody increases EAE scores. This model can be used to evaluate whether rhAbs contribute to CNS damage manifesting as increased EAE scores, decreased grip strength and loss of rotarod performance over control mice that receive a rhAb that does not bind mouse brain tissue.

For example, for the mild EAE model, C57BL/6 female mice (8-12 weeks of age) are immunized s.c. with 100 μg human MOG35-55 on day 0 and treated with 200 ng pertussis toxin i.p. on day 0 and 2. On day 17 post-immunization, mice with similar disease score range, mean and medium (10 mice/group; mean disease score for each group of ~1) are divided into groups and injected i.v. with 200 μg of the anti-MOG rhAb as a positive control, 200 μg of a rhAb that has been documented with no binding properties to brain tissue as a negative control, and 200 μg of each individual rhAb documented to bind brain tissue as the experimental agents. Disease severity (as measured by EAE scores), grip strength testing and rotarod testing is scored for an additional 13 days.

For the neurorepair model, a disease model using cuprizone may be employed. Cuprizone is a neurotoxin that causes profound demyelination in mice following 5 weeks of exposure. This model can be used to determine the neurorepair capability of certain rhAbs. CNS recovery as measured by remyelination occurs over the next two weeks once the mice are returned to a normal diet. For the cuprizone model, 6 to 8 week old C57BL/6 female mice are fed chow mixed with 0.2% cuprizone for 5 weeks to promote demyelination in the brain. The mice are then returned to a normal chow diet at which time CNS recovery as measured by remyelination occurs over the next two weeks.

For example, on Day 1 of the return to normal chow, 200 μg of rhAb is injected intraperitonially. This delivery system demonstrates efficient binding of human IgG1 to mouse brain. During this two-week period, the mice are subjected to grip strength testing and rotarod testing which have been demonstrated to improve during the recovery period. Y-maze and Novel Object tests are used to further evaluate behavior, as performance in these tests are also improved during the recovery period of cuprizone-treated mice.

Other measurements of CNS damage including demyelination may be evaluated, for example, using Luxol fast blue, enumeration of infiltrating lymphocytes (e.g., using hematoxylin/eosin), and enumeration of injured axons (e.g., using R-APP). Since astrocyte loss can lead to oligodendrocyte loss prior to detection of demyelination, the number of astrocytes using GFAP and the number of mature and precursor oligodendrocytes using Nogo-A and Olig2, respectively, can be enumerated. Detection of binding by the rhAbs to mouse CNS tissue may also be performed to confirm exposure of the CNS to the rhAbs.

Other useful models include the monophasic model (induction with MOG35-55 in C57Bl/6 mice) as reported by Sosa et al. (2013), and the RRMS to SPMS model (Biozzi ABH induced with syngeneic spinal cord homogenate), disclosed in Al-Izki et al. (2012) and Hampton et al. (2008).

Where antibodies are identified that positively impact neuroprotection or repair processes, an antibody can be formulated for delivery as a therapeutic agent.

In other aspects, the disclosure provides pharmaceutical compositions to stimulate neuroprotection or repair processes in neurodegenerative diseases, such as MS. In some embodiments, the pharmaceutical composition comprises an effective amount of a VH4 antibody or antigen-binging portion thereof and a pharmaceutically acceptable carrier, the antibody or antigen-binding portion having at least two mutations selected from 31B, 32, 40, 56, 57, 60, 81, and 89, and which binds to an antigen in human gray matter and exhibit neuroprotection or repair. The antibody may exhibit neuroprotection in the EAE model, and/or neurorepair activity in cuprizone model. In some embodiments, the VH4 antibody has a set of heavy chain CDRs as in any one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61 and 63, and a set of light chain CDRs as in any one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, and 64.

In still other embodiments, the VH4 antibody has a set of mutations selected from Table 1. For example, the VH4 antibody may have a set of heavy chain CDRs as in any one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61 and 63, and/or a set of light chain CDRs as in any one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, and 64.

In other aspects, the disclosure provides pharmaceutical compositions to block or reduce binding of pathologic antibodies. The compositions may comprise an anti-idiotypic antibody specific for a VH4 antibody having a set of mutations selected from Table 1. For example, the anti-idiotypic antibody may be specific for a VH4 antibody having a set of heavy chain CDRs as in any one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61 and 63, and a set of light chain CDRs as in any one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, and 64.

In still other embodiments, the VH4 antibody has a set of mutations selected from Table 1, wherein the antibody lacks an Fc domain or has a derivatized Fc domain to alter one or more effector functions. For example, the VH4 antibody may have a set of heavy chain CDRs as in any one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61 and 63, and/or a set of light chain CDRs as in any one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, and 64, and which lacks an Fc domain or has a derivatized Fc domain to alter one or more effector functions.

In some embodiments, the VH4 antibody is a Single Chain Variable Fragment (scFv), which is a fusion of the variable regions of the heavy and light chains of immunoglobulins, linked together with a short (usually serine, glycine) linker. This chimeric molecule, also known as a single domain antibody, retains the specificity of the original immunoglobulin, despite removal of the constant regions and the introduction of a linker peptide. This modification usually leaves the specificity unaltered. Single domain or single chain variable fragments lack the constant Fc region found in complete antibody molecules.

Flexible linkers generally are comprised of helix- and turn-promoting amino acid residues such as alaine, serine and glycine. However, other residues can function as well.

In some embodiments, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Alternative antibody and antigen-binding platforms are described herein, which can be used for the pharmaceutical compositions in this aspect of the disclosure.

Antibody (or related) therapeutics can be formulated to contain from about 0.1 mg to about 100 mg of active agent per dose in some embodiments (e.g., at a concentration of about 0.1 mg to about 100 mg per mL).

In other embodiments, the disclosure provides an oligonucleotide comprising a nucleotide sequence that is complementary to a nucleotide sequence encoding a VH4 heavy chain CDR sequence selected from any one of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61 and 63, or complementary to a nucleotide sequence encoding a VH4 light chain CDR sequence of any one of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, and 64. For example, the oligonucleotide may have a nucleotide sequence that is complementary to an RNA encoding a VH4 CDR region comprising at least two AGS codons. For example, the nucleotide sequence may comprise a sequence that is complementary to a sequence within one of SEQ ID NOS: 65-128. In some embodiments, the oligonucleotide is an antisense oligonucleotide or is a siRNA.

Antisense oligonucleotides are typically in the range of 8 to 30 nucleotides in length (e.g., 12 to 20 nts in length), and may contain one or more chemical modifications to impart stability and/or increase affinity for the target sequence. Exemplary chemical modifications include backbone modifications (e.g., phosphorothioate or phosphorodiamidate morpholino), as well as 2' modifications (e.g., 2' O-methyl) and bridging modifications (e.g., locked nucleic acid, or other 2' to 4' bridge structure), base modifications, and/or cap structures. Exemplary modifications are described in U.S. Pat. Nos. 9,163,235 and 8,642,751, which are hereby incorporated by reference in their entireties.

RNA interference (RNAi) is a mechanism by which gene expression can be reduced or eliminated. siRNAs are designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective, but sequences in the range of 20-25 base pairs in length can be used. This length reflects the lengths of digestion products resulting from the processing of much longer RNAs. Several further modifications to siRNA sequences may be employed to alter their stability or improve their effectiveness. For example, synthetic complementary 21-mer RNAs may have di-nucleotide overhangs (i.e., 19 complementary nucleotides+3' non-complementary dimers), which may provide a greater level of suppression. These siRNAs use a sequence of two (2'-deoxy) thymidine nucleotides as the di-nucleotide overhangs.

RNA for use in siRNA may be chemically or enzymatically synthesized.

In some embodiments, the siRNA or antisense oligonucleotide targets and reduces the expression of VH4 antibodies generally. Nucleotide sequences that are specific for VH4 antibodies over other families are described in U.S. Patent Publication 2014/0371103, which is hereby incorporated by reference in its entirety.

The structure, formulation, and delivery of siRNA therapeutics are described in U.S. Patent Publication 2014/0161894, U.S. Patent Publication 2014/0024699, U.S. Patent Publication 2015/0197746, and U.S. Patent Publication 20160076040, which are hereby incorporated by reference in its entirety.

The present disclosure provides pharmaceutical compositions comprising antibody inhibitory substances. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Other suitable pharmaceutical excipients include starch, glucose, lactose, sucrose, saline, dextrose, gelatin, malt, rice, flour, chalk, silica gel, sodium stearate, glycerol monostearate, talc, sodium chloride, dried skim milk, glycerol, propylene glycol, water, ethanol and the like.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The formulations of the present disclosure may include classic pharmaceutical preparations. Administration of these compositions according to the present disclosure will be via any common route so long as the target tissue is available via that route. In some embodiments administration may be by intradermal, subcutaneous, intramuscular, intraperitoneal, intravenous, intrathecal injection, or other route.

In various embodiments, the active agents are used to treat a neurodegenerative disease, and in particular neuroimmunological or demyelinating diseases, such as MS, autoimmune encephalitis, neuromyelitis optica, optic neuritis, and transverse myelitis.

In some embodiments, the patient has clinically isolated syndrome (CIS). A clinically isolated syndrome (CIS) is a single monosymptomatic attack compatible with MS, such as optic neuritis, brain stem symptoms, and partial myelitis. Patients with CIS that experience a second clinical attack are generally considered to have clinically definite multiple sclerosis (CDMS). Over 80 percent of patients with CIS and MRI lesions go on to develop MS, while approximately 20 percent have a self-limited process. Patients who experience a single clinical attack consistent with MS may have at least one lesion consistent with multiple sclerosis prior to the development of clinically definite multiple sclerosis. In various embodiments, the present methods are used to treat CIS so it does not develop into MS.

In various embodiments, the present methods are used to treat radiologically isolated syndrome (RIS). In RIS, incidental imaging findings suggest inflammatory demyelination in the absence of clinical signs or symptoms. In various embodiments, the present methods are used to treat RIS so it does not develop into MS.

In various embodiments, the active agents are used to treat benign multiple sclerosis; relapsing-remitting multiple sclerosis (RRMS); secondary progressive multiple sclerosis (SPMS); progressive relapsing multiple sclerosis (PRMS); and primary progressive multiple sclerosis (PPMS).

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis. In various embodiments, the present methods are used to treat benign multiple sclerosis so it does not develop into MS.

Patients suffering from RRMS experience sporadic exacerbations or relapses, as well as periods of remission. Lesions and evidence of axonal loss may or may not be visible on MRI for patients with RRMS. In various embodiments, the present methods are used to treat RRMS. A clinical relapse, which may also be used herein as "relapse," "confirmed relapse," or "clinically defined relapse," is the appearance of one or more new neurological abnormalities or the reappearance of one or more previously observed neurological abnormalities.

SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS. In various embodiments, the present methods are used to treat RRMS so it does not develop into SPMS.

PPMS is characterized by a steady progression of increasing neurological deficits without distinct attacks or remissions. Cerebral lesions, diffuse spinal cord damage and evidence of axonal loss are evident on the MRI of patients with PPMS. PPMS has periods of acute exacerbations while proceeding along a course of increasing neurological deficits without remissions. Lesions are evident on MRI of patients suffering from PRMS. In various embodiments, the present methods are used to treat RRMS and/or SPMS so it does not develop into PPMS.

In some embodiments, the present methods are used to treat relapsing forms of MS. In some embodiments, the present methods are used to treat relapsing forms of MS to slow the accumulation of physical disability and/or reduce the frequency of clinical exacerbations, and, optionally, for patients who have experienced a first clinical episode and have MRI features consistent with MS. In some embodiments, the present methods are used to treat worsening relapsing-remitting MS, progressive-relapsing MS or secondary-progressive MS to reduce neurologic disability and/or the frequency of clinical exacerbations. In some embodiments, the present methods can effectively reduce the frequency and/or severity of relapses.

EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Selection of AGS Enriched rhAbs and their Binding to Brain Tissues

Materials and Methods

Patient Sample Acquisition and Processing. CSF was obtained by lumbar puncture from patients recruited into the study in accordance with The University of Texas Southwestern Medical Center (UTSWMC) Institutional Review Board (IRB). This study includes patient samples as previously published by the inventor's group (Cameron et al., 2009 and Ligocki et al., 2013) containing patients with clinically definite multiple sclerosis (CDMS), clinically isolated syndrome optic neuritis ($ON_{CIS}$), and clinically isolated syndrome transverse myelitis ($TM_{CIS}$). The samples were stained with fluorescently labeled antibodies and sorted for single CD19+ B cells through a $CD45^+$ lymphocyte gate as previously described into 96-well plates using either the BD FACSAria flowcytometer (Becton Dickinson, San Jose, CA) or the MoFlo High-Performance Cell Sorter (Cytomation, Ft Collins, CO) (Ligocki et al., 2013).

Single-cell PCR and genetic analysis of VH and Vic genes. After the single cell sort and cell lysis, either gDNA was amplified for the CDMS patient samples or cDNA was generated for the $ON_{CIS}$ and $TM_{CIS}$ patient samples as previously described (Ligocki et al., 2013). Multi-plexed nested PCR was performed to amplify and the Immunoglobulin (Ig) heavy chain and corresponding Ig kappa light chain from each individually sorted CSF B cell. The products were purified, sequenced, catalogued, and analyzed for gene and mutation characteristics (Ligocki et al., 2013).

Germline rearrangements were identified using the IMGT/V-QUEST Ig blasting tool (world-wide-web at imgt.org/IMGT_vquest/share/textes/). Antibody variable heavy ($V_H$) and variable kappa (Vi) sequences were analyzed and compiled using a Perl program developed at UTSWMC (Ligocki et al., 2010 and Ligocki et al., 2013) using IMGT/V-QUEST as the initial source for sequence alignment.

Cloning of full-length recombinant human IgG antibodies (rhAbs). Sequences from CDMS, $ON_{CIS}$, and $TM_{CIS}$ patients were chosen as candidates for cloning into full-length expression vectors based on their VH genetics. The criteria was: expressing a VH4 gene and have 2 or more of the 6 AGS codons mutated (Cameron et al., 2009; Ligocki et al., 2010). 60% were also clonally expanded by identifying another VH sequence within the same patient with identical amino acids in the CDR3 region. The corresponding Vκ sequence was amplified from the same well as the VH sequence to identify the antibody binding region of the single CSF B cell. Sequence and patient details for each selection are shown in Table 5 and Table 6. Additional rounds of PCR were done to add restriction enzyme sites to both the 5' and 3' ends of the original PCR products to allow for insertion into the expression vectors using modifications of previously published primers (Yurasov et al., 2005). Some heavy and light chain rearrangement sequences were purchased from Integrated DNA Technologies (IDT, IA, USA) for extraction into the expression vectors. Dr. Michel Nussenzweig provided the backbone expression vectors for both chains. These vectors and the procedure have been extensively described for the production of monoclonal human IgG1 (Tiller et al., 2008). Briefly, AgeI was used as the 5' restriction enzyme site for both the VH and Vic inserts and plasmid backbone and SalI and BsiWI were used as the 3' restriction enzyme site for the VH and VL respectively (NEB, MA. USA). After digestion, ligation of both the insert and the corresponding expression vector backbone was performed using T4 ligase (NEB). DH5a cells were transformed with a plasmid and individual colonies from the plate were grown for miniprep (Qiagen, CA, USA). The vectors were sequenced in order to confirm that the insert matched the original patient heavy and light chain rearrangements captured by PCR and that the coding region remained in frame. Midiprep DNA (Qiagen) was used for transformation and production of rhAbs in culture. Sequences were validated after each growth.

Two control rhAbs were provided that were cloned from systemic lupus erythematosus (SLE) patient derived B cells. B1 has been shown to not bind to mouse brain and G11 has been shown to bind to NMDARs in the mouse brain as well as dsDNA (Zhang et al., 2009). These two antibodies have been studied and published and were used as controls for the full-length IgG1 rhAb construct in all the experiments presented in this current study.

Production of monoclonal rhAbs. Human embryonic kidney fibroblast (HEK) 293T cells were grown to 50-80% confluency in a 10 cm dish in DMEM media supplemented with FCS (Gibco, Life Technologies). The cotransfection of paired cloning vectors corresponding to the IgK and the IgH of a rhAb were mixed (12.5 μg total DNA) with JetPEI solution (Polyplus transfection) and added dropwise to the cells. The plates were incubated in a 5% $CO_2$ water-jacketed incubator (Nuaire, MN, USA) at 37° C. in 20 ml DMEM media supplemented with ultra-low IgG FCS media (Gibco). Supernatant was harvested and fresh media added on days 3, 5, 7, and 10. ELISAs were used to determine the yield and the concentration of the rhAbs produced in culture. Goat anti-human IgG Fc antibody (Santa Cruz. TX, USA) was used as the coating antibody and serially diluted samples were incubated for 2 hrs at room temperature. Plates were probed with goat anti-human IgG Fc HRP-conjugated antibody (Santa Cruz) for 1 hr and developed using tetramethylbenzidine (TMB) substrate solution (Ebioscience, CA, USA) and stopped with 1 M HCl. The plates were read at 450 nm using the Epoch Nano (Biotek, VT, USA). Standard curves and rhAb concentrations were interpolated using GraphPad Prism 6 (CA, USA). Supernatants were concentrated using the 10 kDa MWCO Amcion Ultra centrifugal filter units (Millipore, MA, USA) following manufacturer's recommendations. A second ELISA was performed on the concentrated stocks of rhAbs and then aliquoted and stored at −80° C. Additionally, a non-transfected cell culture supernatant was confirmed to not contain any IgG above ELISA detection. These concentrated rhAbs were used as primary antibodies for all mouse brain immunohistochemistry.

Biotinylation of monoclonal rhAbs. A set of ten AGS rhAbs and 2 control rhAbs were purified by passing supernatant through a column with a bed of protein G sepharose beads followed by dialysis in PBS and DPBS (Life Technologies). Purity and yield were determined by SDS-page gel stained with coomasie blue and ELISA as described above. Each rhAb was biotinylated using 100 μg of column-purified product and following manufacturer's instructions for the Thermo Scientific EZ-Link Micro NHS-PEG4-Biotinylation kit (Thermo Scientific, MA, USA). These biotinylated rhAbs were used as primary antibodies for all human brain immunohistochemistry.

Processing of frozen brain tissue. Mice were sacrificed 2-3 days post stroke induction as previously described (Stowe et al., 2011) and perfused with 4% paraformaldehyde. The brains were extracted and preserved in 4% paraformaldehyde for 48 hrs at 4° C. followed by cryoprotection in sequential 15% and 30% sucrose solutions. Post-mortem human brain samples were provided by the Human Brain and Spinal Fluid Resource Center (UCLA, Los Angeles, CA). Three samples were used for the studies: white matter (WM) from a healthy control without neurological complications (HC), white matter plaque from a patient with clinically definite MS (MS-P), normal appearing WM from the same MS patient (MS-WM), and normal appearing gray matter (MS-GM). Mean time to sampling from time of death was 16 hrs. Upon removing from −80° C., they were preserved similarly to mouse brains with 4% paraformaldehyde for 48 hrs at 4° C. followed by cryoprotection in sequential 15% and 30% sucrose solutions. All tissues were embedded in O.C.T freezing compound and stored at −20° C. until cryosectioned. Tissue sections (12-16 μm) were cut and attached to charged glass slides using a cryostat (Thermo Scientific MICROM) and frozen at −20° C. Tissues were stained with cresyl violet to validate the integrity of the preservation of the tissue.

Diaminobenzidine (DAB)-immunohistochemistry (IHC) staining of mouse tissue. Tissue sections were subjected to antigen retrieval for 2 min using low pH Antigen Unmasking Solution (Vector Laboratories, Burlingame, CA, USA). Endogenous biotin was blocked using 3% $H_2O_2$ solution for 5 min at room temperature and then washed. The sections were blocked with 3% normal goat serum in PBS for 10 min at room temperature, washed with PBS, and then were incubated overnight at 4° C. with 1 μg rhAb (10 ng/μl) per brain slice. The next day, sections were washed and DAB staining was conducted following the manufacturer's instructions using a biotinylated secondary goat anti-human IgG Fc antibody (Vector Laboratories, Burlingame, CA, USA). The slides were dehydrated and cleared with sequential washes in increasing percentages of EtOH, from 70% to 100%, with two final washes in xylenes. Slides were mounted with a permount:xylene solution and imaged using a 40× brightfield lens on the NanoZoomer (Hammatsu, Japan). Images were visualized using NDP.view software (Hammatsu, Japan) and 20× images were exported for visualization and adjustments to brightness and contrast were done with ImageJ software (NIH, USA).

DAB-IHC staining of human tissue. Initial processing of the human brain tissue sections remained the same as the mouse tissue. After blocking with 3% normal goat serum in PBS for 10 min at room temperature, an additional blocking step was performed with BloxAll for 10 min at room temperature (Vector Laboratories, Burlingame, CA, USA). Tissues were incubated overnight at 4° C. with 1 μg biotinylated-rhAb (10 ng/μl) per brain slice. The next day, these biotinylated-rhAbs were detected without a secondary antibody and instead with ABC reagent alone (Vector Laboratories, Burlingame, CA, USA). Dehydration, clearing, mounting, and visualization of the human tissue followed the same procedure as the mouse tissue.

Immunofluorescence (IFC) staining of mouse tissue. Ten AGS rhAbs and 2 control rhAbs from the DAB panel were selected for further experiments using IFC (Table 5). Tissue sections were subjected to antigen retrieval for 2 min using low pH Antigen Unmasking Solution (Vector Laboratories, Burlingame, CA, USA). The sections were blocked with 1% normal goat serum and 1% Tween-20 in PBS for 1 hr at room temperature. Due to the presence of IgG deposits even in healthy brain and as an artifact of post-mortem tissue preparation, the set of 10 rhAbs and the 2 control rhAbs used in the mouse brain IFC were biotinylated to eliminate the need for a species specific secondary antibody. Most of the rhAbs were diluted in blocking solution. Pierce Immunostain Enhancer (Thermo Scientific) was used as the diluent for the primary rhAb incubation as well as the secondary Alexa Fluor488 for the following two rhAbs: AJL03, AJL15. Slides were washed with PBS, and then incubated overnight at 4° C. with 1 μg rhAb (10 ng/μl) per brain slice. Next day, the sections were washed and incubated for 1 hr at room temperature with the secondary antibody Alexa Fluor 488 goat anti-human IgG Fc (Life Technologies). Then a colocalization marker, either GFAP (Abcam) or NeuN (Chemicon) were used at 1:1000 and 1:100 dilutions respectively, was incubated for 1 hr at room temperature and then incubated for an additional hour with the appropriate secondary antibody Alexa Fluor 594 anti-rabbit IgG Fc for GFAP or Alexa Fluor 594 anti-mouse IgG Fc for NeuN detection (Life Technologies). Next, the stained tissue sections were incubated for three minutes with DAPI (1:1000) as a counterstain for nuclei (Life Technologies). The sections were washed and wet mounted with Fluoro-Gel (Electron Microscopy Diatome). Slides were viewed with a fluorescent Leica TCS SP5 confocal microscope (Leica microsystems) and viewed and adjusted in brightness and contrast using ImageJ software (NIH, USA).

IFC staining of human tissue. Initial processing of the human brain tissue sections remained the same as the mouse tissue above. After the initial blocking, endogenous biotin was blocked per manufacturer's instructions using the streptavidin-biotin blocking kit (Vector Laboratories, Burlingame, CA, USA). Pierce Immunostain Enhancer (Thermo Scientific) was used as the diluent for the primary rhAb incubation as well as the secondary Alexa Fluor 488 for all human tissue IFC. Slides were washed with PBS, and then incubated overnight at 4° C. with 2 μg rhAb (20 ng/μl) per brain slice. Next day, the sections were washed, and incubated for 1.5 hrs at room temperature with the secondary antibody Alexa Fluor 488 goat anti-streptavidin (Life Technologies). The colocalization with either GFAP or NeuN, DAPI counterstain, mounting and visualization followed the same procedure as the mouse brain tissue.

Results

Selection of AGS enriched rhAb. The inventor has previously shown that CIS patients at risk to convert and those with CDMS harbor B cells in the CSF with a unique mutational pattern in their VH4 repertoires termed the Antibody Gene Signature (AGS) (Cameron et al., 2009 and Ligocki et al., 2010). A shared pattern of increased replacement mutations at 6 specific codons within VH4 genes suggests selection and recognition of a shared set of antigens. Therefore, she sought to determine the biological significance of this mutational pattern by testing the binding ability of AGS-enriched antibodies to brain tissue. Using single cell sorting of CSF derived B cells from CDMS, $ON_{CIS}$, and $TM_{CIS}$ patients, the inventor was able to determine the exact antibody-binding variable regions from PCR amplified VHJH and VκJκ sequences. Using a full-length recombinant human IgG1 antibody expression vector system, variable regions were cloned and expressed for further study. Only those B cells expressing a VH4 family gene with mutations in 2 or more of the 6 AGS codons were considered for this analysis.

A total of 32 rhAbs were chosen for expression. The details of 10 rhAbs are shown in Table 5 and the remaining 22 in Table 6. Briefly, all rhAbs contained mutations at 2 or more of the 6 AGS codons, and the majority (66%) contained 3 or more AGS mutations. Additionally, 60% were also clonally expanded, suggesting an antigen driven process. These rhAbs were cloned from 10 CSF patient repertoires: 9 rhAbs from 4 CDMS patients, 14 rhAbs from 3 $ON_{CIS}$ patients, and 9 rhAbs from 3 $TM_{CIS}$ patients. Two control rhAbs cloned from SLE patient B cells were provided by Dr. Betty Diamond as controls for the human IgG construct. The expected binding of this control set has been extensively published using mouse tissue. B1, the negative control, does not react to brain, whereas G11, the positive control, reacts to NMDARs in the brain as well as dsDNA (Zhang et al., 2009).

TABLE 5

Patient, Gene and Staining Overview of the 10 rhAbs used for DAB and IFC

| Patient # | Diagnosis | rhAb | $V_H$;$J_H$[1] | $V_K$; $J_K$[2] | Clone | # AGS[3] | $V_HJ_H$ SHM[4] | Mouse Liver[5] | Mouse Stroke/ EAE Brain[6] | Human Fixed/ Unfixed Brain[7] | NeuN[8] | GFAP[9] |
|---|---|---|---|---|---|---|---|---|---|---|---|---|
| 1 | CDMS | AJL02 | 4-31; 4 | 1-39; 2 | No | 2 | 8.96% | − | +/+ | +/+ | + | + |
| | | AJL03 | 4-39; 1 | 1-33; 2 | No | 2 | 7.96% | − | +/+ | +/+ | + | − |
| 2 | $ON_{CIS}$ | AJL10 | 4-4; 6 | 2-28; 5 | No | 4 | 12.63% | + | +/+ | +/+ | + | − |
| | | WR12 | 4-30; 4 | 2-28; 4 | Yes | 2 | 12.44% | − | +/+ | +/+ | − | + |
| | | WR13 | 4-30; 4 | 2-28; 2 | Yes | 2 | 11.94% | − | +/+ | +/+ | − | + |
| 3 | $ON_{CIS}$ | AJL07 | 4-59; 4 | 1-13,2 | Yes | 3 | 9.23% | − | +/+ | +/+ | + | + |
| 4 | $TM_{CIS}$ | AJL01 | 4-34; 3 | 3-20; 5 | Yes | 3 | 11.28% | − | +/+ | +/+ | − | + |
| | | WR10 | 4-4; 6 | 3-20; 5 | Yes | 2 | 4.55% | − | +/+ | +/+ | + | + |
| 5 | $TM_{CIS}$ | AJL15 | 4-39; 5 | 2-29; 2 | Yes | 4 | 7.46% | − | +/+ | +/+ | + | − |
| 6 | $TM_{CIS}$ | AJL19 | 4-34; 3 | 3-20; 2 | Yes | 3 | 8.21% | − | +/+ | +/+ | + | + |

Abbreviations:
CDMS: clinically definite multiple sclerosis,
$ON_{CIS}$: clinically isolated syndrome- optic neuritis,
$TM_{CIS}$: clinically isolated syndrome- transverse myelitis,
rhAb: recombinant human antibody,
VH: variable heavy chain,
JH: variable heavy chain J segment,
Vk: variable kappa chain,
JK: variable kappa chain J segment,
AGS: antibody gene signature,
$V_HJ_H$ MF: variable heavy chain rearrangement mutation frequency,
EAE: experimental autoimmune encephalomyelitis,
NeuN: neuronal nuclei,
GFAP: glial fibrillary acid protein
[1]Variable heavy and J segment usage by the rhAb.
[2]Variable kappa and J segment usage by the rhAb.
[3]Number of mutated AGS codons (6 total possible) in the $V_H4$ gene of the rhAb.
[4]Somatic hypermutation frequency for the heavy chain rearrangement of the rhAb.
[5]Positive (+) or negative (−) staining as determined by DAB staining on mouse liver tissue.
[6]Positive (+) or negative (−) staining as determined by DAB staining on mouse post-stroke brain or EAE tissue.
[7]Positive (+) or negative (−) staining as determined by DAB staining on human brain fixed with 4% paraformaldehyde or unfixed frozen brain. Positive (+) or negative (−) colocalization as determined by the mouse brain tissue IFC experiments.

TABLE 6

Patient, gene, and staining overview of the 22 rhAbs used only for mouse brain tissue DAB.[1]

| Patient # | Diagnosis | rhAb | Clone | # AGS[2] |
|---|---|---|---|---|
| 2 | $ON_{CIS}$ | AJL11 | no | 3 |
| 3 | $ON_{CIS}$ | AJL06 | no | 3 |
| | | AJL08 | yes | 3 |
| | | AJL09 | yes | 2 |
| | | AJL13 | yes | 3 |
| 4 | $TM_{CIS}$ | WR11 | yes | 2 |
| 5 | $TM_{CIS}$ | AJL14 | no | 3 |
| | | AJL16 | yes | 3 |
| 6 | $TM_{CIS}$ | AJL18 | yes | 5 |
| | | AJL20 | no | 3 |
| 7 | CDMS | WR01 | yes | 2 |
| | | WR02 | yes | 2 |
| 8 | CDMS | WR03 | no | 3 |
| | | WR04 | no | 3 |
| | | WR05 | no | 4 |
| | | WR06 | no | 3 |
| 9 | CDMS | WR07 | no | 4 |
| 10 | $ON_{CIS}$ | AJL04 | yes | 3 |
| | | AJL05 | yes | 4 |

TABLE 6-continued

| Patient, gene, and staining overview of the 22 rhAbs used only for mouse brain tissue DAB.[1] | | | | |
|---|---|---|---|---|
| Patient # | Diagnosis | rhAb | Clone | # AGS[2] |
| | | AJL12 | no | 3 |
| | | WR08 | yes | 2 |
| | | WR09 | yes | 2 |

Abbreviations:
CDMS: clinically definite multiple sclerosis,
$ON_{CIS}$: clinically isolated syndrome- optic neuritis,
$TM_{CIS}$: clinically isolated syndrome- transverse myelitis,
rhAb: recombinant human antibody,
AGS: antibody gene signature
[1]See DAB images of tire rhAbs listed here
[2]Number of mutated AGS codons (6 total possible) in the Vh4 gene of the rhAb.

AGS-enriched rhAbs bind to mouse brain tissue. The panel of 32 experimental AGS-enriched and clonally expanded rhAbs as well as the 2 control rhAbs was first tested for targeting to mouse brain tissue using DAB. This methodology offers sensitive detection of primary rhAb binding to the tissue. Due to previous work from other laboratories demonstrating a lack of binding of antibodies cloned from CDMS CSF B cells to normal brain tissue or WM (Owens et al., 2009 and von Budingen et al., 2008), the inventor chose to utilize brain tissue from a mouse model of transient stroke as a source of inflammation (Stowe et al., 2011). This provided generalized non-antigen directed inflammation to minimize bias of any specific CNS antigen. The secondary antibody used for detection, goat anti-human IgG, did not react to mouse brain alone (FIG. 1A). As expected, the negative construct control rhAb B1 also did not react to mouse brain, while the positive control rhAb G11 showed recognition to brain and thus validated the assay (FIG. 1A).

The full panel of 32 rhAbs was tested on mouse brain by DAB. There was a wide range of staining intensity. However, all but two of the 32 rhAbs, WR01 and WR11, displayed binding to brain tissue (FIGS. 1A-1D and FIGS. 6A-6C). There was no difference of rhAb staining patterns amongst the three patient groups used to derive the rhAbs. A common feature was that the binding appears cellular in the cortex and midbrain and was either absent or sparse along the heavily myelinated corpus callosum.

Figure 2A:
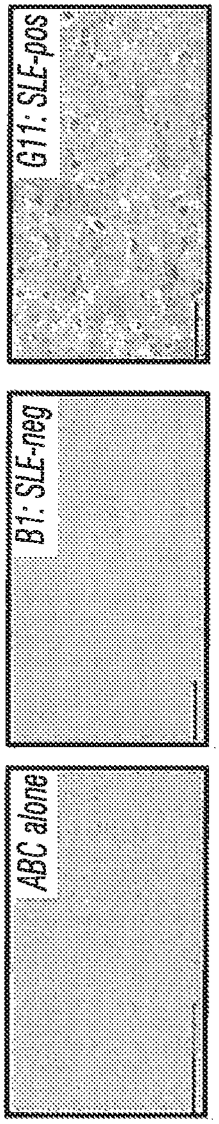
FIGS. 2A-2D show that AGS-enriched rhAbs bind to human multiple sclerosis gray matter (GM) brain tissue. DAB images are shown at 20× magnification of MS-GM. The rhAbs in each row are grouped as follows: controls (FIG. 2A), CDMS (FIG. 2B), $ON_{CIS}$ (FIG. 2C), and $TM_{CIS}$ (FIG. 2D). The rhAb designation, patient type, and patient number are shown in the upper right corner of each panel. Data are representative of three MS-GM sections per rhAb. Scale bar represents 100 μm.
Figure 2B:
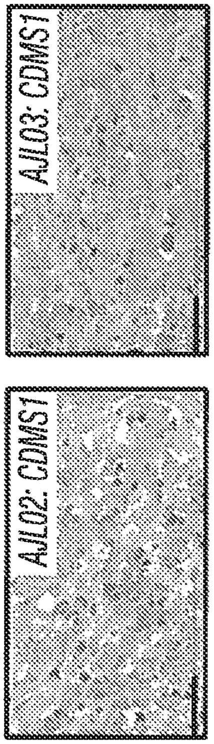
Figure 2C:
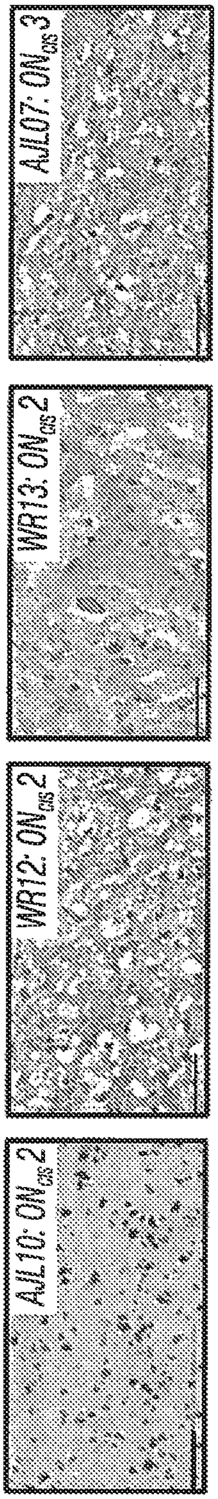
Figure 2D:
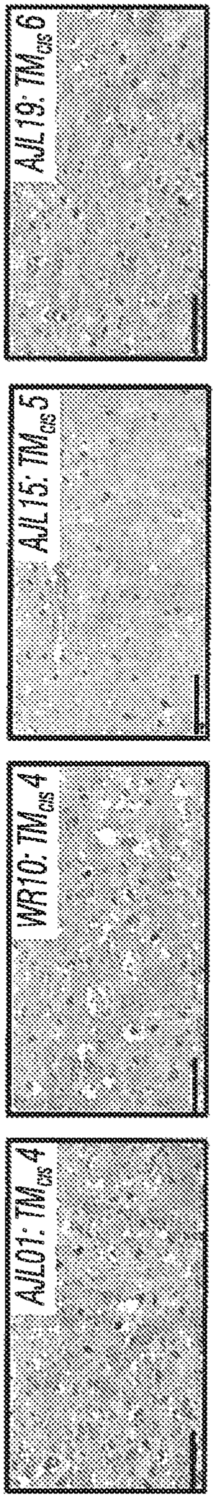

AGS-enriched rhAbs bind to human brain tissue. Four sources of human brain were used for the DAB staining experiments: MS normal appearing gray matter (MS-GM) (FIGS. 2A-2D), MS normal appearing white matter (MS-WM) (FIGS. 7A-7D), MS white matter plaque (MS-P) (FIGS. 8A-8D), and healthy control normal appearing (NA) WM (HC-WM) (FIGS. 9A-9D). Due to the rhAb staining pattern found in the mouse brain, the tissue source of most interest was the MS-GM. The two negative controls, ABC reagent alone and rhAb B1, did not bind to MS-GM whereas the positive control rhAb G11 bound MS-GM (FIG. 2A). The ten AGS-enriched rhAbs from 3 different disease types representing 6 different patients all showed binding to human MS-GM (FIGS. 2B-2D). As with the mouse brain DAB (FIGS. 1A-1D), the staining appeared to be cellular and exhibited similar staining patterns in the human brain DAB (FIGS. 2A-2D).

In contrast, the rhAbs demonstrated poor recognition to MS-WM (FIGS. 7A-7D). Plaque tissue from the MS patient showed evidence of damage, and the binding was diminished or absent in MS-P tissue (FIGS. 8A-8D). The rhAbs also had weak or no binding to HC-WM (FIGS. 9A-9D). A common feature shared by the rhAbs was that testing on all sources of WM tissue resulted in weaker staining patterns than was seen in GM tissue.

Figures 17A, 17B, 17C:
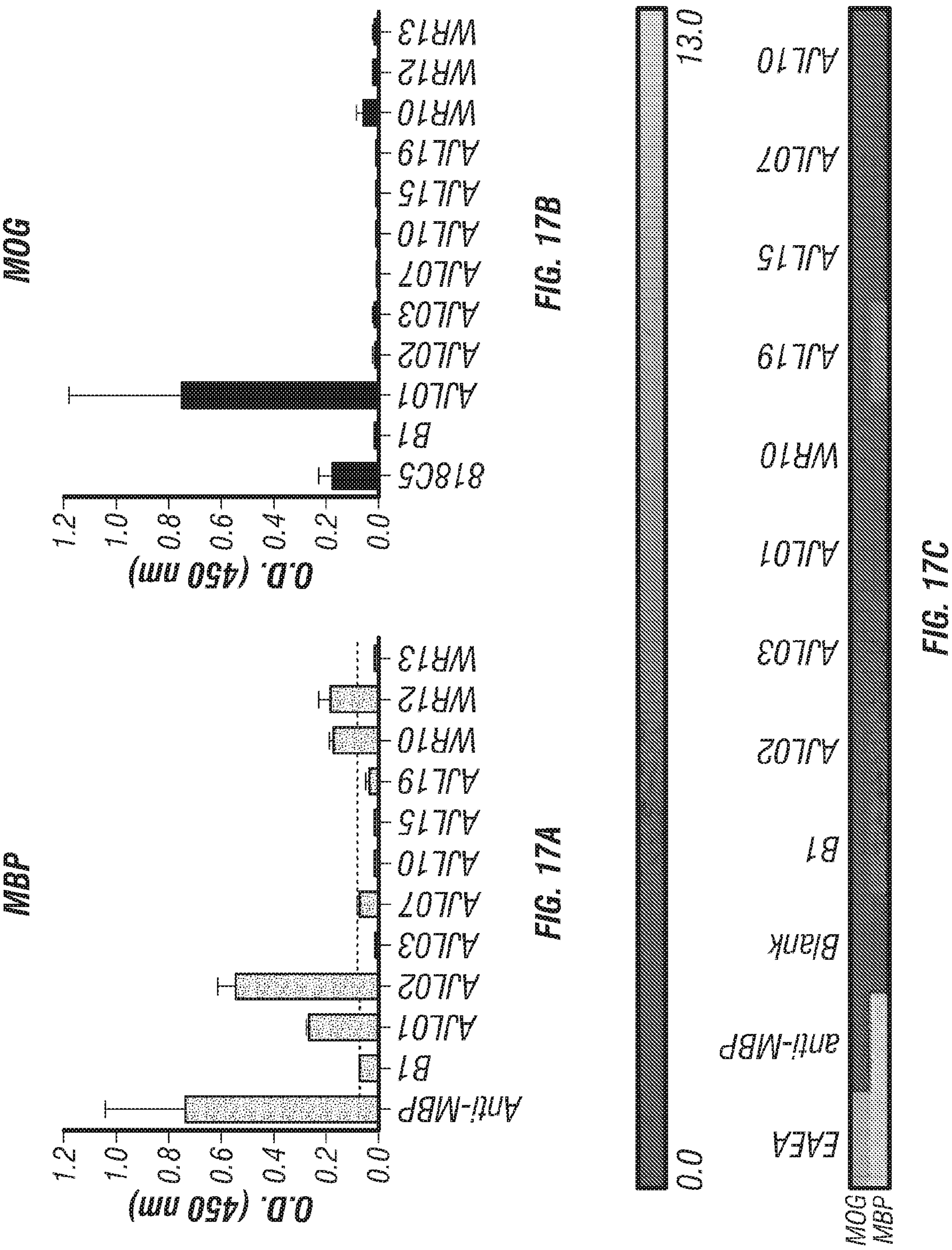
FIGS. 17A-17D show that AGS-enriched rhAbs do not bind strongly to myelin components.
Figure 17D:
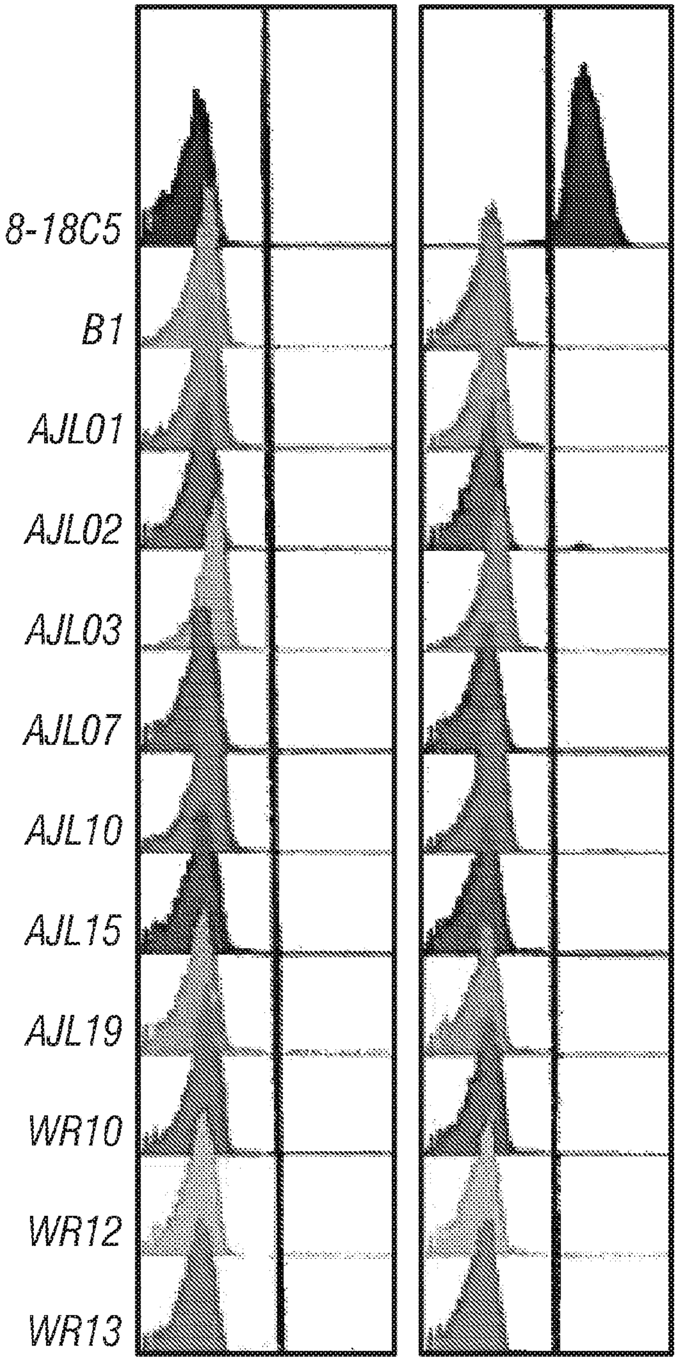
Figures 18A, 18B, 18C, 18D, 18E, 18F:
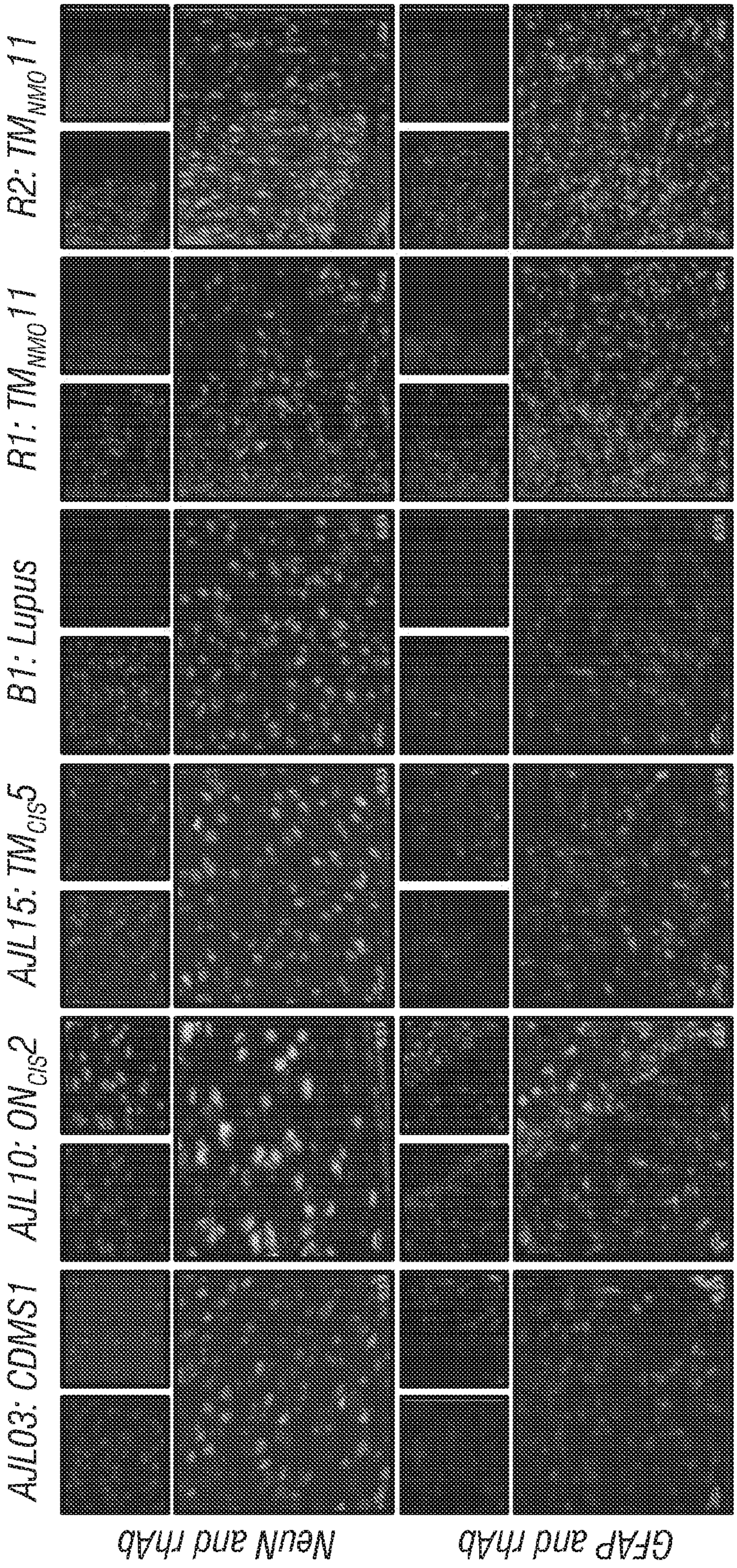
FIGS. 18A-18M show AGS-enriched rhAbs demonstrate reactivity to neurons and astrocytes.
Figures 18G, 18H, 18I:
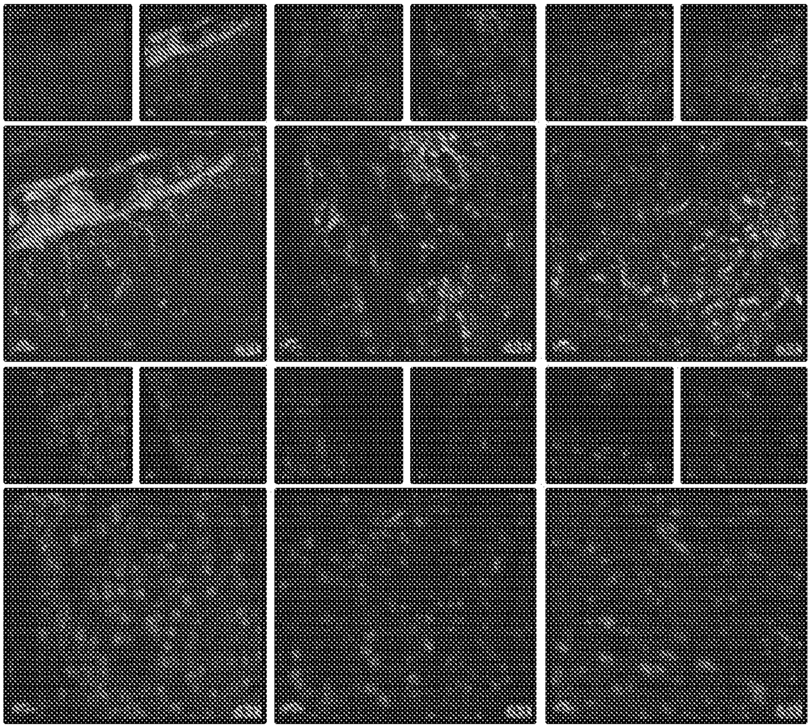
Figures 18J, 18K, 18L, 18M:
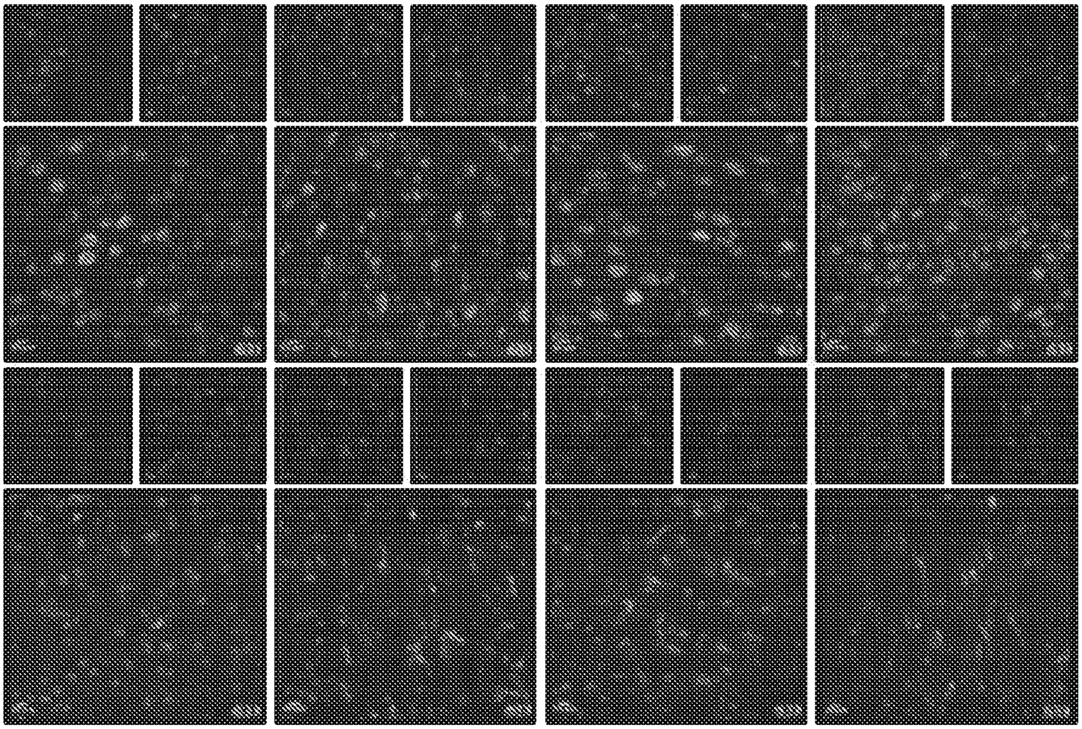

To confirm the paucity of rhAb reactivity to myelinated tracts, the inventor evaluated binding of the subset of rhAbs to myelin basic protein (MBP) and myelin oligodendrocyte glycoprotein (MOG), two myelin components of considerable interest in MS.21 With the exception of AJL01, which was reactive to both MBP and MOG, all of the rhAbs tested negative to binding MBP and MOG by ELISA (FIGS. 17A-17B). In addition, none of the subset rhAbs reacted to MBP or MOG in a myelin array that has been previously described (FIG. 17C). Finally, none of these rhAbs reacted to MOG expressed on the cell surface of HeLa cells as assessed by flow cytometry (FIG. 17D).

Figure 3A:
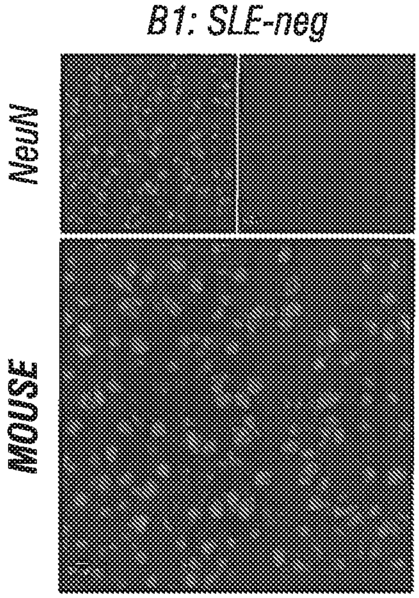
FIGS. 3A-3H show that IFC of AGS-enriched rhAbs target neuronal nuclei in both mouse and human-GM brain tissue: AJL03, AJL10, and AJL15. Confocal images are shown at 63× magnification with the colocalization marker for NeuN (for neuronal nuclei) shown as red (Alexa Fluor 594). The primary rhAb is shown as green (Alexa Fluor 488) and nuclei are counterstained blue (DAPI). The images are shown as independent red and green channels above the overlay including DAPI. B1 (−SLE) and G11 (+SLE) negative and positive controls respectively on mouse brain tissue are shown in FIGS. 3A and 3B. Mouse and human GM brain tissue IFC are shown for each rhAb labeled above the column: AJL03 (CDMS1) (FIGS. 3C, 3D), AJL10 ($ON_{CIS}2$) (FIGS. 3E, 3F), and AJL15 ($TM_{CIS}5$) (FIGS. 3G, 3H). Data are representative of six coronal sections per rhAb on mouse tissue and three sections per rhAb on GM tissue. Scale bar represents 10 μm.
Figure 3B:
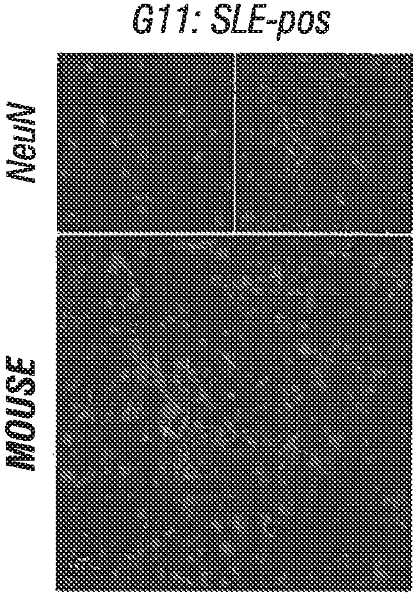
Figure 10A:
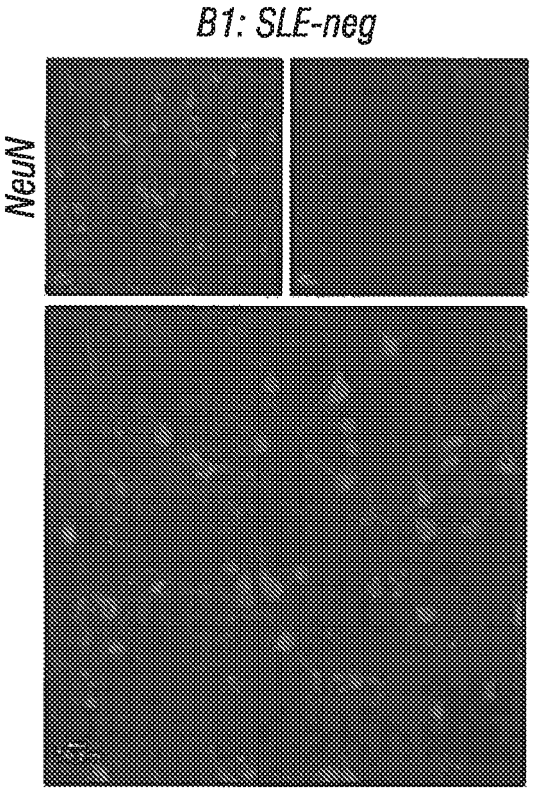
FIGS. 10A-10B show IFC of control rhAbs on human MS-GM brain: B1 (FIG. 10A) and G11 (FIG. 10B). Confocal images are shown at 63× magnification with the colocalization marker for NeuN (for neuronal nuclei) shown as red (Alexa Fluor 594), the primary rhAb as green (Alexa Fluor 488), and nuclei counterstained blue (DAPI). The images are shown as independent red and green channels above the overlay including DAPI with the rhAb label above each panel. Data are representative of three MS-GM sections per rhAb. Scale bar represents 10 μm.
Figure 10B:
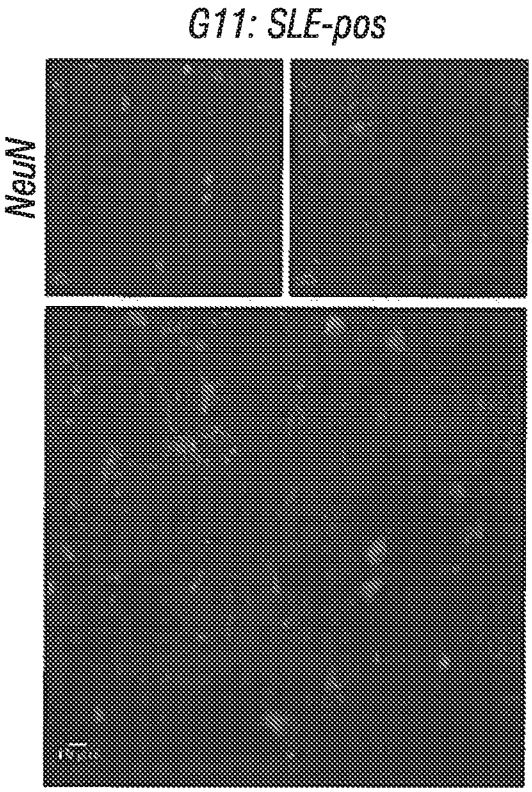

AGS-enriched rhAbs target neurons and astrocytes in both mouse and human brain tissue. Due to the location and appearance of the DAB staining, the inventor hypothesized that the rhAbs were binding to either of two major cell types in the brain, neurons and/or astrocytes. Therefore, IFC colocalization experiments were performed on 10 of the rhAbs from the initial cohort of 32. These 10 were chosen to sample all three disease subtypes and the same source of mouse brain tissue was utilized in these experiments. B1 and G11 were again used as negative and positive controls for the assay respectively. B1 did not recognize brain tissue (FIGS. 2A, 3A), but G11 did recognize mouse brain tissue (FIGS. 2B, 3B) as evidenced in both the NeuN and the GFAP colocalization experiments. Similar staining pattern of both B1 and G11 was confirmed in human MS-GM (FIGS. 10A, 10B).

Figure 3C:
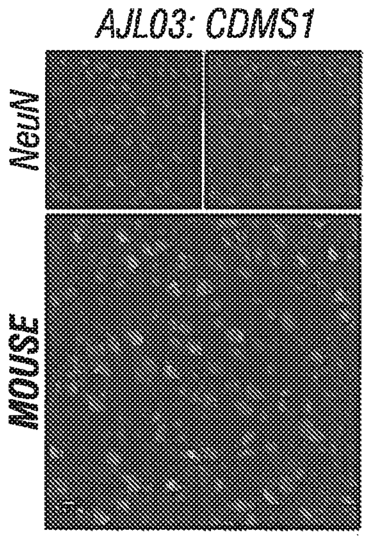
Figure 3E:
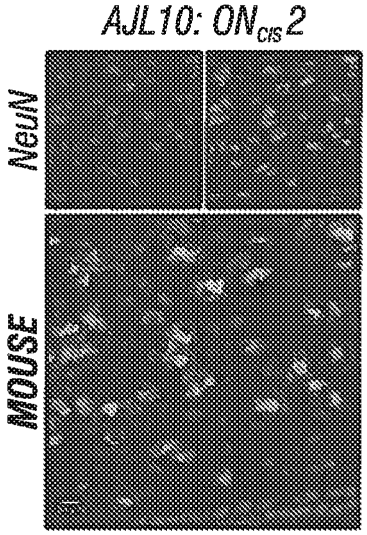
Figure 3G:
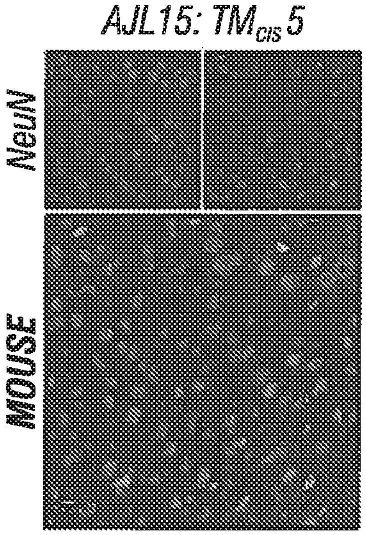
Figure 3D:
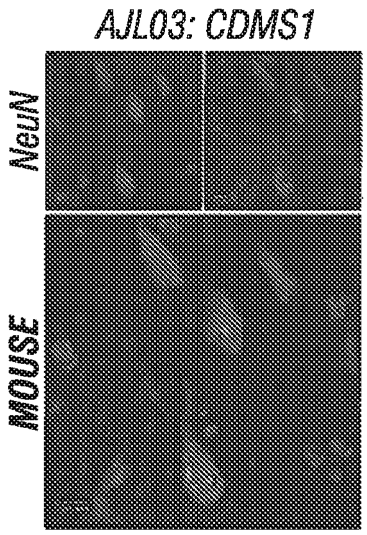
Figure 3F:
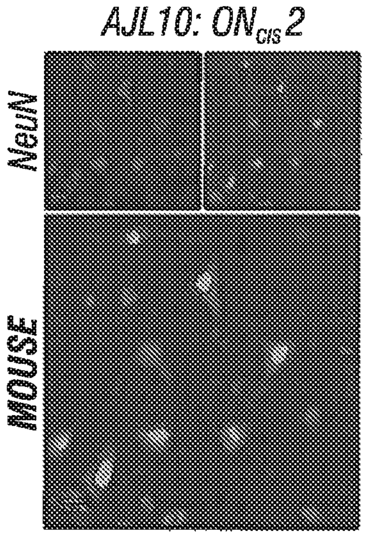
Figure 3H:
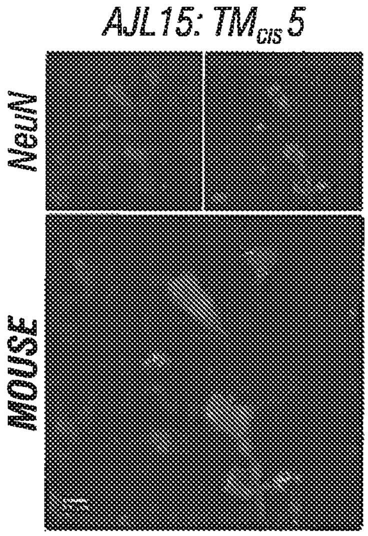

Three rhAbs, one from each patient type, colocalized with neuronal nuclei identified by NeuN in both mouse and human brain. AJL03 from patient CDMS1 showed similar staining of neuronal nuclei in both species tissue type (FIGS. 3C, 3D). AJL10, from patient $ON_{CIS}2$, showed colocalization with neuronal nuclei with the human targeting being very concentrated in the nucleus compared to a more diffuse staining pattern in mouse (FIGS. 3E, 3F). Additionally, there were areas of AJL10 binding that were independent of NeuN but were still associated with nuclei as marked by DAPI (FIG. 3E). AJL15 from patient $TM_{CIS}5$ also colocalized with neuronal nuclei in both mouse and human tissue (FIGS. 3G, 3H). AGS-enriched B cells that recognize neuronal nuclei in the GM are found in all disease presentations and have conserved recognition between mouse and human species.

Figure 4A:
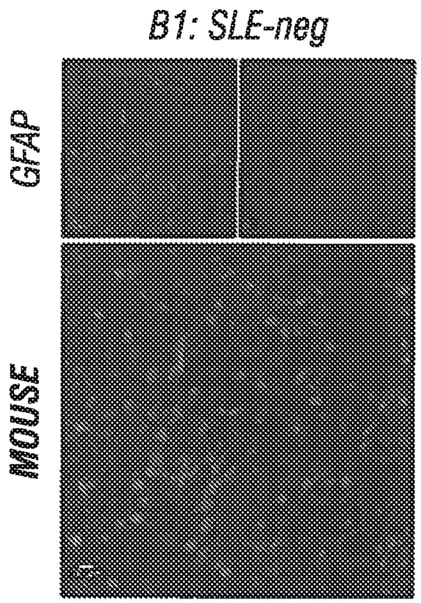
FIGS. 4A-4H show that IFC of AGS-enriched rhAbs target astrocytes in both mouse and human GM brain tissue: WR12, WR13, and AJL01. Confocal images are shown at 63× magnification with the colocalization marker for GFAP (for astrocytes) shown as red (Alexa Fluor 594). The primary rhAb is shown as green (Alexa Fluor 488) and nuclei are counterstained blue (DAPI). The images are shown as independent red and green channels above the overlay including DAPI. B1 (−SLE) and G11 (+SLE) negative and positive controls respectively on mouse brain tissue are shown in FIGS. 4A and 4B. Mouse and human GM brain tissue IFC are shown for each rhAb labeled above the column: WR12 ($ON_{CIS}2$) (FIGS. 4C, 4D), WR13 ($ON_{CIS}2$) (FIGS. 4E, 4F), and AJL01 ($TM_{CIS}4$) (FIGS. 4G, 4H). Data are representative of six coronal sections per rhAb on mouse tissue and three sections per rhAb on MS-GM tissue. Scale bar represents 10 μm.
Figure 4B:
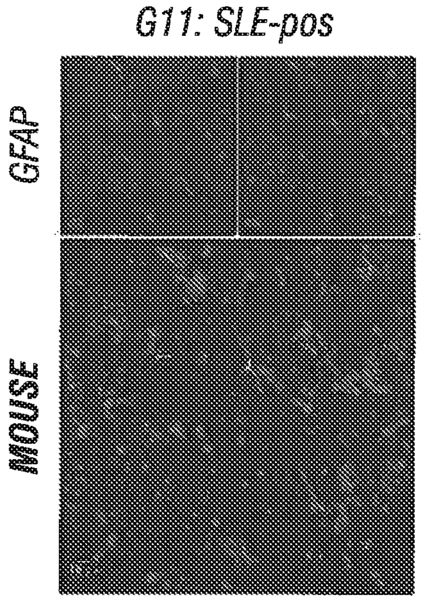
Figure 4C:
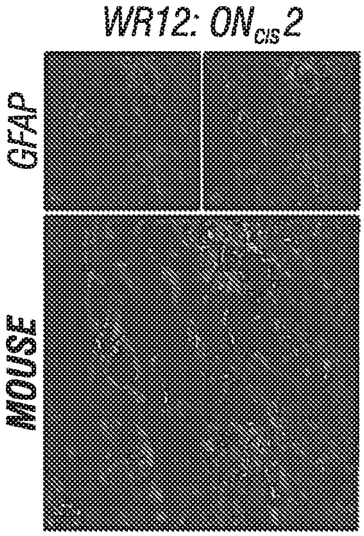
Figure 4E:
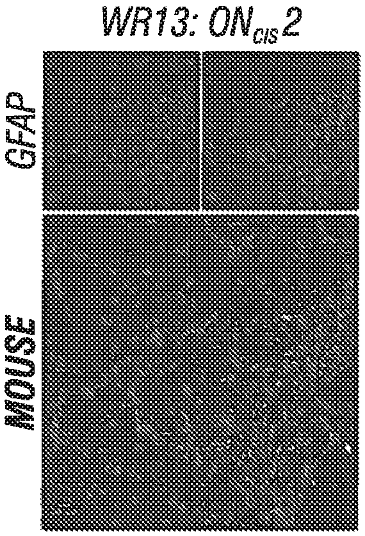
Figure 4G:
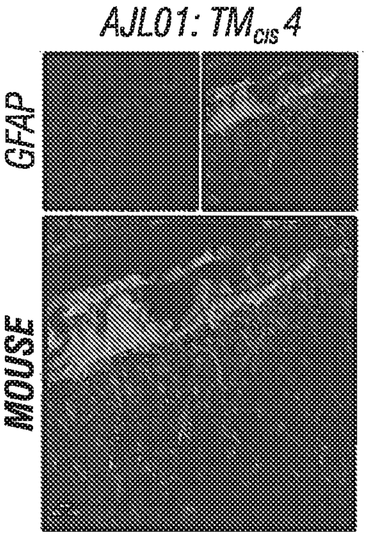
Figure 4D:
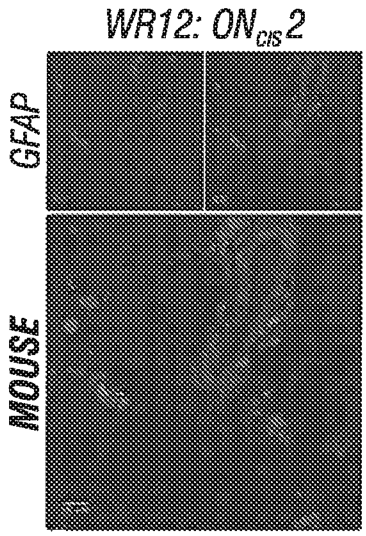
Figure 4F:
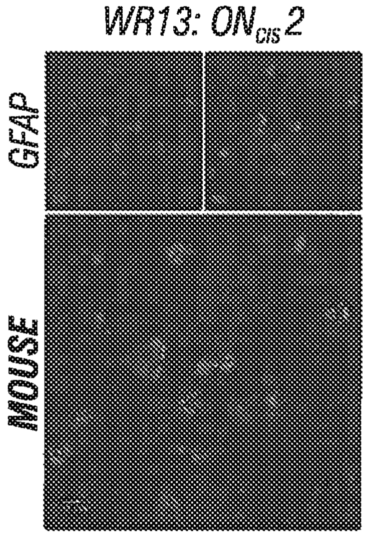
Figure 4H:
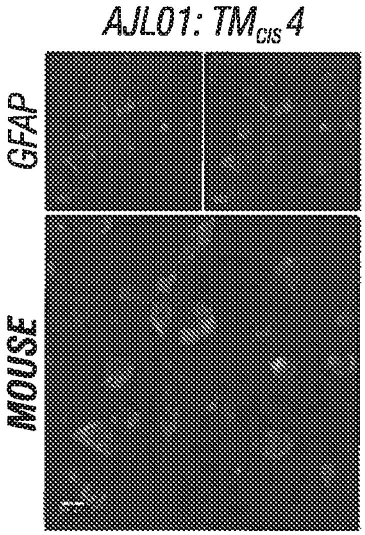

In order to see if targeting to astrocytes was present, the other major cell type in the GM in addition to neurons, IFC with GFAP was tested. WR12 and WR13 from the same patient, $ON_{CIS}2$, colocalized with astrocytes and their processes in mouse tissue (FIGS. 4C, 4E). In human tissue, both rhAbs recognized GFAP-positive astrocyte bodies with additional vessel staining seen with WR12 (FIGS. 4D, 4F). AJL01 from patient $TM_{CIS}4$ predominately colocalized with astrocytes with additional staining along the periventricular lining in mouse (FIG. 4G). AJL01 colocalized to astrocyte endfeet within a vessel in addition to the astrocyte bodies in MS-GM shown (FIG. 4H). In addition to AGS-enriched B cells that recognize neurons, this mutational pattern also imparts recognition to astrocytes.

Figure 5A:
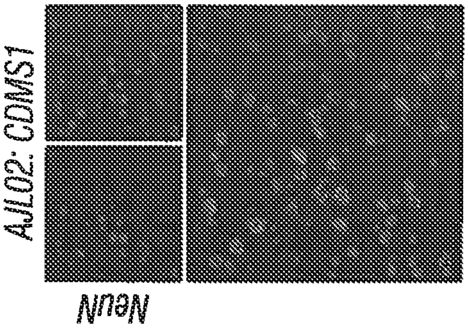
FIGS. 5A-5L show that IFC of AGS-enriched rhAbs target both neuronal nuclei and astrocytes in both mouse and human GM brain tissue: AJL02, AJL07, WR10 and AJL19. Confocal images are shown at 63× magnification with the colocalization marker for NeuN (for neuronal nuclei) across the first row and GFAP (for astrocytes) across the second row shown as red (Alexa Fluor 594). The primary rhAb is shown as green (Alexa Fluor 488) and nuclei are counterstained blue (DAPI). The images are shown as independent red and green channels above the overlay including DAPI. The top two rows are NeuN and GFAP staining on mouse brain tissue with the bottom row showing human GM brain tissue with labels of the colocalization marker above the red panel. Each rhAb is labeled above the column: AJL02 (CDMS1) (FIGS. 5A-C), AJL07 ($ON_{CIS}3$) (FIGS. 5D-F), WR10 ($TM_{CIS}4$) (FIGS. 5G-I), and AJL19 ($TM_{CIS}6$) (FIGS. 5J-L). Data are representative of six coronal sections per rhAb on mouse tissue and three sections per rhAb on human MS-GM tissue. Scale bar represents 10 μm.
Figure 5B:
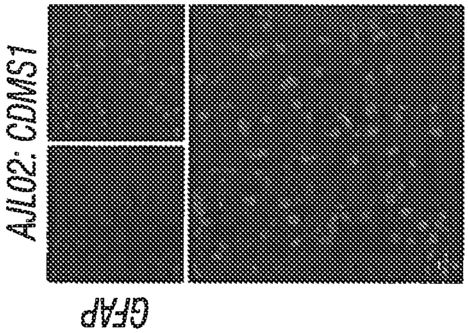
Figure 5D:
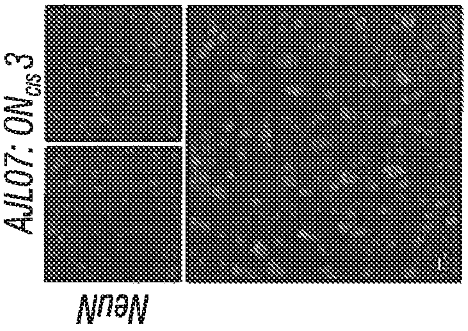
Figure 5E:
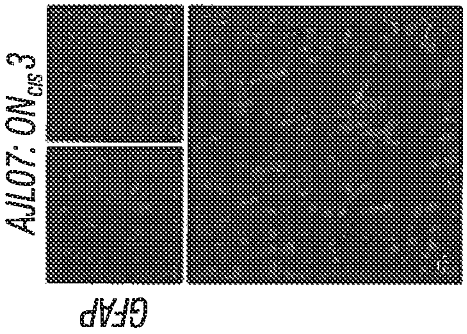
Figure 5G:
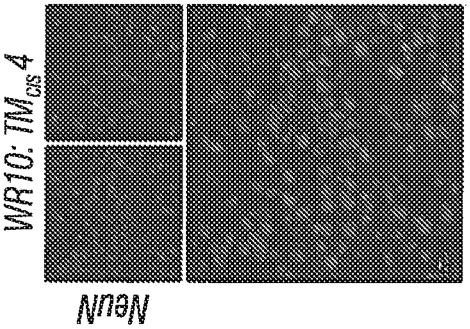
Figure 5H:
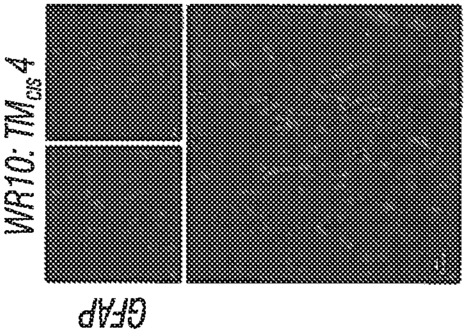
Figure 5J:
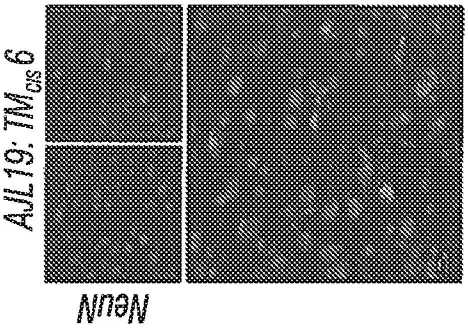
Figure 5K:
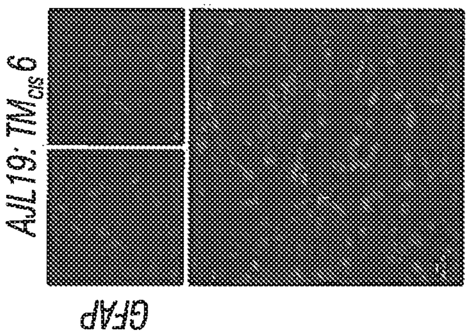
Figure 5C:
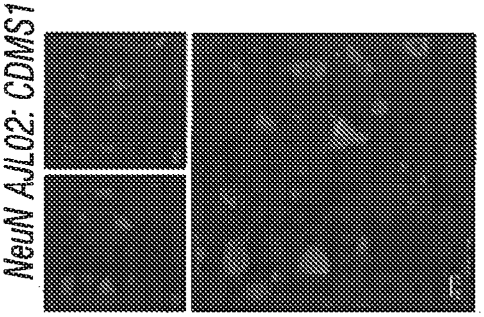
Figure 5F:
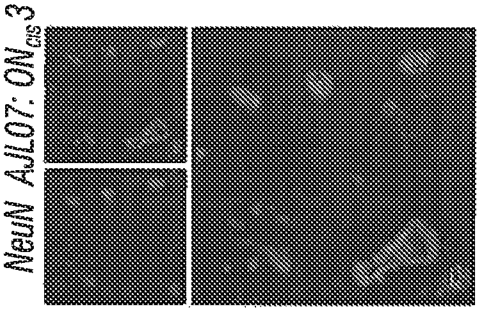
Figure 5I:
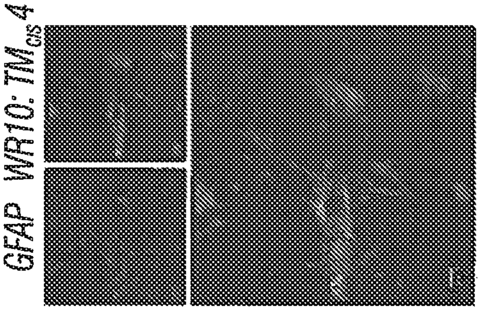
Figure 5L:
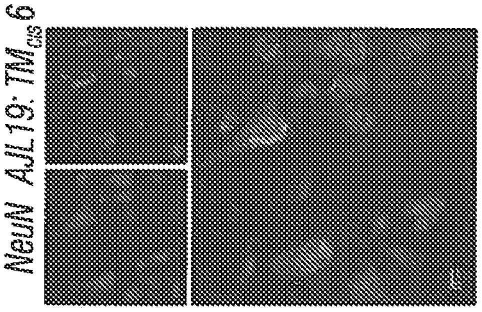
Figure 6A:
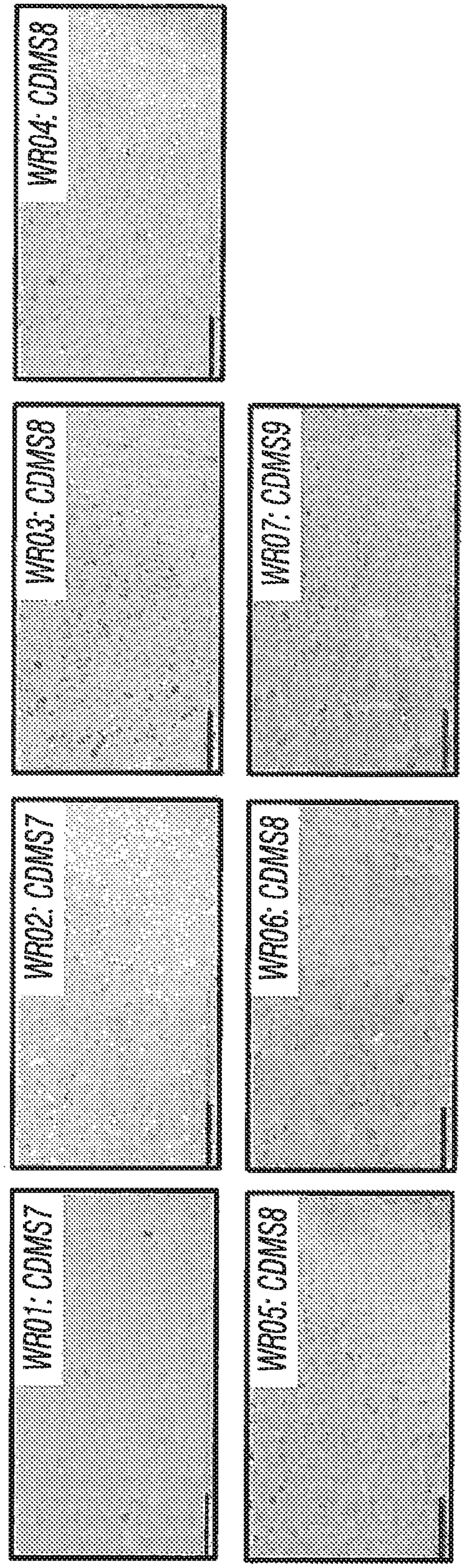
FIGS. 6A-6C show AGS-enriched rhAbs bind to mouse brain. The remaining 22 rhAbs not in FIG. 1 are shown here. DAB images are shown at 20× magnification of the cortex and corpus callosum. The rhAbs in each section are grouped as follows: CDMS (FIG. 6A), $ON_{CIS}$ (FIG. 6B), and $TM_{CIS}$ (FIG. 6C). The rhAb designation, patient type, and patient number are shown in the upper right corner of each image. Data are representative of three coronal sections per rhAb. Scale bar represents 100 μm.
Figure 6B:
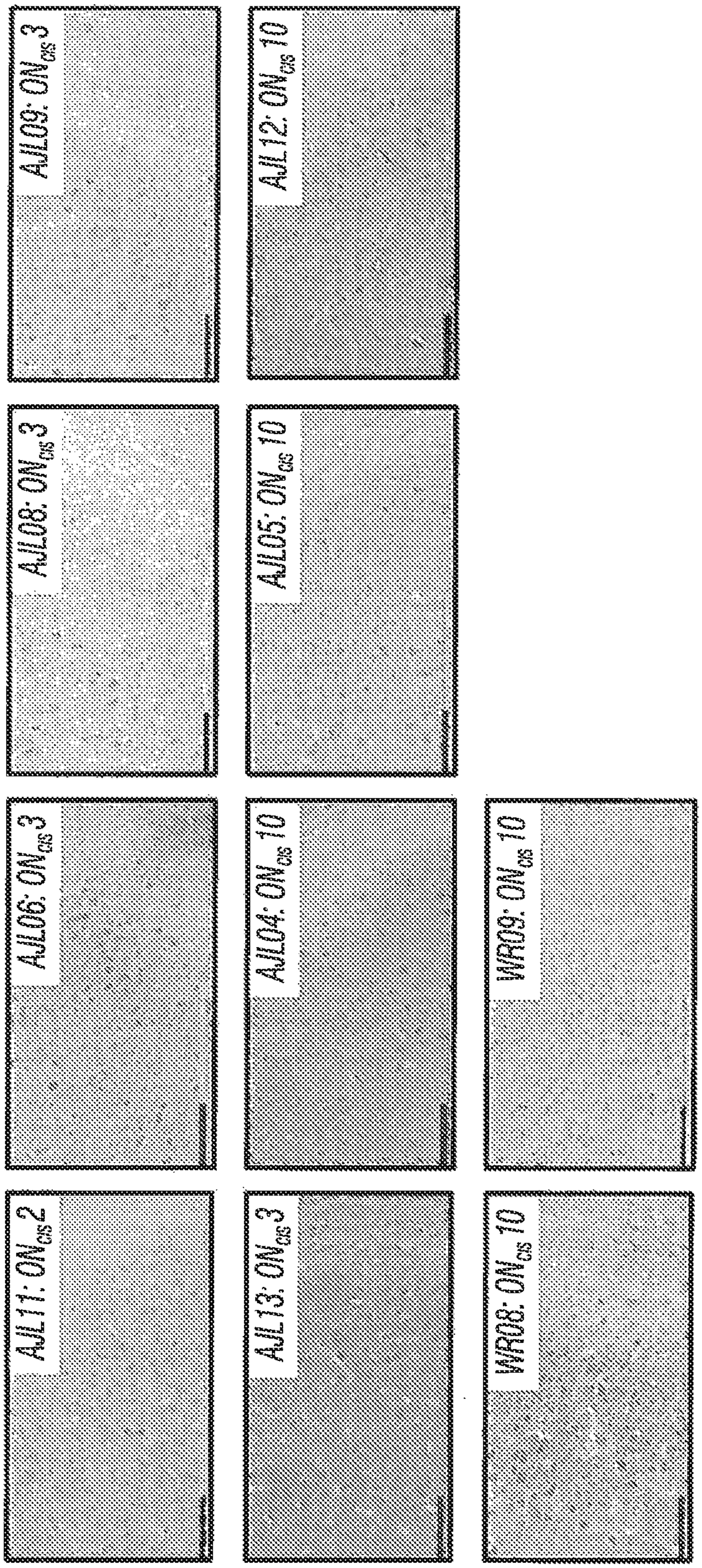
Figure 6C:
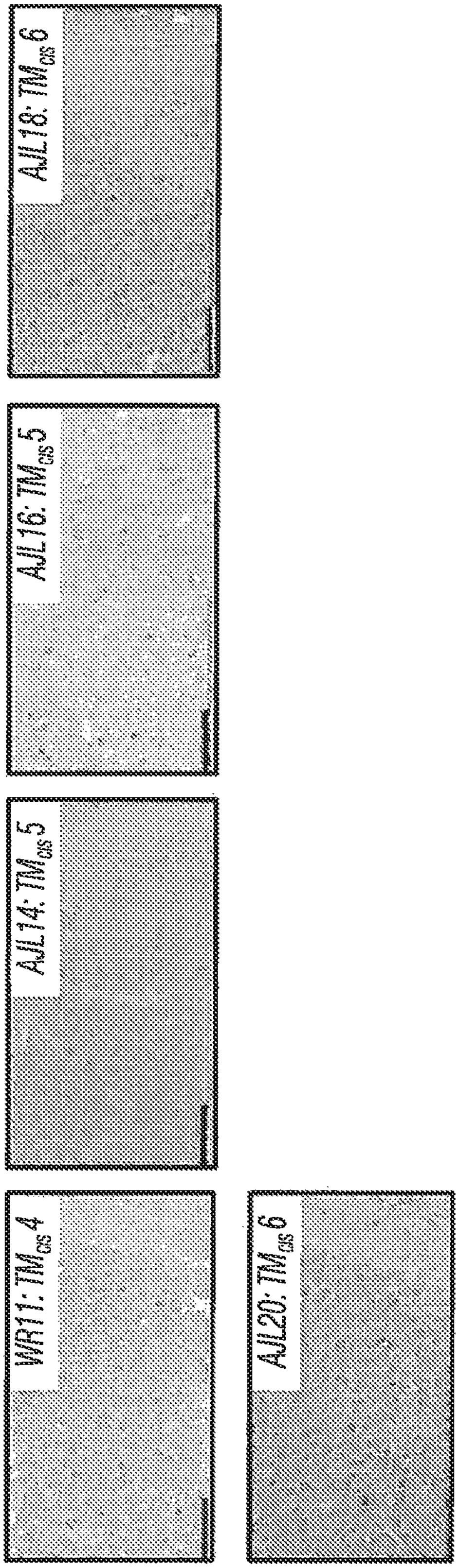
Figure 7A:
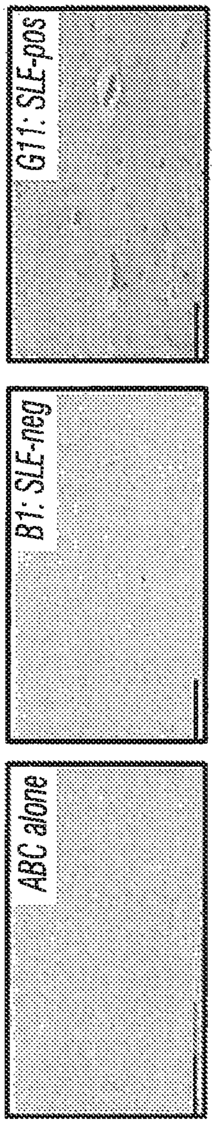
FIGS. 7A-7D show AGS-enriched rhAb DAB staining on human multiple sclerosis white matter (MS-WM) brain. DAB images are shown at 20× magnification of MS-WM. The rhAbs in each row are grouped as follows: controls (FIG. 7A), CDMS (FIG. 7B), $ON_{CIS}$ (FIG. 7C), and $TM_{CIS}$ (FIG. 7D). The rhAb designation, patient type, and patient number are shown in the upper right corner of each panel. Data are representative of three MS-WM sections per rhAb. Scale bar represents 100 μm.
Figure 7B:
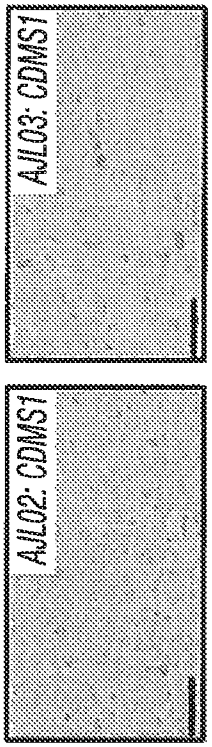
Figure 7C:
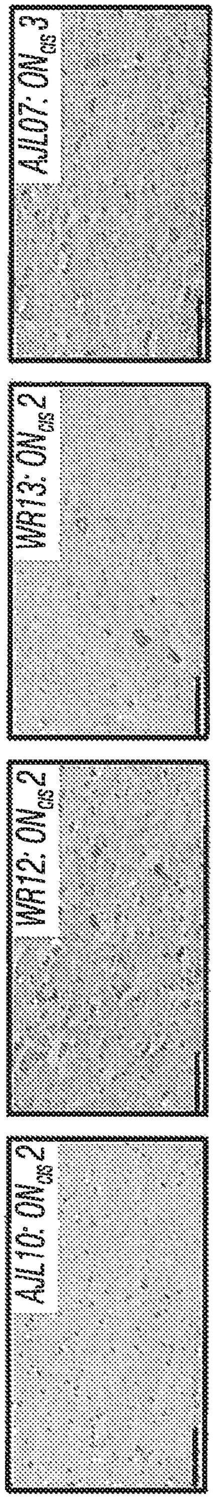
Figure 7D:
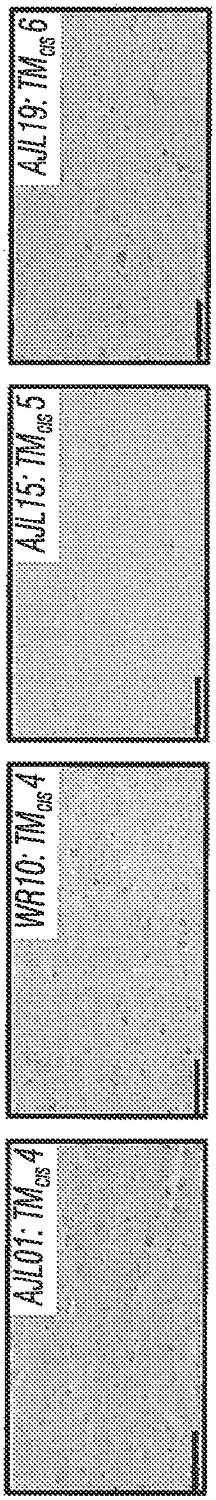
Figure 8A:
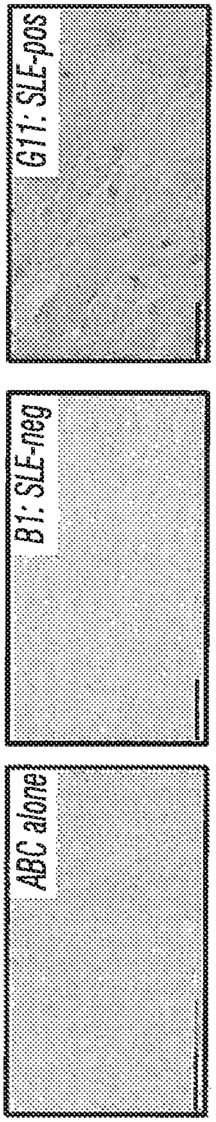
FIGS. 8A-8D show AGS-enriched rhAb DAB staining on human brain MS plaque (MS-P). DAB images are shown at 20× magnification of MS-P. The rhAbs in each row are grouped as follows: controls (FIG. 8A), CDMS (FIG. 8B), $ON_{CIS}$ (FIG. 8C), and $TM_{CIS}$ (FIG. 8D). The rhAb designation, patient type, and patient number are shown in the upper right corner of each panel. Data are representative of three MS-P sections per rhAb. Scale bar represents 100 μm.
Figure 8B:
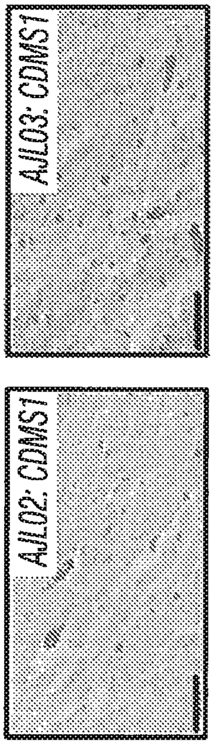
Figure 8C:
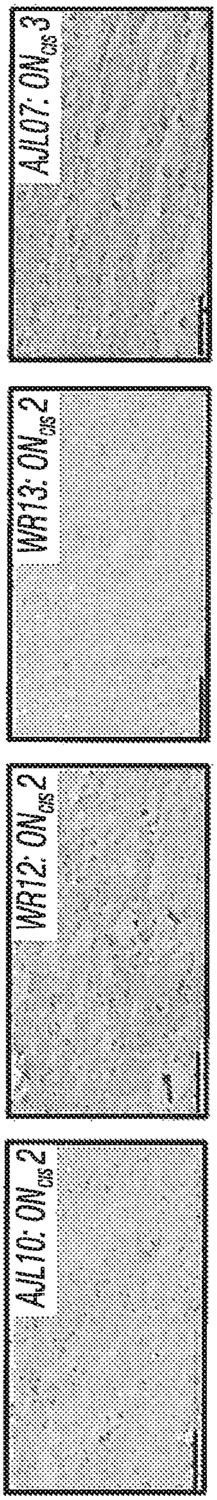
Figure 8D:
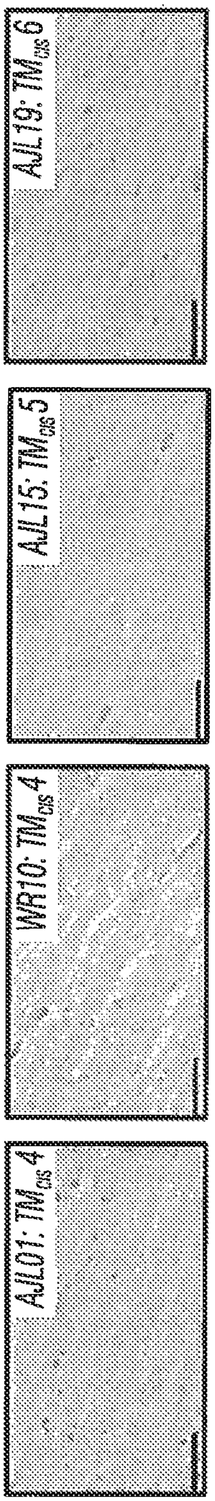
Figure 9A:
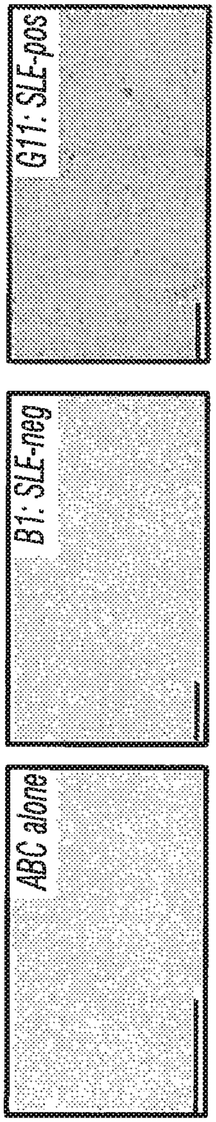
FIGS. 9A-9D show AGS-enriched rhAb DAB staining on healthy human control white matter (HC-WM) brain tissue. DAB images are shown at 20× magnification of HC-WM. The rhAbs in each row are grouped as follows: controls (FIG. 9A), CDMS (FIG. 9B), $ON_{CIS}$ (FIG. 9C), and $TM_{CIS}$ (FIG. 9D). The rhAb designation, patient type, and patient number are shown in the upper right corner of each panel. Data are representative of three HC-WM sections per rhAb. Scale bar represents 100 μm.
Figure 9B:
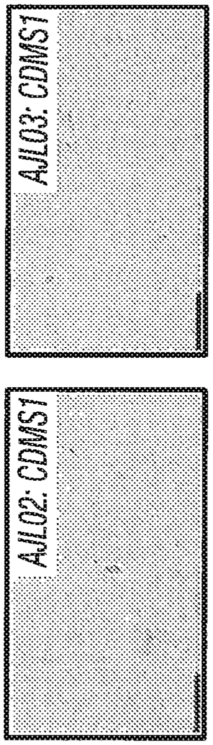
Figure 9C:
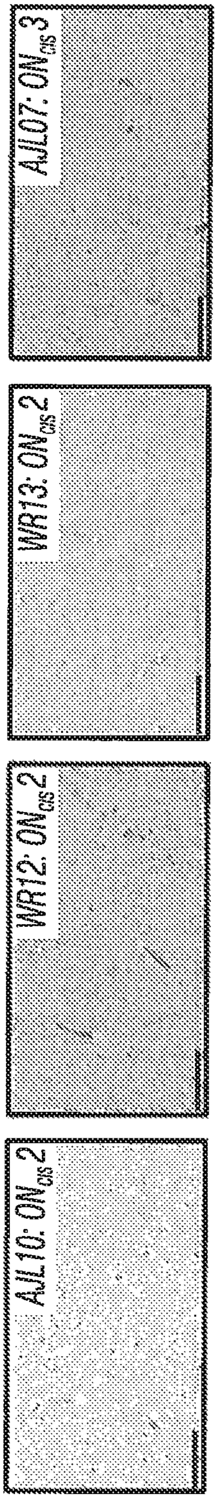
Figure 9D:
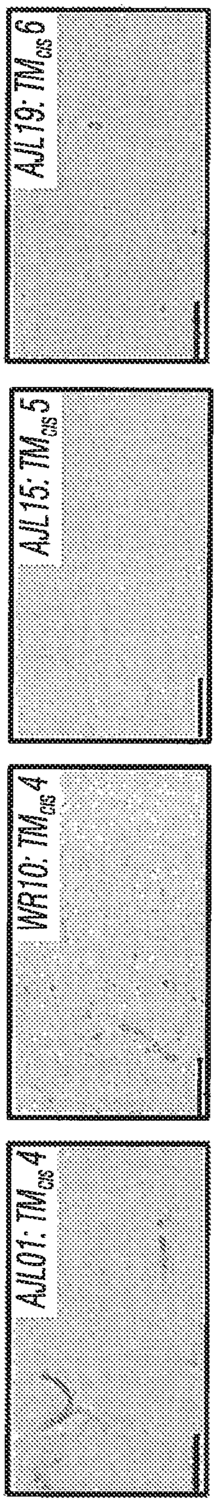

Four AGS-enriched rhAbs from all 3 patient types displayed dual-cell targeting. AJL02 from patient CDMS1 predominantly colocalized with NeuN in a ring-like fashion within the nuclei (FIG. 5A) with minor colocalization with GFAP astrocyte processes (FIG. 5B). This ring-like staining pattern around neuronal nuclei was also seen in human tissue (FIG. 5C). AJL07 was cloned from patient $ON_{CIS}3$, and displayed dual-cell targeting to both neurons and astrocytes in mouse brain (FIGS. 5D, 5E). In MS-GM AJL07 principally stained neuronal nuclei and also a vessel (FIG. 5F), keeping with the dual-cell targeting observed in mouse. From patient $TM_{CIS}$ 4, WR10 displayed dual-cell targeting with colocalization to both the edges of neuronal nuclei and astrocyte processes in mouse brain (FIGS. 5G, 5H). WR10 stained astrocyte bodies, endfeet around a vessel, as well as a neuron seen at the top of the panel in MS-GM (FIG. 5I). AJL19 from patient $TM_{CIS}$6 reacted similarly to WR10 with dual-cell targeting as it colocalized with both neuronal nuclei and astrocytes (FIGS. 5J, 5K). Colocalization of AJL19 with neuronal nuclei was also seen in MS-GM (FIG. 5L).

Due to the focused cellular binding of these rhAbs by DAB, the inventor hypothesized that the rhAbs were binding to either neurons and/or astrocytes in the gray matter. Therefore, IFC colocalization experiments were performed on the subset of rhAbs. In both mouse and human brain tissues, NeuN was utilized as a marker for neuronal nuclei and GFAP was utilized as a marker for astrocytes. FIGS. 13A-F and FIGS. 14A-F feature four of these rhAbs and the remaining six are summarized in FIGS. 15A-F (CDMS derived rhAbs) and FIGS. 16A-L (CIS derived rhAbs).

Figure 13A:
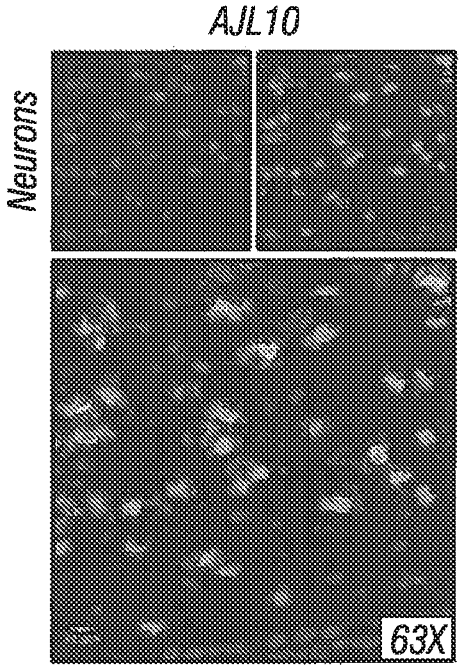
FIGS. 13A-13F show IFC of AGS-enriched rhAbs targeting neuronal nuclei in both mouse and human GM brain tissue: AJL10 ($ON_{CIS}2$) and AJL07 ($ON_{CIS}3$). Confocal images are shown at 63× magnification for the mouse tissue (FIGS. 13A and 13C.
Figure 13B:
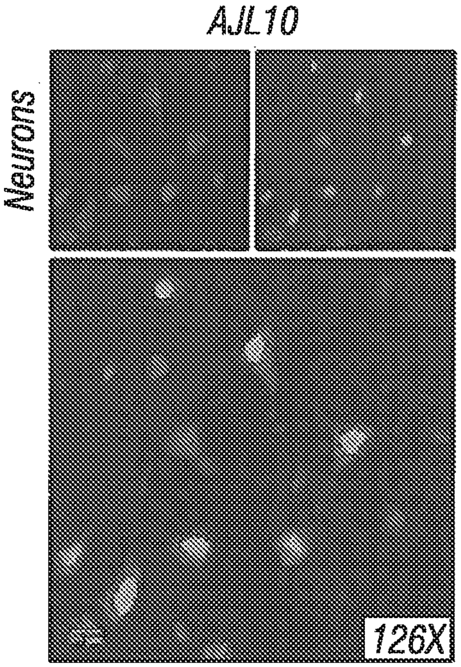
Figure 13C:
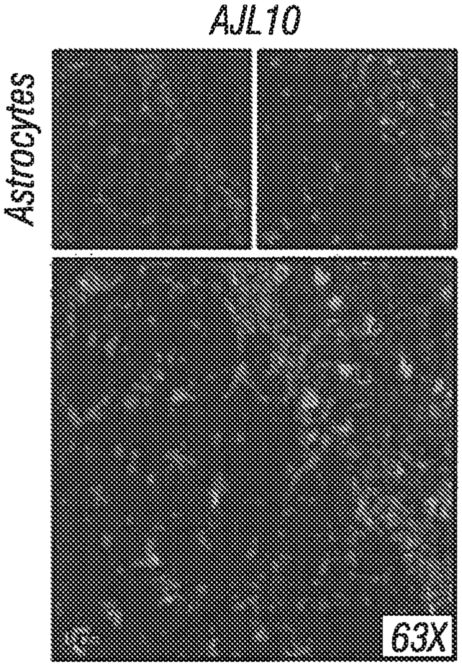
Figure 13D:
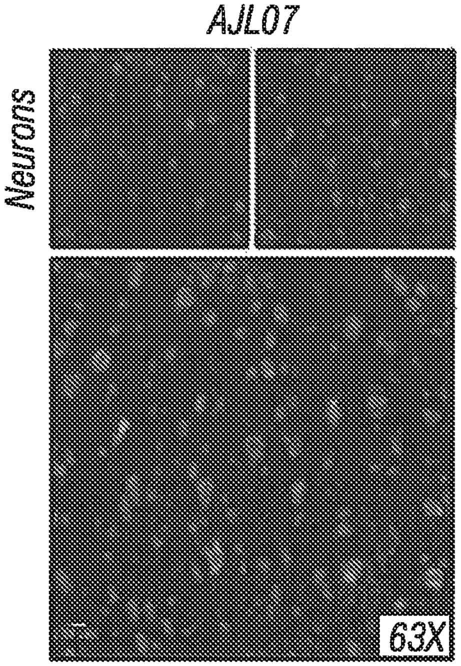
Figure 13E:
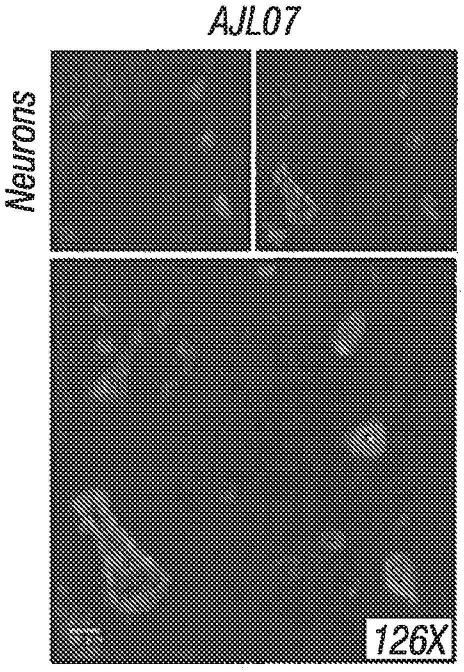
Figure 13F:
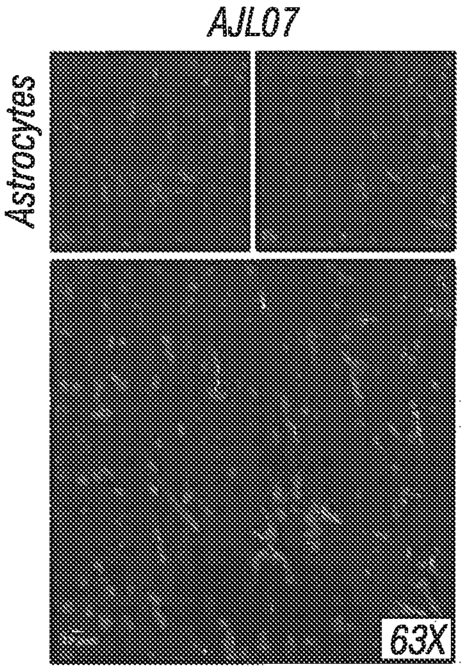

AJL10 is a rhAb cloned from patient $ON_{CIS}$2 that had an AGS score of 6.07 and converted to MS 2.5 years after sampling. This antibody utilizes the VH4-4 gene paired with a JH6 segment and also uses a VK light chain. AJL10 has replacement SHM at 4 of the 6 AGS codons (40, 56, 81, and 89) with an overall high mutation frequency of 12.63% (Table 5). No additional clones of this B cell were detected in the patient's CSF. As shown in FIGS. 13A-F, AJL10 demonstrated co-localization with neuronal nuclei in both mouse (FIG. 13A), and human (FIG. 13B) gray matter. AJL10 did not cross-react with astrocytes as demonstrated by the lack of co-localization with the astrocyte specific antibody, GFAP (FIG. 13C). AJL07 is a rhAb cloned from a different CIS patient, $ON_{CIS}$3, that had an AGS score of 10.68 and converted to MS 1 month after sampling. This antibody utilizes the VH4-59 gene paired with a JH4 segment and also uses a VK light chain. AJL07 has replacement SHM at 3 of the 6 AGS codons (56, 57, and 81) with an overall high mutation frequency of 9.23% (Table 5). Three additional clones of this B cell were detected in the patient's CSF. AJL07 co-localized with NeuN in both mouse and human gray matter (FIGS. 13D-E) and also cross-reacted with astrocytes as demonstrated by GFAP co-localization (FIG. 13F). Interestingly, AJL07 also bound to the vasculature in human gray matter (FIG. 13E).

Figure 14A:
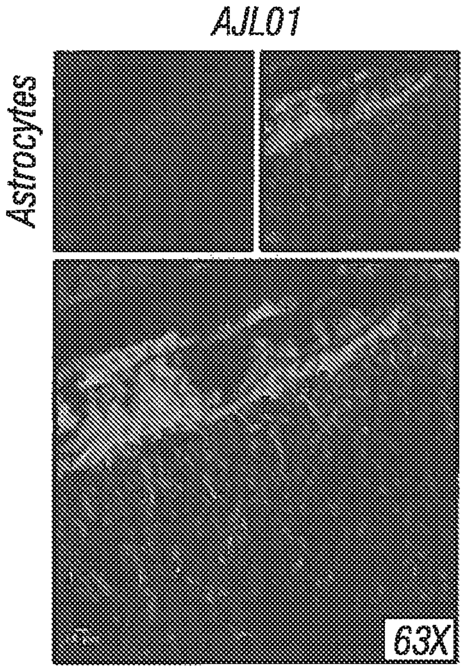
FIGS. 14A-14F show IFC of AGS-enriched rhAbs target astrocytes in both mouse and human GM brain tissue: AJL01 ($TM_{CIS}$4) and WR13 ($ON_{CIS}$2). Confocal images are shown at 63× magnification for the mouse tissue (FIGS. 14A and 14C.
Figure 14B:
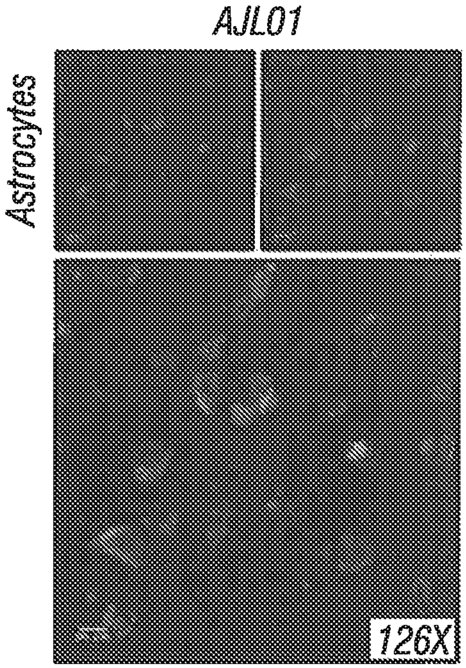
Figure 14C:
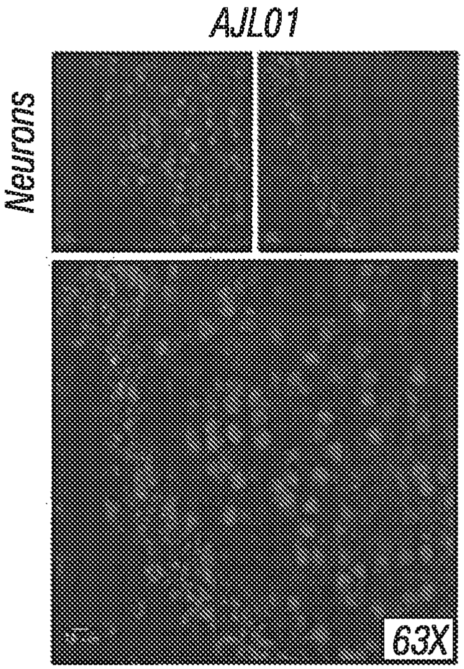
Figure 14D:
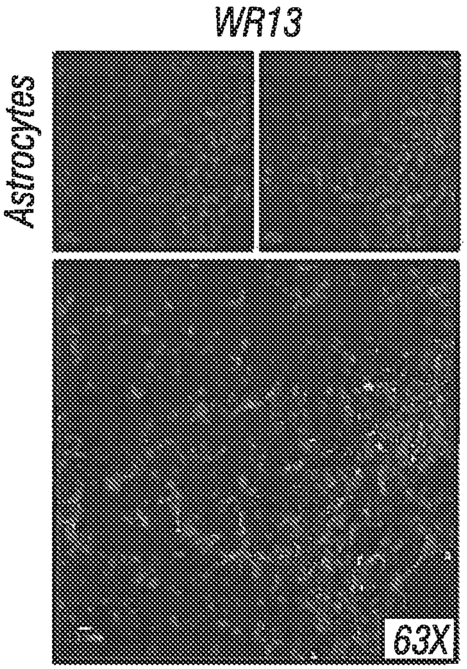
Figure 14E:
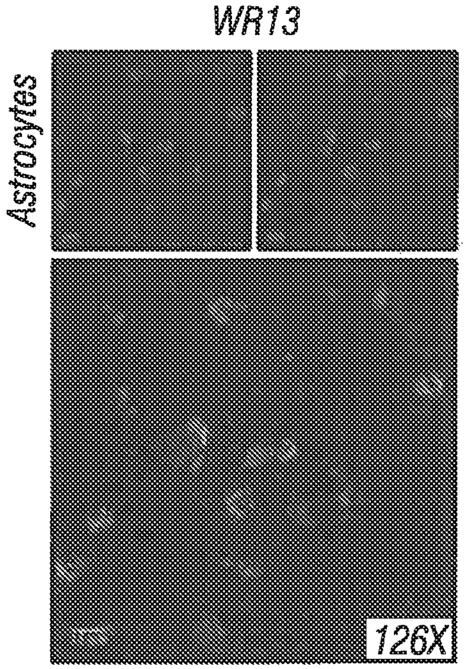
Figure 14F:
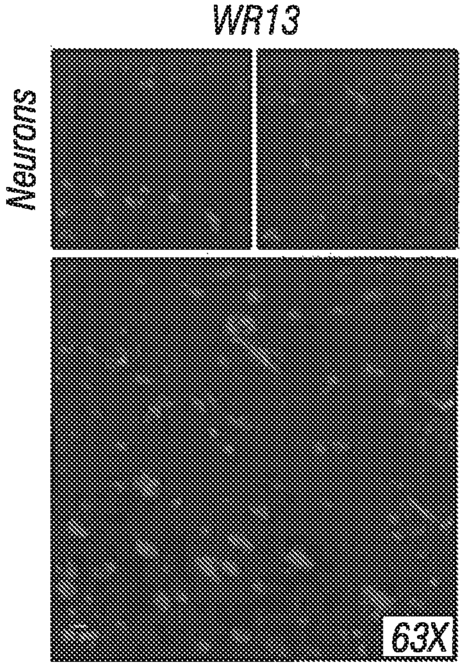
Figure 15A:
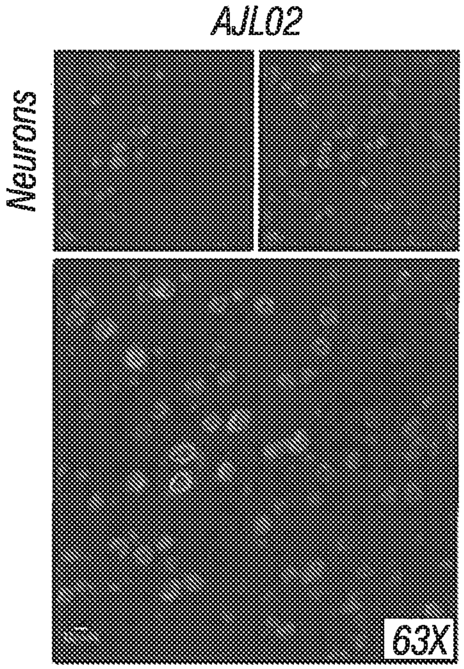
FIGS. 15A-15F show that CDMS derived AGS-enriched rhAbs demonstrate reactivity to neuronal nuclei and astrocytes: AJL02 and AJL03 (CDMS1). Confocal images are shown at 63× magnification for the mouse tissue (FIGS. 15A-B.
Figure 15B:
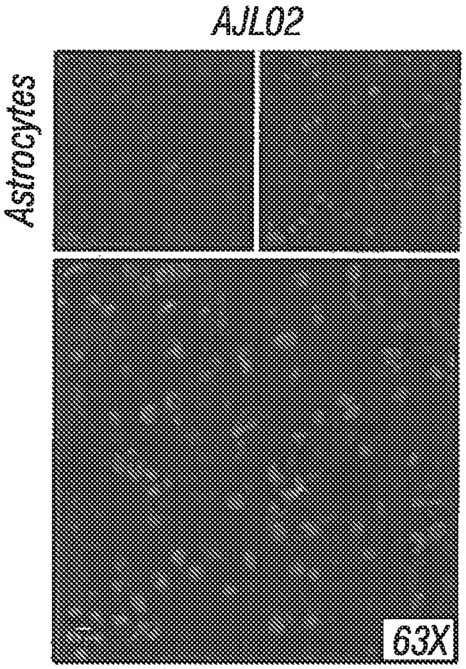
Figure 15C:
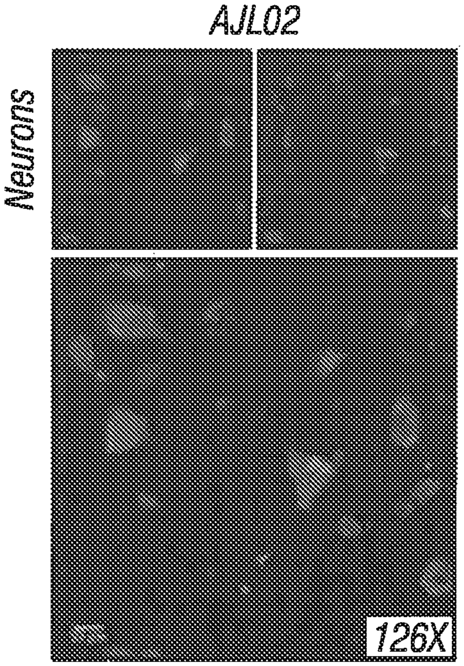
Figure 15D:
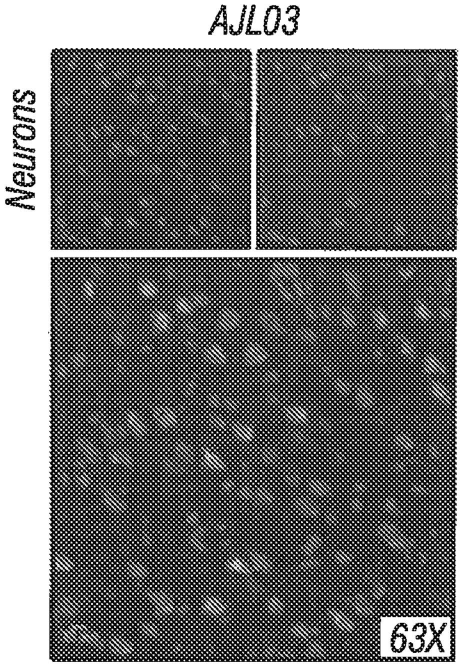
Figure 15E:
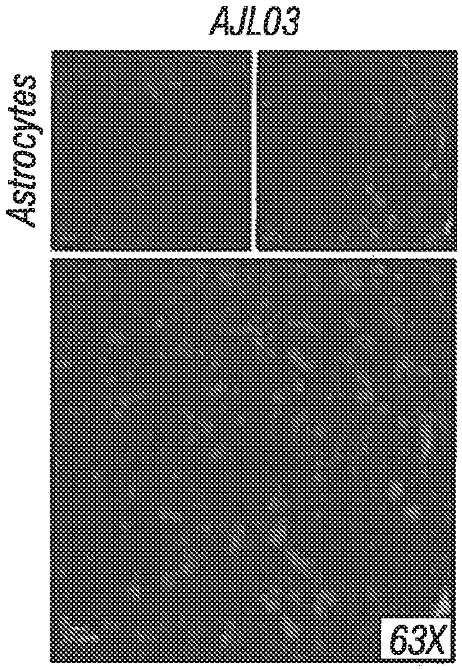
Figure 15F:
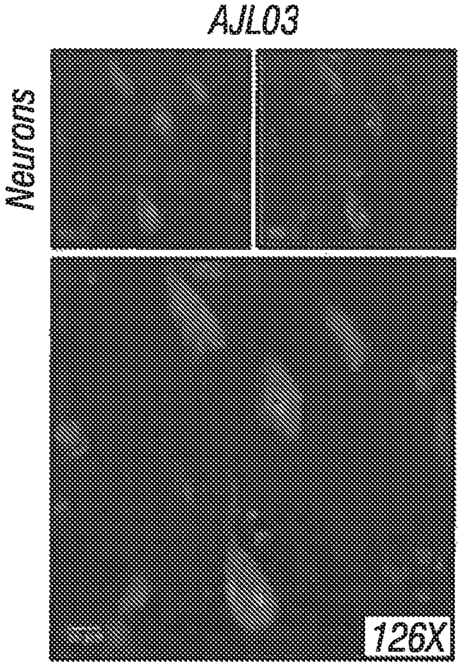
Figure 16A:
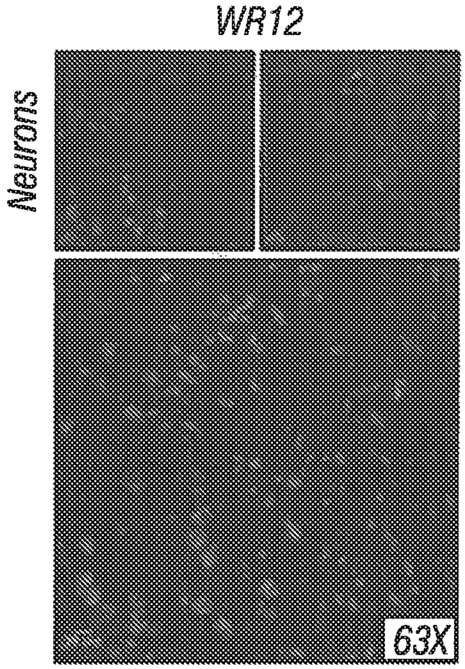
FIGS. 16A-16L show that CIS derived AGS-enriched rhAbs demonstrate reactivity to neuronal nuclei and astrocytes: WR12 ($ON_{CIS}$2), WR10 ($TM_{CIS}$4), AJL15 ($TM_{CIS}$5), and AJL19 ($TM_{CIS}$ 6). Confocal images are shown at 63× magnification for the mouse tissue (FIGS. 16A, 16B, 16D, 16E, 16G, 16H, 16J, 16K) and 126× for the human tissue (FIGS. 16C, 16F, 16I, 16L) with the colocalization marker for NeuN (neuronal nuclei) or GFAP (for astrocytes) shown as red (Alexa Fluor 594). The primary rhAb is shown as green (Alexa Fluor 488) and nuclei are counterstained blue (DAPI). The images are shown as independent red and green channels above the overlay including DAPI. Data are representative of six coronal sections per rhAb on mouse brain tissue and three sections per rhAb on human GM brain tissue. Scale bar represents 10 μm.
Figure 16B:
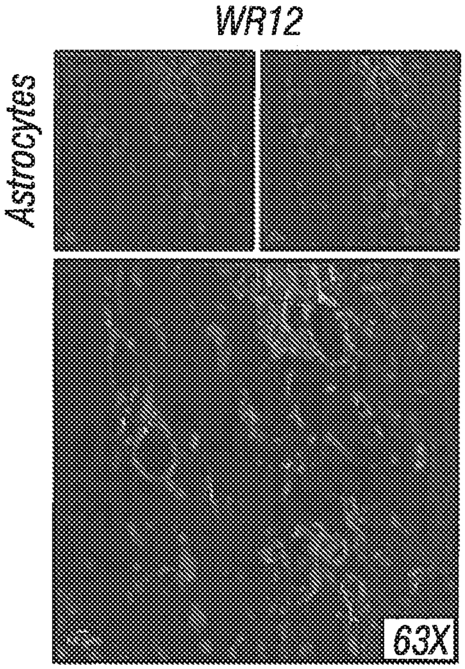
Figure 16C:
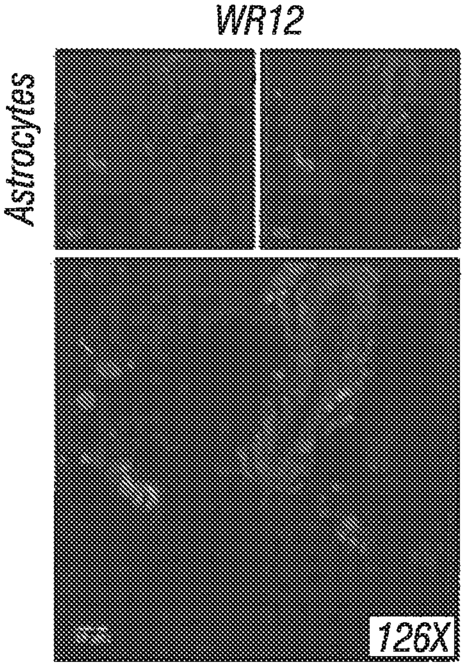
Figure 16D:
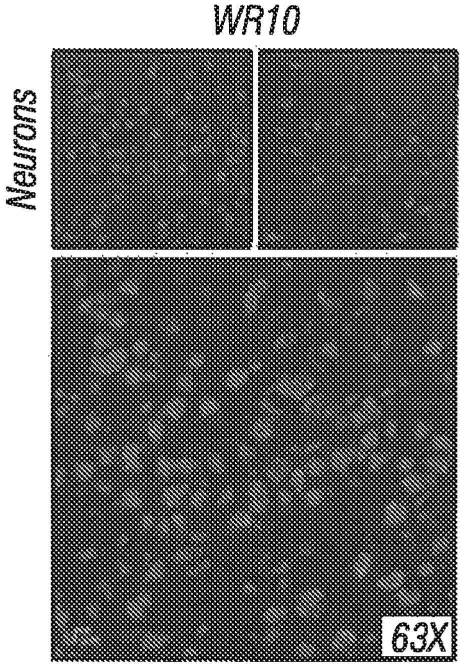
Figure 16E:
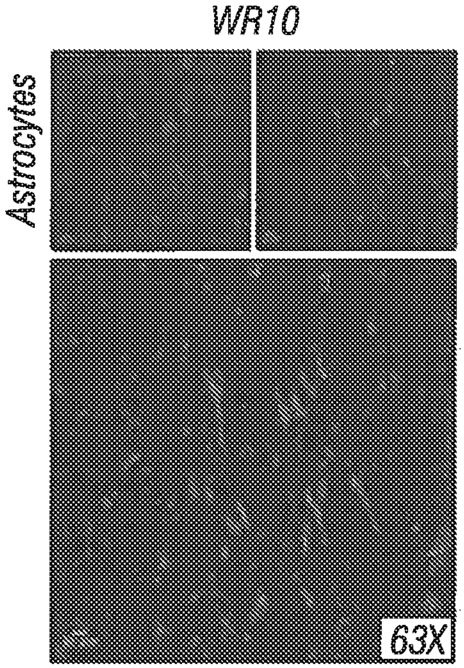
Figure 16F:
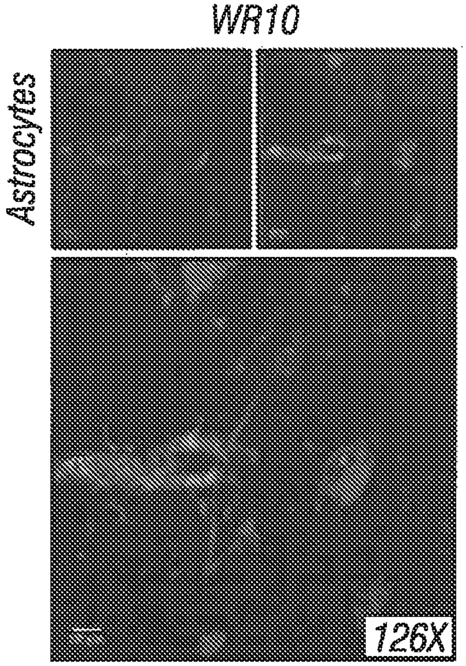
Figure 16G:
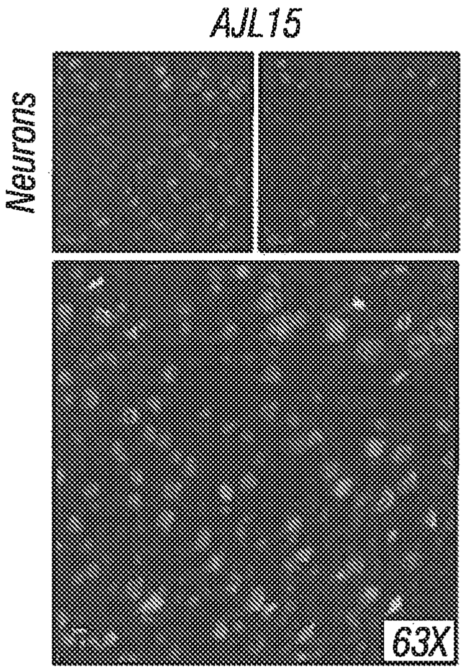
Figure 16H:
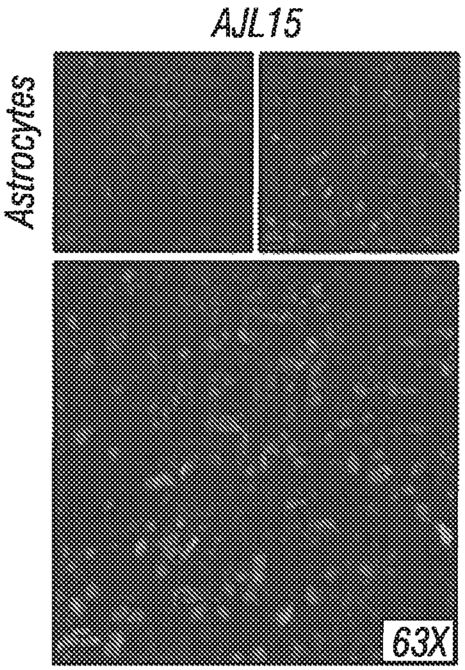
Figure 16I:
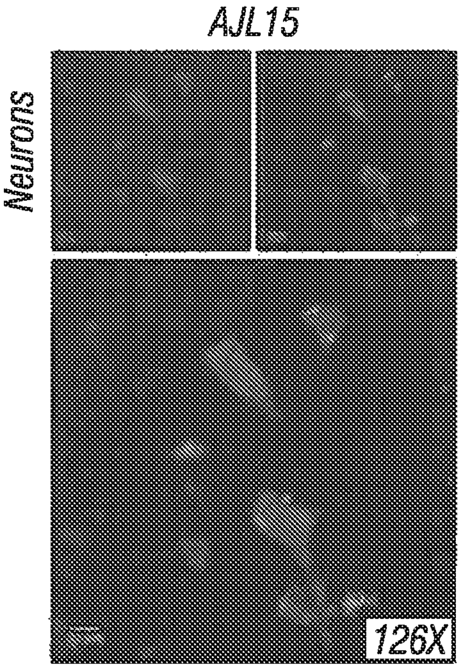
Figure 16J:
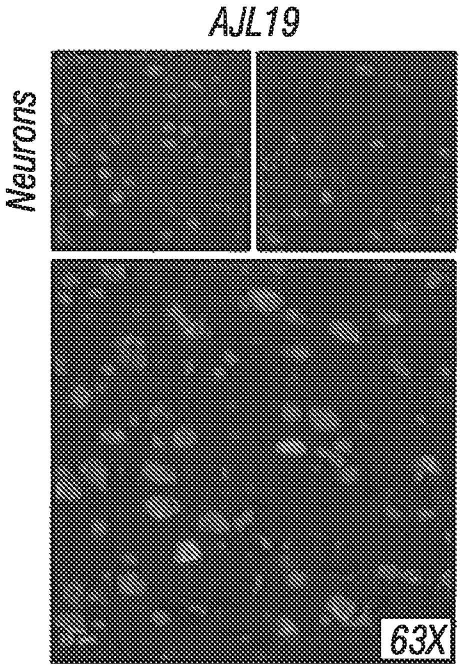
Figure 16K:
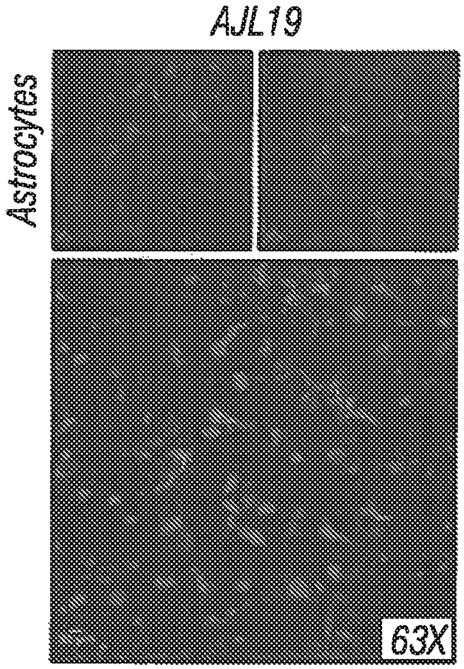
Figure 16L:
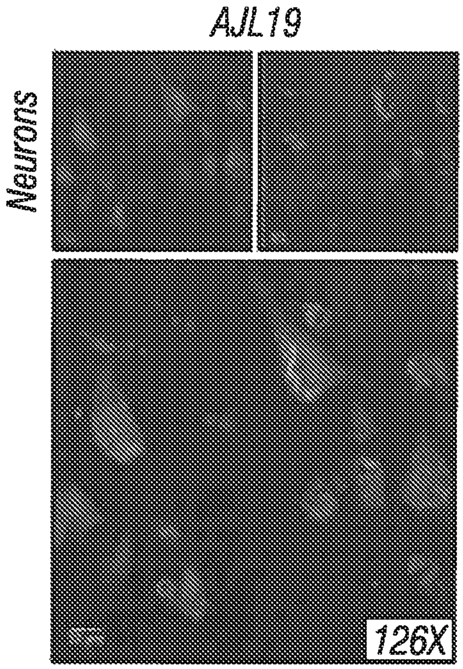

Next, the inventor wanted to see if CIS patients presenting with TM would also display gray matter binding by their AGS-enriched rhAbs (FIGS. 14A-F). AJL01 is a rhAb cloned from patient $TM_{CIS}$4 that had an AGS score of 17.90 and converted to MS 8 months after sampling. This antibody utilizes the VH4-34 gene paired with a JH3 segment and also uses a VK light chain. AJL01 has replacement SHM at 3 of the 6 AGS codons (56, 57, and 81) with an overall high mutation frequency of 11.28% (Table 5). This was detected as a four member clone within the patient's CSF. AJL01 colocalized to astrocyte endfeet within the blood-brain barrier in addition to the astrocyte bodies shown in both mouse and human GM (FIGS. 14A-B). AJL01 did not cross-react with neurons in mouse GM (FIG. 14C). Another AGS-enriched rhAb, WR13, also bound to astrocytes. This rhAb was cloned from the same ONCIS2 patient as AJL10. This antibody utilizes the VH4-30 gene paired with a JH4 segment and also uses a VK light chain. WR13 has replacement SHM at 2 of the 6 AGS codons (56 and 81) with an overall mutation frequency of 11.94% (Table 5). Similar to AJL01 from a $TM_{CIS}$ patient, WR13 from an $ON_{CIS}$ patient co-localized to astrocytes in both mouse and human GM (FIGS. 14D-14E) and did not cross-react with neurons (FIG. 14F). A clonally related rhAb also detected in this patient's CSF, WR12, was tested and demonstrated the same staining pattern (FIGS. 16A-16L).

Of the 32 rhAbs that were evaluated for binding to brain tissue, 30 bound to brain tissue by DAB staining. Of those, 10 were evaluated for binding to neurons and astrocytes by IFC. Of those 10, 4 bound to both neurons and astrocytes, 3 bound to neurons only and 3 bound to astrocytes only. Some of the results are shown in FIGS. 18A-18M. Further investigation of the 6 AGS codons revealed that all brain binding antibodies must have replacement mutations in at least two of the AGS codons. One of these mutations is typically an "R" or "N" replacement result at codon 81. Antibodies that do not have a mutation at codons 31b, 40, or 89 but have a "T" or "R" replacement result at codon 56 bind astrocytes, but not neurons. Antibodies that do not meet the astrocyte binding criteria bind neurons, and also have an "S" replacement result at codon 40. Those antibodies that bind neurons and astrocytes do not have a mutation at codon 31b and no "R" replacement result at codon 56. This finding could have profound implications in the diagnostic and therapeutic treatment of CNS disease, such as Multiple Sclerosis.

FIGS. 43-44 and Table 4 illustrate the sequenced heavy and light chains, and their staining patterns.

TABLE 4

AGS Mutations and Binding Patterns

| | | AGS Codon | | | | | | | | | | | | | | | | | |
|---|---|---|---|---|---|---|---|---|---|---|---|---|---|---|---|---|---|---|---|
| | | 36 (31b) | | | | | | 45 (40) | | | | | | 64 (56) | | | | | |
| | Gene | 4-30 | 4-31 | 4-34 | 4-39 | 4-4 | 4-59 | 4-30 | 4-31 | 4-34 | 4-39 | 4-4 | 4-59 | 4-30 | 4-31 | 4-34 | 4-39 | 4-4 | 4-59 |
| | AA | D | G | — | S | — | — | P | H | P | P | P | P | S | S | S | S | S | S |
| | Nuc. | gat | ggt | — | agt | — | — | ccc | cac | ccc | ccc | ccc | ccc | agc | agc | agc | agc | agc | agc |
| Dual Binding | AJL02 | — | G | — | — | — | — | — | S | — | — | — | — | — | S | — | — | — | — |
| | | — | ggt | — | — | — | — | — | tcc | — | — | — | — | — | agc | — | — | — | — |
| | AJL07 | — | — | — | — | — | — | — | — | — | — | — | P | — | — | — | — | — | N |
| | | — | — | — | — | — | — | — | — | — | — | — | ccc | — | — | — | — | — | aat |
| | AJL19 | — | — | — | — | — | — | — | — | P | — | — | — | — | — | D | — | — | — |
| | | — | — | — | — | — | — | — | — | ccc | — | — | — | — | — | gat | — | — | — |
| | WR10 | — | — | — | — | — | — | — | — | — | — | S | — | — | — | — | — | G | — |
| | | — | — | — | — | — | — | — | — | — | — | tcc | — | — | — | — | — | ggc | — |

TABLE 4-continued

AGS Mutations and Binding Patterns

| | | | | | | | | | | | | | | | | | | | |
|---|---|---|---|---|---|---|---|---|---|---|---|---|---|---|---|---|---|---|---|
| Astrocyte | AJL01 | — | — | — | — | — | — | — | — | P | — | — | — | — | — | R | — | — | — |
| | | — | — | — | — | — | — | — | — | ccc | — | — | — | — | — | aga | — | — | — |
| | WR12 | D | — | — | — | — | — | P | — | — | — | — | — | T | — | — | — | — | — |
| | | gat | — | — | — | — | — | ccc | — | — | — | — | — | acc | — | — | — | — | — |
| | WR13 | D | — | — | — | — | — | P | — | — | — | — | — | T | — | — | — | — | — |
| | | gat | — | — | — | — | — | ccc | — | — | — | — | — | acc | — | — | — | — | — |
| Neuron | AJL03 | — | — | — | R | — | — | — | — | — | P | — | — | — | — | — | S | — | — |
| | | — | — | — | cgt | — | — | — | — | — | ccc | — | — | — | — | — | agc | — | — |
| | AJL10 | — | — | — | — | — | — | — | — | — | — | S | — | — | — | — | — | T | — |
| | | — | — | — | — | — | — | — | — | — | — | tcc | — | — | — | — | — | act | — |
| | AJL15 | — | — | — | N | — | — | — | — | — | S | — | — | — | — | — | S | — | — |
| | | — | — | — | aat | — | — | — | — | — | tcc | — | — | — | — | — | agc | — | — |

| | | AGS Codon | | | | | | | | | | | | | | | | | |
|---|---|---|---|---|---|---|---|---|---|---|---|---|---|---|---|---|---|---|---|
| | | 65 (57) | | | | | | 90 (81) | | | | | | 101 (89) | | | | | |
| | Gene | 4-30 | 4-31 | 4-34 | 4-39 | 4-4 | 4-59 | 4-30 | 4-31 | 4-34 | 4-39 | 4-4 | 4-59 | 4-30 | 4-31 | 4-34 | 4-39 | 4-4 | 4-59 |
| | AA | T | T | T | T | T | T | K | K | K | K | K | K | V | V | V | V | V | V |
| | Nuc. | acc | acc | acc | acc | acc | acc | aag | aag | aag | aag | aag | aag | gtg | gtg | gtg | gtg | gtg | gtg |
| Dual | AJL02 | — | T | — | — | — | — | — | R | — | — | — | — | — | V | — | — | — | — |
| Binding | | — | acc | — | — | — | — | — | agg | — | — | — | — | — | gtc | — | — | — | — |
| | AJL07 | — | — | — | — | — | I | — | — | — | — | — | N | — | — | — | — | — | V |
| | | — | — | — | — | — | att | — | — | — | — | — | aac | — | — | — | — | — | gtg |
| | AJL19 | — | — | A | — | — | — | — | — | K | — | — | — | — | — | L | — | — | — |
| | | — | — | gcc | — | — | — | — | — | aag | — | — | — | — | — | tta | — | — | — |
| | WR10 | — | — | — | — | T | — | — | — | — | — | K | — | — | — | — | — | V | — |
| | | — | — | — | — | acc | — | — | — | — | — | aag | — | — | — | — | — | gtg | — |
| Astrocyte | AJL01 | — | — | A | — | — | — | — | — | N | — | — | — | — | — | V | — | — | — |
| | | — | — | gcc | — | — | — | — | — | aac | — | — | — | — | — | gtc | — | — | — |
| | WR12 | T | — | — | — | — | — | R | — | — | — | — | — | V | — | — | — | — | — |
| | | acc | — | — | — | — | — | agg | — | — | — | — | — | gtc | — | — | — | — | — |
| | WR13 | T | — | — | — | — | — | R | — | — | — | — | — | V | — | — | — | — | — |
| | | acc | — | — | — | — | — | agg | — | — | — | — | — | gtc | — | — | — | — | — |
| Neuron | AJL03 | — | — | — | T | — | — | — | — | — | N | — | — | — | — | — | V | — | — |
| | | — | — | — | act | — | — | — | — | — | aac | — | — | — | — | — | gtg | — | — |
| | AJL10 | — | — | — | — | T | — | — | — | — | — | R | — | — | — | — | — | I | — |
| | | — | — | — | — | act | — | — | — | — | — | agg | — | — | — | — | — | ata | — |
| | AJL15 | — | — | — | D | — | — | — | — | — | R | — | — | — | — | — | V | — | — |
| | | — | — | — | gac | — | — | — | — | — | agg | — | — | — | — | — | gtg | — | — |

It has been well-established in the literature that somatic hypermutations in the variable antibody gene regions enable antibodies to bind their cognate antigen with greater affinity. In fact, some studies have demonstrated that loss of particular mutations at certain codons in a single antibody gene can abrogate binding of the particular antibody to its cognate antigen. In the case of these AGS-enriched antibodies, the inventor describes, for the first time, a commonality of somatic hypermutation to particular replacement amino acids among a panel of antibodies expressed by individual B cells with distinct CDR3 regions that bind neurons, astrocytes, both neurons and astrocytes or neither cell type. Thus, by following the Decision Tree based on the amino acid resulting from somatic hypermutation at particular codons, one can predict whether the antibody will bind neurons, astrocytes, both neurons and astrocytes or neither cell type (FIG. 19).

Example 2—VH4+ Plasmablasts Demonstrate Autoreactive B Cell Expansion Toward Brain Antigens in Early Multiple Sclerosis Patients

Materials and Methods

Patient Sample Processing. Treatment naïve clinically isolated syndrome (CIS) patients included in this study had partial transverse myelitis symptoms (PTM) and were at high risk for developing multiple sclerosis (details in Table 8). Neuromyelitis optica (NMO) patients had established disease and were either on Cellcept therapy or no therapy. Only the NMO patients not on immune modulatory therapy were included as comparators for immunoglobulin gene analysis and antibody cloning. Blood was collected from CIS-PTM and NMO patients according to the University of Texas Southwestern Medical Center (UTSWMC) institutional review board. Peripheral blood mononuclear cells (PBMCs) were isolated by Ficoll separation and stained with fluorescent antibodies as previously described. Either memory B cells (CD19+CD27+) or plasmablasts (CD19+ CD27hi) as defined by others were sorted individually into 96-well plates using the BD FACSAria flow cytometer (Becton Dickinson, San Jose, CA).

Single Cell Polymerase Chain Reaction and Immunoglobulin Gene Analysis. Individually sorted B cell subpopulations were flash frozen and lysed. Upon thawing, immunoglobulin mRNA was reverse transcribed and amplified with multiple rounds of PCR as previously described. Sanger sequencing was used at the UTSWMC sequencing core to generate the antibody variable domain reads. Sequences were analyzed using the IgBlast component of the VDJServer online repertoire analysis tool (https://vdjserver.org/). This output was filtered to remove any sequence which met at least one of the following criteria: out-of-frame junction, missing CYS or TRP/PHE to anchor CDR3, stop codon, out of frame sequence, missing CDR3 or truncated read length (sequence alignment starts after CDR1). Peter Lipsky at UTSWMC provided the data from healthy donor CD19+ cells and the antibody repertoire data from influenza responding plasmablasts was previously described.

Antibody Cloning and Production. Plasmablasts from CIS-PTM and NMO patients expressing highly mutated VH4 or VH3 heavy chains were selected for production. The variable domains were synthesized (Integrated DNA Technologies, Corallville, IA) and bi-directionally cloned into an IgG1 backbone provided by Michel Nussenzweig at the Rockefeller University as previously described. The 6 IgG1 antibodies cloned from one healthy donor used as controls were previously also described. Betty Diamond at the Hofstra Northwell School of Medicine provided the DNA for two control IgG1 antibodies, B1 and G11, which serve as isotype negative and positive controls, respectively. All recombinant human antibodies (rhAbs) were transiently transfected into HEK293T cells (ATCC, Manassas, VA) with the lipid transfection reagent JetPEI (PolyPlus Transfection, Illkirch, France). Supernatants from these cultures were collected on days 3, 5, 7 and 10, and antibody was purified from these on a column of sepharose Protein G beads (Life Technologies, Grand Island, NY), dialyzed into dPBS (HyClone, Logan, UT), and concentrated to between 0.2 and 1.2 mg/ml. The exact concentration of the antibodies was measured by ELISA (Bethyl Laboratories, West Grove, PA).

Tissue and Antigen ELISAs. Mouse brain and kidney lysates were made as described elsewhere and the following protocol was adapted from this reference. Plates were coated with 10 μg/ml of human brain or kidney lysate in bicarbonate buffer overnight at 4° C. The next day plates were blocked with 10% BSA in PBST for 2 hours at room temperature and primary antibodies were added at 20 μg/ml or patient serum was diluted to 1:100, 1:250, 1:500 and 1:1000 in 5% BSA and incubated overnight at 4° C. The following day 1 μg/ml of biotinylated anti-human (eBioscience, San Diego, CA) in 3% BSA was incubated fro 2 hours at room temperature, followed by 1 hour with a 1:2000 dilution of streptavidin-HRP (BD Pharmigen, San Jose, CA) in 3% BSA. Plates were developed for 30 seconds with TMB substrate and neutralized with 1 M HCl before reading at 450 nm with an Epoch Microplate Spectrophotometer (BioTek, Winooski, VT). Thresholds for determining binding in this human brain and kidney lysate ELISAs were set by averaging the absorbance values of control antibodies and adding two standard deviations.

Histology. Healthy and diseased (EAE or stroke) mouse brains were preserved and cryosectioned as described previously but stored at −80° C. until use. Slides were briefly warmed, washed in PBS and antigens were uncovered by boiling for 2 minutes in unmasking solution (Vector Labs, San Mateo, CA). Slides were blocked for 2 hours at room temperature with 1% goat serum in PBS with 0.1% Triton X. Primary rhAbs were added at 20 μg/ml in blocking buffer overnight. The next day goat anti-human AlexaFluor 488 (Life Technologies, Grand Island, NY) was incubated with the slides for 1 hour, followed by re-blocking for 2 hours. Primary antibodies for NeuN, GFAP (Abcam, Cambridge, MA), or PDGFR (Santa Cruz Biotechnology, Dallas, TX) were incubated for 1 hour followed by 1 hour with anti-rabbit AlexaFluor 594 (Life Technologeis, Grand Island, NY). Slides were stained with DAPI (Sigma Aldrich, St. Louis, MO) for 4 minutes at room temperature, sealed with VectaShield (Vector Labs, San Mateo, CA), and imaged on a Zeiss LSM780 upright confocal microscope (Zeiss, Oberkochen, Germany). Blinded experts in histology and pathology (co-authors RC, DR and AS) assessed staining of the rhAbs.

Immunocytochemistry. Hep2 immunocytochemistry (ICC) was performed with a Hep-2 Substrate Slide anti-nuclear antibody kit according to the manufacturers instructions (MBL International, Woburn, MA). For SH-Sy5y staining, glass coverslips were coated with laminin at 50 μg/ml in dPBS for 2 hours at 37° C., washed once with PBS and SH-Sy5y were plated overnight. The following day, cells were fixed with 4% PFA and permeabilized with 0.2% Triton X in 2 mg/ml BSA. Cells were blocked with 1% goat serum, 3% BSA and 0.1% Triton X for 2 hours at room temperature before adding primary rhAbs or commercial anti-Hsp70 (Abcam, Cambridge, MA) at 20 μg/ml overnight at 4° C. The next day, secondary anti-human AlexaFluor 488 or anti-rabbit AlexaFluor 594 (Life Technologies, Grand Island, NY) was added and the slides incubated for 1 hour at room temperature. Cells were then stained with DAPI (Sigma Aldrich, St. Louis, MO) for 4 minutes at room temperature. Coverslips were sealed onto a glass slide using VectaShield (Vector Labs, San Mateo, CA), and imaged on a Zeiss Axioscan slide scanner (Zeiss, Oberkochen, Germany).

IHC and ICC signal affinity verification. Antibody affinity for these cell types in tissue sections was validated using a lambda scan on the Ziess LSM780 Upright Confocal/Multiphoton microscope (Zeiss, Oberkochen, Germany). The image area is scanned at various wavelengths recording signal intensity so that points of interest can be selected and compared to background fluorescence. Only antibodies with a signal to noise ratio above 1.5 near the emission wavelength for AlexaFluor488 (519 nm) were considered positive (FIGS. 34A-34D). Many of the antibodies well exceeded this ratio, demonstrating high affinity binding.

Flow Cytometry. Cells were lifted with Accutase for 5 minutes at 37° C. (Innovative Cell Technologies, San Diego, CA). Fc receptors were blocked with rat anti-mouse CD16 Fc block for 10 minutes at room temperature (BD Biosciences, Franklin Lakes, NJ). For intracellular staining, cells were fixed and permeabilized with BD fixation/perm solution for 30 minutes at room temperature (BD Biosciences, Franklin Lakes, NJ). 1 μg of rhAb was added to the intracellular stains and 5 μg of rhAb was added to the extracellular stains for 1 hour at room temperature. Secondary anti-human-APC (BD Pharmigen, San Jose, CA) or anti-rabbit-FITC (BD Pharmigen, San Jose, CA) was incubated with the cells for 30 minutes at room temperature. Data was collected on a FACSAria (Becton Dickenson, San Jose, CA) or LSR (Becton Dickenson, San Jose, CA) flow cytometer.

Results

Figure 20A:
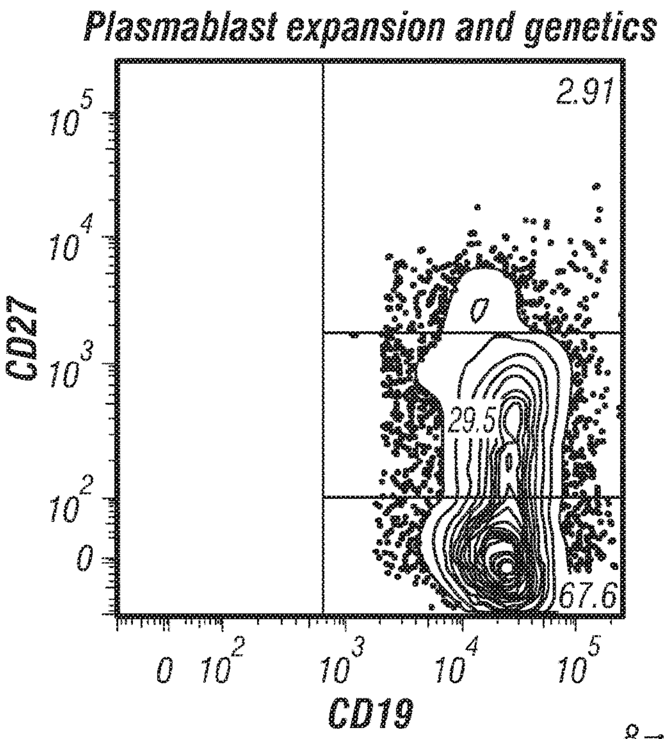
FIGS. 20A-20D. Plasmablast expansion and genetics.
Figure 20B:
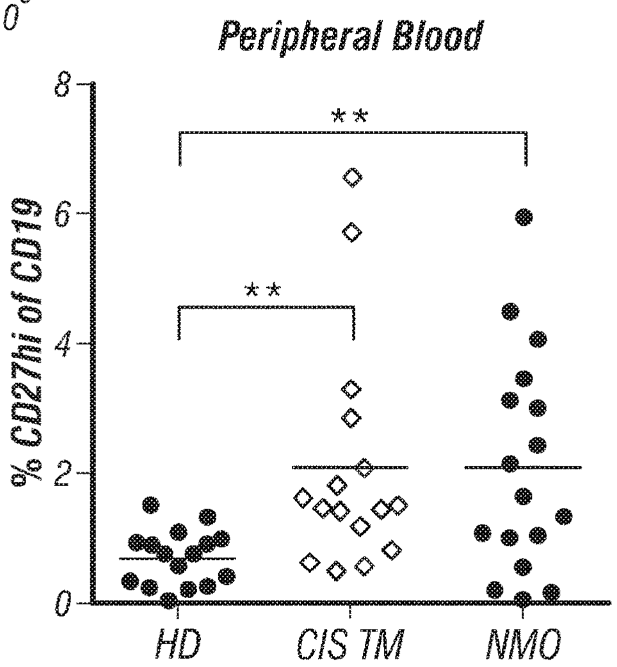

Expansion of peripheral PBs is common to patients experiencing transverse myelitis symptoms. Previously, the inventor's laboratory demonstrated that peripheral plasmablasts are expanded in clinically isolated syndrome (CIS) patients experiencing their first partial transverse myelitis attack (CIS-PTM). Plasmablasts are also increased in Neuromyelitis Optica (NMO), a neurological disease where patients also experience transverse myelitis symptoms, but without brain inflammation. To ascertain the extent of this increase, the inventor determined the frequency of CD19+CD27high plasmablasts in PBMCs from healthy donors, CIS-PTM patients and NMO patients by flow cytometry (FIG. 20A). As expected, peripheral plasmablasts were present in CIS-PTM and NMO patients to a similar extent (2.10% vs 2.12%, p=0.98), and both were elevated over steady state production in healthy donors (2.10% vs 0.71%, p=0.005) (FIG. 20B).

Expanded peripheral PBs in CIS-PTM patients over-utilize VH4 antibody genes. B cells create their unique antigen receptor by processes of immunoglobulin gene segment recombination, light and heavy chain pairing, and somatic hypermutation. Previous data from the inventors' laboratory demonstrate that B cells in the CSF of CIS-PTM patients at high risk to convert to MS tend to over-utilize immunoglobulin heavy chain V-region subgroup 4 (VH4) gene segments. VH4 family genes are also associated with autoreactivity in MS patients and other autoimmune diseases such as systemic lupus erythematosus. To determine whether peripheral plasmablasts tend to utilize VH4 genes, the inventor isolated and sequenced the variable domain of immunoglobulins of individual peripheral plasmablasts from CIS-PTM and NMO patients. Antibody repertoire data from these peripheral plasmablasts were compared to published control databases of healthy total peripheral B cells and flu-responding peripheral plasmablasts.

Figure 20C:
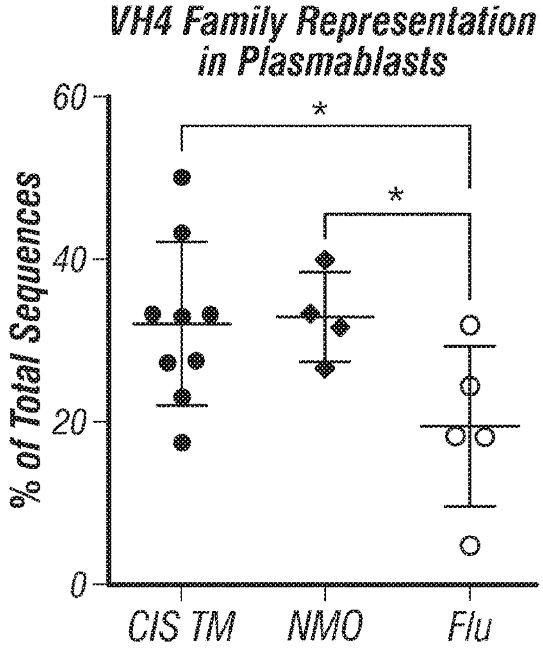
Figure 20D:
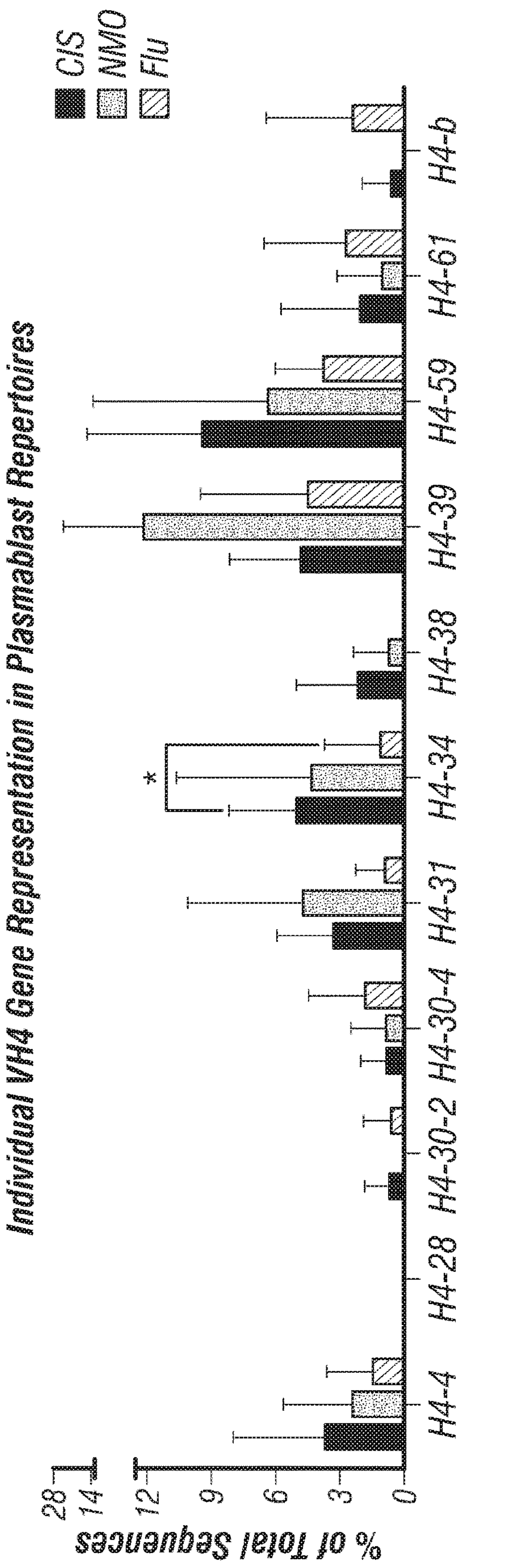

Approximately 19% of peripheral plasmablasts from healthy donors responding to influenza infection utilize VH4 genes (FIG. 20C), which is a similar proportion to that of healthy donor total peripheral B cells. In contrast, 32% of peripheral plasmablasts from CIS-PTM patients utilize VH4 genes, which was statistically higher than flu-responding peripheral plasmablasts (p=0.04) (FIG. 20C). Plasmablasts from NMO patients demonstrated a similar expansion of VH4 usage compared to CIS-PTM patients (33% v 32%, p=0.88). When individual genes within the VH4 family are assessed, the frequency of VH4-34 was statistically elevated in plasmablasts from CIS-PTM patients compared to plasmablasts responding to influenza (p=0.04) (FIG. 20D). VH4-31 was statistically elevated in plasmablasts from CIS-PTM patients compared to healthy donor total peripheral B cells (3.25% vs 0.0%, p=0.02), but not plasmablasts responding to influenza (p=0.05). Normally these genes are selected against due to their natural propensity for autoreactivity. No other genes within the VH4 family were statistically elevated in CIS-PTM patients compared to controls as well as other V gene families. A more comprehensive antibody genetic analysis is provided in FIGS. 21A-21F and 22A-22E.

CIS-PTM peripheral plasmablasts bind strongly to brain antigens. The researchers next sought to examine whether antibodies expressed by the peripheral plasmablasts of CIS-PTM patients are autoreactive. To do this, the inventor generated recombinant human antibodies (rhAbs) from 38 peripheral plasmablasts isolated from 7 CIS-PTM patients. The researchers also generated 10 rhAbs from 4 NMO patients and 6 rhAbs from 1 healthy donor as controls. Of those CIS-PTM rhAbs from which the inventor could determine isotype, 85% were IgG+ and all had significant mutation accumulation that marked them as having undergone affinity maturation (Table 8).

Figure 23A:
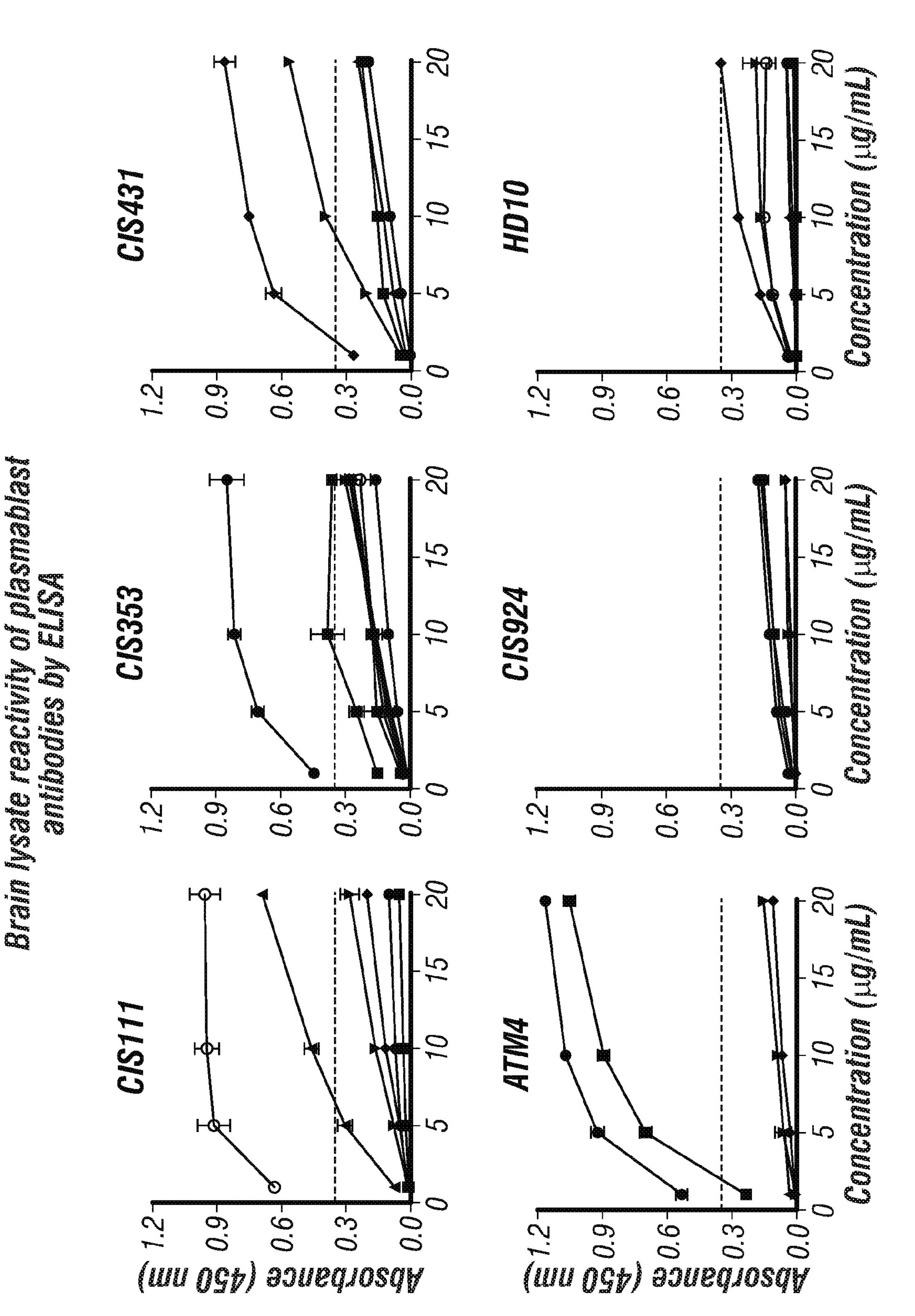
FIGS. 23A-23B. Brain lysate reactivity of plasm blast antibodies by ELISA.
Figure 23A:
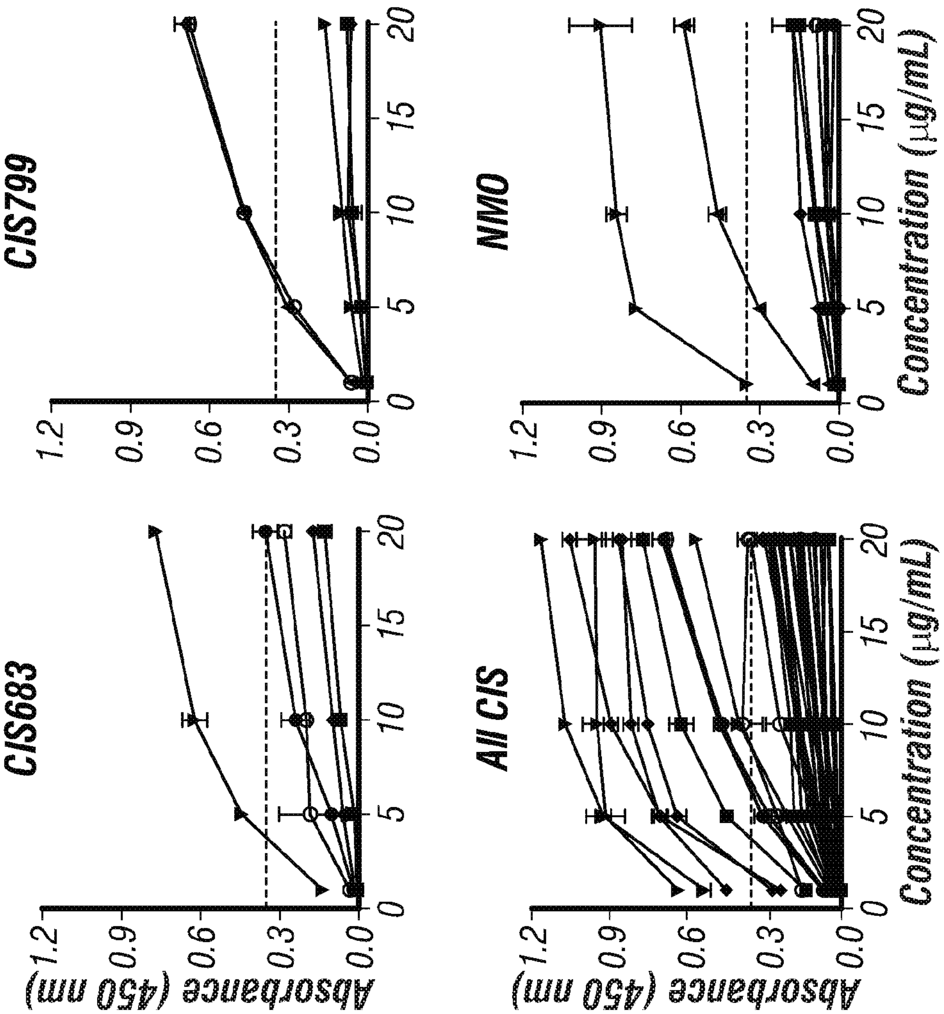
Figure 23B:
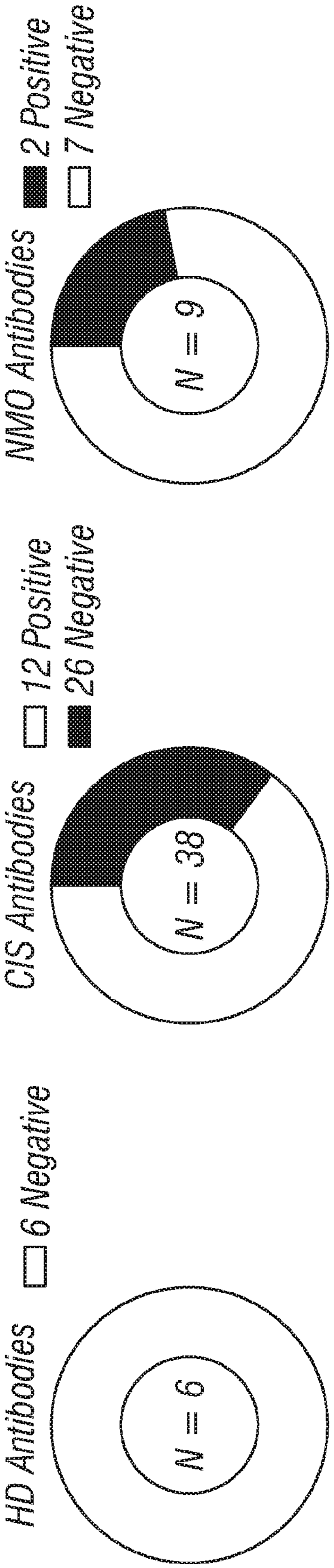
Figure 24A:
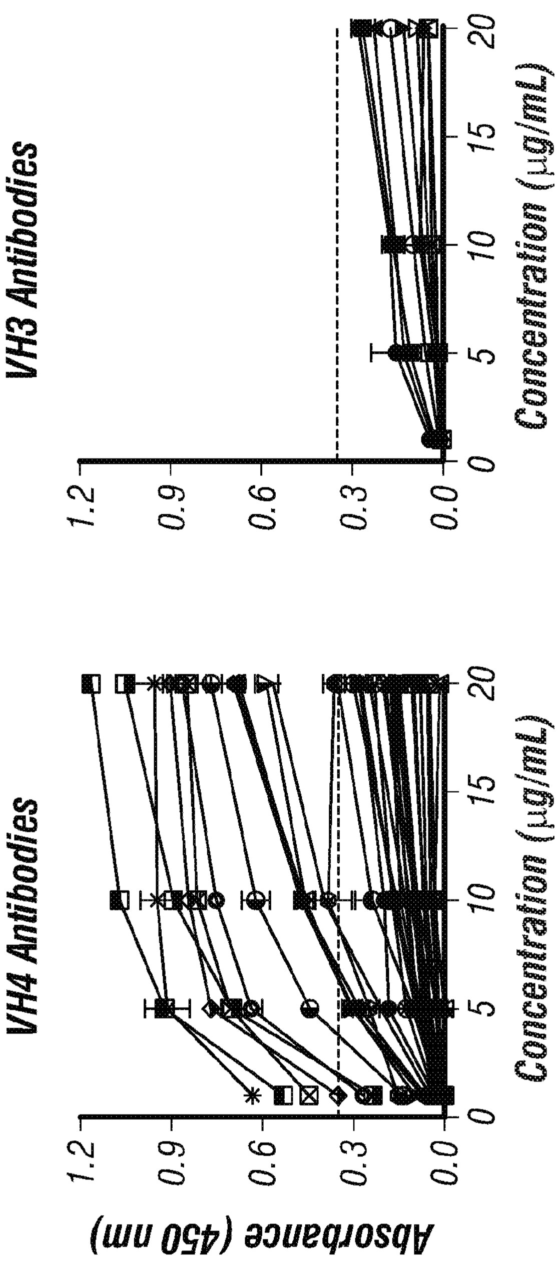
FIGS. 24A-24C. Comparison of VH4 and VH3 antibodies.
Figure 24B:
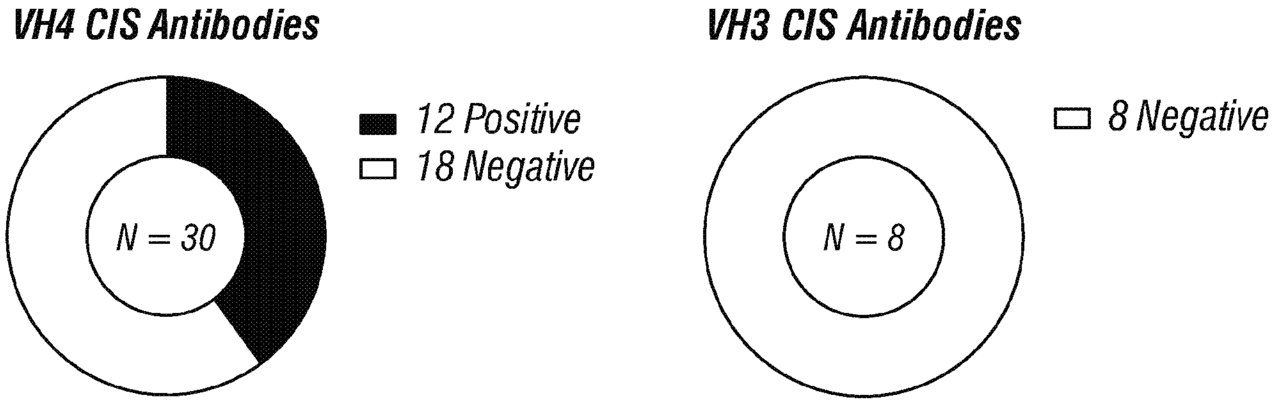
Figure 24C:
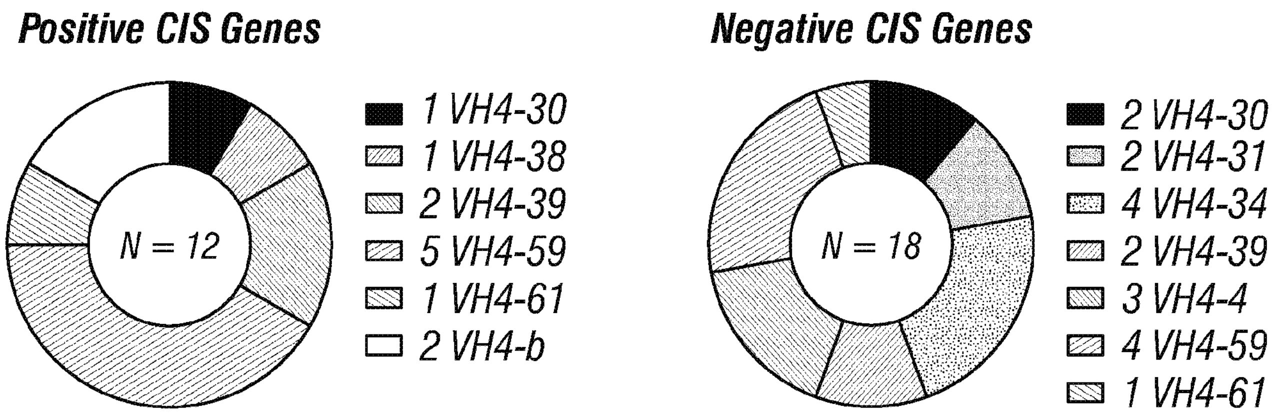
Figure 25A:
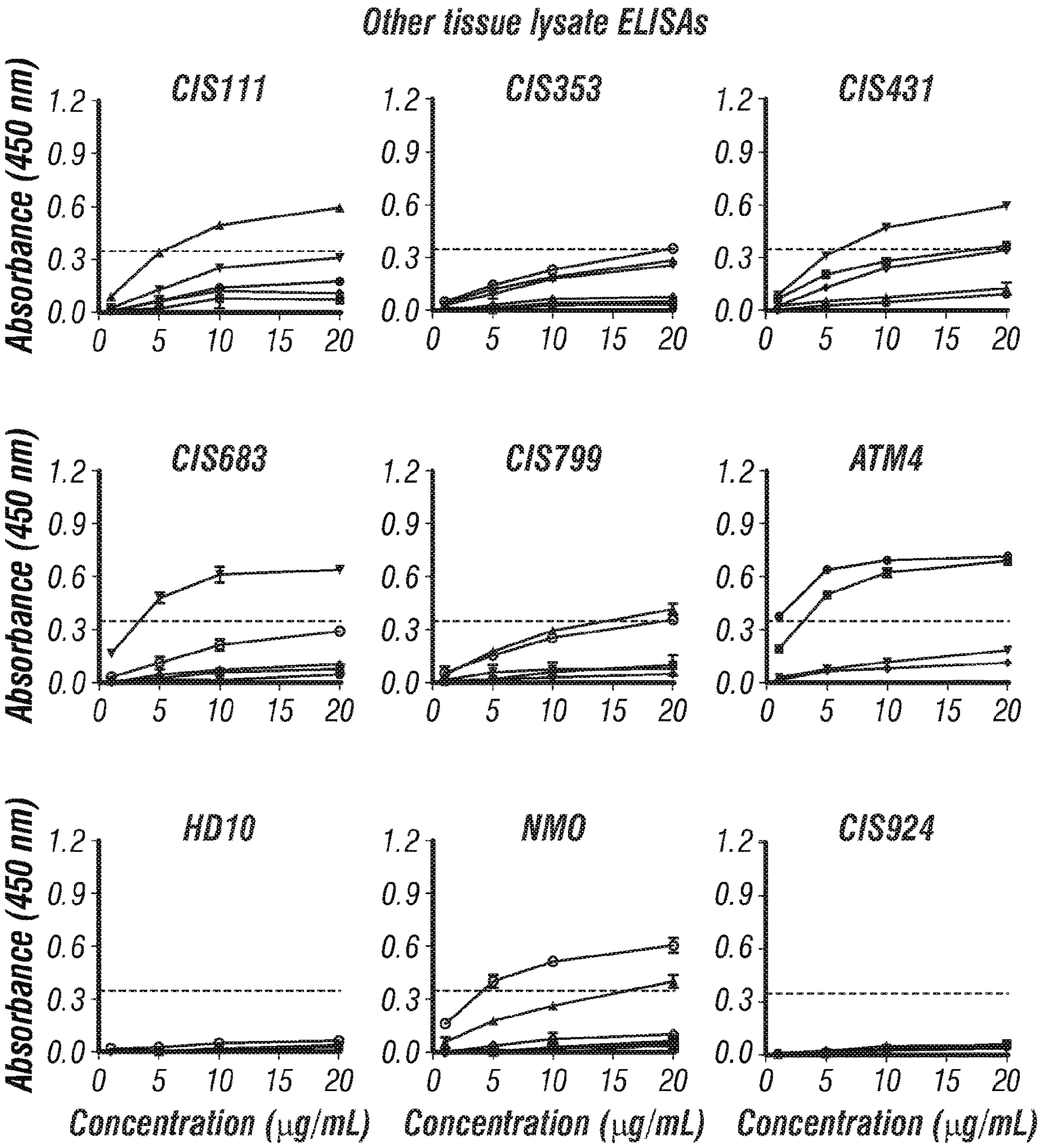
FIGS. 25A-25C. Other tissue lysate ELISAs (FIG. 25A) Kidney ELISA results grouped by patient.
Figure 25B:
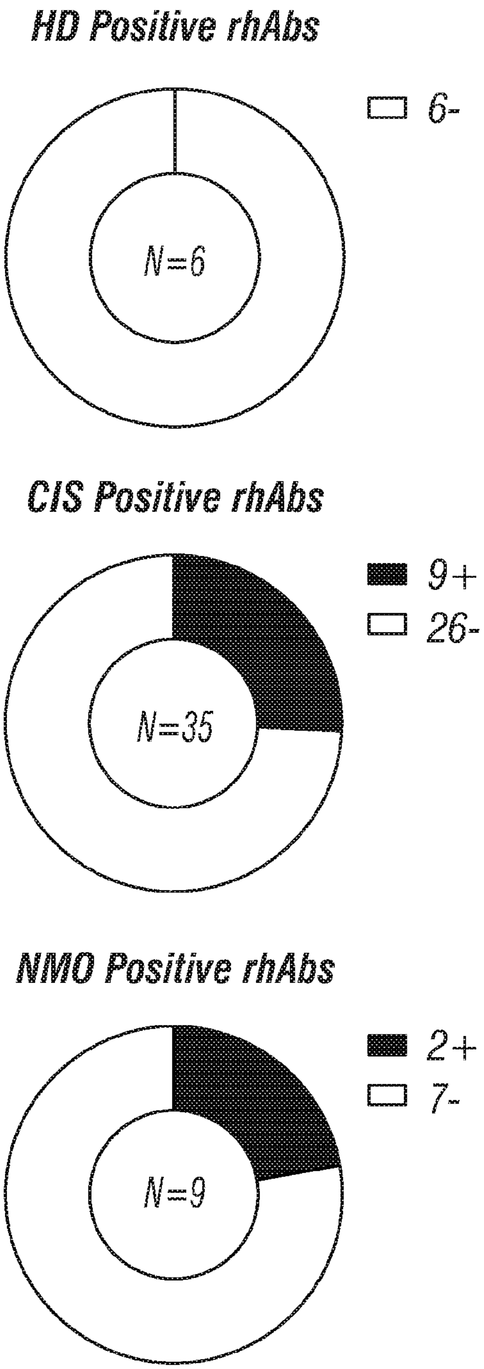
Figure 25C:
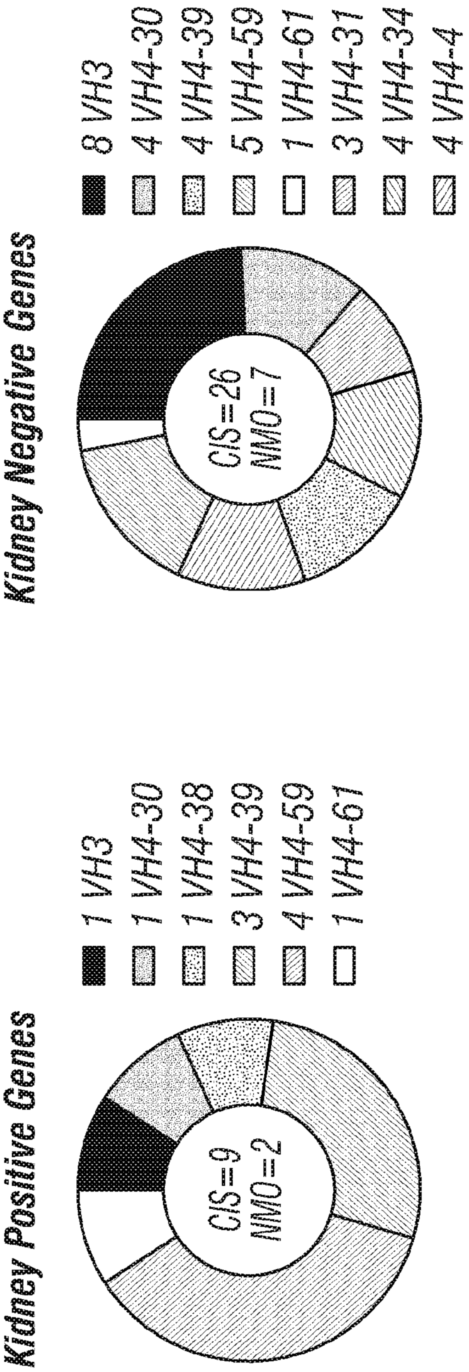

The researchers first tested these recombinant human antibodies (rhAbs) for binding to brain antigens using a brain lysate ELISA. The six rhAbs from healthy donor peripheral B cells were used as negative controls and were not reactive in this assay (FIGS. 23A-23B). In contrast, 32% of the rhAbs (12 out of 38) from the CIS-PTM cohort recognized brain lysate by ELISA, and 22% of the rhAbs (2 out of 9) from the NMO cohort recognized brain lysate by ELISA. Of the 12 CIS-PTM rhAbs that demonstrated positive reactivity to brain lysate by ELISA, 7 of them also recognized kidney lysate, indicating autoreactivity to more ubiquitous antigens in some cases (FIGS. 24A-24C). Both of the NMO rhAbs that bound to brain lysate were reactive to kidney lysate (Table 8).

Next, the inventor binned the 38 rhAbs from the CIS-PTM patients by their use of VH4 or VH3 genes, and observed that the rhAbs reacting strongly to brain lysate utilized VH4 genes (FIG. 24A, 24B). None of the rhAbs utilizing VH3 genes reacted to brain lysate despite high mutation frequencies (FIG. 24A, 24B). Positive reactivity to brain lysate by ELISA was noted for rhAbs using 6 of the 9 VH4 genes, while rhAbs using one of the other 3 VH4 genes (VH4-4, 4-31, and 4-34) were not reactive in this assay (FIG. 24C). However it should be noted that the relative representation of antigens in the lysate might encourage false negatives.

Figure 26A:
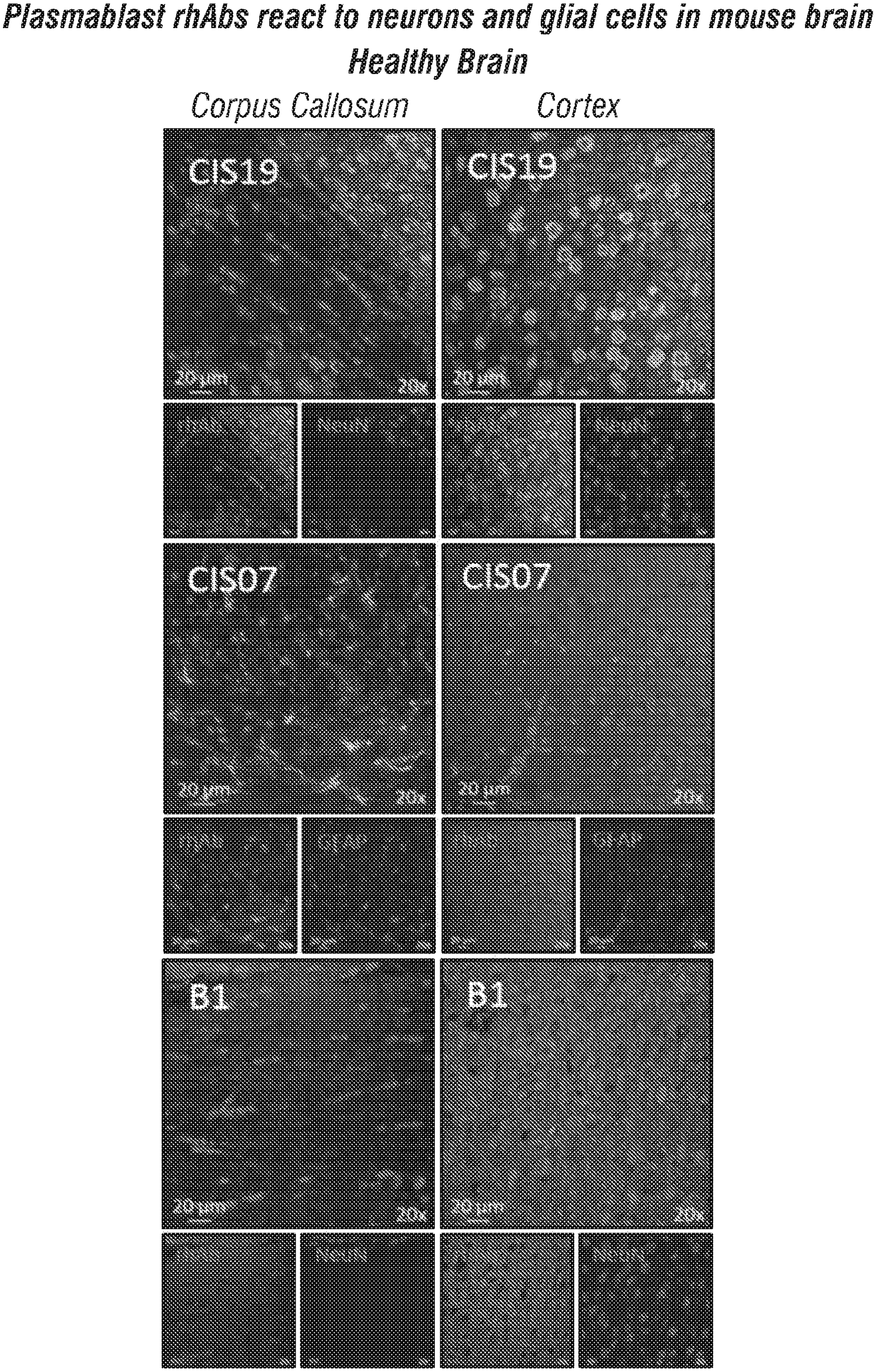
FIGS. 26A-26E. Plasmablast rhAbs react to neurons and glial cells in mouse brain. 20× images of rhAbs staining neurons and glia in the white (corpus callosum, left) and gray (cortex, right) matter of healthy mouse brain (FIG. 26A), stroke brain (FIG. 26B) and EAE brain (FIG. 26C); rhAbs that recognized neurons did so in a ring-like pattern around the nucleus and rhAbs that recognized glia bound to cell body processes (FIG. 26D). One quarter of the CIS rhAbs that were positive by ELISA recognized exclusively glia and the remaining three quarters recognized both glia and neurons (FIG. 26E).
Figure 26B:
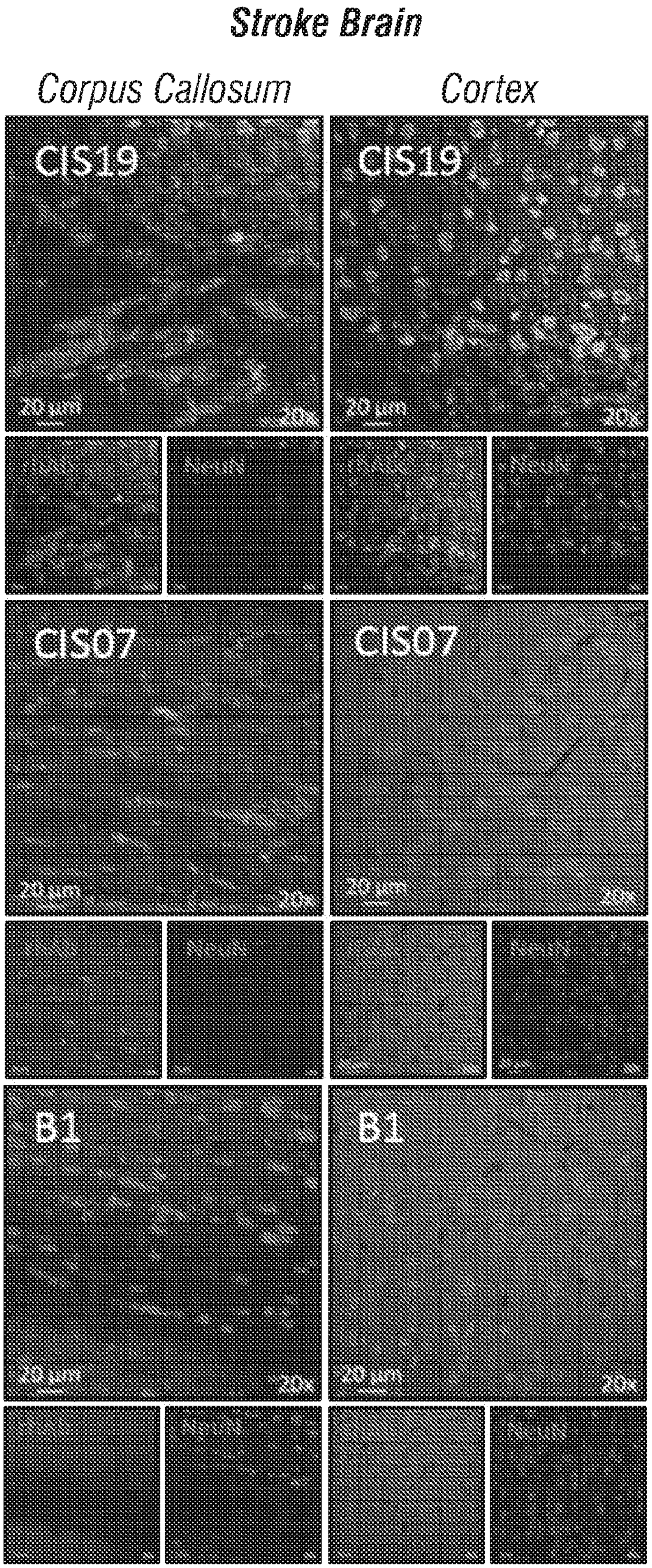
Figure 26C:
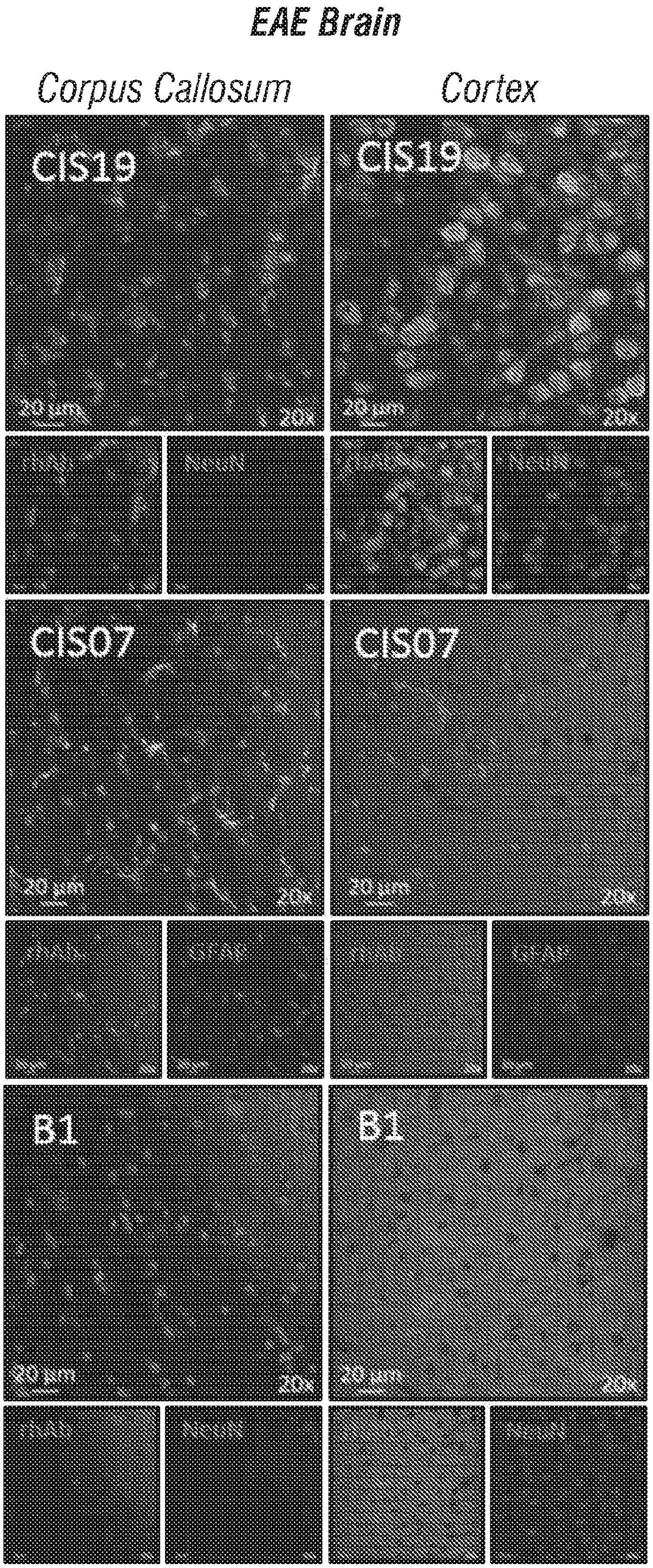
Figure 26D:
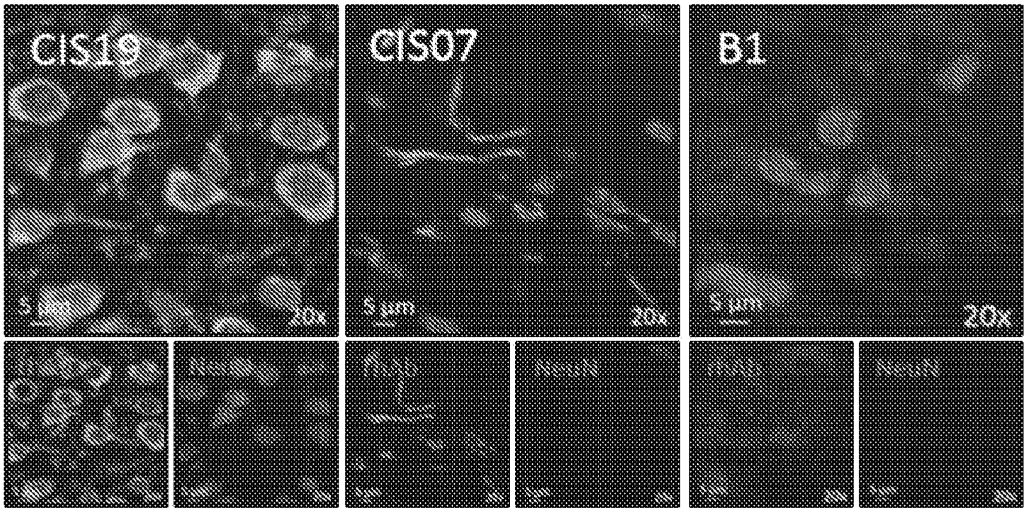
Figure 26E:
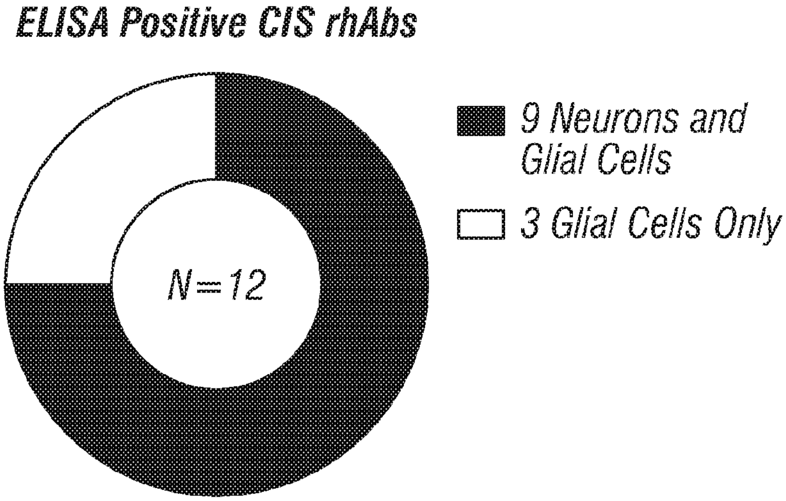
Figure 27:
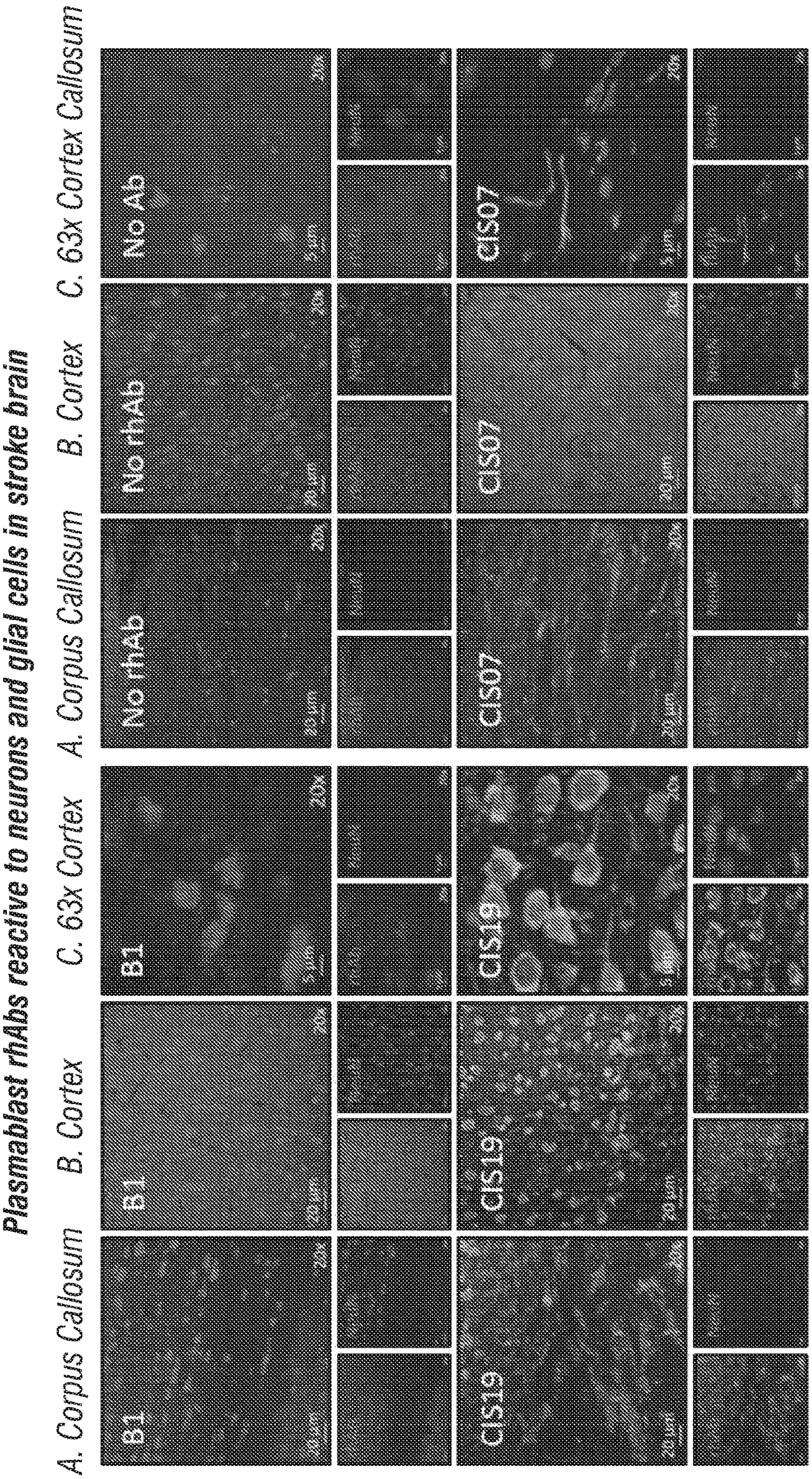
FIGS. 27A-27C. Plasmablast rhAbs reactive to neurons and glial cells in stroke brain.
Figure 27:
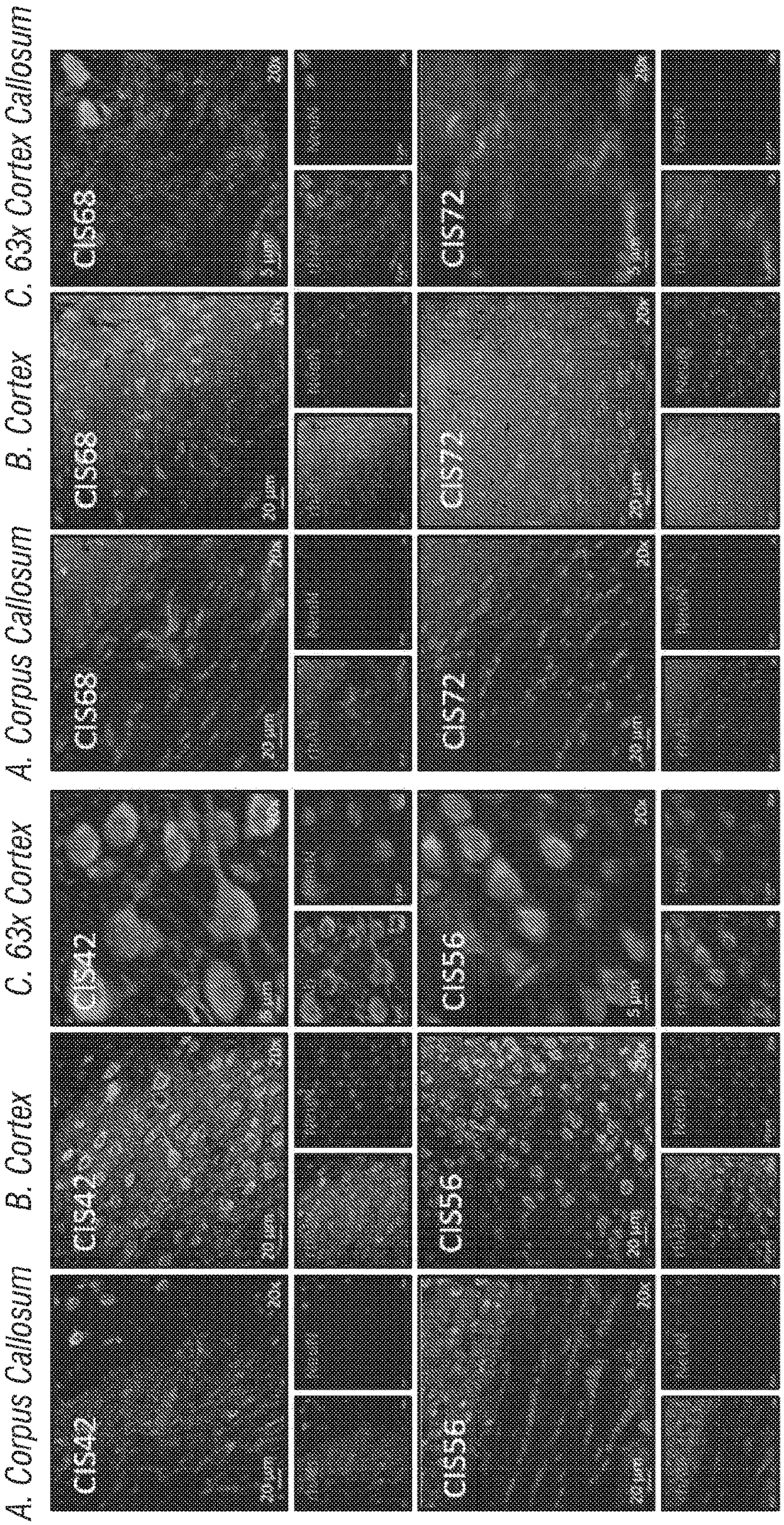
Figure 27:
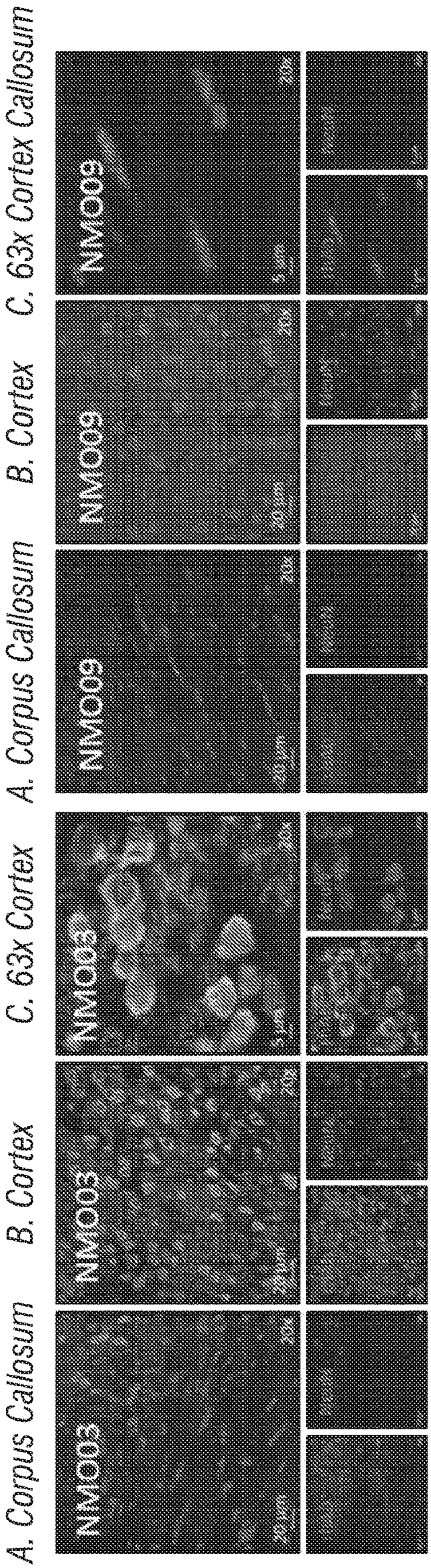
Figure 28:
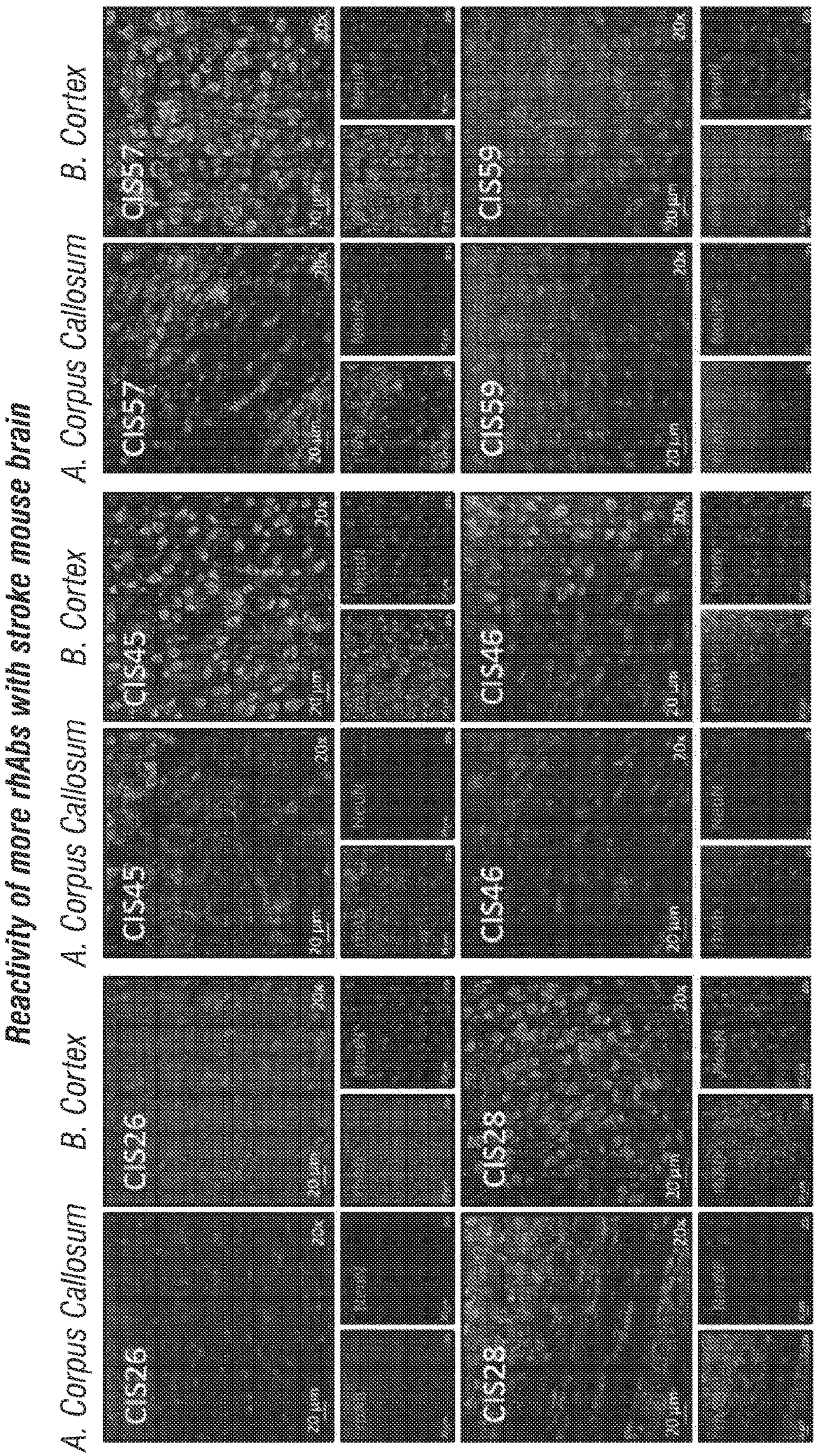
FIGS. 28A-28B. Reactivity of more rhAbs with stroke mouse brain.
Figure 28:
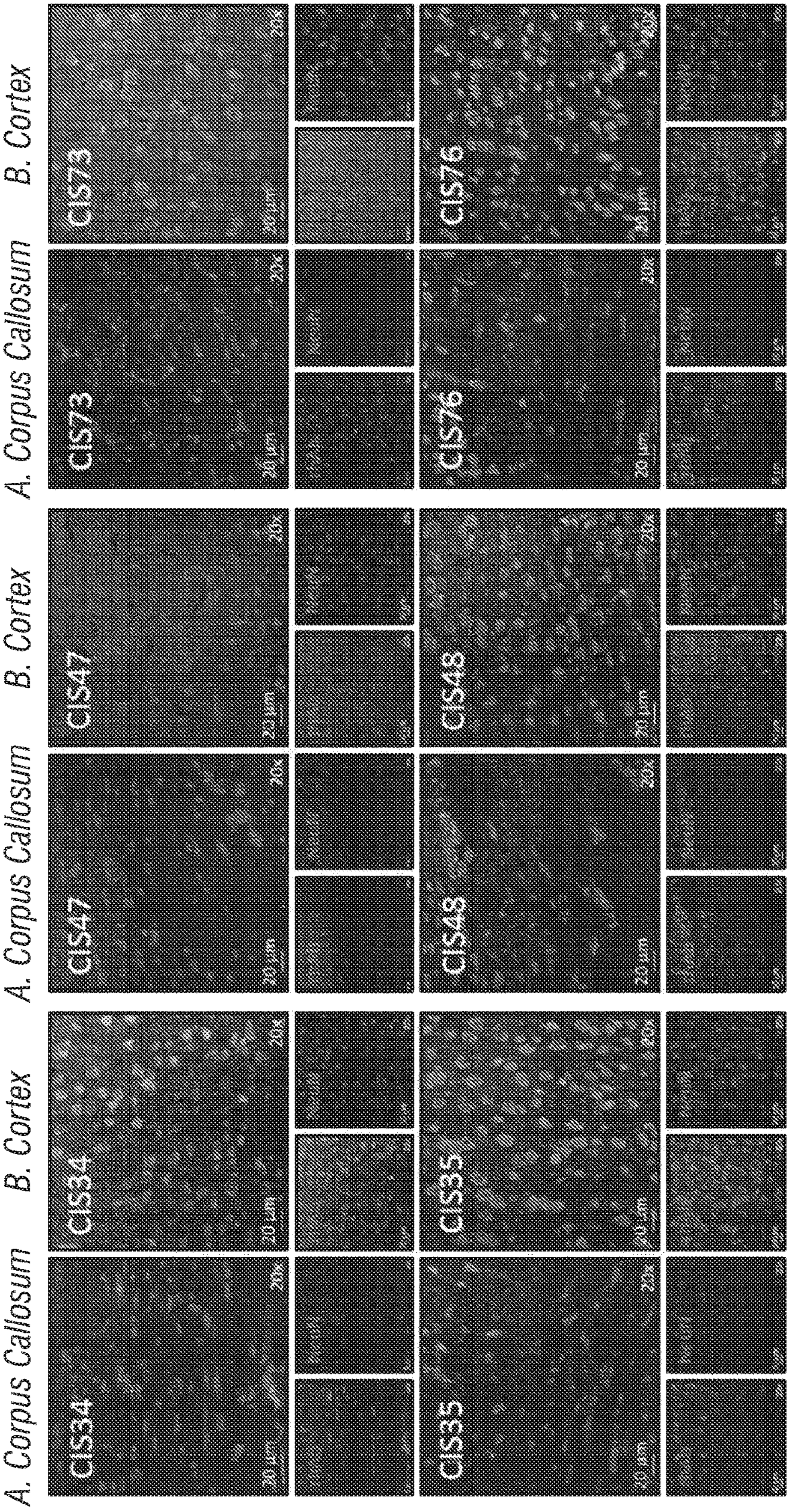
Figure 28:
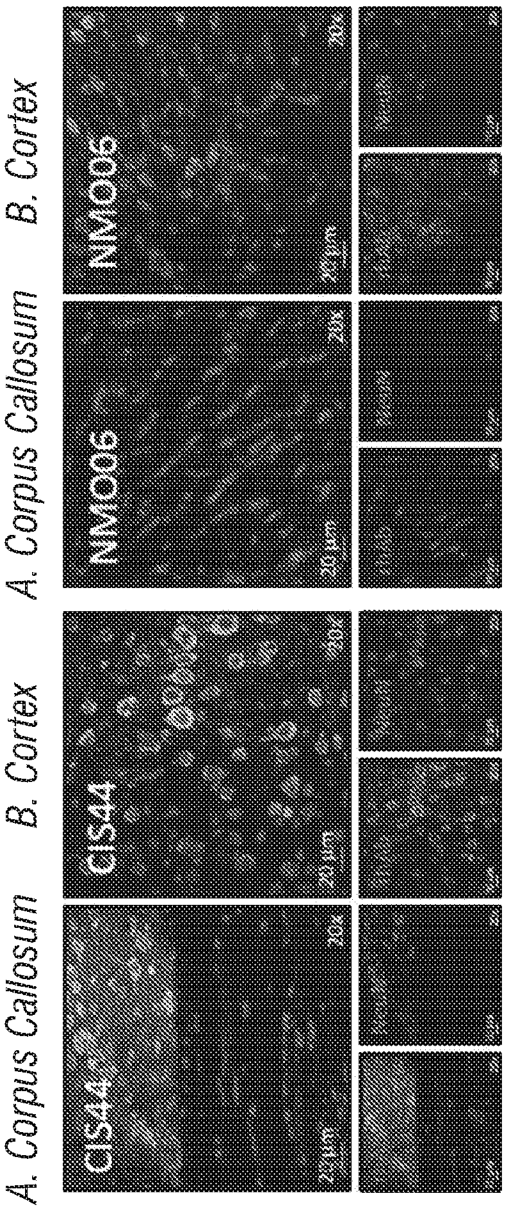
Figure 29:
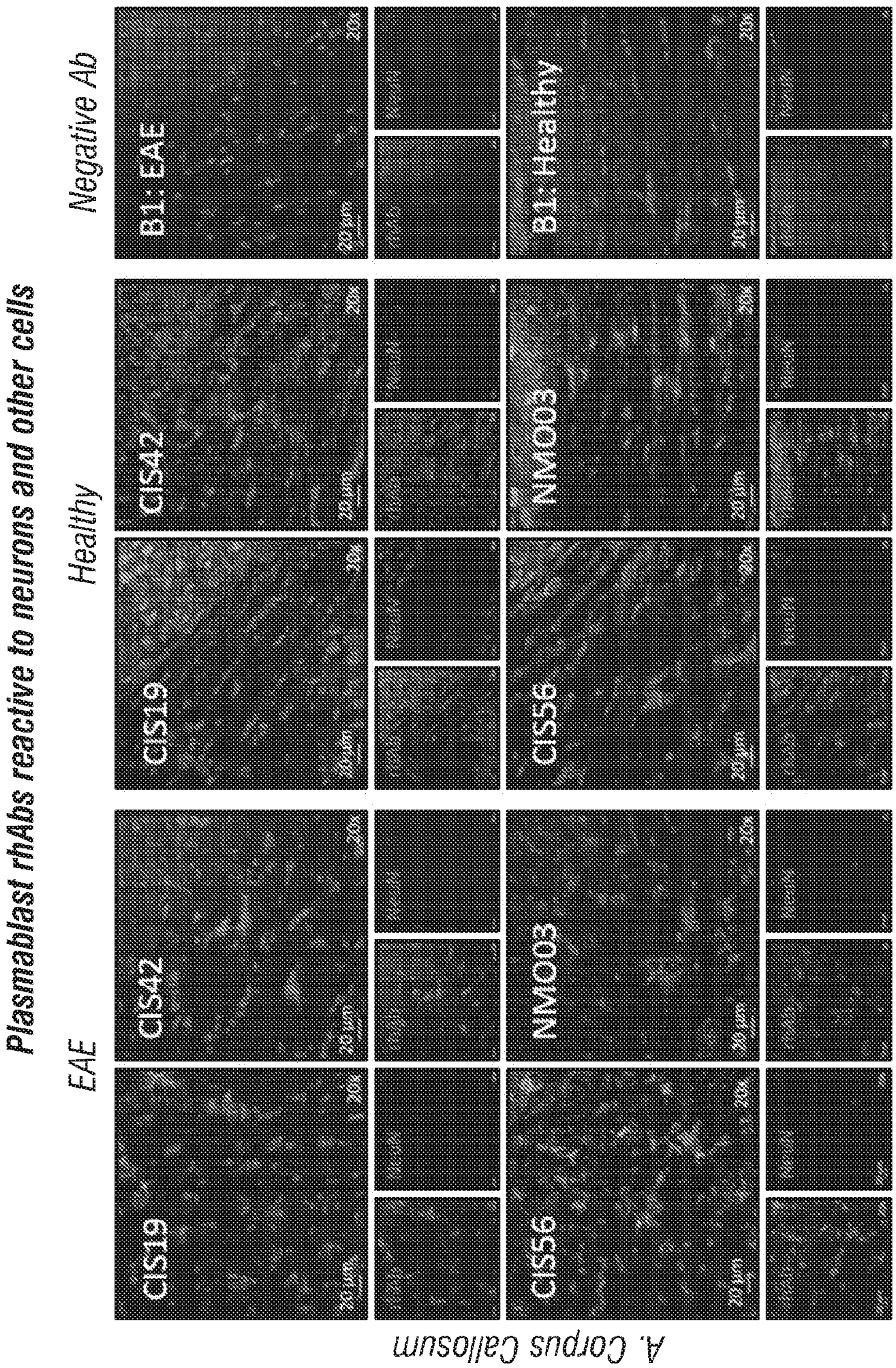
FIGS. 29A-29B. Plasmablast rhAbs reactive to neurons and other cells. Figures show the representative rhAb binding to EAE and healthy mouse corpus callosum (FIG. 29A) and cortex (FIG. 29B). The pattern of rhAb recognition was similar in all three types of mouse brain tissue (FIGS. 27A-27C) and for these examples recognized primarily neuronal bodies, as shown by colocalization with NeuN. Isotype control antibody B1 did not bind EAE and healthy corpus callosum and cortex brain tissue.
Figure 29:
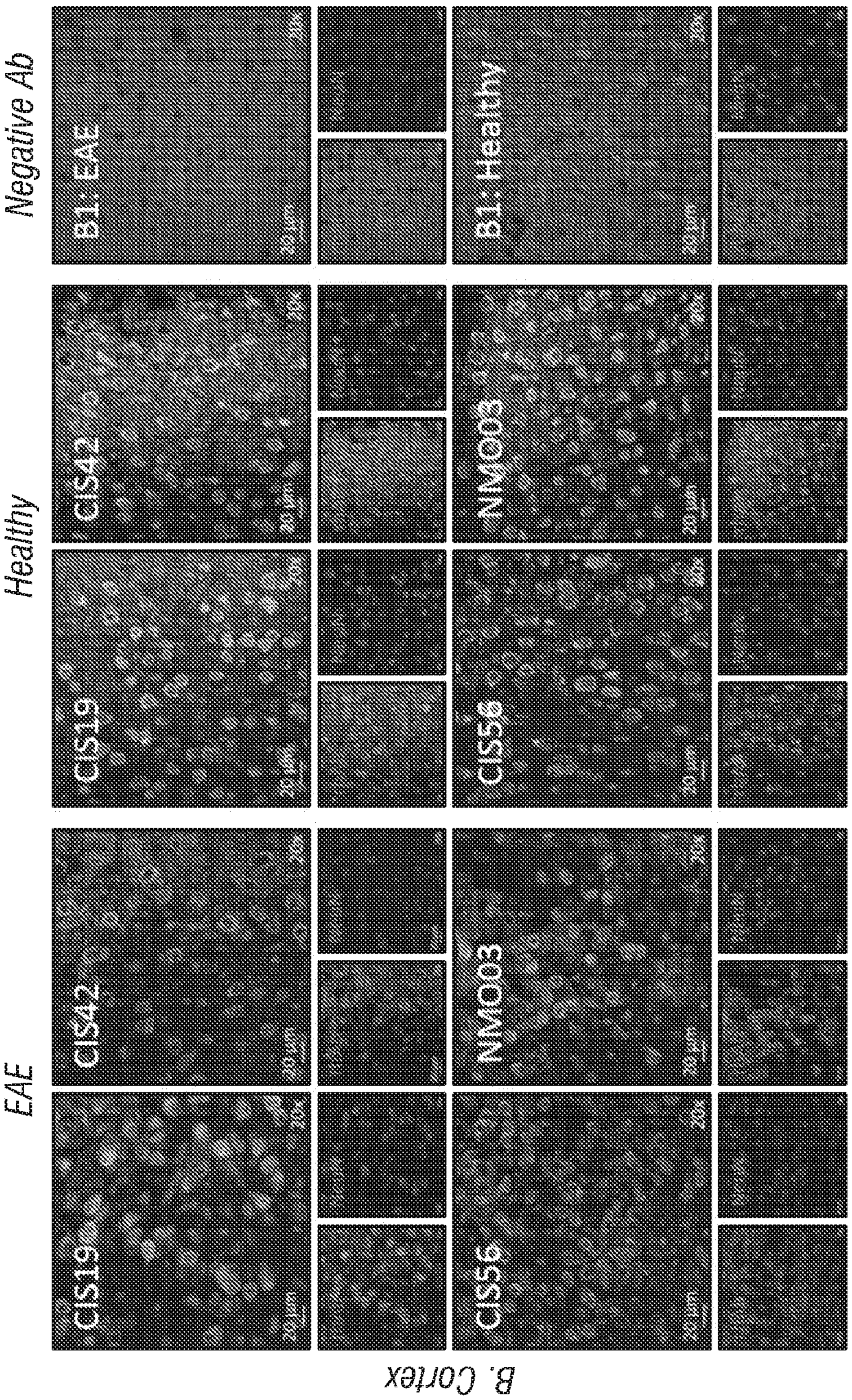
Figure 30:
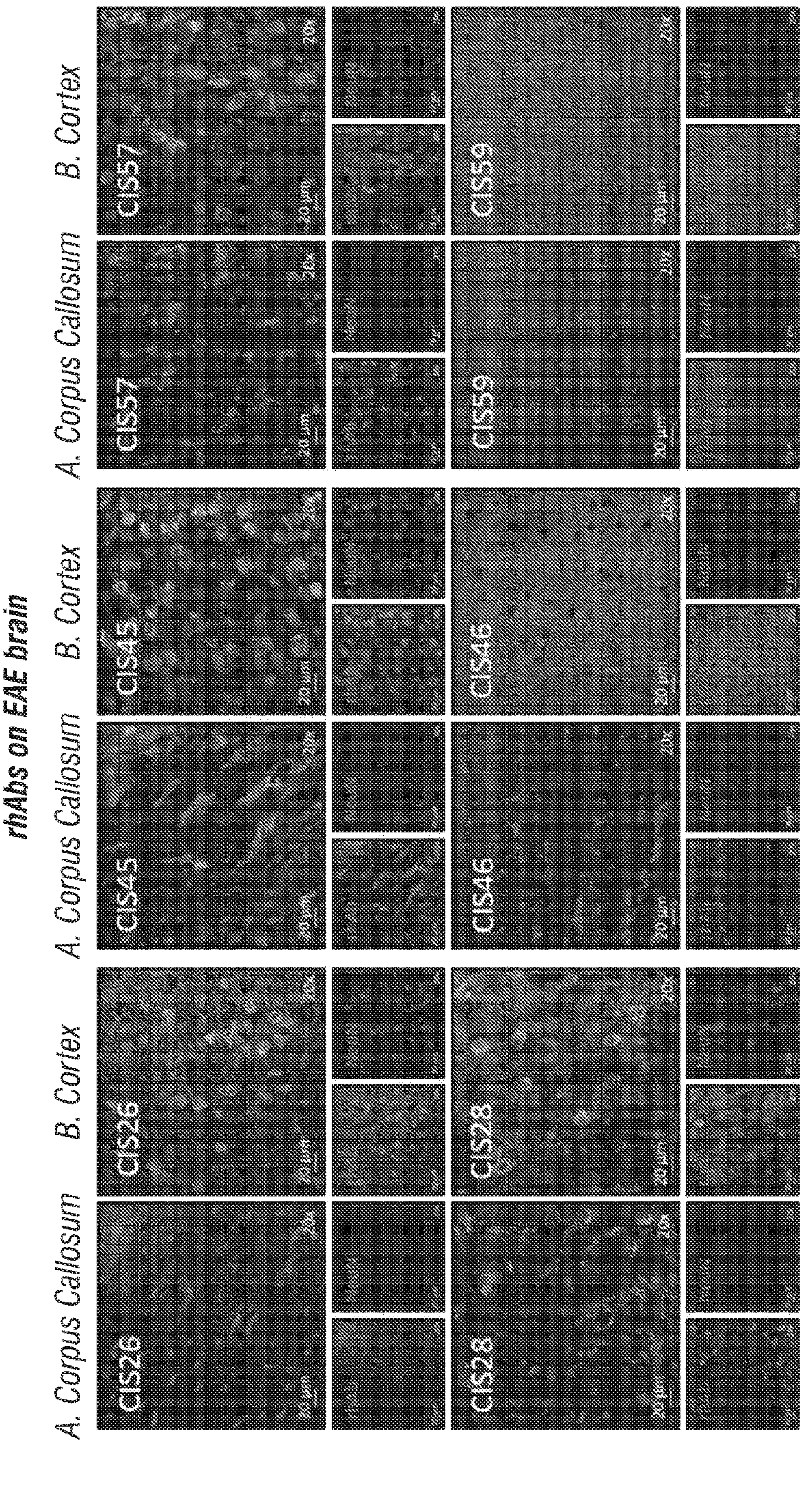
FIGS. 30A-30B. rhAbs on EAE brain. Figures show representative images of additional rhAbs binding to the corpus callosum (FIG. 30A) and cortex (FIG. 30B) of EAE brain tissue. Similar patterns of recognition were observed in many of the rhAbs with neurons and glial cells being the primary targets.
Figure 30:
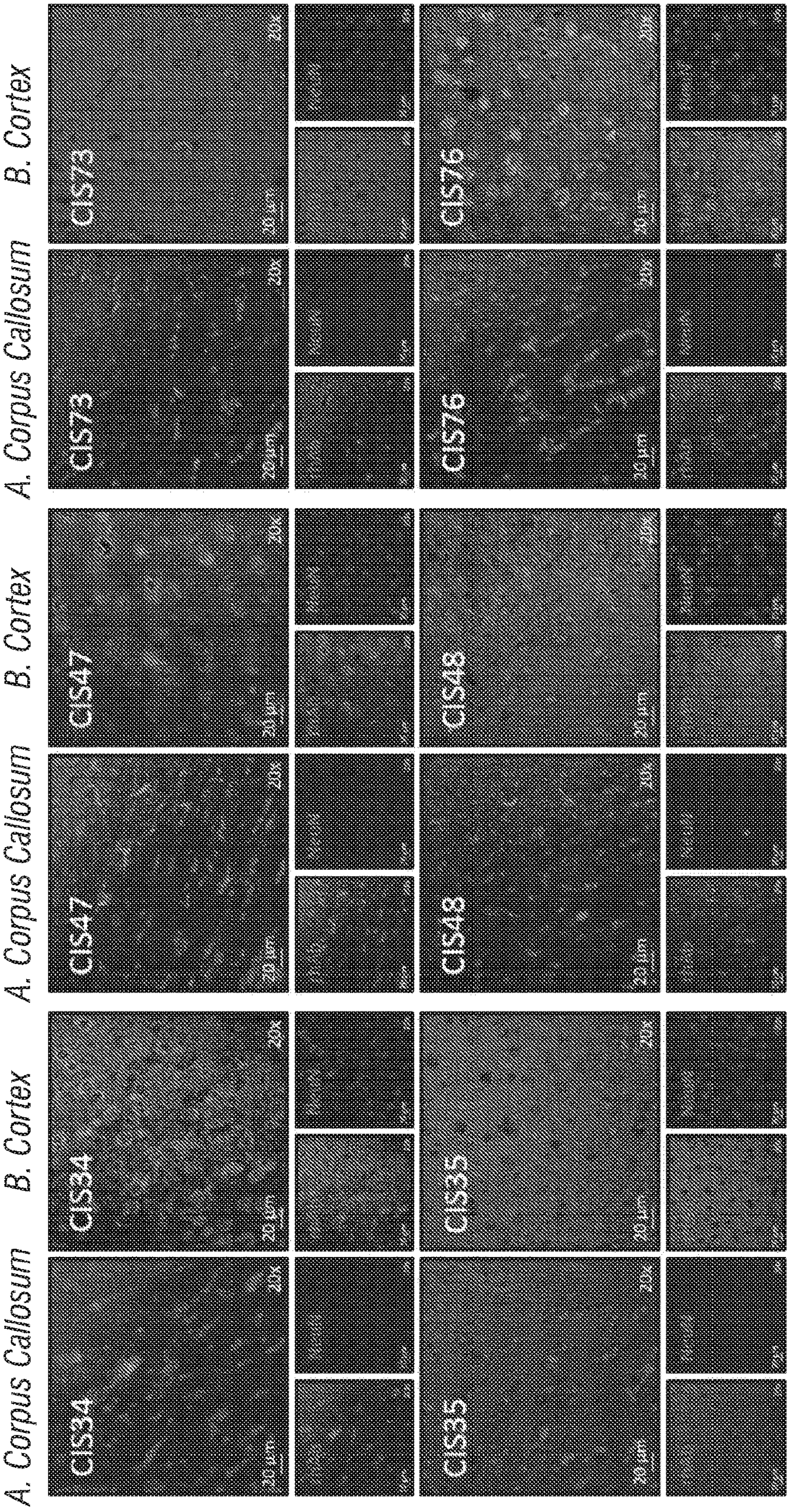
Figure 30:
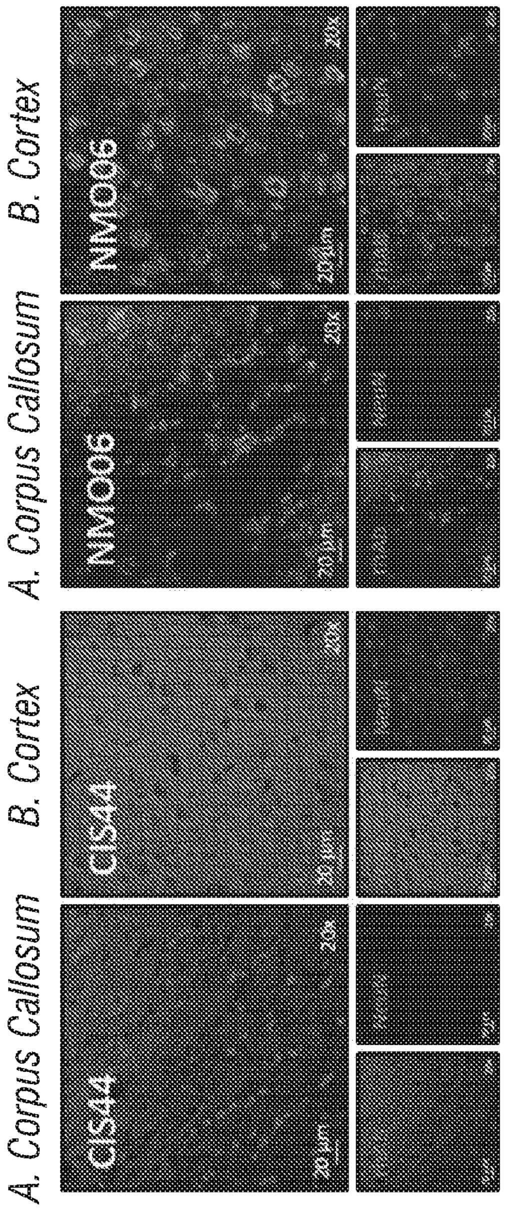
Figure 31:
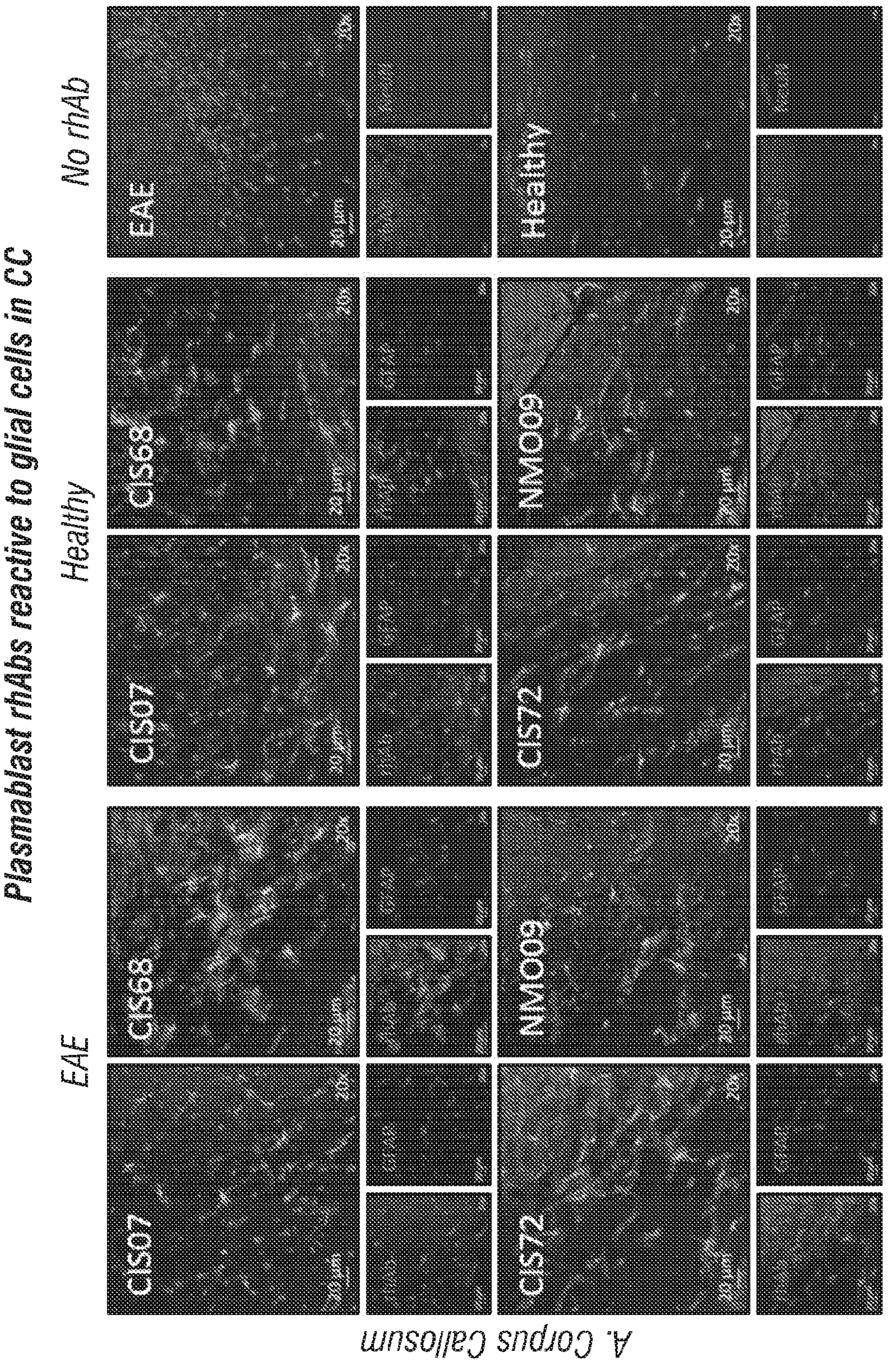
FIGS. 31A-31B. Plasmablast rhAbs reactive to glial cells in CC. Figures show representative rhAb binding to EAE and healthy mouse corpus callosum (FIG. 31A) and cortex (FIG. 31B). The pattern of rhAb recognition was similar in both tissues (FIGS. 27A-27C). The rhAbs shown here primarily colocalized with GFAP, indicating their binding to astrocytes. When no rhAb was incubated on EAE and healthy mouse brain, no flurochrome signal was detected.
Figure 32:
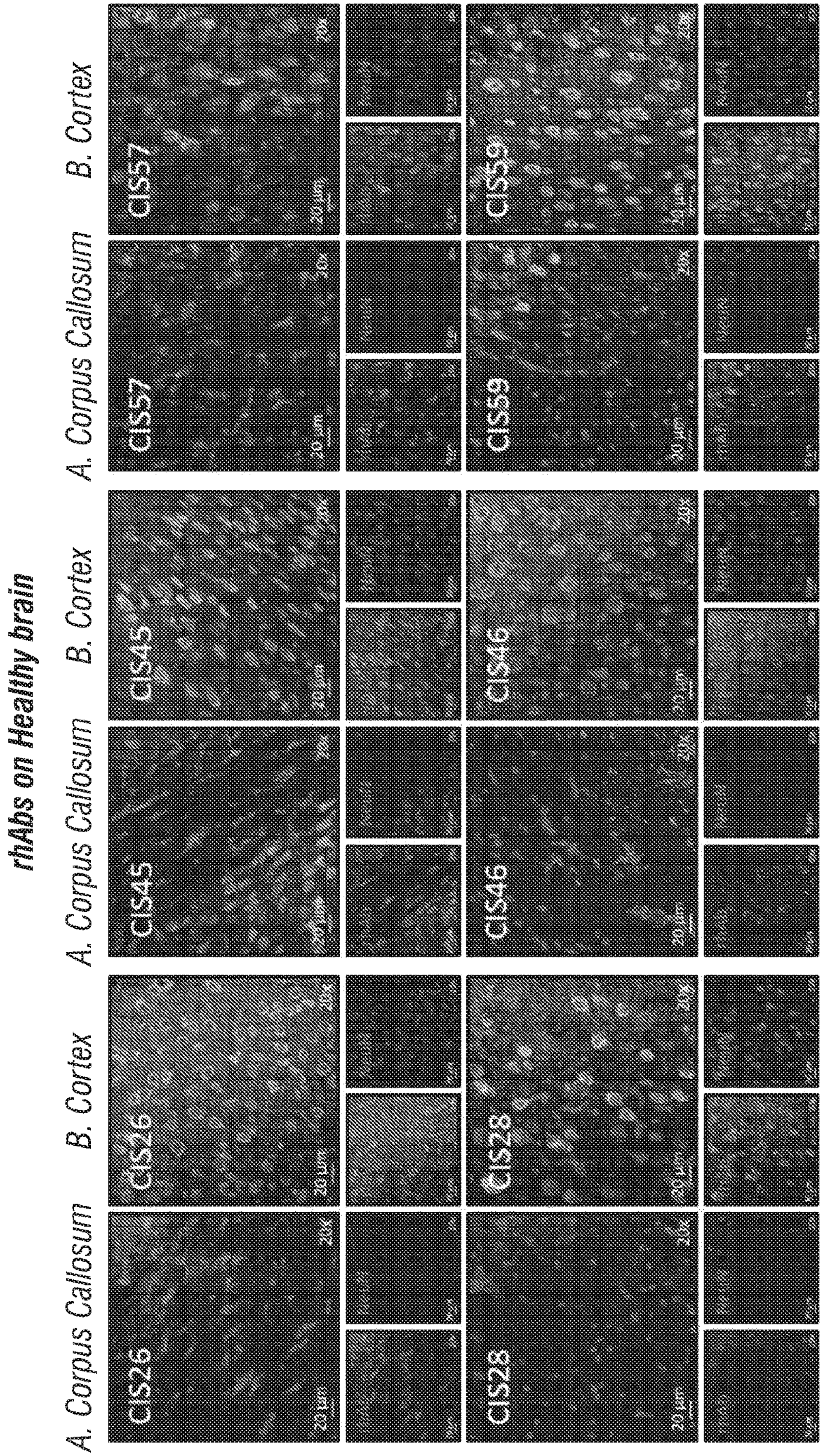
FIGS. 32A-32B. rhAbs on healthy brain. Figures show representative images of additional rhAbs binding to the corpus callosum (FIG. 32A) and cortex (FIG. 32B) of healthy brain tissue. Similar patterns of recognition were observed in many of the rhAbs with neurons and glial cells being the primary targets.
Figure 32:
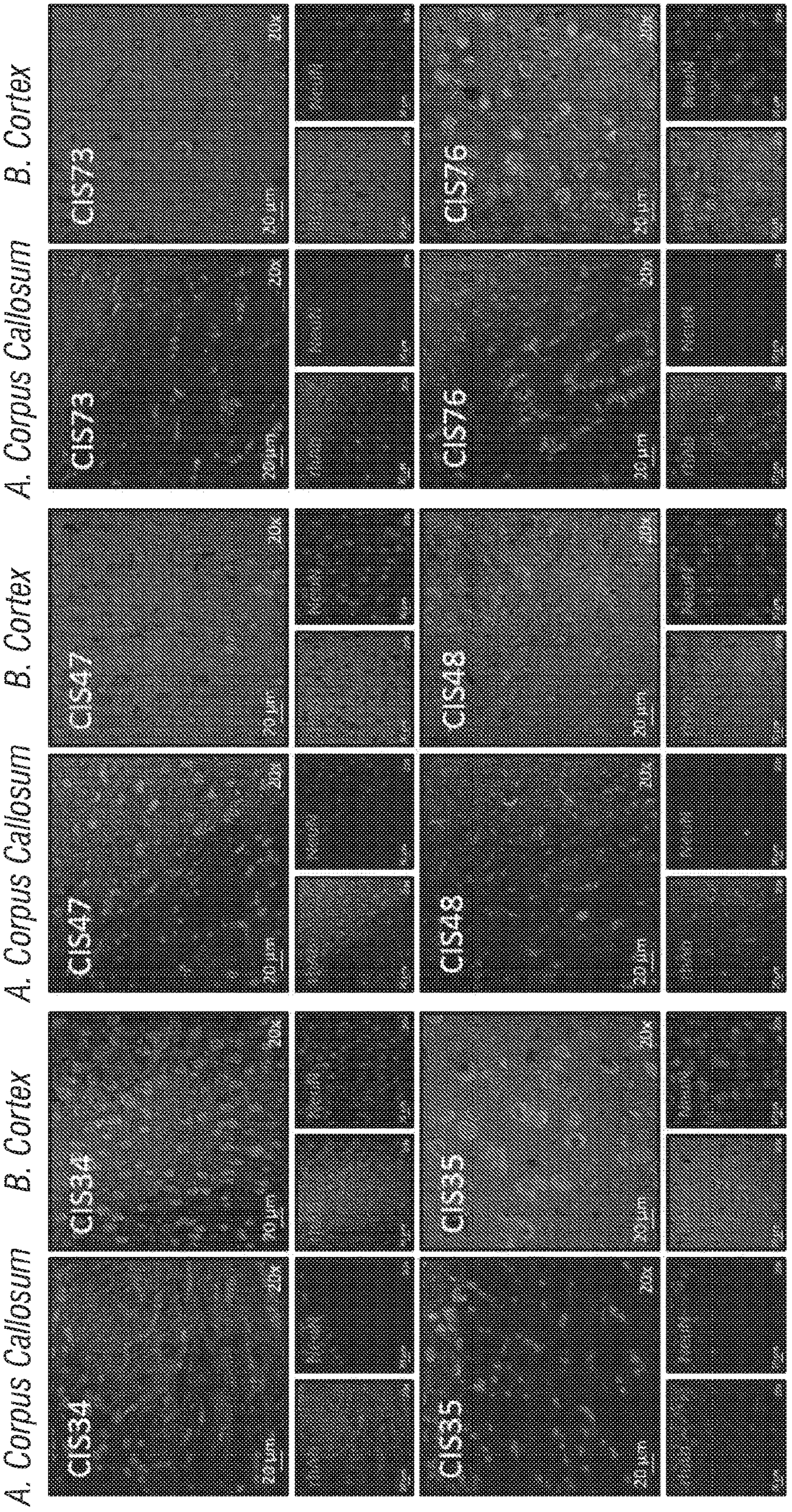
Figure 32:
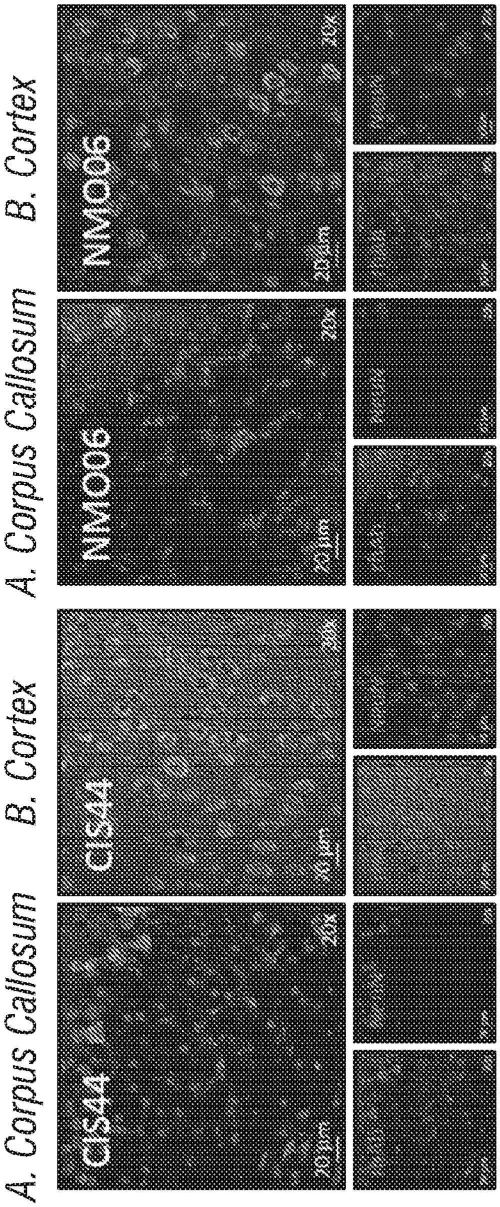
Figure 33:
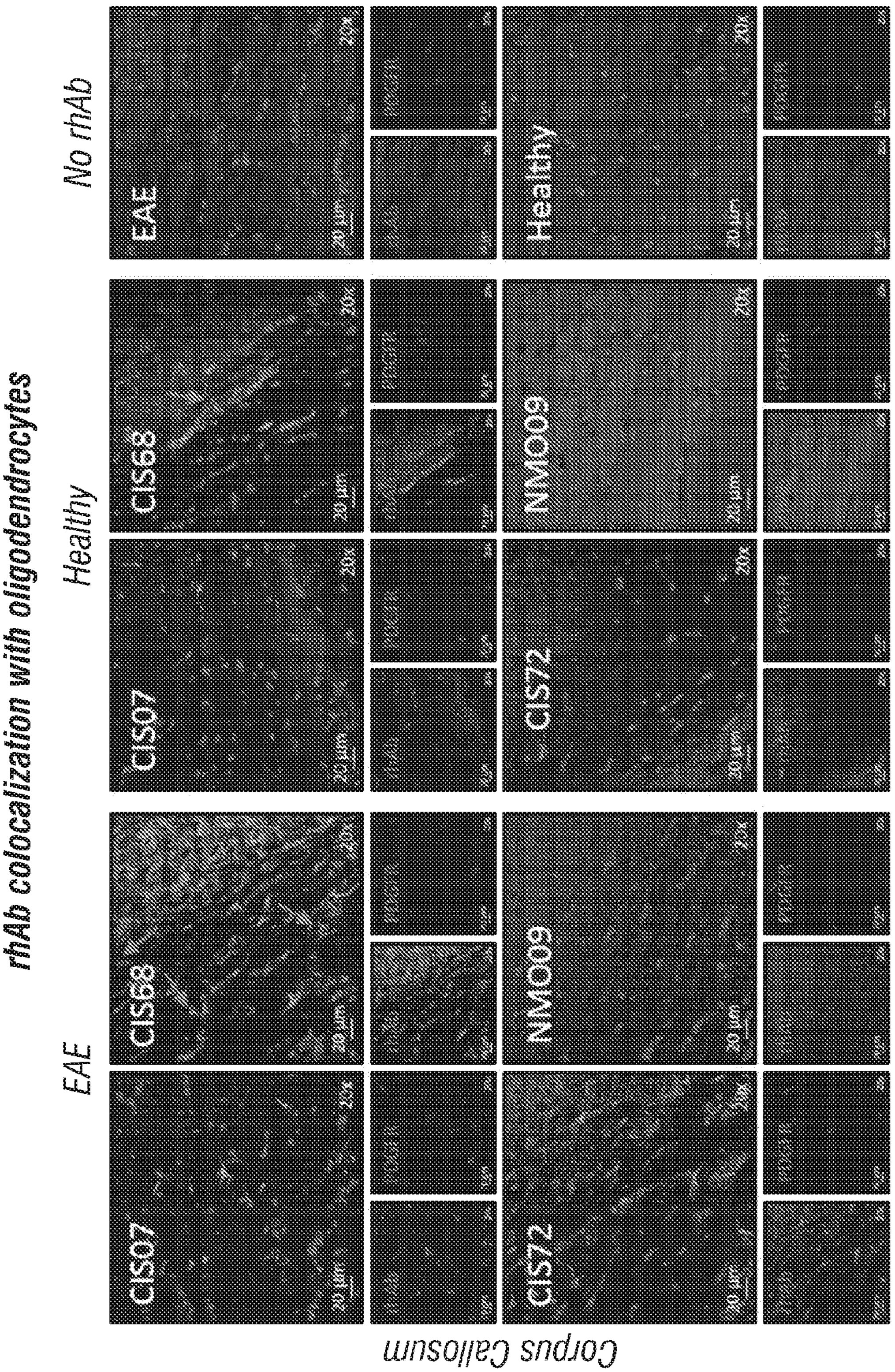
FIGS. 33A-33B. rhAbs colocalization with oligodendrocytes. Figures show representative images of rhAb binding to EAE and healthy mouse corpus callosum (FIG. 33A) and cortex (FIG. 33B). rhAb colocalization with PDGFR indicates oligodendrocyte binding. From this panel of rhAbs, only CIS68 showed some colocalization with this marker.
Figure 34A:
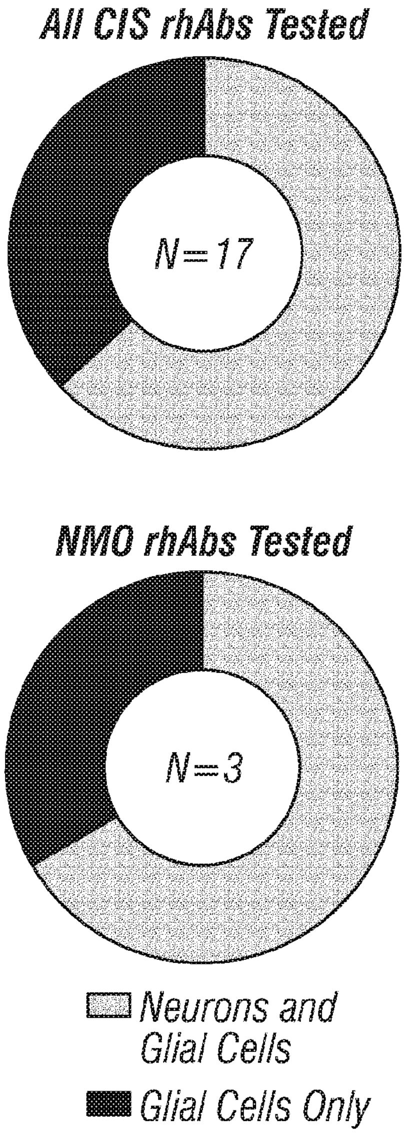
FIGS. 34A-34B: Plasmablast rhAbs binding evaluation by histology.
Figure 34B:
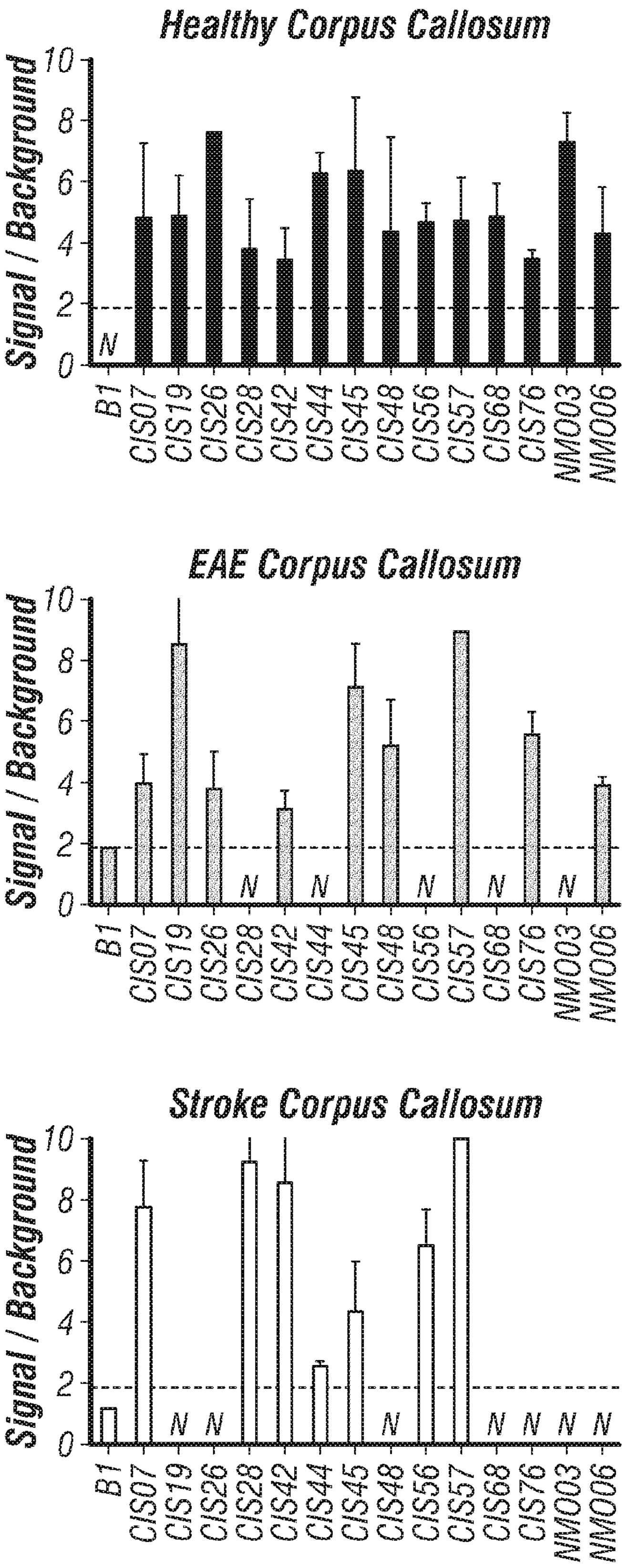
Figure 34B:
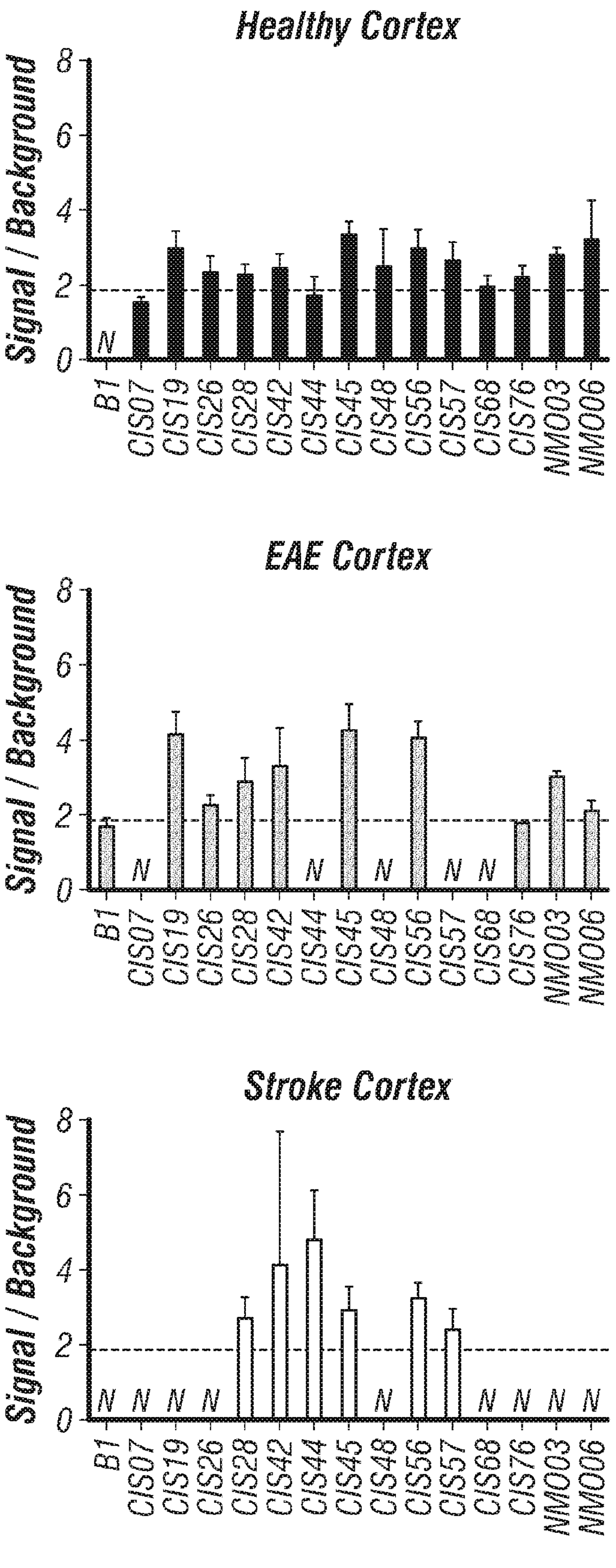

CIS-PTM peripheral plasmablasts bind primarily to neurons and astrocytes. Next, the 12 CIS-PTM rhAbs that demonstrated strong reactivity in the brain lysate ELISA were tested for binding to brain tissue by histology (FIGS. 26A-26E). NMO rhAbs (n=3) were included as comparators and two control antibodies from lupus patients were utilized in this part of the study (B1 as a negative control and G11 as a positive control). Healthy mouse brain was used to investigate binding to normal tissue, stroke mouse brain was used to test reactivity to generally inflamed tissue, and EAE brain was used to study reactivity to inflamed tissue in the context of an MS model (FIGS. 26A-26E). One negative control rhAb (B1) and two rhAbs (CIS19 and CIS07) from CIS-PTM patients are shown here as examples (FIGS. 26A-26E). All 12 CIS-PTM rhAbs that displayed strong binding by brain lysate ELISA also bound cellular targets in mouse brain tissue (FIGS. 26A-26E and FIGS. 27-33). Two structures were most commonly recognized: glial cells in the corpus callosum and neuronal bodies in the cortex. The CIS19 rhAb is presented in FIGS. 26A-26E as an example of binding to neuronal bodies, and CIS07 rhAb is presented in FIGS. 26A-26E as an example of binding to glial cells. Overall, the majority of highly mutated VH4 expressing CIS-PTM plasmablast rhAbs recognized both neurons and glial cells in multiple brain tissue types (Table 8, FIGS. 27-33), with a smaller portion recognizing only glial cells (FIG. 26E).

Of those rhAbs that recognized neuronal bodies, the majority recognized the cytoplasm in a ring-like structure around the nucleus as illustrated by CIS19 (FIGS. 26A-26D, top and left images). Of those rhAbs that recognized glial cells, the majority bound bodies and cell processes in the corpus callosum as illustrated by CIS07 rhAb (FIGS. 26A-26D, middle). In general there was a preference for astrocytes over oligodendrocytes, as the inventor rarely observed colocalization with the oligodendrocyte marker PDGFR (FIGS. 31A-31B and 33A-33B). One exception was CIS68 rhAb, which bound to both glial cell types (FIG. 33A-33B).

Figure 21A:
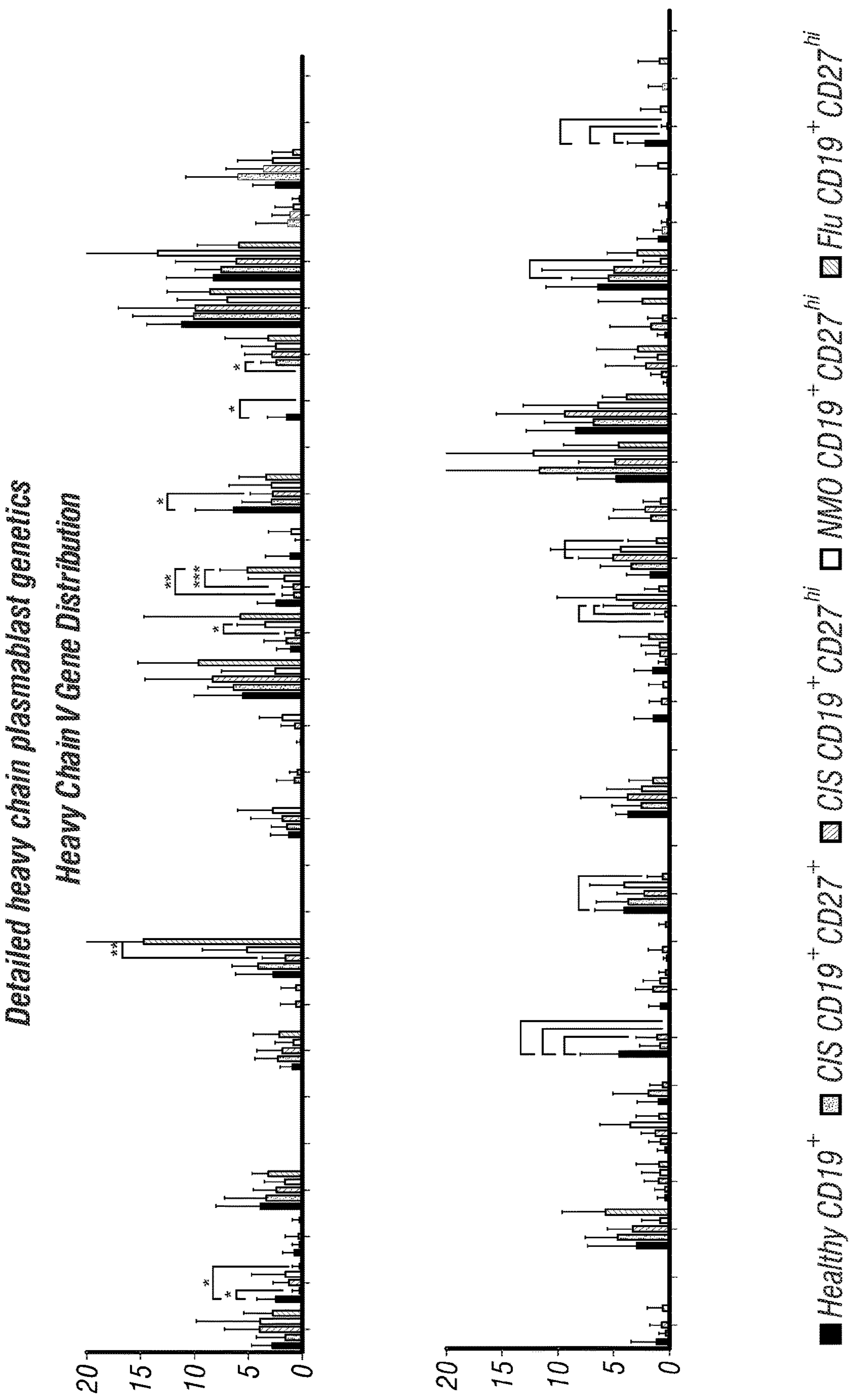
FIGS. 21A-21F. Detailed heavy chain plasmablast genetics.
Figure 21B:
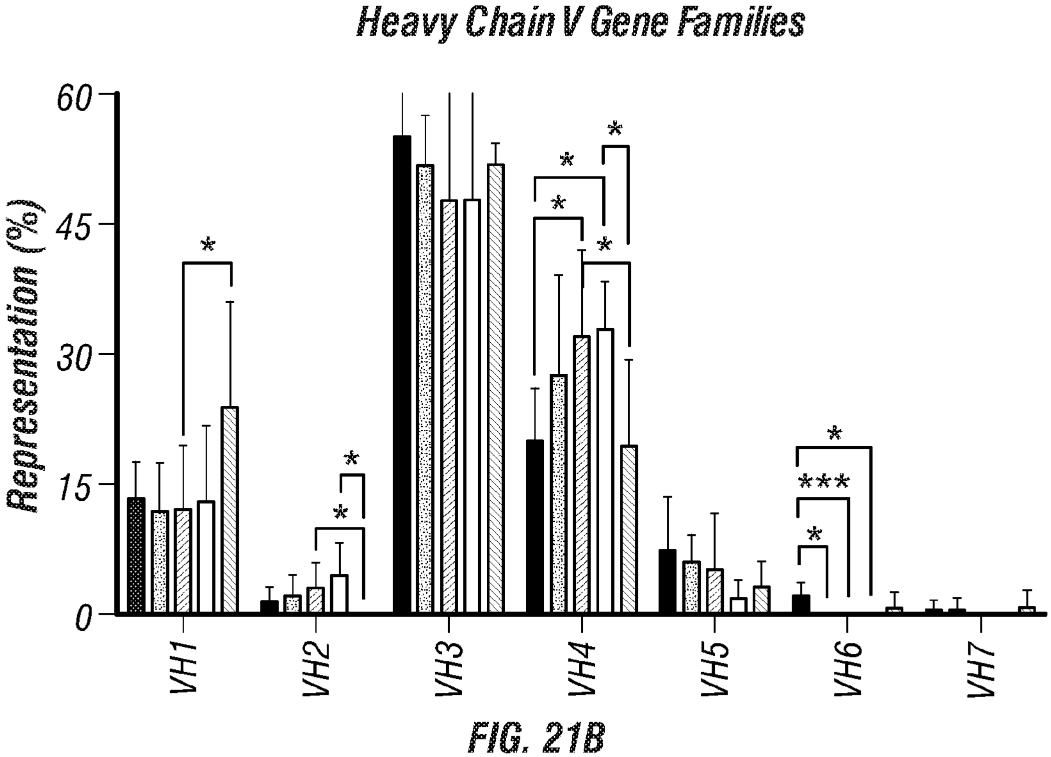
Figure 21C:
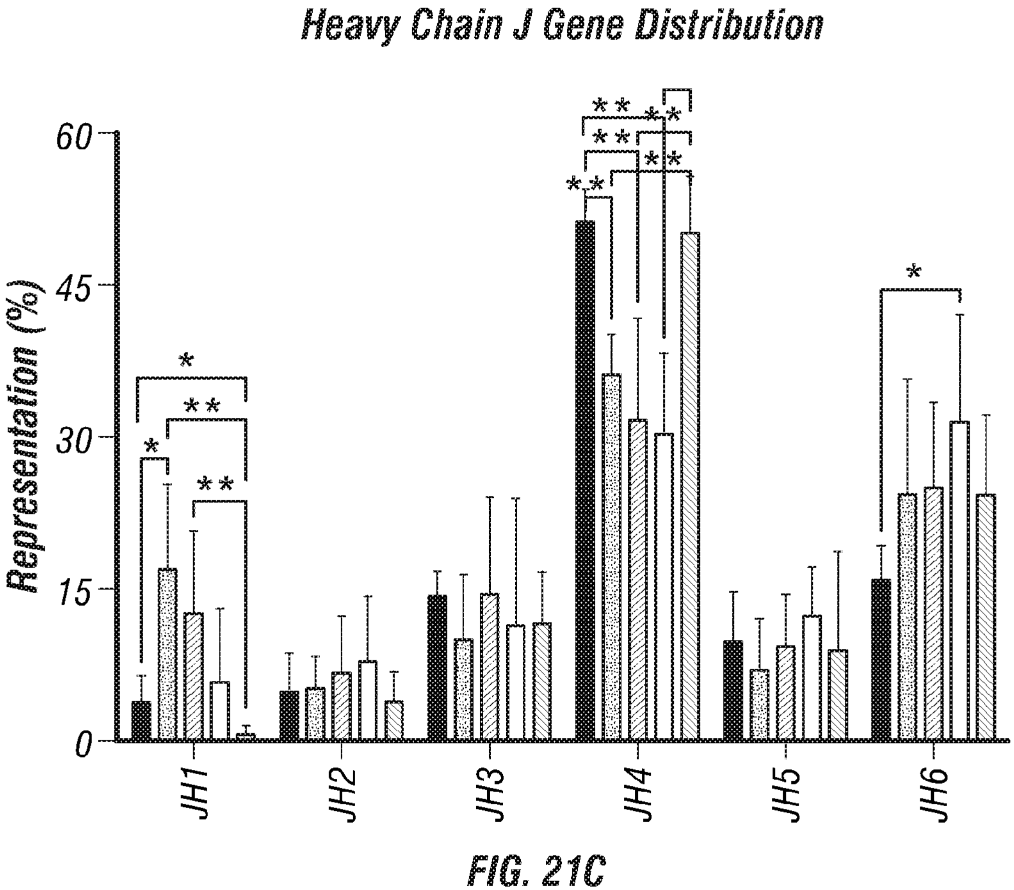
Figure 21D:
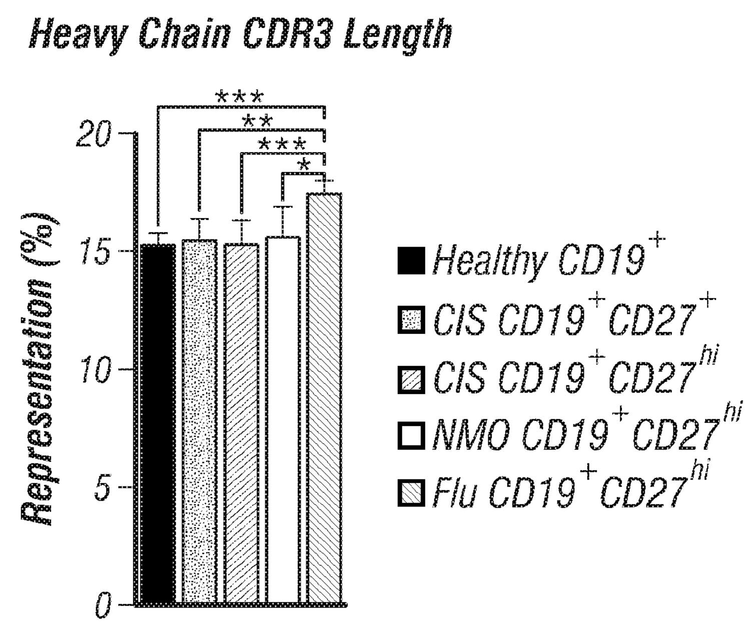
Figure 21E:
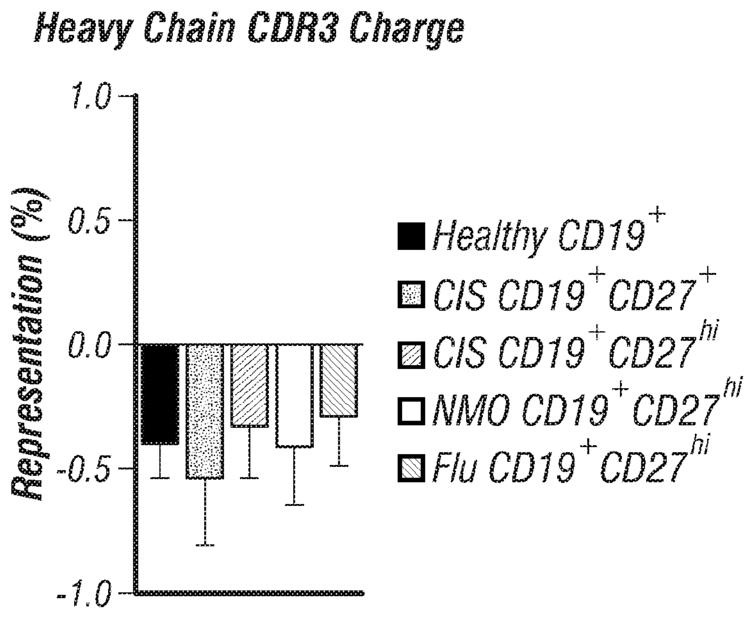
Figure 21F:
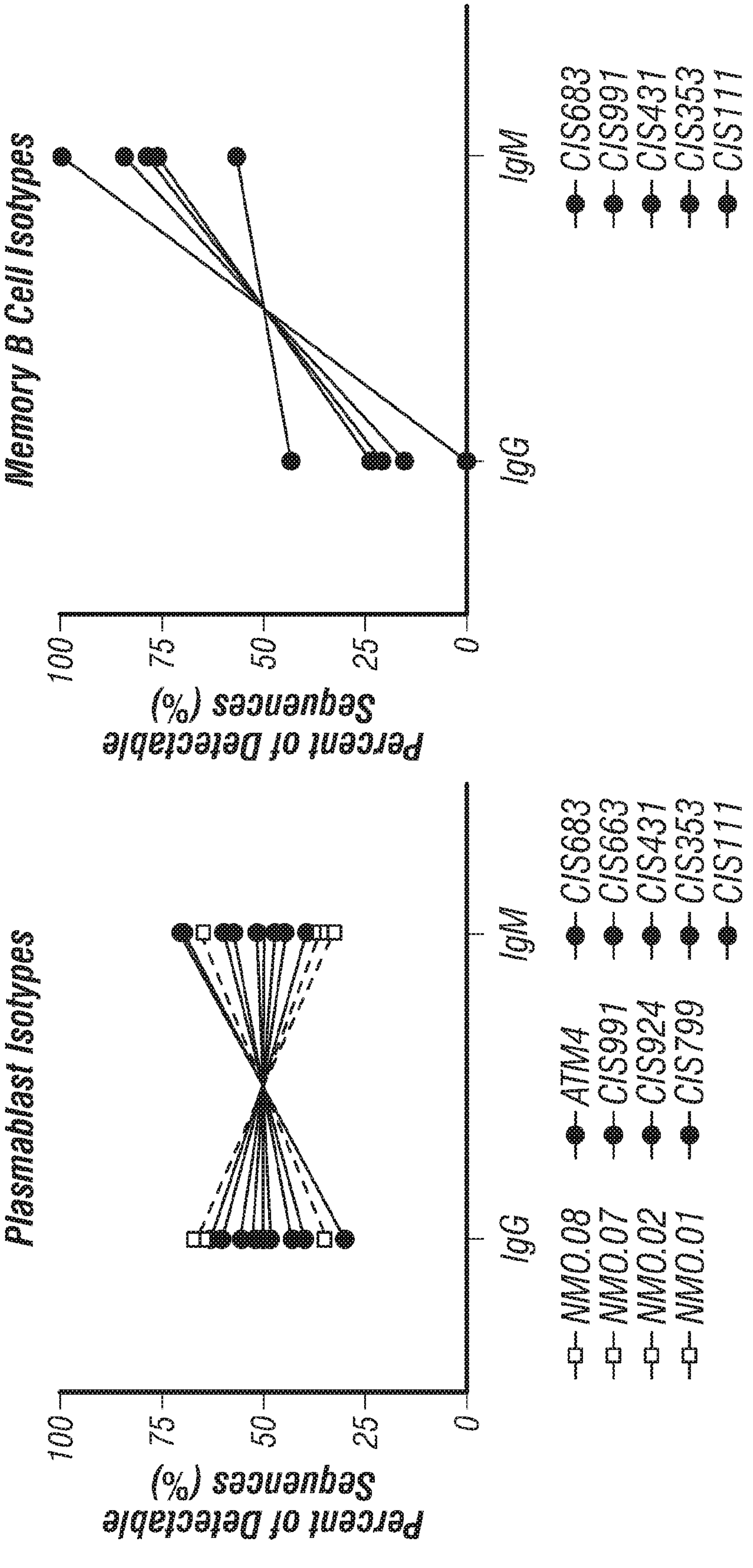
Figure 22A:
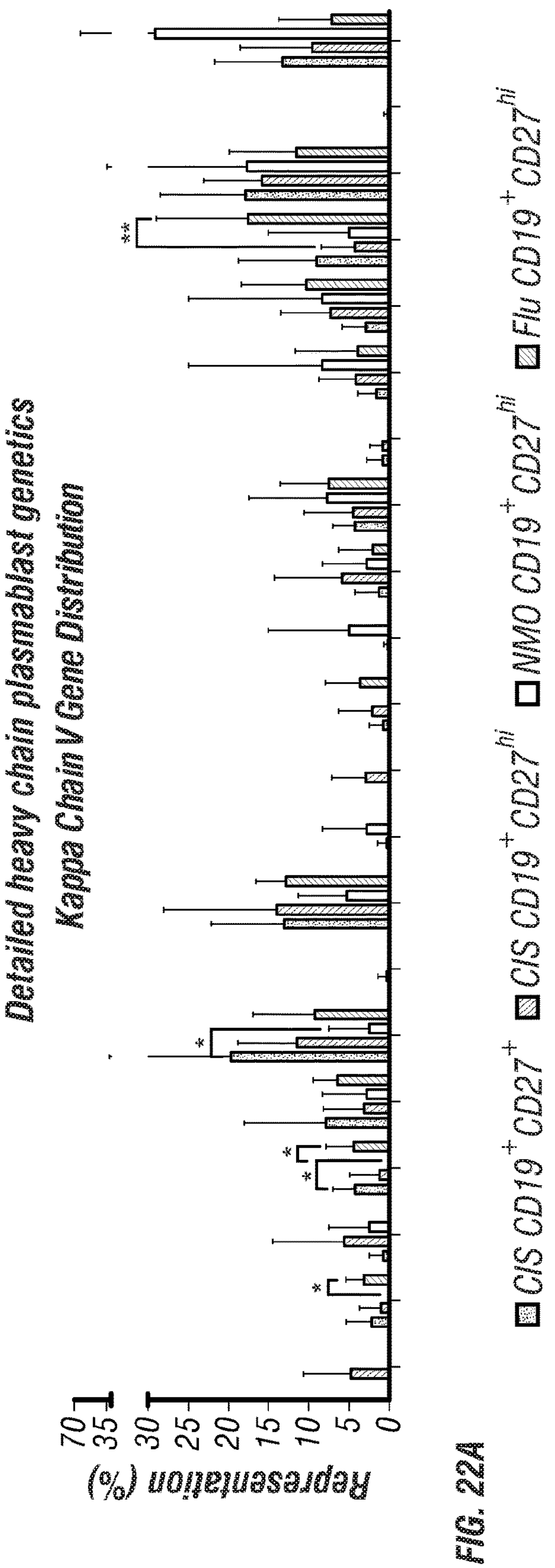
FIGS. 22A-22F. Detailed heavy chain plasmablast genetics.
Figure 22B:
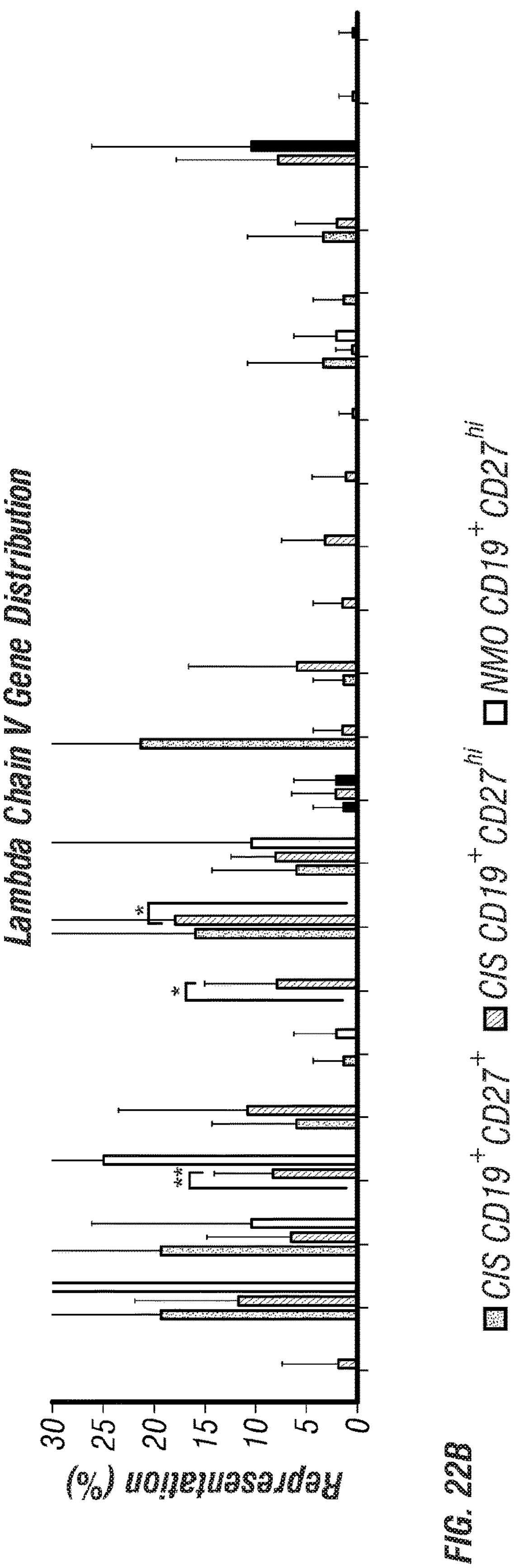
Figure 22C:
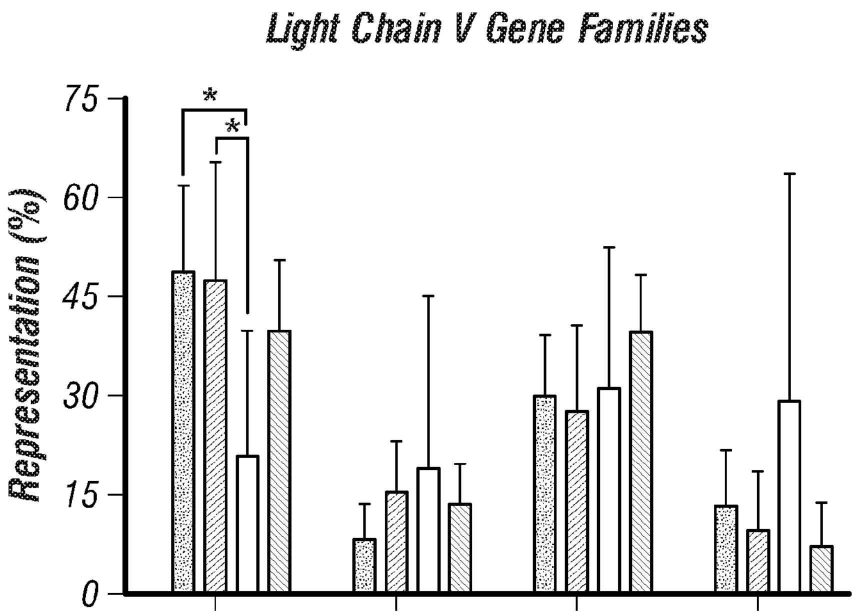
Figure 22D:
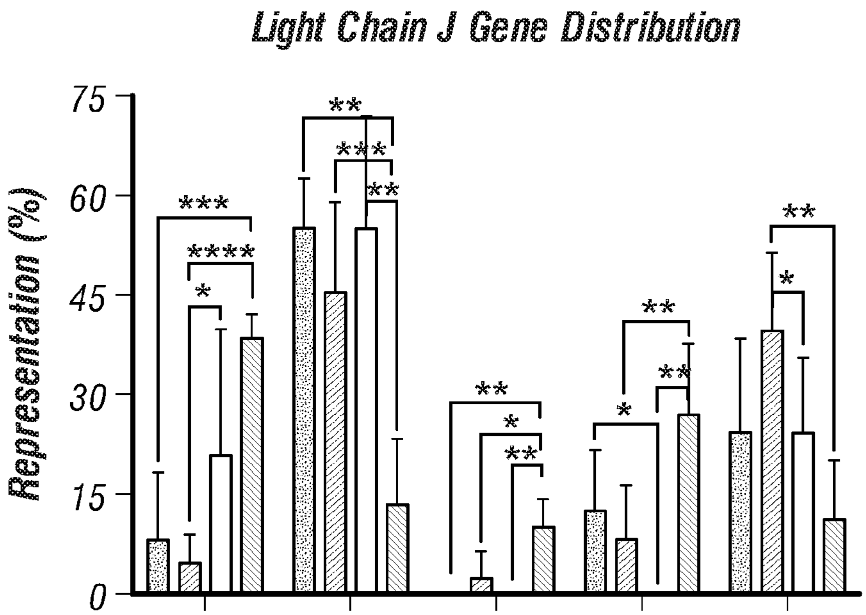
Figure 22E:
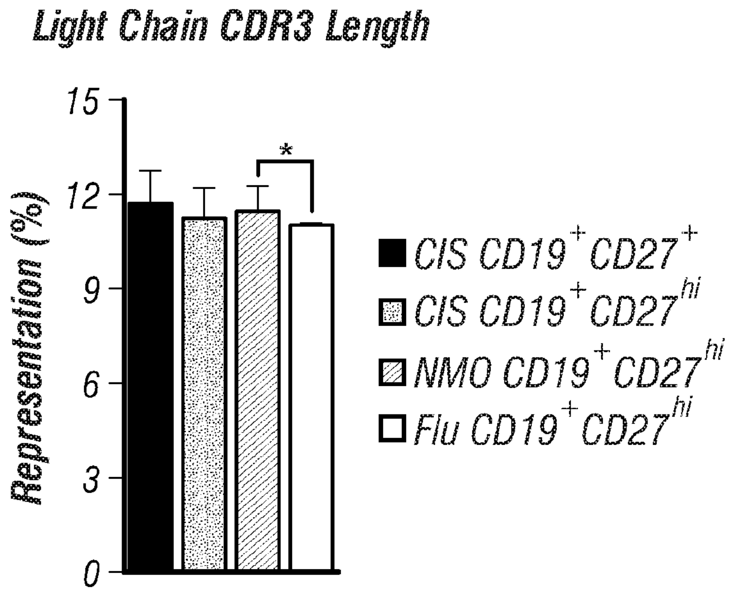
Figure 22F:
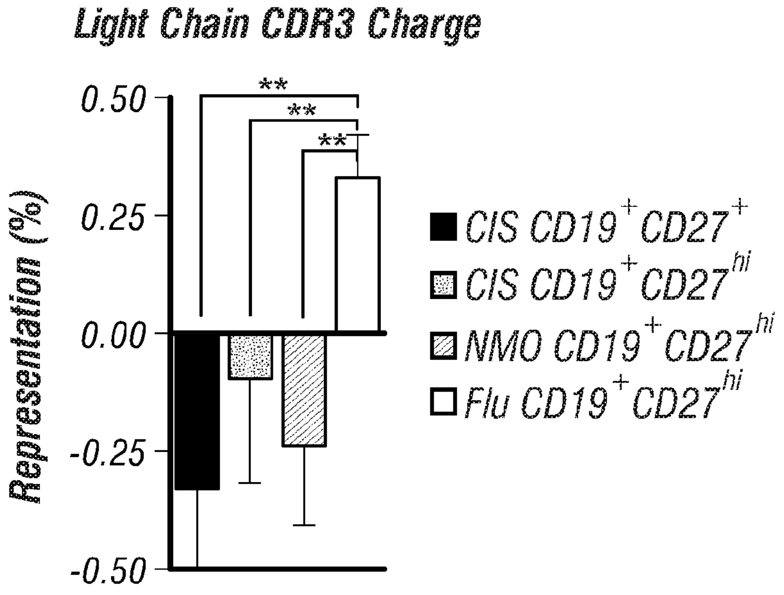
Figure 37A:
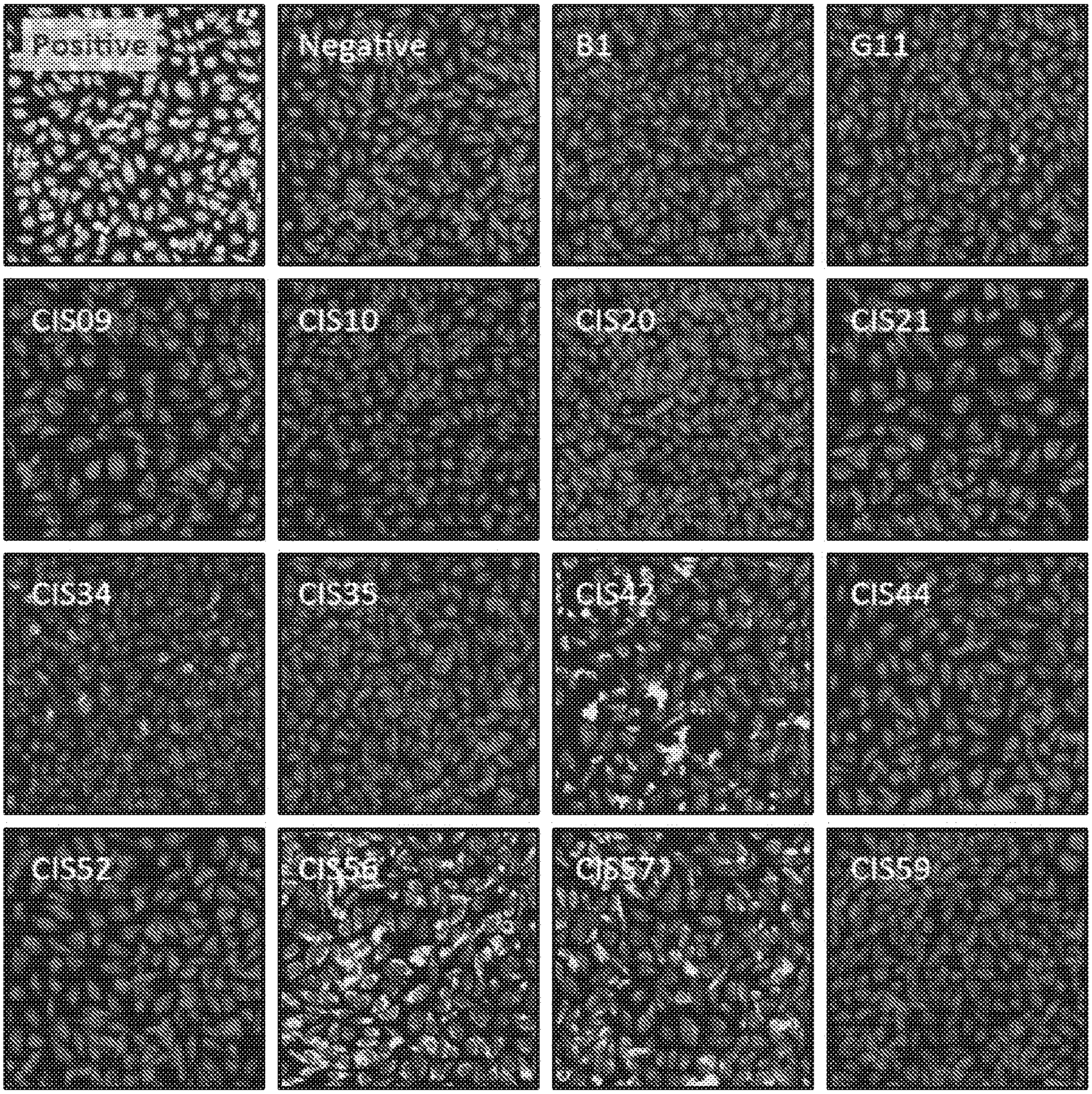
FIGS. 37A-37B. Reactivity to Hep2 by ICC.
Figure 37A:
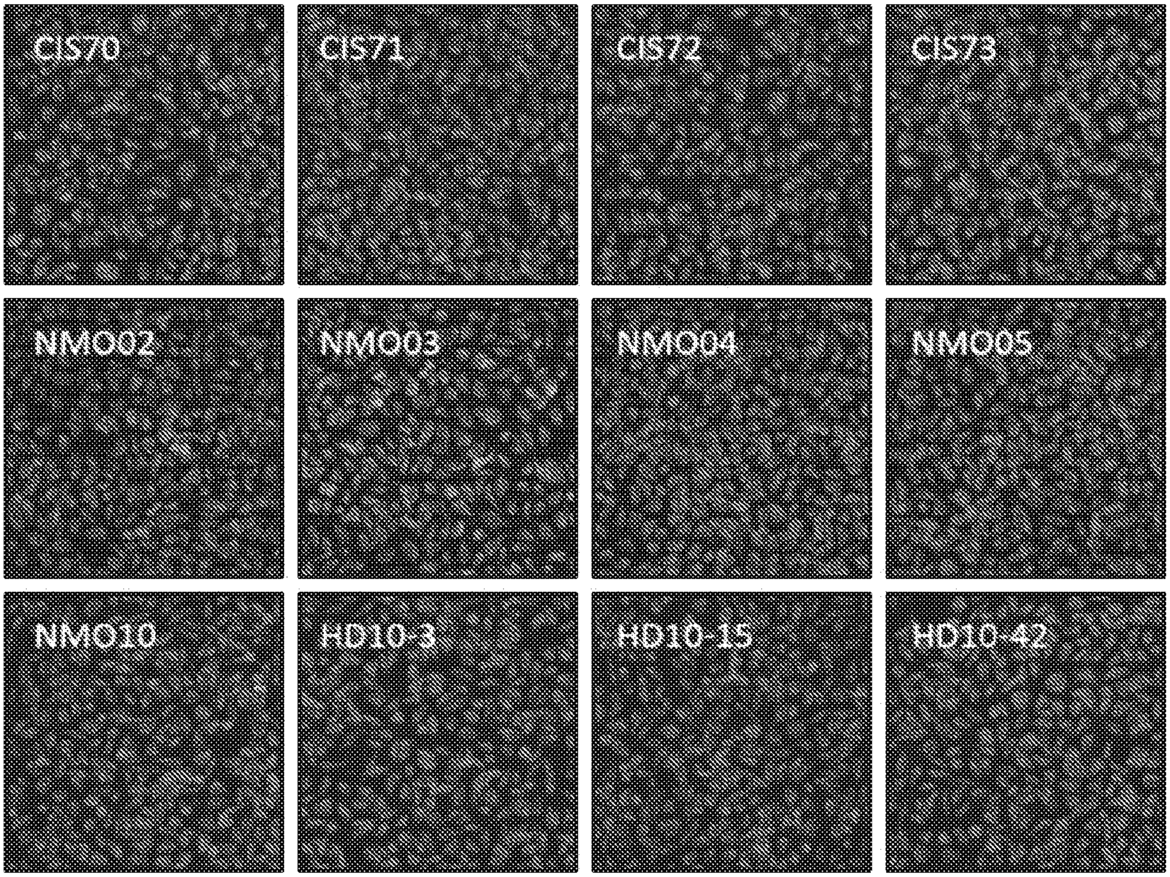
Figure 37A:
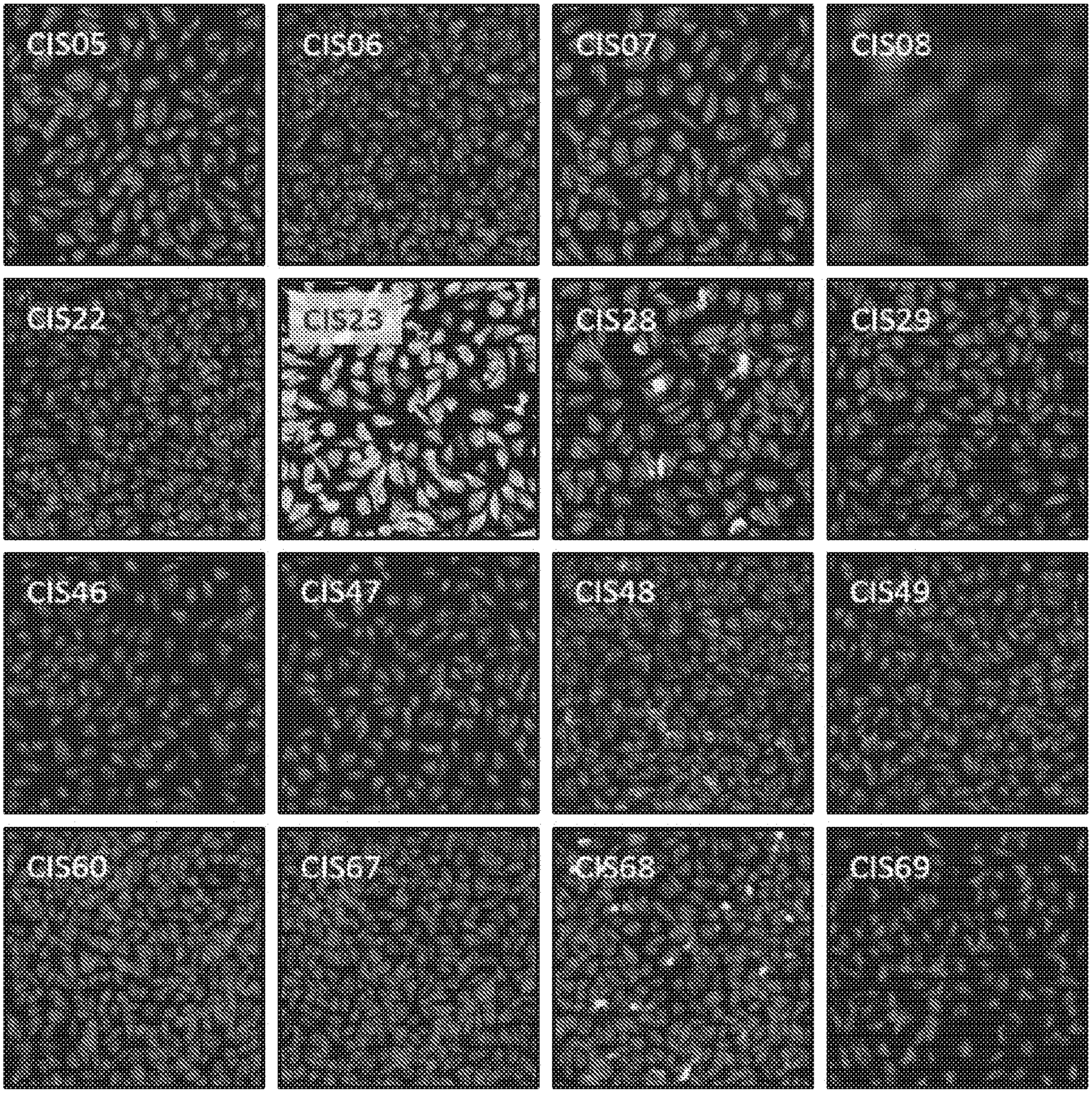
Figure 37A:
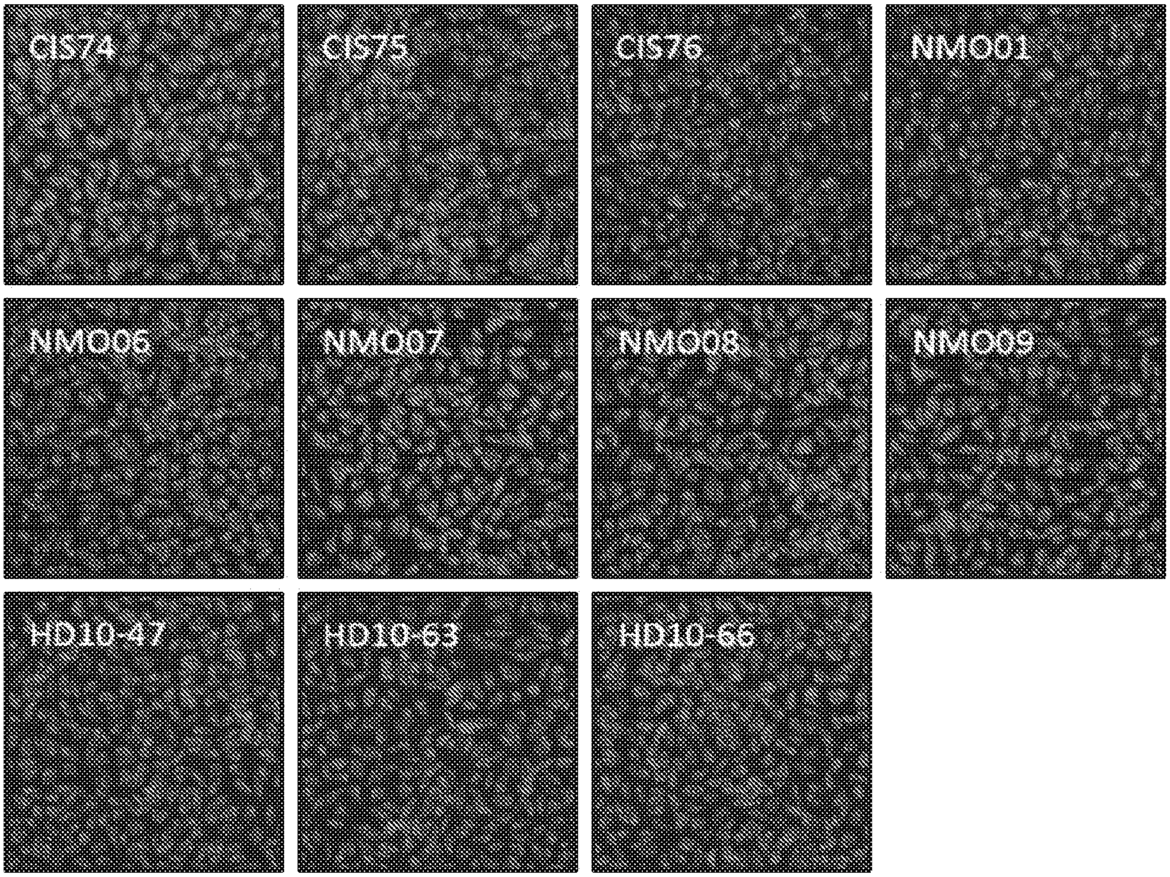
Figure 37B:
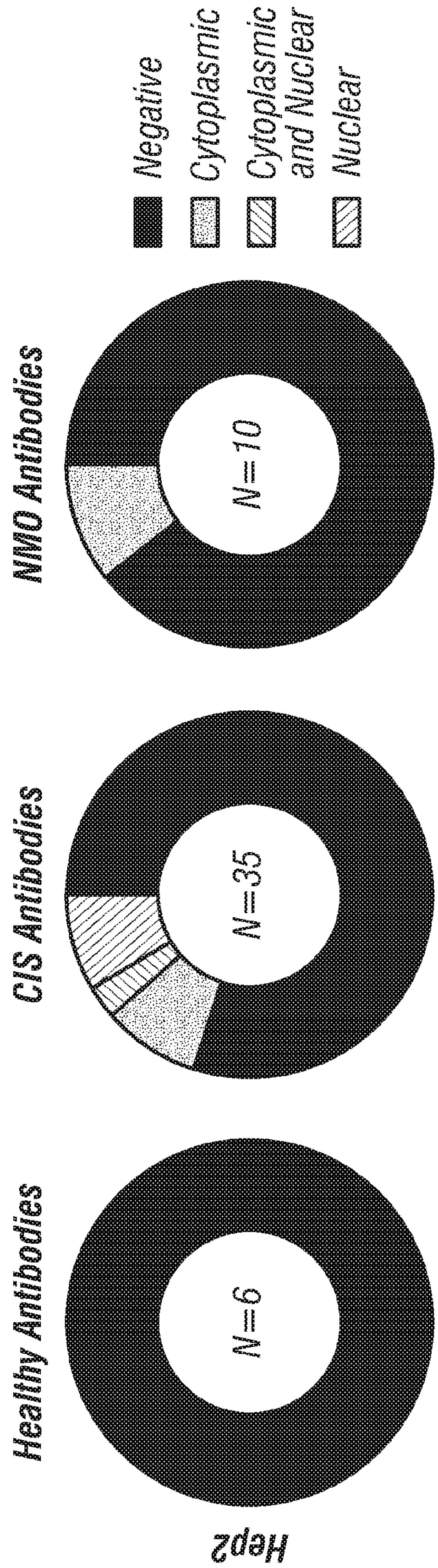

The researchers also included 6 additional CIS-PTM rhAbs that were negative by the brain lysate ELISA (FIGS. 23A-23B), but utilized VH4-31 or VH4-34 genes, which were over-represented in the heavy chain repertoire analysis (FIG. 20D and FIG. 21A). Notably, even though rhAbs expressing VH4-34 and VH4-31 antibody genes did not bind strongly by brain lysate ELISA, these rhAbs bound less abundant cell types in the brain such as glial cells in the corpus callosum (FIG. 37A).

Figure 35A:
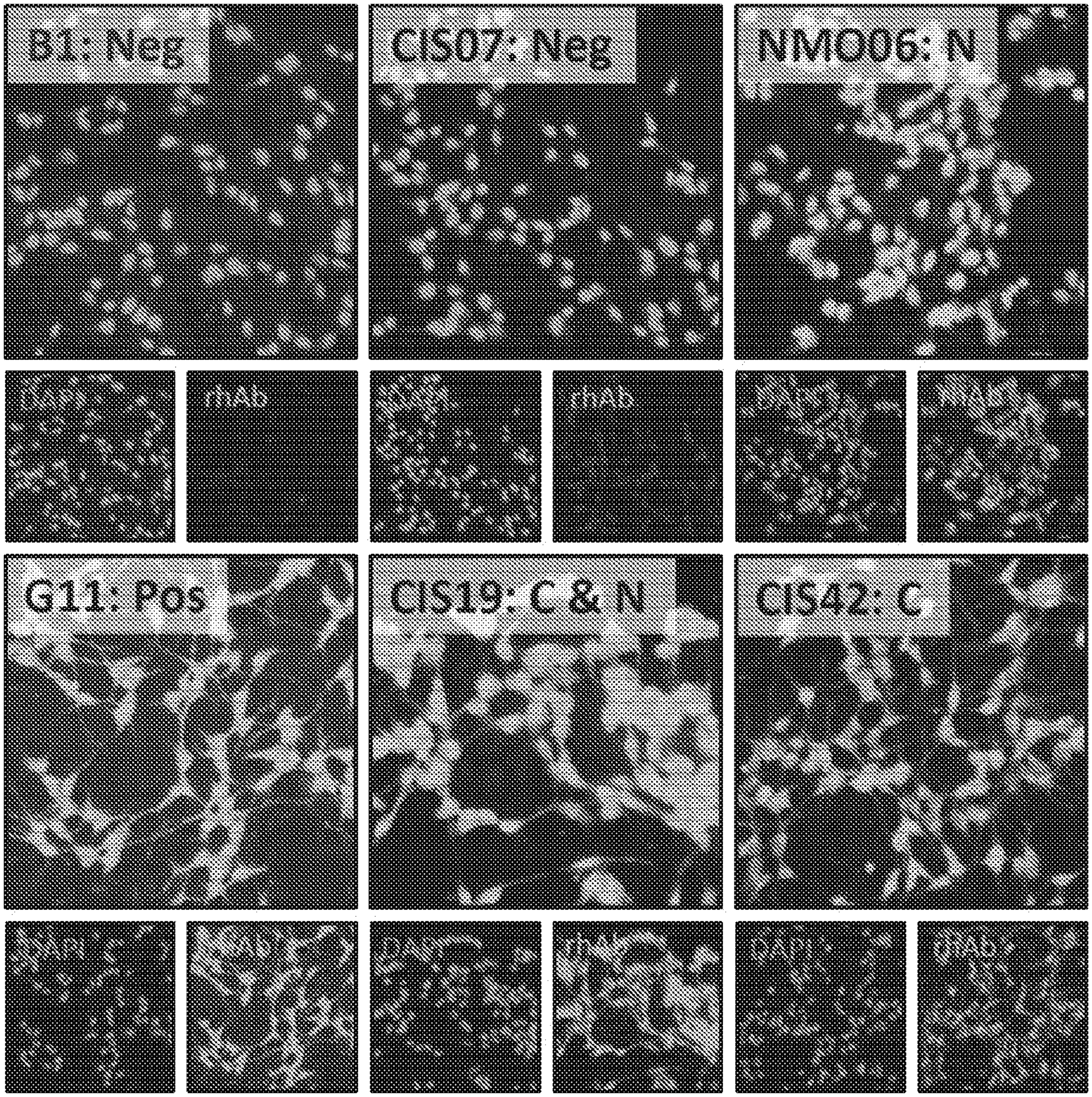
FIGS. 35A-35B. Reactivity to Sy5y by ICC.
Figure 35B:
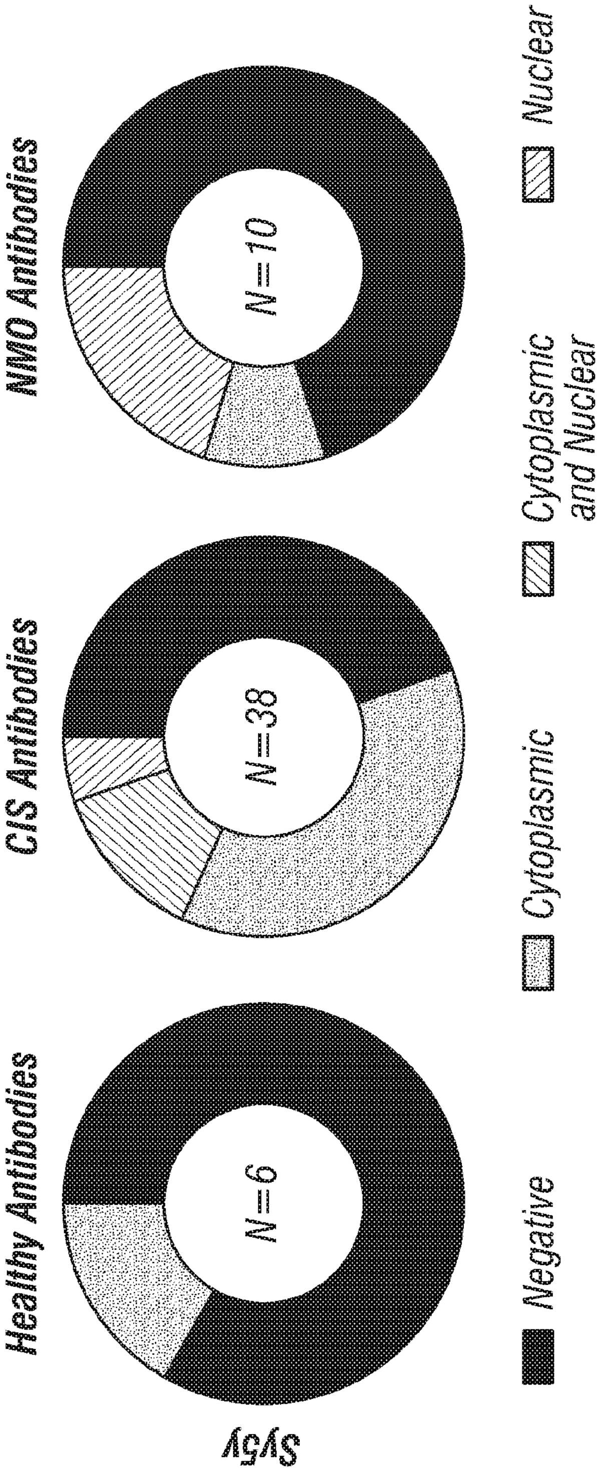
Figure 36:
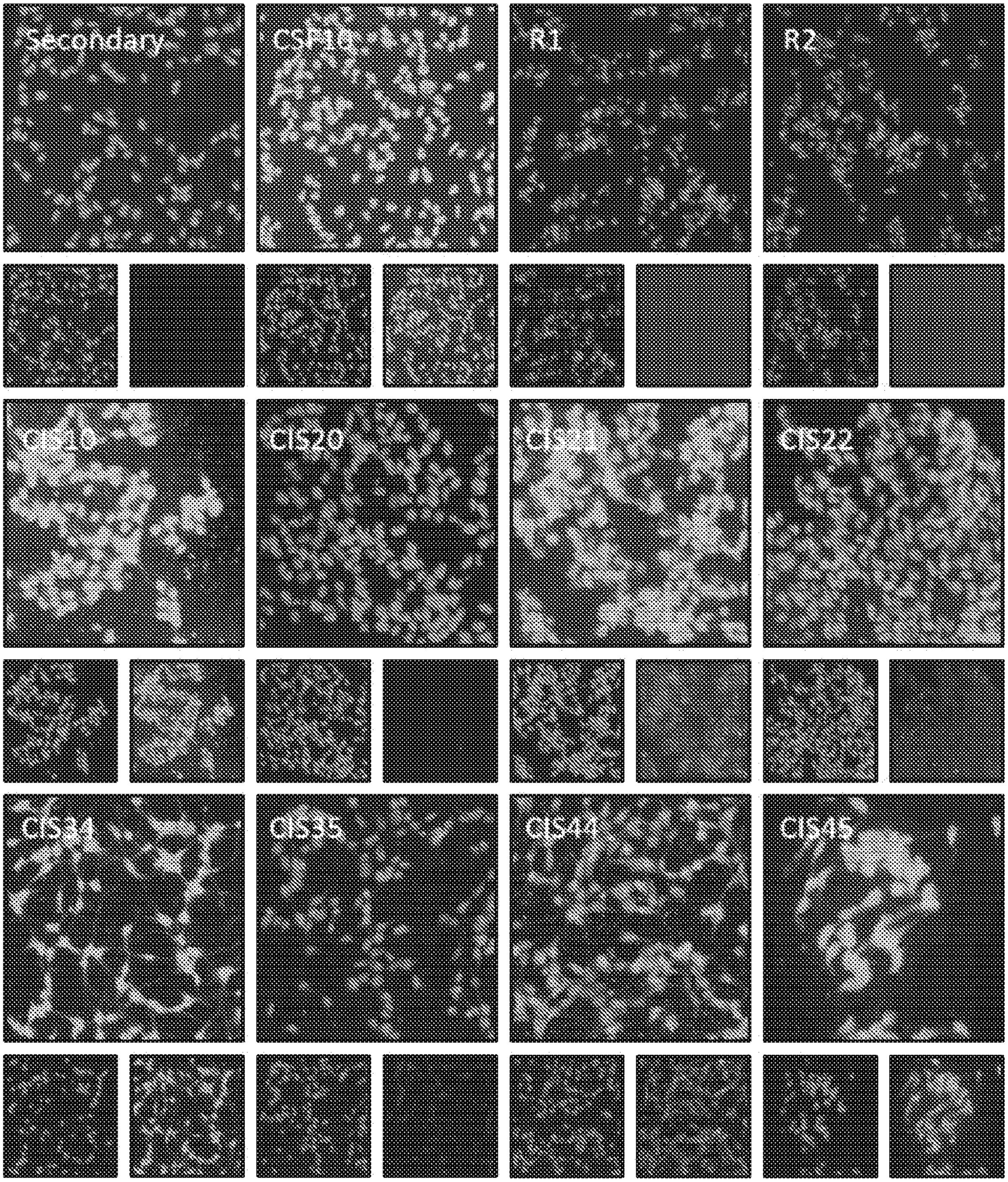
FIG. 36. Reactivity to Sy5y by ICC. Figure shows all remaining images of rhAb binding to SH-Sy5y cells by ICC. R1, R2, and CSF10 served as additional negative and positive controls.
Figure 36:
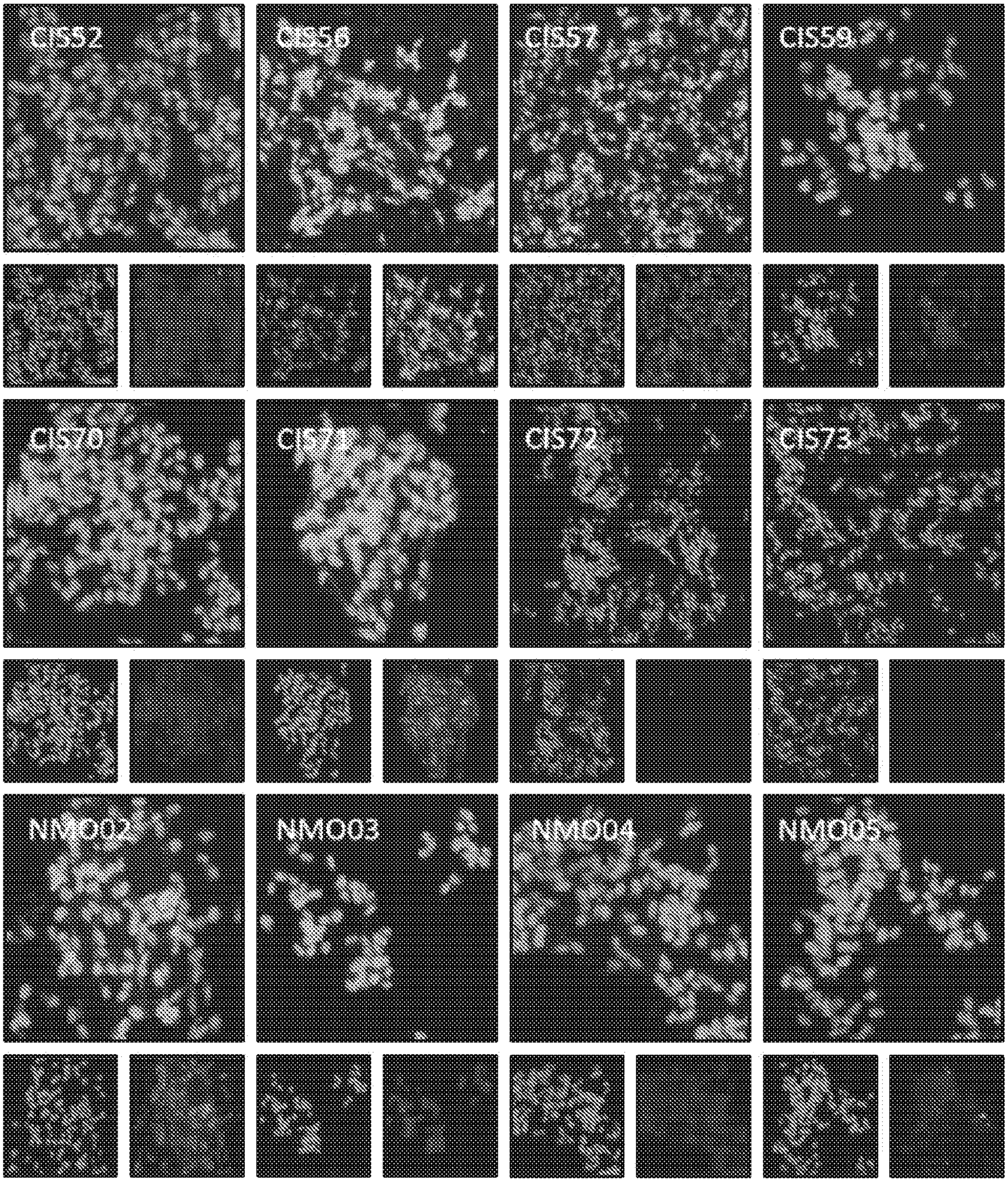
Figure 36:
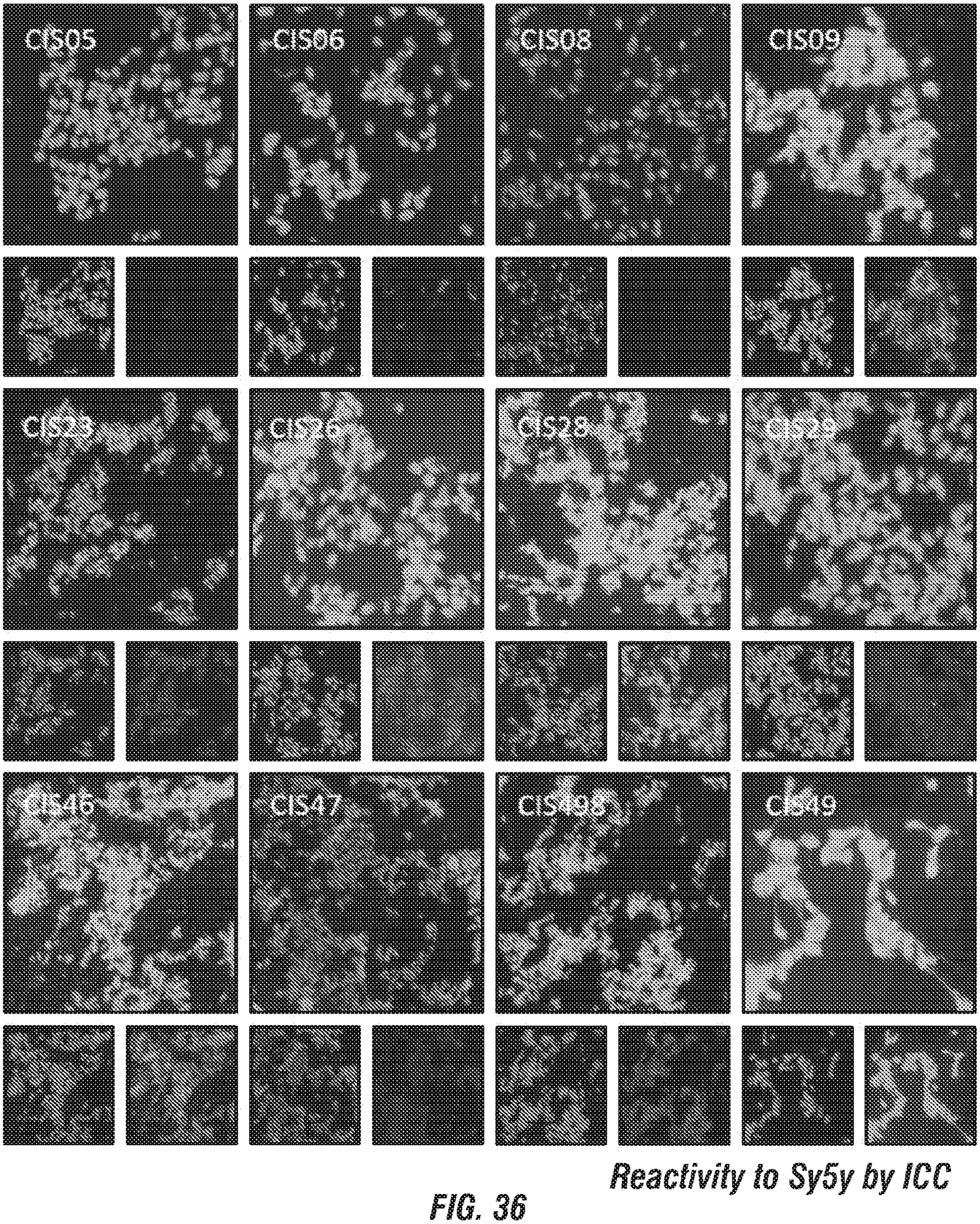
Figure 36:
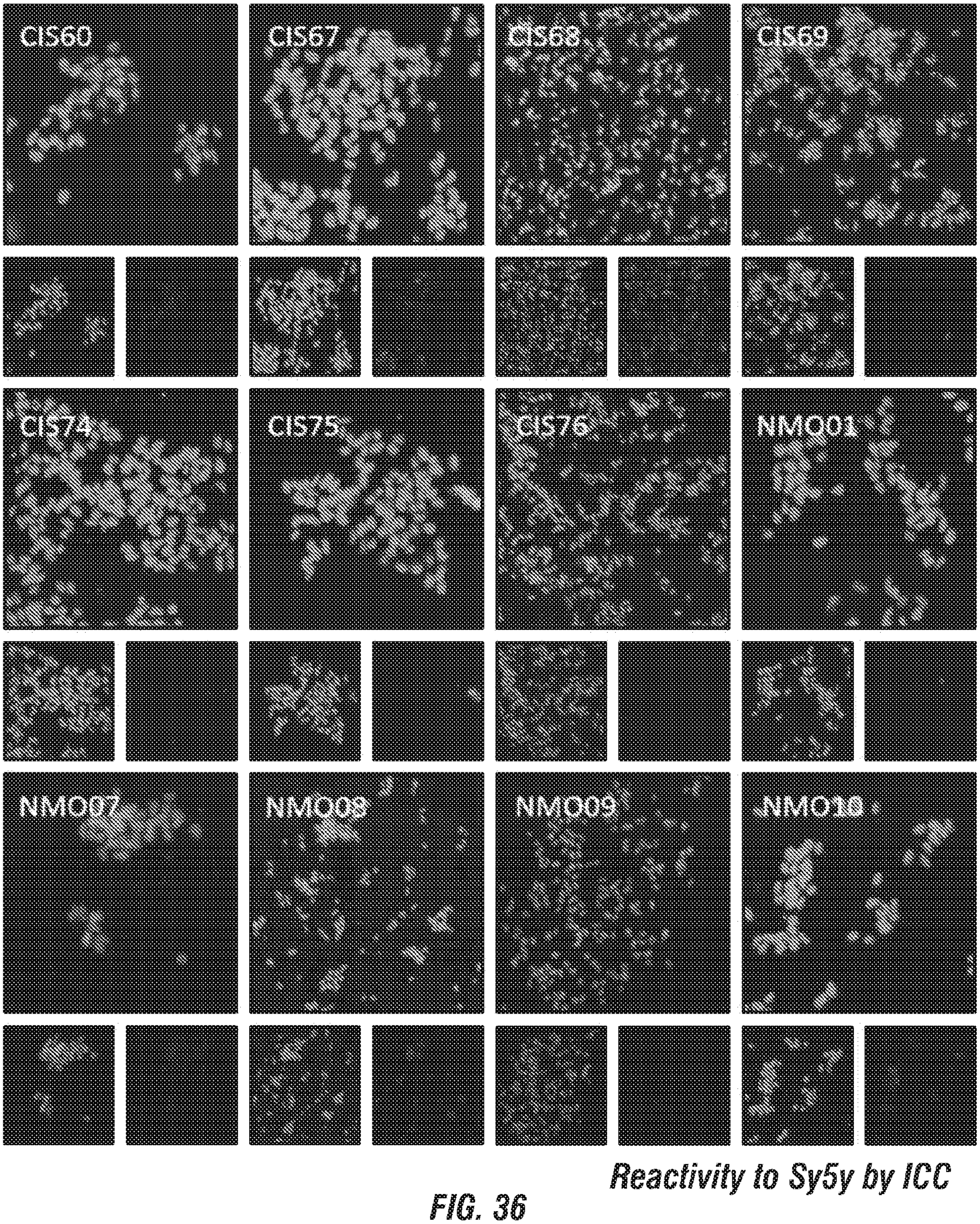
Figure 36:
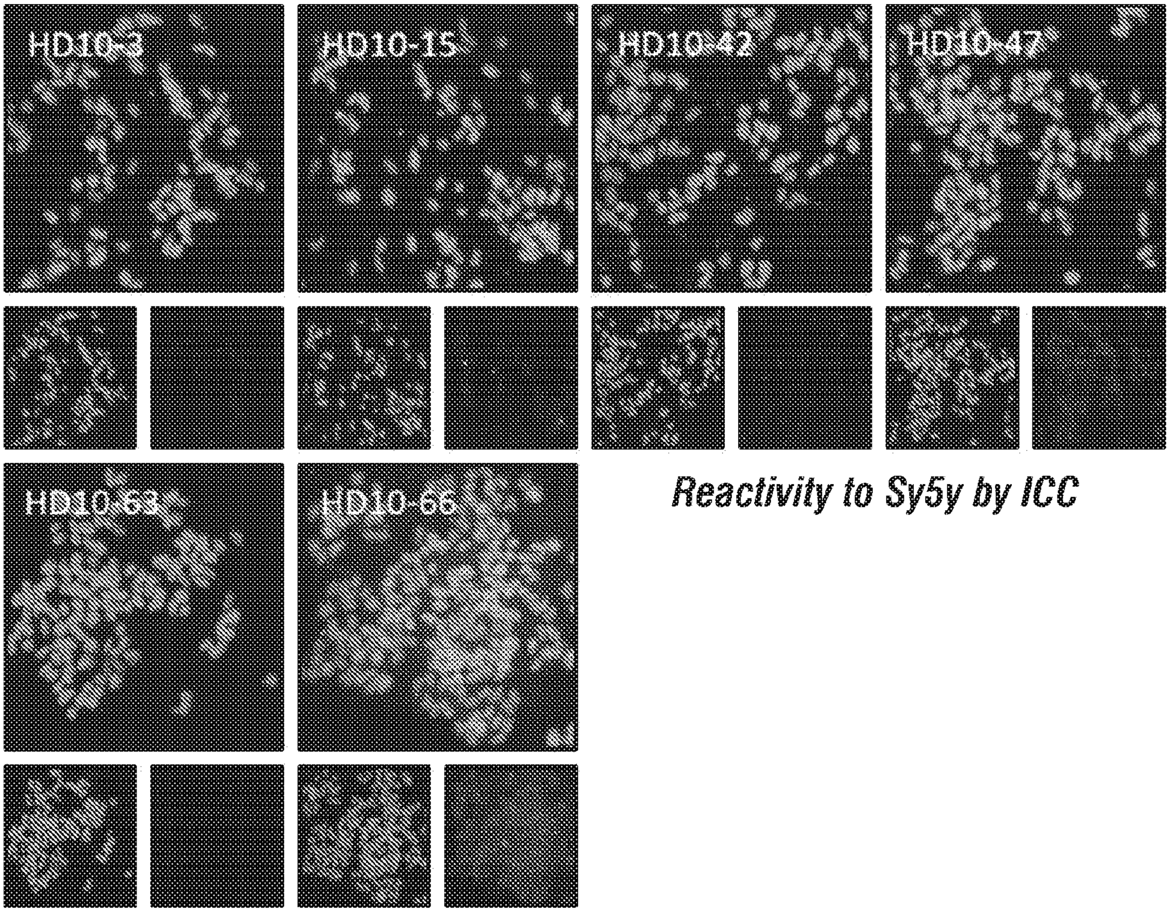

Peripheral plasmablasts from CIS-PTM patients recognize cytoplasmic and nuclear targets on human neurons. The researchers used immunocytochemistry (ICC) to further investigate the binding of CIS-PTM peripheral plasmablast rhAbs to nuclear and cytoplasmic targets on the human neuroblastoma cell line, SH-Sy5y (FIGS. 35A-35B). B1 is presented as a negative control, G11 is presented as a positive control, and 4 rhAbs are presented as examples in FIGS. 35A-35B. Each type of binding pattern is represented (negative, nuclear only, cytoplasmic only, nuclear and cytoplasmic) and G11 demonstrates both cytosolic and nuclear recognition of the cell line. Of the 38 CIS-PTM rhAbs, 21 of them (55%) bound SH-Sy5y, including 9 of the 12 CIS-PTM rhAbs that demonstrated strong binding by the brain lysate ELISA. The majority of these 21 CIS-PTM rhAbs bound to cytoplasmic targets, with some binding to both cytoplasmic and nuclear targets, and only one binding to nuclear targets alone. Of the 10 NMO rhAbs, 3 of them bound SH-Sy5y; 2 to nuclear targets alone and 1 to both cytoplasmic and nuclear targets. Only one of the HD rhAbs bound to cytoplasmic targets on SH-Sy5y. The rhAbs were additionally probed for binding to the Hep-2 cell line, a test commonly used to identify generic anti-nuclear antibodies in lupus patients. One NMO plasmablast rhAb and 20% of the CIS-PTM plasmablast rhAbs also recognized the Hep-2 cells, but most were not anti-nuclear in nature (FIG. 36).

Figure 38A:
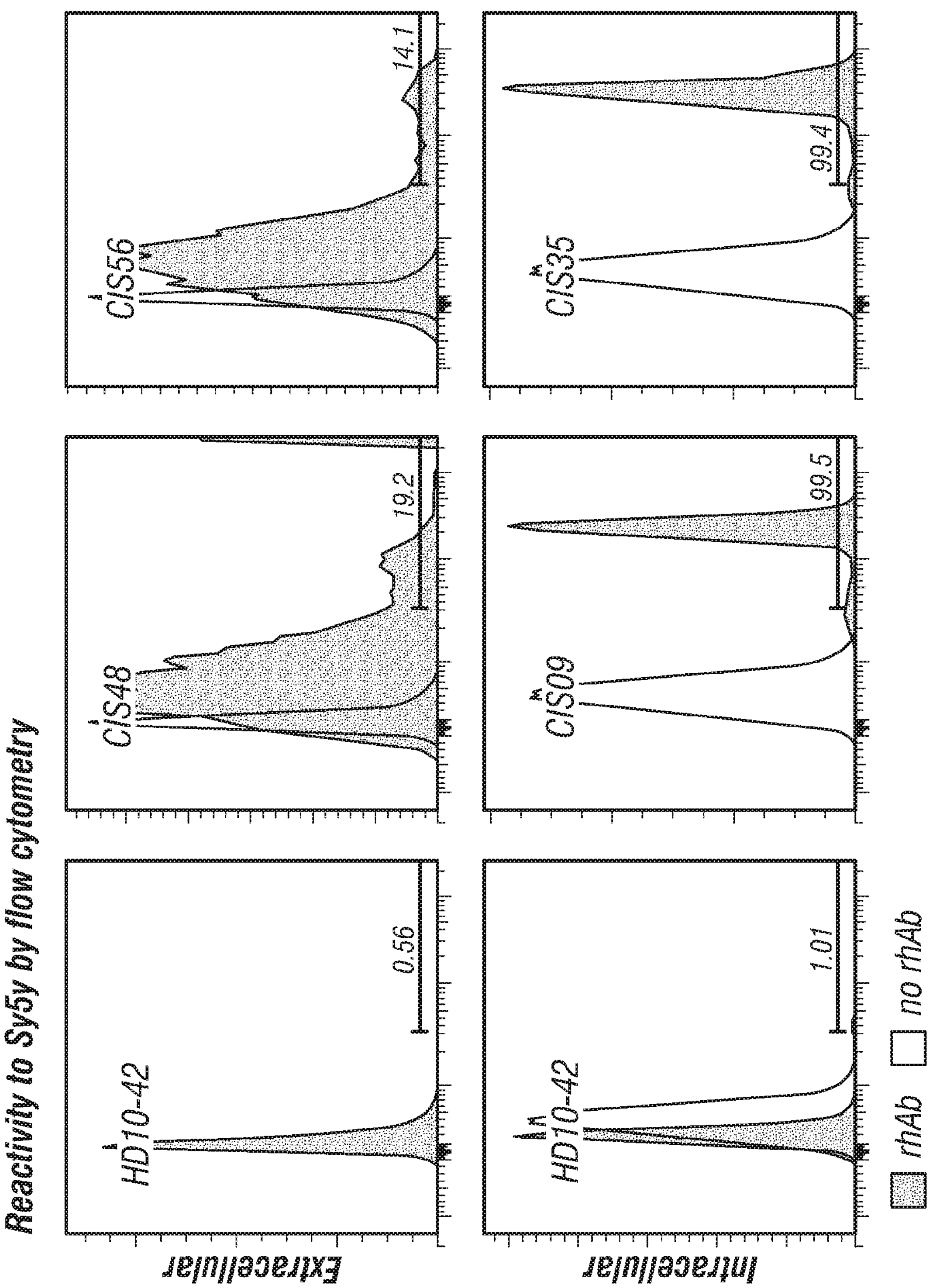
FIGS. 38A-38B. Reactivity to Sy5y by flow cytometry.
Figure 38B:
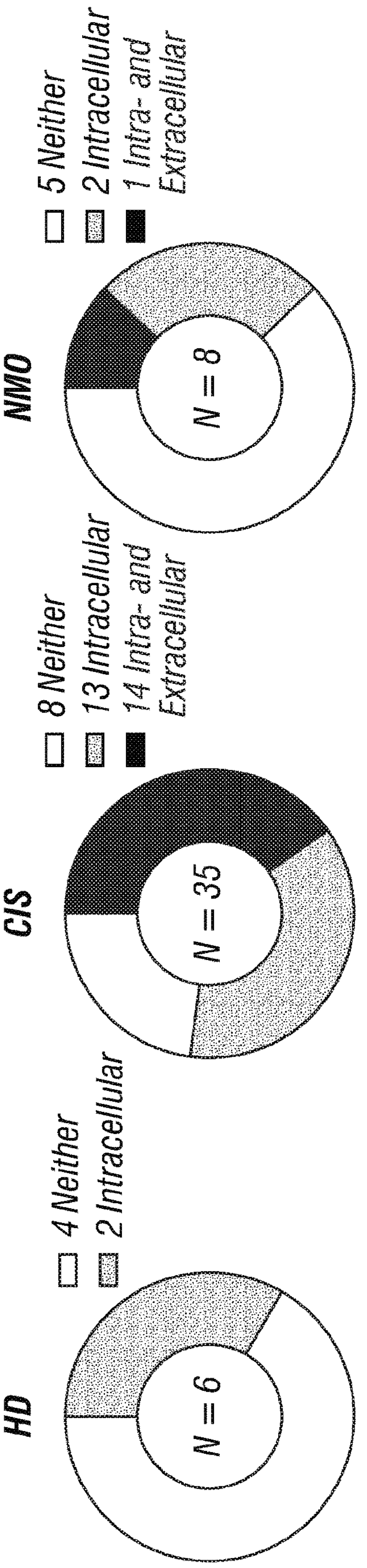
Figure 39:
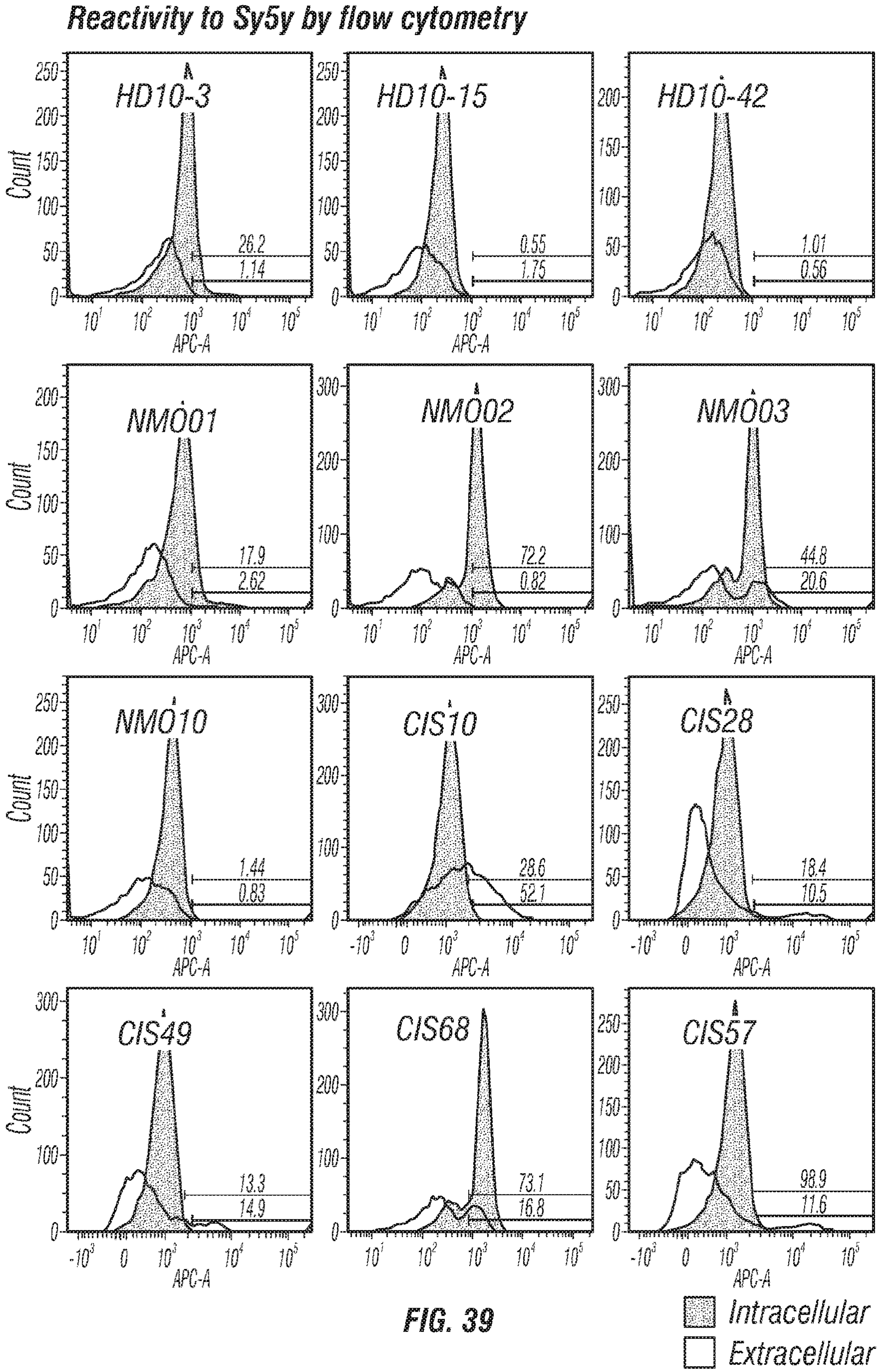
FIG. 39. Reactivity to Sy5y by flow cytometry. Figure shows histogram data with intracellular and extracellular rhAb recognition of SH-Sy5y cells by flow cytometry.
Figure 39:
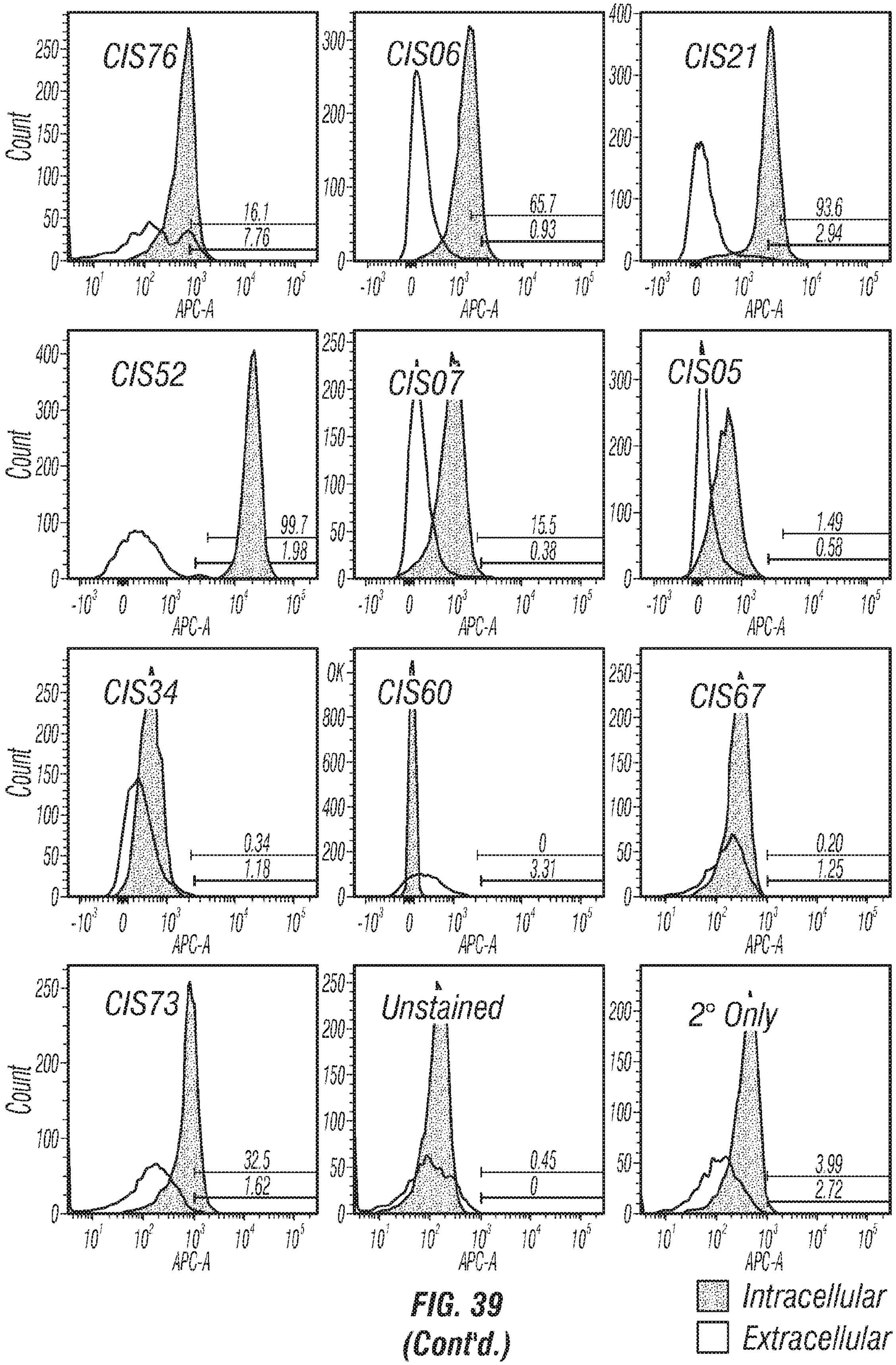
Figure 39:
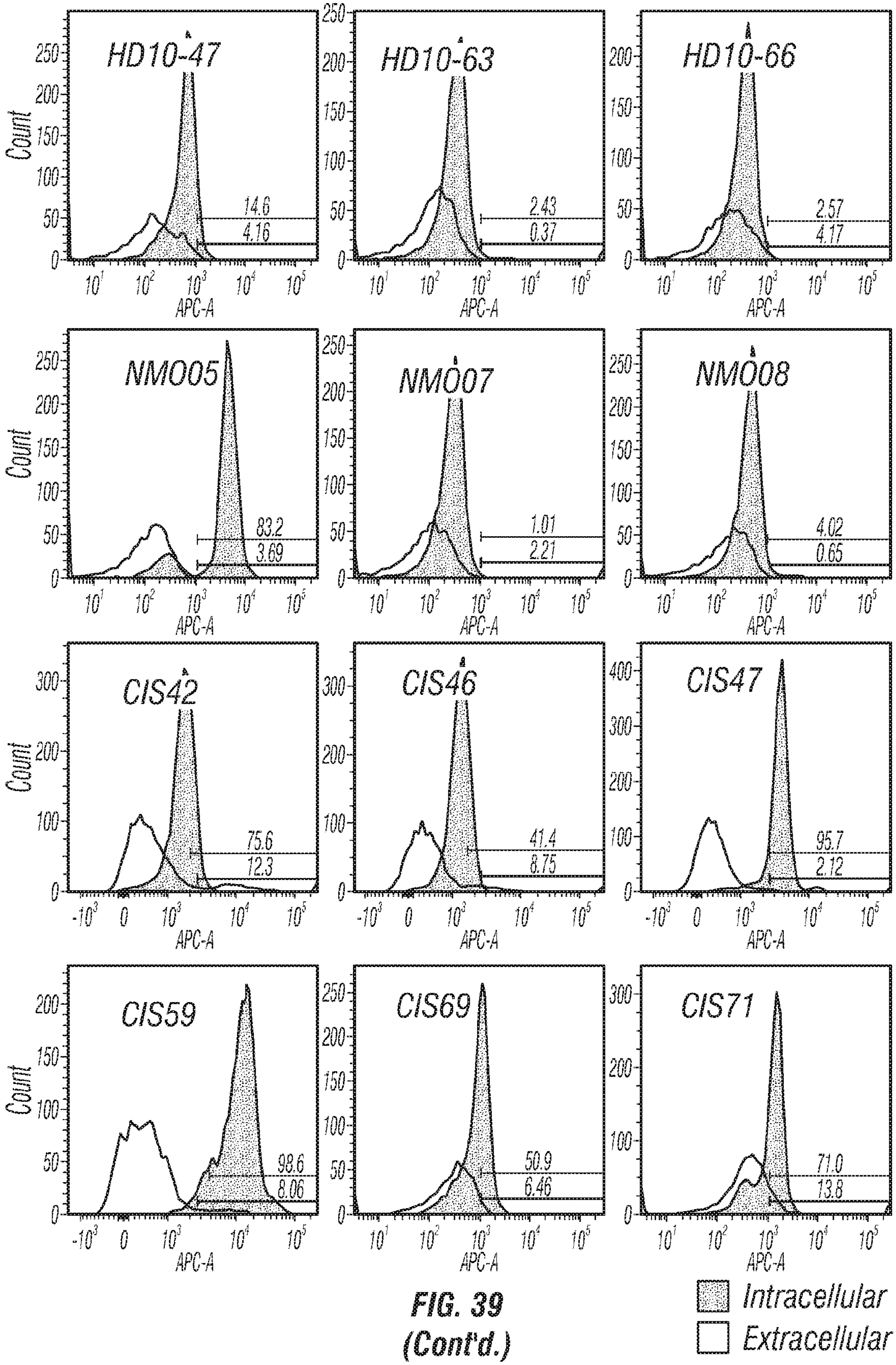
Figure 39:
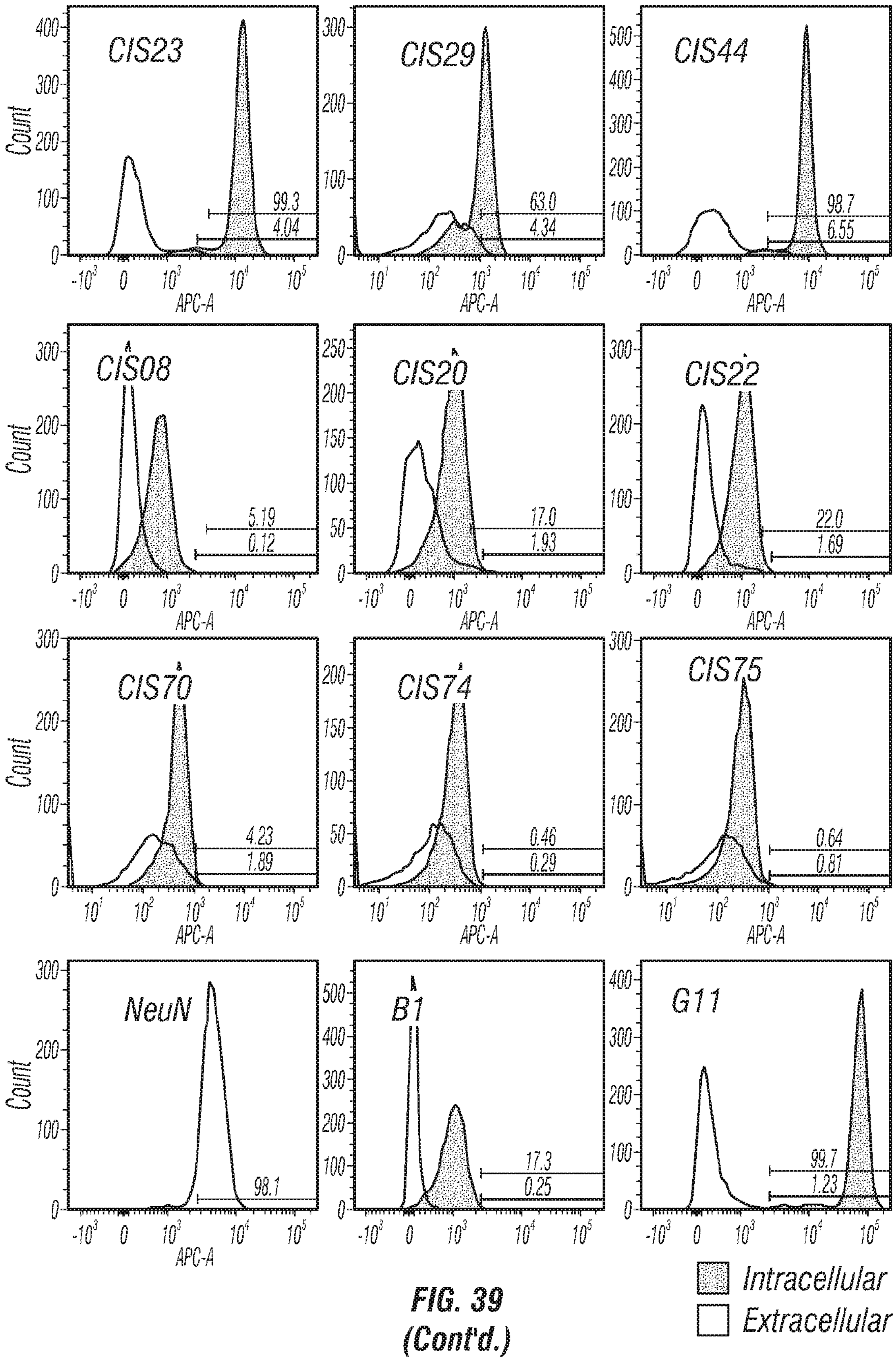
Figure 39:
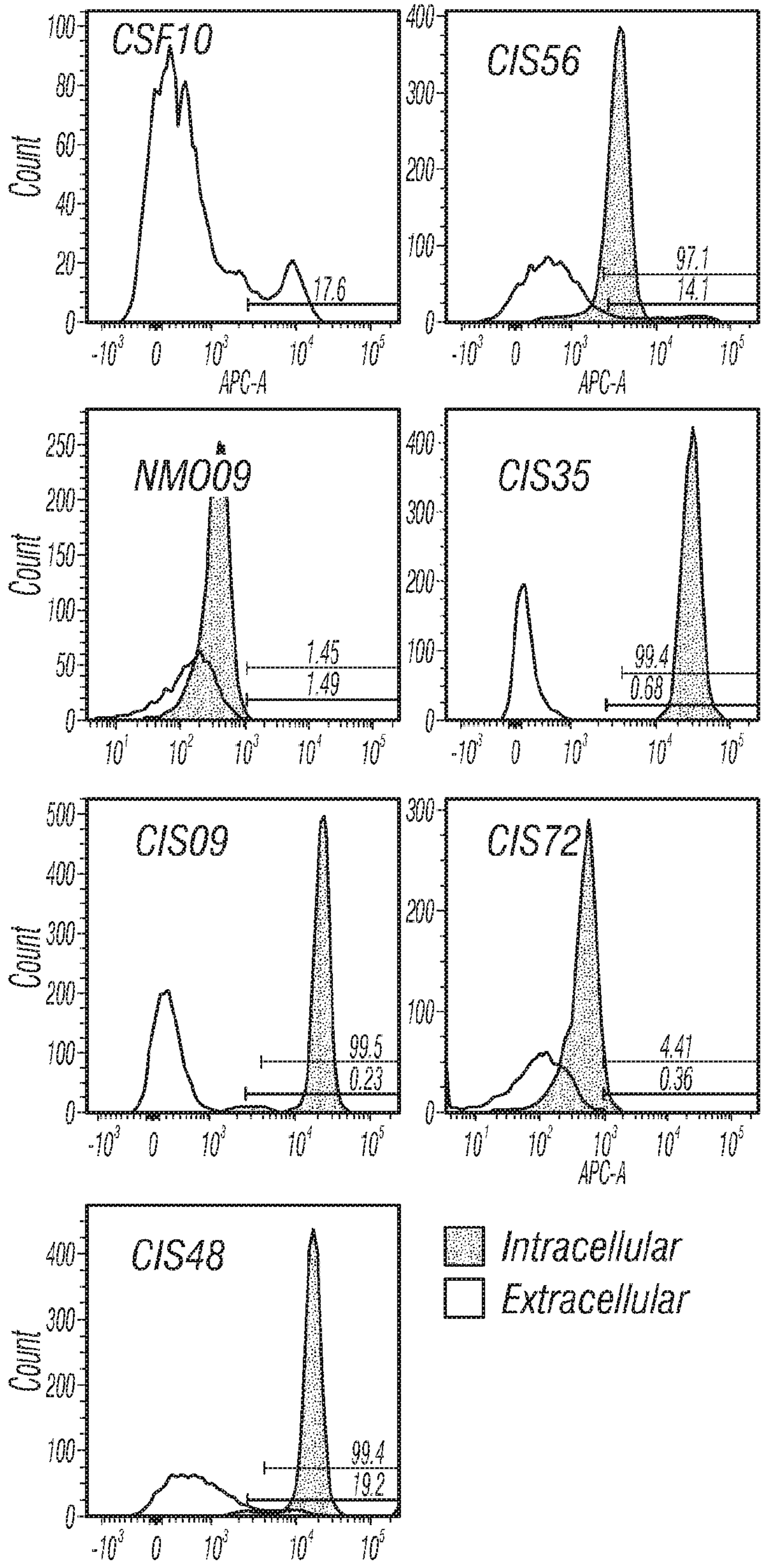
Figure 40A:
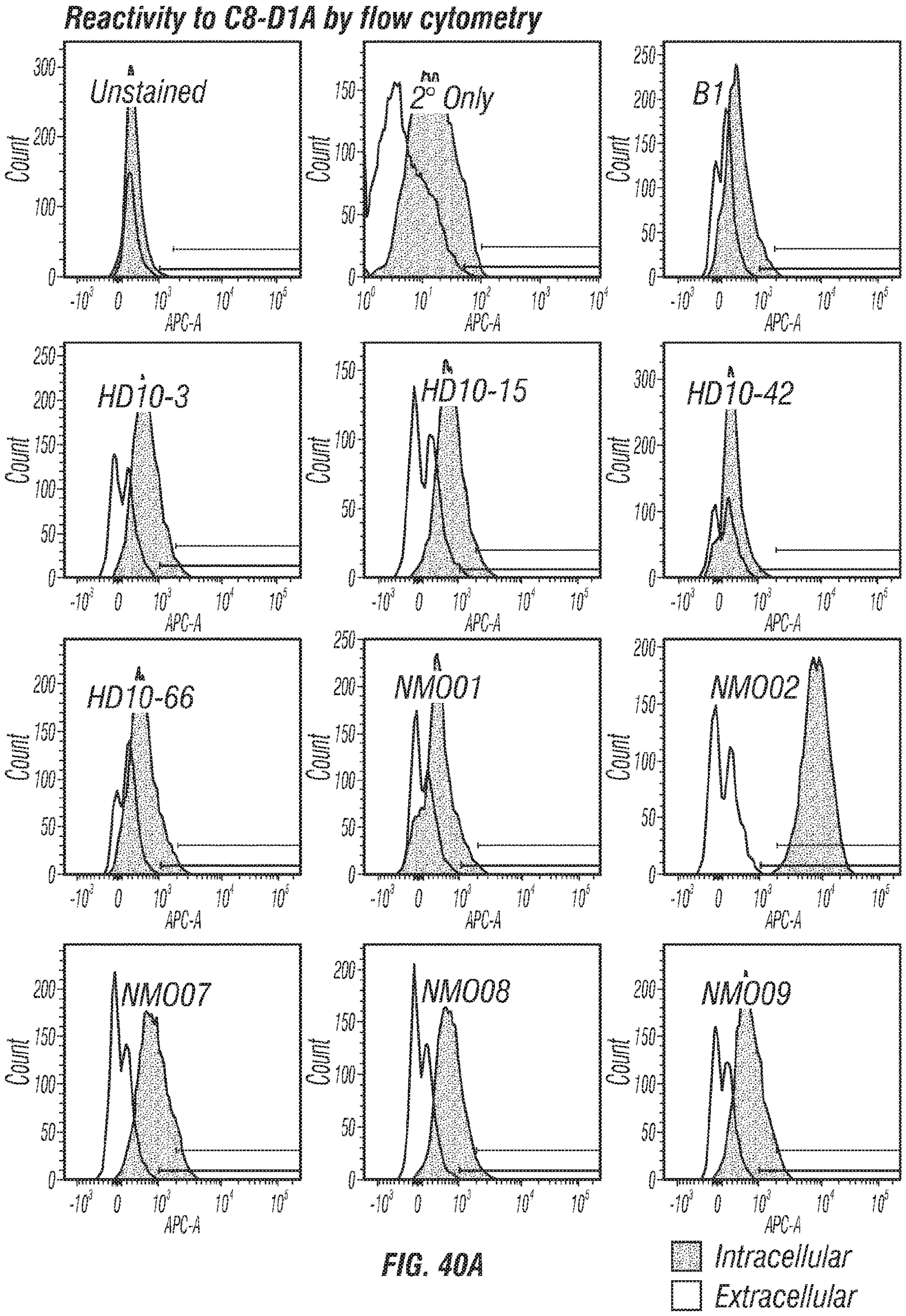
FIGS. 40A-40B. Reactivity to C8-D1A by flow cytometry.
Figure 40A:
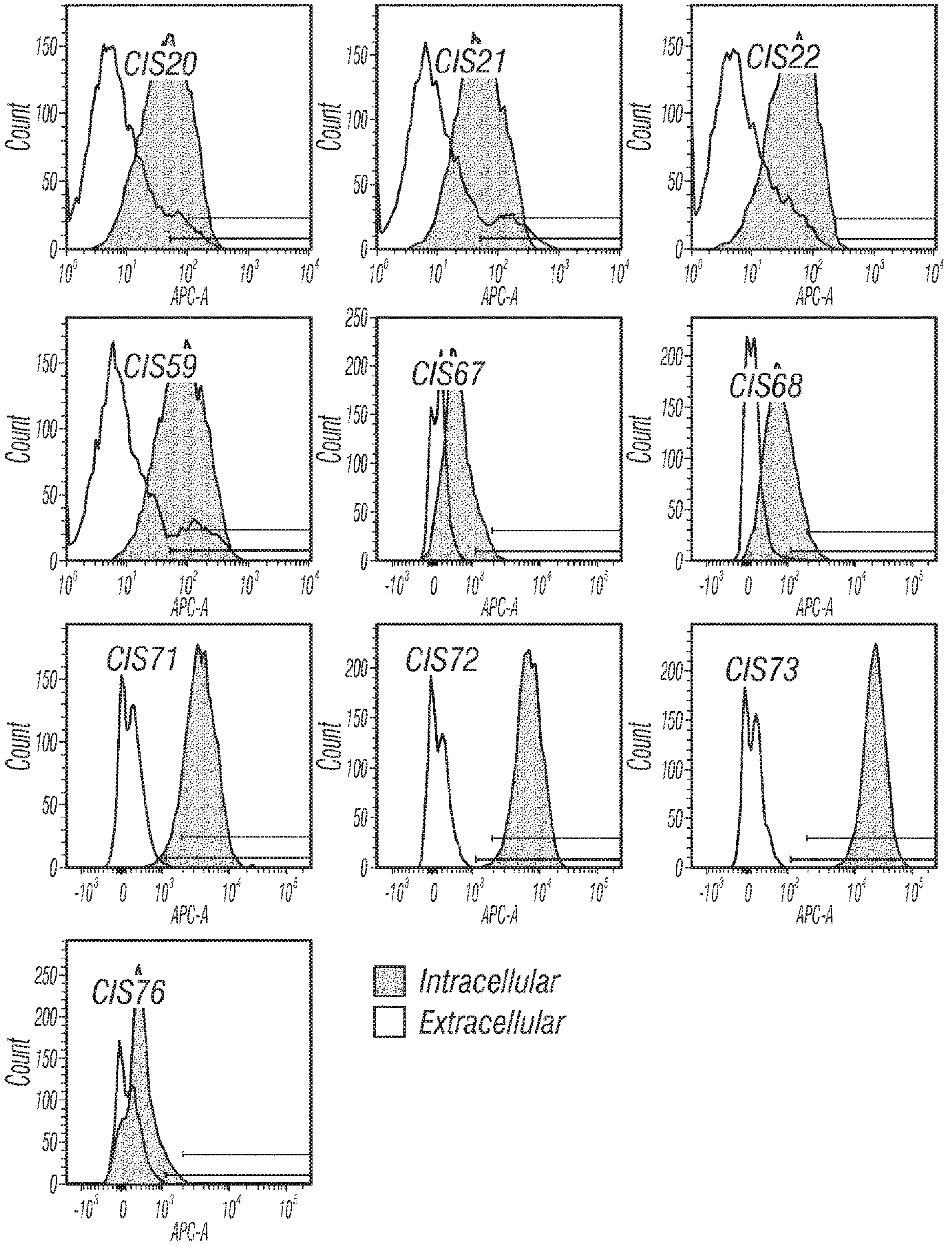
Figure 40A:
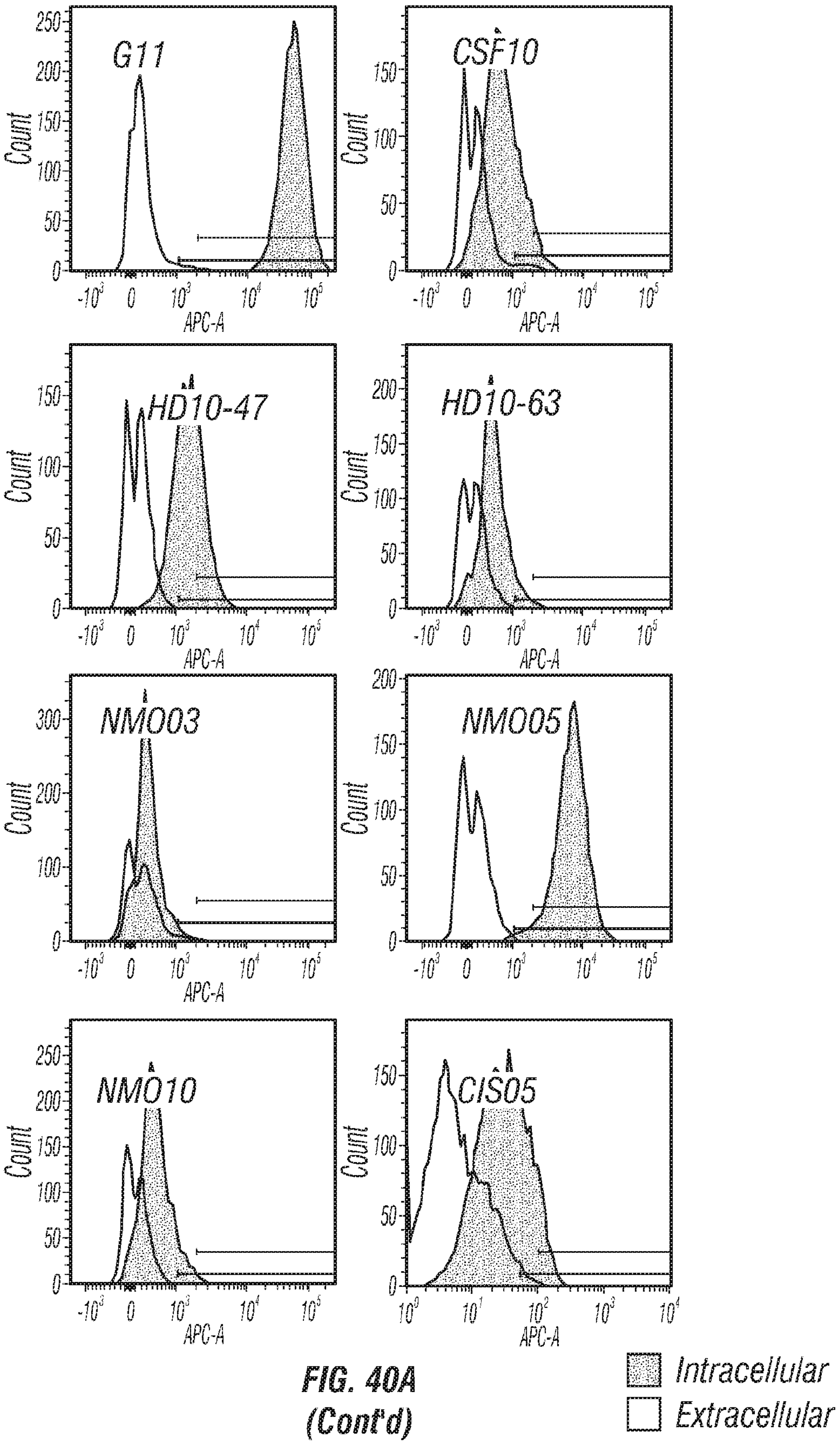
Figure 40A:
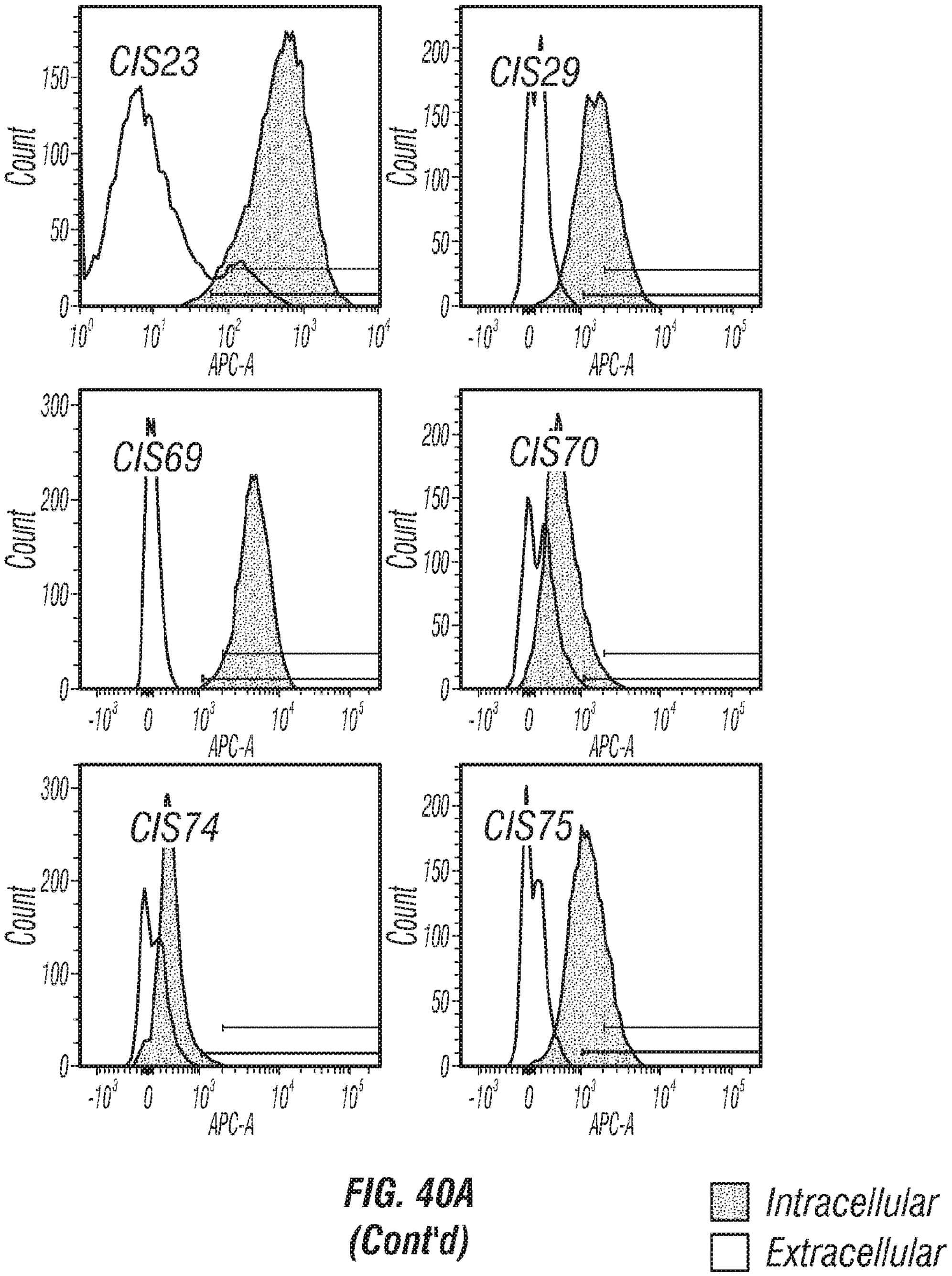
Figure 40B:
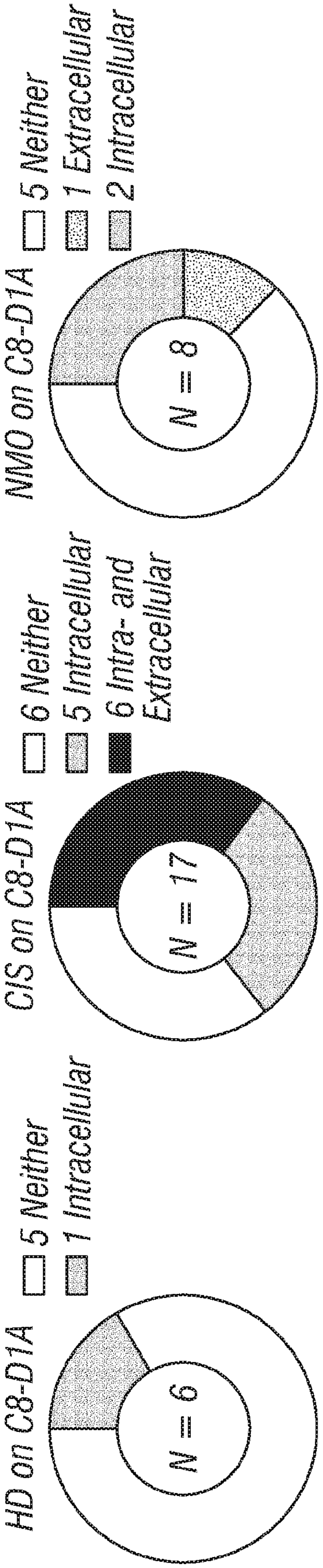
Figure 41A:
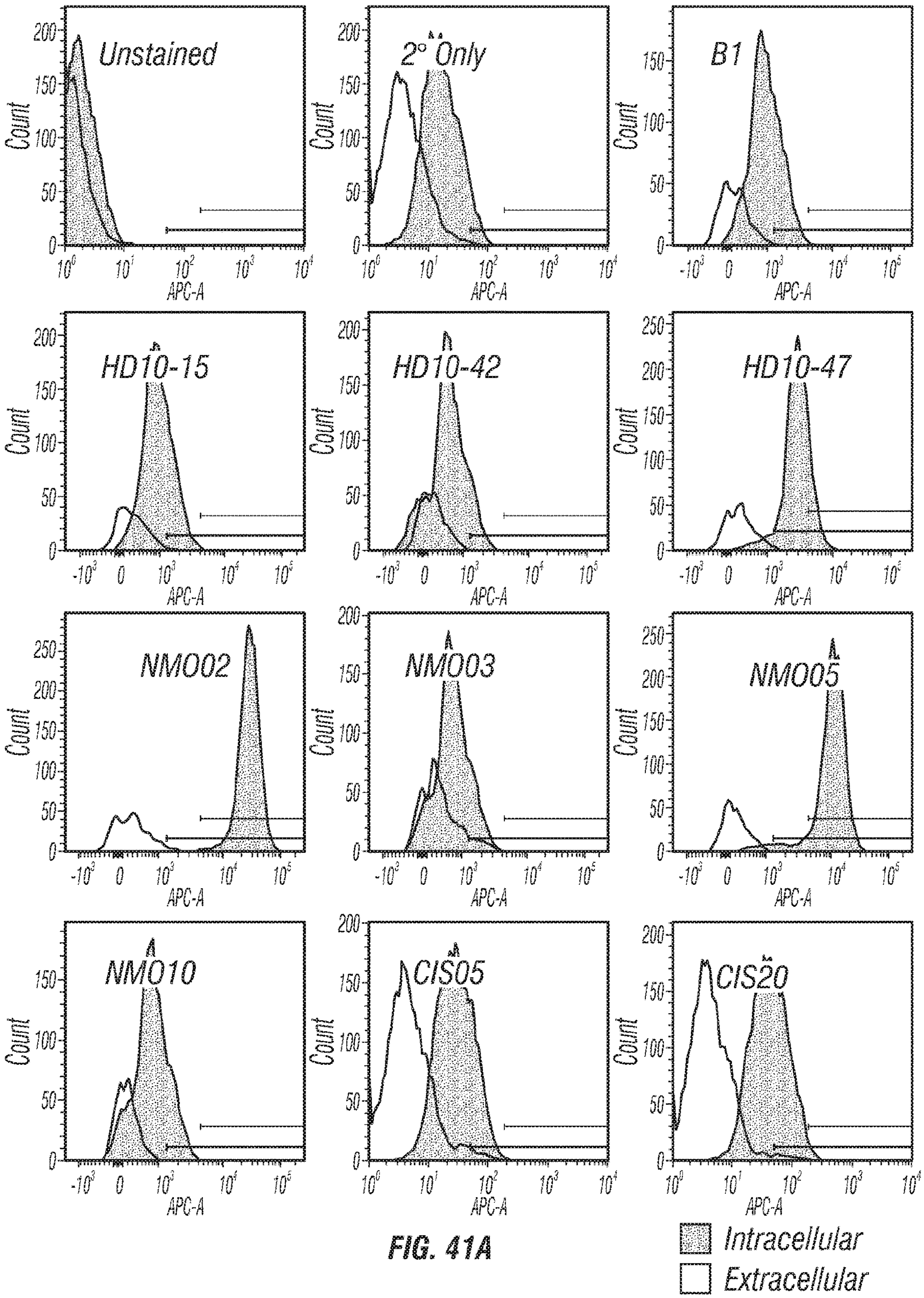
FIGS. 41A-41B. Reactivity to Neuro-2a by flow cytometry.
Figure 41A:
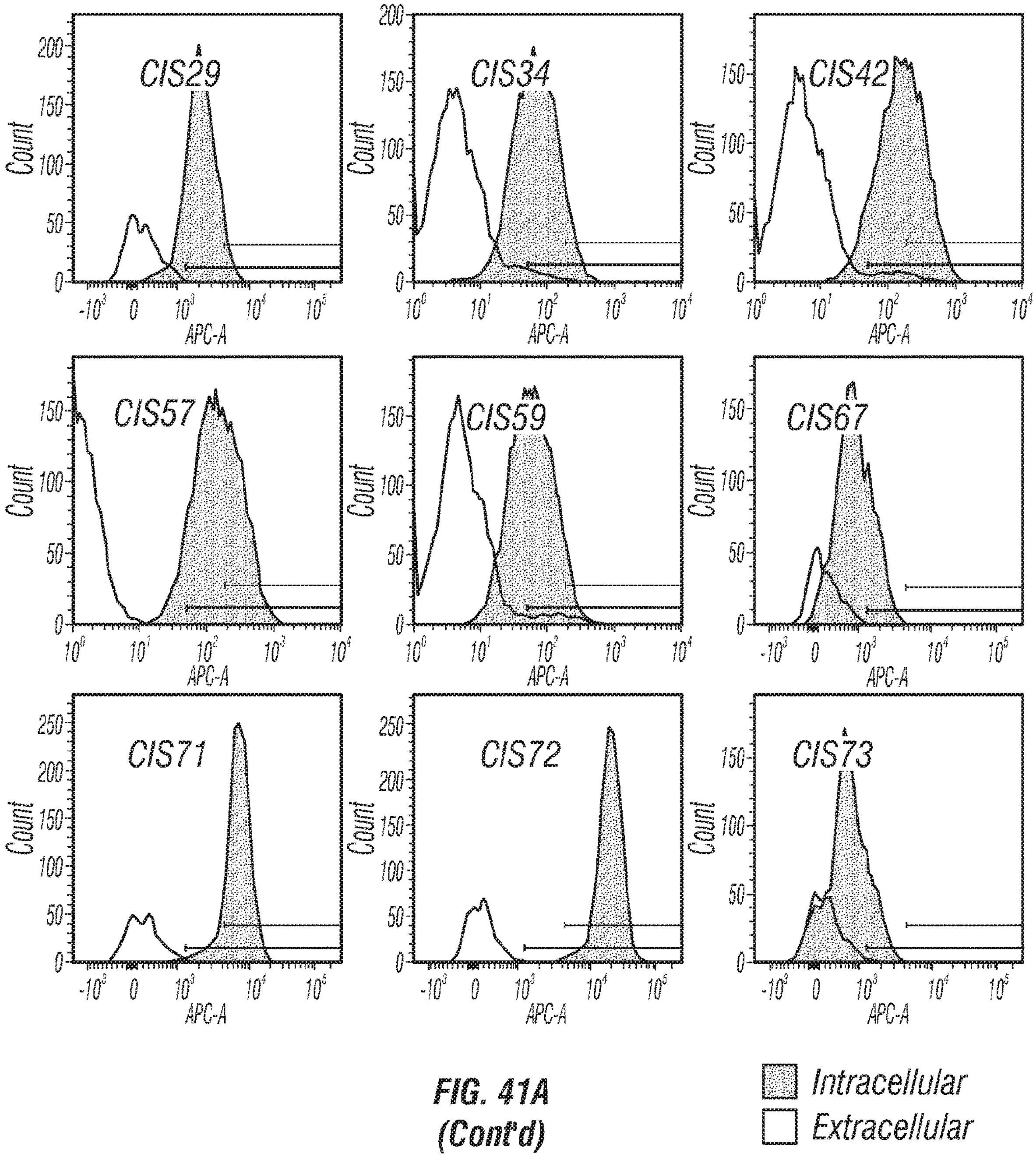
Figure 41A:
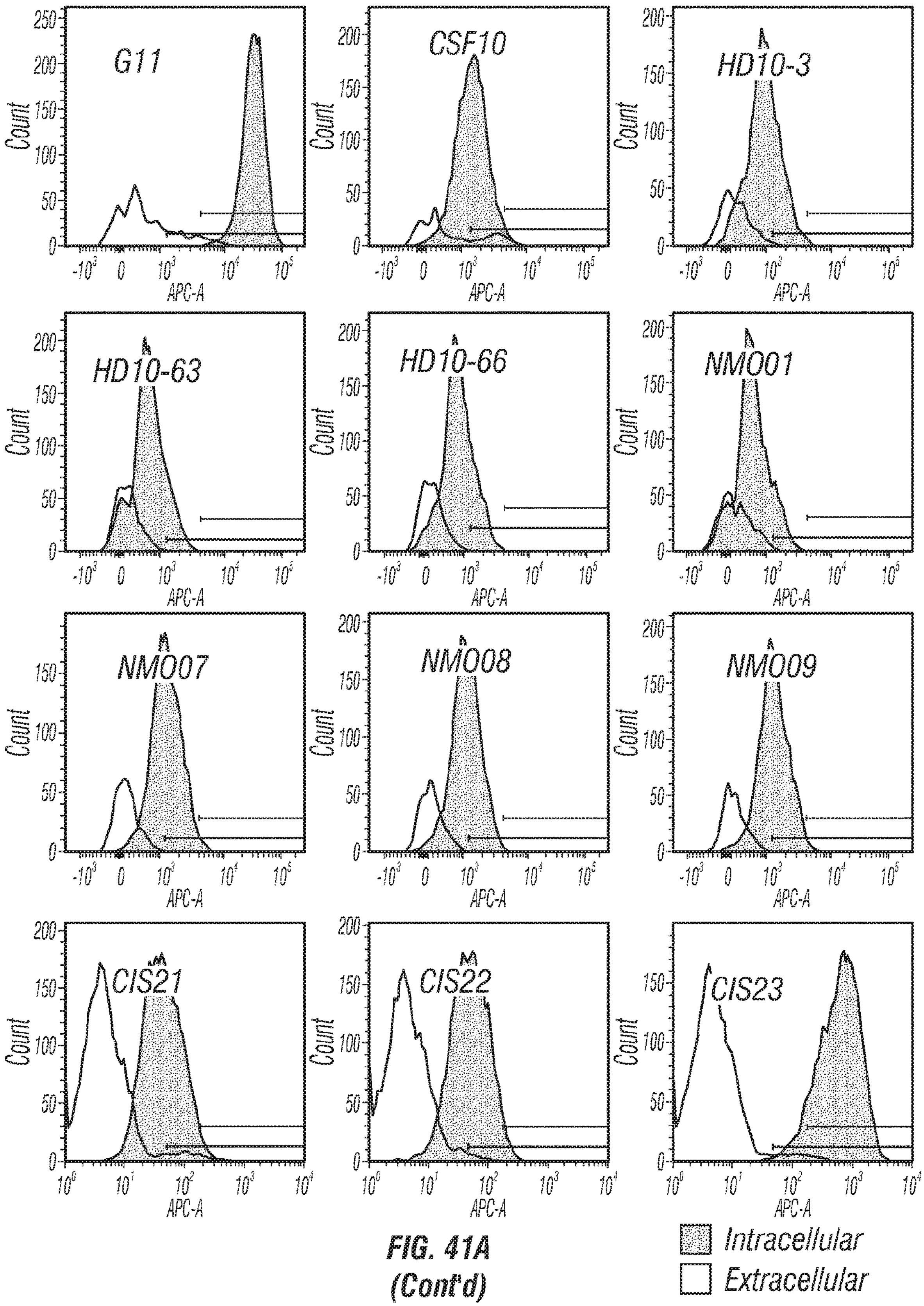
Figure 41A:
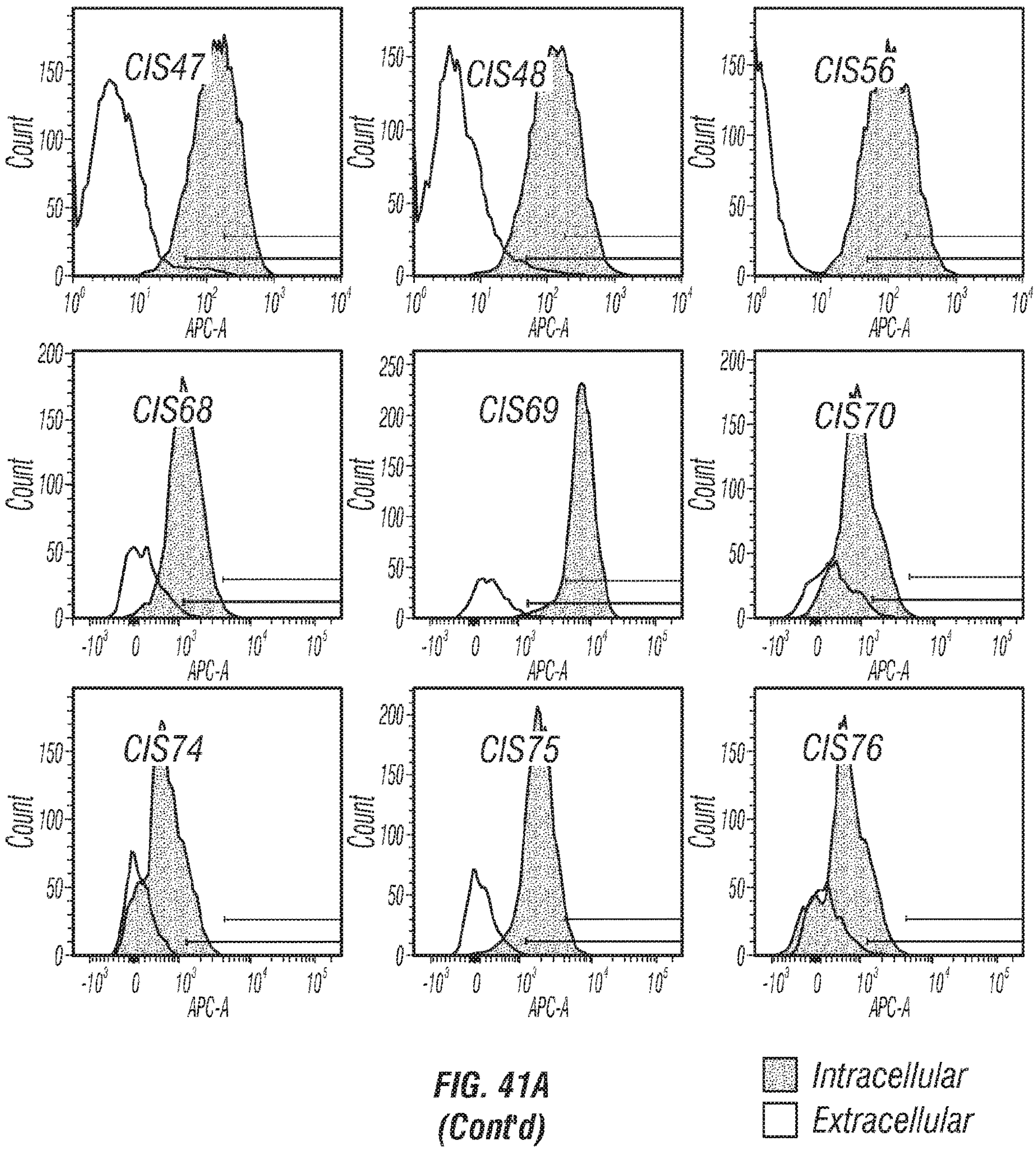
Figure 41B:
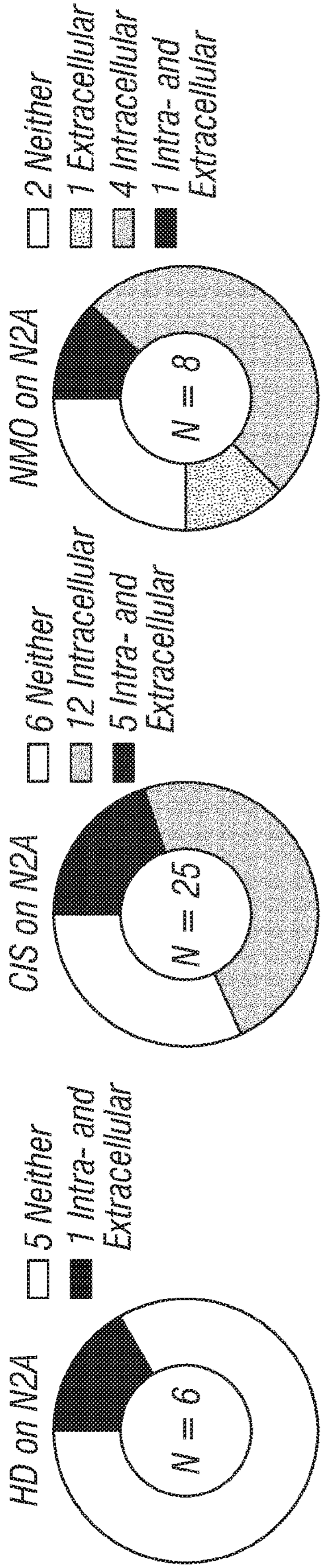

CIS-PTM peripheral plasmablasts bind both intracellular and extracellular antigens. To further verify the cellular specificity observed by histological methods, the inventor used flow cytometry to determine whether the 38 CIS-PTM plasmablast rhAbs were binding intracellular and/or extracellular antigens. The human neuroblastoma line SH-Sy5y (FIG. 38A-38B and FIG. 39), mouse neuroblastoma line Neuro-2a (FIGS. 40A-40B), and mouse astrocytoma line C8-D1A (FIGS. 41A-41B) were all tested by this method. In FIGS. 38A-38B, B1 is presented as a negative control, G11 is presented as a positive control for intracellular targets, and 6 rhAbs are presented as examples of each type of binding pattern (negative, intracellular, or extracellular). With only 2 exceptions (CIS19 and CIS68), the rhAbs that recognized either neurons or glial cells by histology recognized their corresponding cell type by this method (Table 8). Not surprisingly some discrepancies exist between the recognition of mouse brain and human neuroblastoma cell lines by individual rhAbs (Table 8). The rhAbs demonstrated multiple patterns of recognition ranging from only intracellular (i.e., CIS35, 99.4%) to primarily extracellular antigens (i.e., CIS44, 98.7%) (FIGS. 38A-38B, FIG. 39, FIGS. 40A-40B and FIGS. 41A-41B). Of the 27 CIS-PTM rhAbs that recognized SH-Sy5y cells, 14 recognized both intracellular and extracellular antigens, while 13 recognized only intracellular antigens (FIG. 38B).

Figure 42A:
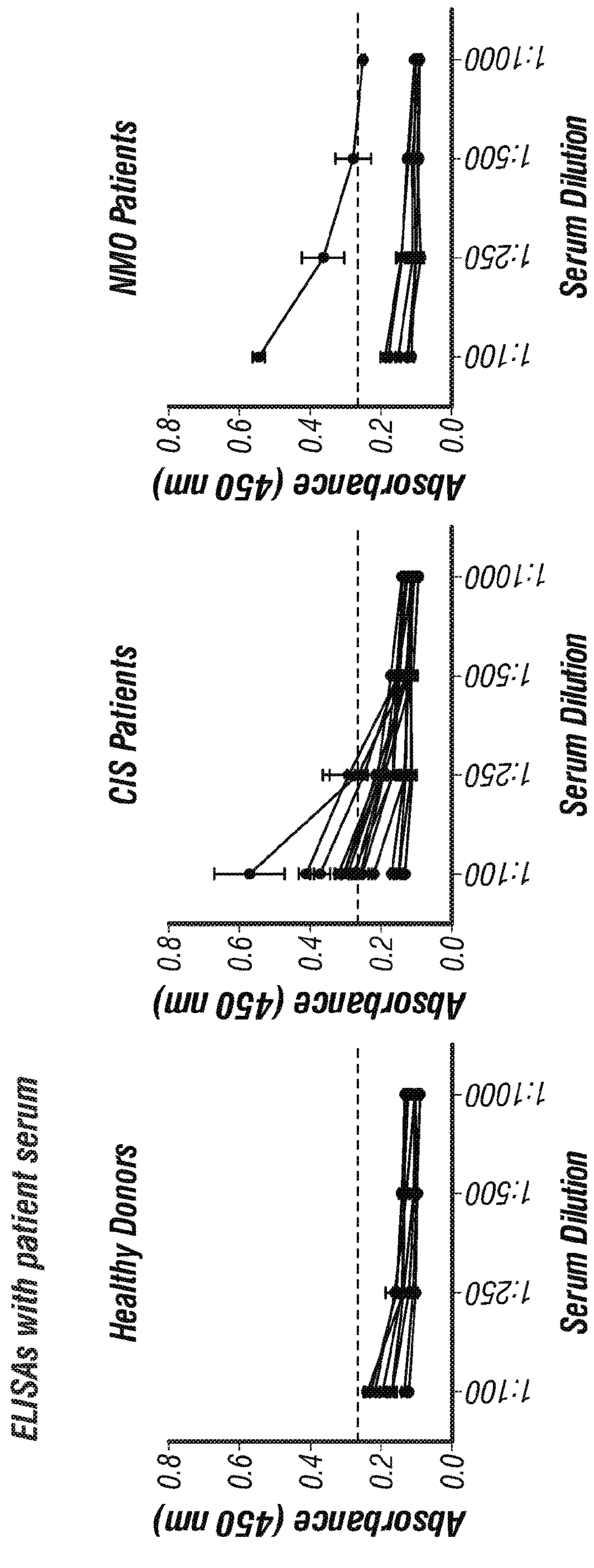
FIGS. 42A-42B. ELISAs with patient serum. Figures show brain lysate ELISA results with dilutions of plasma taken from 7 healthy donors responding to influenza vaccination, 7 NMO patients, and 16 CIS patients.
Figure 42B:
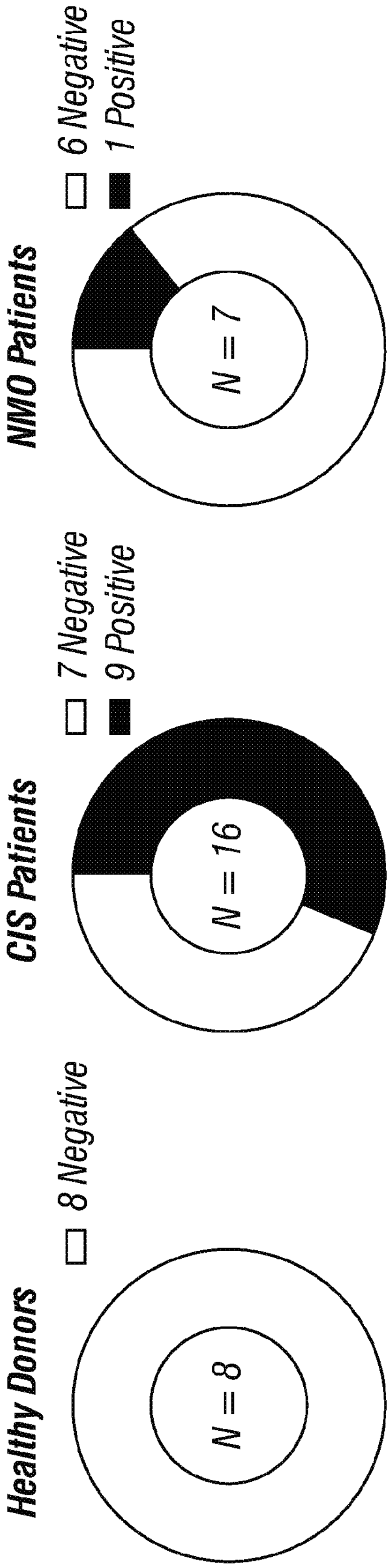

CIS-PTM plasmablast antibodies are well represented in the plasma pool. Even when expanded, plasmablasts are only a small portion of the peripheral B cell pool, and thus may have a small impact on the ongoing auto-reactivity associated with MS. To assess whether this small expansion could lead to an observable increase in autoreactive antibodies in the plasma, the inventor tested plasma samples from 7 NMO patients, 8 healthy donors with plasmablasts responding to recent influenza vaccination, and 16 treatment naïve CIS-PTM patients for reactivity to brain lysate by ELISA (FIGS. 42A-42B), including all 7 of the CIS-PTM patients from which the inventor cloned rhAbs. Plasma samples from all 8 healthy donors and 6 of the 7 NMO patients were not reactive (FIG. 42A). Notably, the one NMO patient with high binding to brain lysate was treatment naïve while the remaining NMO patients were on Cellcept therapy (Table 8). Of the 16 CIS-PTM patients, 9 show plasma reactivity at least 2 standard deviations above the mean of healthy donors (FIG. 42B). Plasma from the 6 patients whose rhAbs were reactive to brain lysate also had higher antibody titers in the plasma towards brain lysate in comparison to plasma from healthy donors. The 1 patient who showed little rhAb reactivity also did not display plasma reactivity (FIG. 42A, Table 7).

TABLE 7

Patient Information

| | Patient | Gender | Age | Diagnosis at Draw | Current Diagnosis | Treatment at Draw | Current Treatment | Percent of Plasmablasts in Blood | Percent of Plasmablasts in CSF | Plasma ELISA Result |
|---|---|---|---|---|---|---|---|---|---|---|
| CIS Patients | CIS924* | M | 69 | TM | TM | None | None | 7.1 | 33.3 | − |
| Included in | CIS799* | F | 28 | CIS | RRMS | None | Avonex | 5.74 | 13.3 | + |
| Genetic | CIS991* | F | 34 | CIS | TM | None | Steroids | 3.3 | 15.4 | + |
| Analysis | CIS111*+◆ | F | 62 | CIS | PPMS | None | Avonex | 3.04 | 5.77 | + |
| | CIS663* | F | 32 | TM | TM | None | None | 2.85 | 10.8 | − |
| | CIS431*+◆ | F | 27 | CIS | RRMS | None | Gilenya | 2.07 | 35.9 | + |
| | ATM4 | M | 24 | CIS | RRMS | Prednisone | None | 1.54 | 16.1 | + |
| | CIS353*+◆ | F | 58 | CIS | RRMS | None | Copaxone | 1.45 | 11.4 | + |
| | CIS683*+◆ | F | 39 | CIS | RRMS | None | Tecfidera | 0.82 | 26.6 | + |
| CIS Patients | CIS287*◆ | F | 45 | TM | TM | None | Betaseron | 6.58 | 37.9 | − |
| Not Included | CIS873*◆ | F | 19 | RRMS | RRMS | None | Avonex | 2.98 | 26 | − |
| in Genetic | CIS527*◆ | F | 43 | CIS | RRMS | None | Copaxone | 1.81 | 14.1 | + |
| Analysis | CIS699* | F | 37 | CIS | RRMS | None | Avonex | 1.61 | 7.87 | − |
| | CIS787*◆ | M | 33 | CIS | RRMS | None | Copaxone | 1.45 | 36.9 | − |
| | CIS251*◆ | F | 53 | TM | Sarcoidosis | None | None | 1.43 | 2.57 | − |
| | CIS942* | F | 52 | CIS | CIS | None | Copaxone | 1.19 | 12.2 | |
| | CIS328*◆ | M | 32 | CIS | RRMS | None | Avonex | 0.64 | 2.41 | − |
| | CIS371*◆ | F | 56 | CIS | CIS | None | Copaxone | 0.51 | 13.9 | |
| NMO Patients | NMO.1 | F | 55 | NMO | NMO | None | Cellcept | 3.47 | n/a | + |
| Included in | NMO.2 | F | 36 | NMO | NMO | None | None | 0.22 | n/a | |
| Genetic | NMO.7 | F | 54 | NMO | NMO | None | Cellcept | 4.09 | n/a | |
| Analysis | NMO.8 | F | 64 | NMO | NMO | None | Rituxan | 2.43 | n/a | |
| NMO Patients | NMO.3 | F | 39 | NMO | NMO | Cellcept | Cellcept | 1.05 | n/a | |
| Not Included | NMO.4 | F | 61 | NMO | NMO | Cellcept | Cellcept | 0.09 | n/a | |
| in Genetic | NMO.5 | F | 41 | NMO | NMO | Cellcept | Rituxan | 1.08 | n/a | |
| Analysis | NMO.6 | M | 47 | NMO | NMO | Cellcept | Rituxan | 1.01 | n/a | |
| | NMO.9 | F | 53 | NMO | NMO | Cellcept | Cellcept | 1.34 | n/a | − |
| | NMO.10 | F | 61 | NMO | NMO | Cellcept | Cellcept | 0.17 | n/a | − |
| | NMO.31 | F | 46 | NMO | NMO | AZT | Unknown | 0 | n/a | − |

TABLE 7-continued

| Patient Information | | | | | | | | | | |
|---|---|---|---|---|---|---|---|---|---|---|
| Patient | Gender | Age | Diagnosis at Draw | Current Diagnosis | Treatment at Draw | Current Treatment | Percent of Plasmablasts in Blood | Percent of Plasmablasts in CSF | Plasma ELISA Result |
| NMO.33 | M | 38 | NMO | NMO | Cellcept | Unknown | 5.97 | n/a | − |
| NMO.70 | F | 45 | NMO | NMO | AZT | Unknown | 4.52 | n/a | |
| NMO.260 | F | 47 | NMO | NMO | Cellcept | Unknown | 3.02 | n/a | |
| NMO.626 | M | 36 | NMO | NMO | AZT | Unknown | 2.15 | n/a | |
| NMO.740 | F | 29 | NMO | NMO | AZT | Unknown | 3.13 | n/a | |
| NMO.745 | F | 50 | NMO | NMO | Cellcept | Unknown | 1.66 | n/a | |

*CSF and peripheral B cells previously studied by flow cytometry
♦CSF B cell previously studied by genetic analysis
†Peripheral B cells previously studied by genetic analysis

TABLE 8

| Antibody Information | | | | | | | | | | |
|---|---|---|---|---|---|---|---|---|---|---|
| rhAB | Patient | HC (V) | HC (J) | LC (V) | LC (J) | HC Mut | Isotype | Brain ELSIA | Kidney ELSIA | Sy5y ICC |
| CIS56 | ATM4 | H4-61 | 3 | L3-45 | 7 | 26 | ND | + | + | N + C |
| CIS57 | ATM4 | H4-59 | 6 | K3-20 | 5 | 17 | ND | + | + | N |
| CIS59 | ATM4 | H4-31 | 4 | K2-24 | 2 | 15 | IgG | − | − | C |
| CIS60 | ATM4 | H4-61 | 3 | K2-30 | 2 | 15 | IgM | − | − | − |
| CIS45 | CIS111 | H4-59 | 4 | K1-6 | 2 | 31 | IgG | + | − | C |
| CIS46 | CIS111 | H4-34 | 6 | K1-39 | 2 | 22 | IgG | − | − | C |
| CIS47 | CIS111 | H4-34 | 6 | K4-1 | 5 | 22 | IgG | − | − | − |
| CIS48 | CIS111 | H4-39 | 6 | K1-12 | 2 | 20 | ND | + | + | C |
| CIS49 | CIS111 | H4-34 | 5 | K2-39 | 5 | 17 | ND | − | − | N + C |
| CIS52 | CIS111 | H4-59 | 2 | L1-44 | 7 | 36 | ND | − | − | − |
| CIS05 | CIS353 | H4-39 | 4 | K3-20 | 5 | 17 | ND | − | − | − |
| CIS06 | CIS353 | H3-23 | 3 | K4-1 | 3 | 23 | IgG | − | − | − |
| CIS19 | CIS353 | H4-6 | 3 | K2-5 | 2 | 25 | IgG | + | − | C |
| CIS20 | CIS353 | H4-58 | 3 | K1-33 | 2 | 18 | IgG | − | + | − |
| CIS21 | CIS353 | H4-39 | 5 | K5-20 | 5 | 16 | ND | − | − | C |
| CIS22 | CIS353 | H4-4 | 1 | K1-5 | 2 | 12 | IgG | − | − | C |
| CIS23 | CIS353 | H3-21 | 4 | K3-20 | 5 | 23 | IgG | − | − | C |
| CIS26 | CIS353 | H4-b | 3 | L1-47 | 3 | 38 | IgG | + | − | C |
| CIS09 | CIS431 | H4-4 | 4 | K3-11 | 5 | 10 | ND | − | − | C |
| CIS10 | CIS431 | H3-30 | 4 | K3-5 | 4 | 32 | ND | − | + | N |
| CIS35 | CIS431 | H4-59 | 4 | L2-24 | 1 | 22 | IgM | − | − | − |
| CIS42 | CIS431 | H4-30 | 4 | L2-23 | 7 | 35 | ND | + | + | C |
| CIS44 | CIS431 | H4-59 | 6 | L2-8 | 3 | 20 | ND | + | − | C |
| CIS07 | CIS683 | H4-59 | 5 | K3-20 | 5 | 28 | IgG | + | − | − |
| CIS08 | CIS683 | H3-23 | 6 | K3-11 | 5 | 22 | ND | − | − | − |
| CIS28 | CIS683 | H4-59 | 5 | K3-11 | 3 | 8 | IgG | + | + | N + C |
| CIS29 | CIS683 | H3-23 | 3 | K1-3 | 2 | 20 | IgG | − | − | − |
| CIS34 | CIS683 | H4-34 | 4 | L3-10 | 2 | 5 | IgG | − | − | N + C |
| CIS67 | CIS799 | H4-30 | 4 | K2-30 | 2 | 17 | ND | − | − | − |
| CIS68 | CIS799 | H3-38 | 4 | K1-5 | 5 | 16 | ND | + | + | N |
| CIS69 | CIS799 | H4-30 | 6 | K1-27 | 9 | 12 | ND | − | − | − |
| CIS70 | CIS799 | H3-30 | 4 | K3-20 | 5 | 31 | IgG | − | − | C |
| CIS75 | CIS799 | H4-39 | 2 | L6-57 | 3 | 23 | ND | + | + | − |
| CIS71 | CIS924 | H4-4 | 5 | K1-9 | 2 | 19 | IgG | − | − | C |
| CIS72 | CIS924 | H4-34 | 6 | L2-14 | 2 | 13 | ND | − | − | − |
| CIS73 | CIS924 | H4-31 | 4 | K1-12 | 2 | 12 | IgG | − | − | − |
| CIS74 | CIS924 | H3-30 | 4 | K1-39 | 5 | 26 | IgM | − | − | − |
| CIS75 | CIS924 | H3-23 | 5 | K1-17 | 3 | 20 | ND | − | − | − |
| NMO01 | NMO.01 | H4-30 | 3 | L2-8 | 2 | 27 | IgG | − | − | − |
| NMO02 | NMO.01 | H2-39 | 4 | K1-5 | 2 | 7 | IgM | − | − | C |
| NMO03 | NMO.01 | H4-39 | 4 | L2-23 | 2 | 6 | IgM | + | + | − |
| NMO04 | NMO.01 | H4-39 | 4 | L2-23 | 2 | 3 | IgM | − | − | − |
| NMO05 | NMO.01 | H3-7 | 3 | K2-30 | 2 | 23 | IgM | − | − | − |
| NMO06 | NMO.02 | H4-39 | 6 | L6-57 | 3 | 9 | IgG | + | + | N |
| NMO07 | NMO.07 | H4-4 | 6 | K3-20 | 4 | 11 | IgG | − | − | − |
| NMO08 | NMO.07 | H3-30 | 6 | K2-28 | 2 | 12 | IgG | − | − | N |
| NMO09 | NMO.08 | H4-31 | 4 | K3-20 | 2 | 33 | IgM | − | − | − |
| NMO10 | NMO.08 | H4-39 | 3 | K3-15 | 2 | 12 | ND | − | − | − |

| rhAB | Hep2 ICC | Stoke Brain | EAE Brain | Healthy Brain | Sy5y FC | N2A FC | C8D1A FC | MOG | MBP |
|---|---|---|---|---|---|---|---|---|---|
| CIS56 | C | N + G | N + G | N + G | I + E | I | | + | + |
| CIS57 | C | N + G | N + G | N + G | I + E | I | | + | + |

TABLE 8-continued

| Antibody Information | | | | | | | | | |
|---|---|---|---|---|---|---|---|---|---|
| CIS59 | – | – | – | N + G | I + E | I + E | I + E | – | – |
| CIS60 | – | | | | – | I | | – | – |
| CIS45 | – | N + G | N + G | N + G | – | | | + | + |
| CIS46 | – | N + G | G | N + G | I + E | | | – | – |
| CIS47 | – | – | N + G | G | I | I | | – | – |
| CIS48 | – | N + G | G | G | I + E | I | | – | – |
| CIS49 | – | | | | I + E | I + E | | – | – |
| CIS52 | – | | | | I | | | – | – |
| CIS05 | – | | | | – | – | – | – | – |
| CIS06 | – | | | | I | – | | – | – |
| CIS19 | – | N + G | N + G | N + G | – | | | + | + |
| CIS20 | – | | | | I | – | I + E | – | – |
| CIS21 | – | | | | I | – | I + E | – | – |
| CIS22 | – | | | | I | – | I + E | – | – |
| CIS23 | N + C | | | | I | I | I + E | + | + |
| CIS26 | – | – | N + G | N + G | – | | | – | – |
| CIS09 | – | | | | I | | | – | – |
| CIS10 | – | | | | I + E | | | – | – |
| CIS35 | – | – | – | N + G | I | | | – | – |
| CIS42 | C | N + G | N + G | N + G | I + E | I + E | | + | + |
| CIS44 | – | N + G | – | N + G | I + E | | | – | – |
| CIS07 | – | G | G | G | I | | | – | – |
| CIS08 | – | | | | – | | | – | – |
| CIS28 | N | N + G | N + G | N + G | I + E | | | + | + |
| CIS29 | – | | | | I | I | I | – | – |
| CIS64 | N | N + G | N + G | N + G | – | I | | + | + |
| CIS67 | – | | | | – | – | – | – | – |
| CIS68 | N | N + G | N + G | N + G | I + E | I | – | + | + |
| CIS69 | – | | | | I + E | I + E | I | – | – |
| CIS70 | – | | | | – | I + E | – | – | – |
| CIS75 | – | N + G | N + G | N + G | I + E | – | – | + | – |
| CIS71 | – | | | | I + E | I | I + E | – | + |
| CIS72 | – | G | N + G | G | – | I | I | – | – |
| CIS73 | – | N + G | G | G | I | – | I | – | – |
| CIS74 | – | | | | – | – | – | – | – |
| CIS75 | – | | | | – | I | I | – | – |
| NMO01 | – | | | | I | – | – | – | – |
| NMO02 | – | | | | I | I + E | I | – | – |
| NMO03 | C | N + G | N + G | N + G | I + E | E | E | + | + |
| NMO04 | – | | | | – | | | – | – |
| NMO05 | – | | | | I | I | E | – | – |
| NMO06 | – | N + G | N + G | N + G | – | | | + | + |
| NMO07 | – | | | | – | I | – | – | – |
| NMO08 | – | | | | – | I | – | – | – |
| NMO09 | – | G | G | G | – | I | – | – | – |
| NMO10 | – | | | | – | – | – | – | – |

Bold = VH4 antibodies
Thin = VH3 antibodies
White = VX antibodies
Gray = VL antibodies
ND = Not Detectable
+ = Positive
– = Negative
N = Nuclear
C = Cytoplasmic
N + C = Both
N + G = Neurons + Glia
G = Glia
I = Intracellular
E = Extracellular
I + E = Both

Discussion

Peripheral B cell pools are key components of MS pathogenesis because blocking their entrance to the CNS has a profound effect on disease (Stuve et al., 2006). In this study the focus was on one particular subset of B cell, identified as a plasmablast by the upregulation of CD27 expression and simultaneous expression of CD38 and CD95 (Fink et al., 2012; Jacobi et al., 2010; Frolich et al., 2010; Odendahl et al., 2000; Avery et al., 2005). Previously, the inventor demonstrated that the frequency of CD27-high plasmablasts in the CSF is elevated in patients experiencing their first attack of transverse myelitis (Ligocki et al., 2013). Interestingly, the four patients in that study who later experienced additional MRI activity had elevated frequencies of CD27-high plasmablasts at the time of their initial event, which recapitulated findings by others that the frequency of plasmablasts correlates with parenchymal inflammatory disease activity as disclosed by MRI (Cepok et al., 2005). In this example, the inventor extends those findings by demonstrating an expansion of plasmablasts in the blood of CIS-PTM patients compared to healthy donors. Interestingly, the frequency of peripheral plasmablasts in the current CIS-PTM cohort was similar to that of NMO patients, a CNS autoimmune disease in which patients also experience transverse myelitis symptoms, but without brain inflammation (Parratt et al., 2010). Thus, it is possible that plasmablast expansion in the periphery is a feature shared among patients with CNS diseases who experience transverse myelitis symptoms independent of brain inflammation status. The events that drive CIS-PTM patients to MS rather than NMO remains unknown.

The antibody genetics of a B cell population can have profound impact on the understanding of disease, as the development and function of a B cell is dependent on the antibody it expresses (19, Brezinshcek et al., 1997; Casellas et al., 2001; Meffre et al., 2000; Odendahl et al., 2000; Wardemann et al., 2003). In fact, antibody genetics studies have led to several key discoveries in MS that show expansion of particular genes, excessive receptor editing, dysregulation in B cell selection (Ligocki et al., 2013; Krumbholz et al., 2012; Monson et al., 2005; Harp et al., 2007; Cameron et al., 2009; Owens et al., 1998; Palanichamy et al., 2014; von Budingen et al., 2012; Owens et al., 2003; Ritchie et al., 2004; Qin et al., 1998; Colombo et al., 2000; Colombo et al., 2003; Winges et al., 2007; von Budingen et al., 2008; von Budingen et al., 2010; Bankoti et al., 2014; Rounds et al., 2014; Qin et al., 2003; Haubold et al., 2004), and even a mutational biomarker that identifies patients who will convert to MS with 86-92% accuracy (Rounds et al., 2015). In this example, the inventor demonstrates that the variable heavy chain family 4 (VH4) genes are used more extensively by peripheral plasmablasts from CIS-PTM and NMO patients in comparison to previously published generalized healthy donor B cell pool and healthy donor plasmablasts following flu vaccination. However, 7 of the 9 VH4 family genes were utilized at frequencies similar to these two control populations. This indicates that the VH4 family itself is over-utilized in both CIS-PTM and NMO patient populations, rather than particular VH4 genes driving the over-utilization of the VH4 family. This data also suggests that VH4 expansion may be a generalized feature of patients with CNS diseases who experience transverse myelitis symptoms. Others have demonstrated VH4 family expansion in the CSF of MS patients (Bennett et al., 2008; Owens et al., 2007), which may suggest that VH4 expansion is an early and prolonged feature of particular CNS diseases. Interestingly, B cells from the cerebrospinal fluid of NMO patients are dominated by an expansion of VH2 genes, not VH4 genes (Bennett et al., 2015).

In this study, the inventor demonstrates that the expansion of VH4 utilization in peripheral plasmablasts translates to an increase in autoreactivity toward brain antigens. The inventor used a human brain lysate (hBL) ELISA to initially screen rhAbs cloned from plasmablasts for binding to brain targets, but soon after discovered that this assay often led to false negatives. Several rhAbs exhibited binding to neuron bodies and glial cell processes in the brain, but were not reactive in the hBL ELISA. However, it should be noted that the hBL preparation would consist mainly of cytosolic and easily soluble proteins, and much of it would consist of myelin proteins, which represent as much as 30% of all proteins in the brain (Siegel et al., 1999). Thus, non-myelin and hydrophobic protein targets are under-represented in the hBL antigen pool, diminishing the probability of identifying primary targets not associated with myelin. Furthermore, mild detergents in the buffer easily compromise the conformational integrity of proteins in ELISA platforms (von Budigen et al., 2004; 2002). Thus, the identification of brain-reactive rhAbs relied more heavily on their ability to bind cellular targets by either tissue histology or flow cytometric cell-based assays. Indeed, hBL ELISA positivity was noted for only about half of the CIS-PTM plasma samples from this cohort, despite clinical and immunological evidence of their CNS reactivity. For this reason, the inventor would agree that a multi-tiered pipeline for characterizing the CNS-reactive potential of antibodies in any CNS disease setting with suspected autoimmune components involving humoral immunity is necessary as suggested by others (Zekeridou et al., 2015).

When rhAb reactivity is considered in aggregate, it is interesting to note that whereas the CSF-derived rhAbs from these patients were largely reactive to neurons and astrocytes in the gray matter of the brain (Ligocki et al., 2015), many of the rhAbs generated from the peripheral plasmablasts were directed towards both gray and white matter targets. This data suggests that peripheral plasmablasts have a wider array of autoreactive specificities than CSF-derived B cells. This scenario is consistent with underlying dysregulation in tolerance of peripheral B cells in these CIS-PTM patients, and indeed others have demonstrated that there is a break in the peripheral tolerance checkpoint in MS patients (Tiller et al., 2008). The exact mechanism of CNS-reactive effector B cell development in the blood is still unknown, and this break in tolerance could involve both B cell intrinsic and extrinsic mechanisms. The rapid return of memory B cells in the periphery following B cell depletion as a strong indicator of poor response to therapy further emphasizes the importance of studying the development of autoreactive B cells in the periphery.

During an exacerbation of MS, the blood brain barrier is often compromised, allowing increased exchange of antigen stimulated cells between the CNS and periphery (Minagar and Alexander, 2003; Holman et al., 2011), including intracellular antigens whose ability to drive autoimmunity is only beginning to be understood (Lim et al., 2006; Waldman and Madaio, 2005; Racanelli et al., 2011; Yanase et al., 1997; Jang et al., 2009; Song et al., 2008). There are many scenarios that may account for this discordance in antigen targets of peripheral and CSF-derived B cell subsets. For example, there may be an underlying open access to gray matter targets throughout the disease course, and access to white matter targets primarily during distinct points throughout the disease course. It is also possible that there is less reactivity to white matter targets at later stages of disease due to immune response exhaustion to those targets (Akbar and Henson, 2011; Ratts et al., 2006). Alternatively, gray matter targets may be more immunogenic, considering the more extensive clonal expansion of CSF B cells that bind to these targets as compared to the peripheral plasmablasts. Interestingly, it has been demonstrated that antibodies targeting neurons from clonally expanded CSF B cells from MS patients mediate demyelination of axons in vitro, highlighting their potential to participate in the pathogenesis of disease (Blauth et al., 2015). Delineating the pathway by which autoreactive plasmablasts develop, persist and mediate pathogenesis in MS patients will greatly improve the understanding of the disease, and is particularly important given that the frequency of plasmablasts increases the longer that CIS-PTM patients are left untreated (Ligocki et al., 2013).

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

U.S. Pat. No. 5,475,096
U.S. Pat. No. 5,831,012
U.S. Pat. No. 6,004,746
U.S. Pat. No. 6,794,144
U.S. Pat. No. 6,818,418
U.S. Pat. No. 6,994,982
U.S. Pat. No. 7,166,697
U.S. Pat. No. 7,186,524
U.S. Pat. No. 7,250,297
U.S. Pat. No. 7,417,130
U.S. Pat. No. 7,803,907
U.S. Pat. No. 7,838,629
U.S. Pat. No. 8,394,583
U.S. Patent Publication 2004/023334
U.S. Patent Publication 2004/132094
U.S. Patent Publication 2010/119446
U.S. Patent Publication 2010/239633
U.S. Patent Publication 2014/024699
U.S. Patent Publication 2014/161894
U.S. Patent Publication 2014/371103
U.S. Patent Publication 2015/197746
U.S. Patent Publication 2016/076040
U.S. Patent Publication 2004/146938
U.S. Patent Publication 2004/157209
U.S. Patent Publication 2004/209243
Akbar & Henson, Nat Rev Immunol, 11(4): p. 289-95, 2011.
Avery et al., J Immunol, 174(7): p. 4034-42, 2005.
Bankoti et al., Ann Neurol, 75(2): p. 266-76, 2014.
Bennett et al., J Neuroimmunol, 199(1-2): p. 126-32, 2008.
Bennett et al., Neurol Neuroimmunol Neuroinflamm, 2(3): p. e104, 2015.
Blauth et al., Acta Neuropathol, 130(6): p. 765-81, 2015.
Bo et al., *Arch Neurol.*, January; 64(1):76-80, 2007.
Bo et al., *J Neuropathol Exp Neurol.*, July; 62(7):723-32, 2003.
Brezinschek et al., J Clin Invest, 99(10): p. 2488-501, 1997.
Cameron et al., J Neuroimmunol, 213(1-2): p. 123-30, 2009.
Casellas et al., Science, 291(5508):p. 1541-4, 2001.
Cepok et al., *Brain., July;* 128(Pt 7):1667-76, 2005.
Colombo et al., Eur J Immunol, 33(12): p. 3433-8, 2003.
Colombo et al., J Immunol, 164(5): p. 2782-9, 2000.
Fink et al., Front Immunol, 3:p. 78, 2013.
Fisniku et al., *Ann Neurol., September;* 64(3):247-54, 2008.
Frolich et al., J Immunol, 185(5):p. 3103-10, 2010.
Harp et al., J Neuroimmunol, 183(1-2): p. 189-99, 2007.
Haubold et al., Ann Neurol, 56(1): p. 97-107, 2004.
Holman et al, Biochim Biophys Acta, 1812(2): p. 220-30, 2011.
Jacobi et al., Ann Rheum Dis, 69(1):p. 305-8, 2010.
Jang et al., Cell Mol Life Sci, 66(11-12): p. 1985-97, 2009.
Keegan et al., *Lancet.*, August 13-19; 366(9485):579-82, 2005.
Krumbholz et al., Nat Rev Neurol, 8(11): p. 613-23, 2012.
Lassmann et al., *Brain Pathol., April;* 17(2):210-8, 2007.
Ligocki et al., *J Neuroimmunol.*, September 14; 226(1-2): 192-3, 2010.
Ligocki et al., *Genes Immun.*, Apr. 18, 2013.
Ligocki et al., ASN Neuro, (1759-0914 (Electronic)), 2015.
Lim & Zouali, Immunol Lett, 103(1): p. 17-26, 2006.
Lovato et al., *Brain.*, Jan. 7, 2011.
Lucchinetti et al., *Ann Neurol.*, June; 47(6):707-17, 2000.
Meffre et al., *Nat Immunol,* 1(5): p. 379-85, 2000.
Minagar & J. S. Alexander, Mult Scler, 9(6): p. 540-9, 2003.
Monson et al., J Neuroimmunol, 158(1-2): p. 170-81, 2005.
Obermeier et al., *J Neuroimmunol., April;* 233(1-2):245-8, 2011.
Odendahl et al., J. Immunol, 165:p. 5970-5979, 2000.
Owens et al., Ann Neurol, 43(2): p. 236-43, 1998.
Owens et al., J Immunol, 171(5): p. 2725-33, 2003.
Owens et al., J Immunol, 179(9): p. 6343-51, 2007.
Owens et al., *Ann Neurol.*, June; 65(6):639-49, 2009.
Palanichamy et al., *Sci Transl Med.* 6(248):248ra106, 2014.
Parratt & Prineas, Mult Scler, 16(10):p. 1156-72, 2010.
Qin et al., J Clin Invest, 102(5): p. 1045-50, 1998.
Qin et al., Lab Invest, 83(7): p. 1081-8, 2003.
Racanelli et al., Autoimmun Rev, 10(8): p. 503-8, 2011.
Ratts et al., J Neuroimmunol, 178(1-2): p. 100-10, 2006.
Ritchie et al., J Immunol, 173(1): p. 649-56, 2004.
Rounds et al., Front Neurol, 5: p. 166, 2014.
Rounds et al., Gene, 572(2): p. 191-7, 2015.
Sellebjerg et al., *J Neuroimmunol.*, August 1; 108(1-2):207-15, 2000.
Sellebjerg et al., *J Neurol Sci.*, May 7; 157(2):168-74, 1998.
Siegel et al., Basic Neurochemistry, Molecular, Cellular and Medical Aspects. 6th ed., Philadelphia: Lippincott-Raven, 1999.
Song et al., Eur J Immunol, 38(11): p. 3178-90, 2008.
Stowe et al., *Ann Neurol.*, June; 69(6):975-85, 2011.
Stuve et al., Ann Neurol, 59(5): p. 743-7, 2006.
Tiller et al., J Immunol Methods, 329(1-2): p. 112-24, 2008.
Vercellino et al., *J Neuropathol Exp Neurol.*, December; 64(12):1101-7, 2005.
von Budingen et al., Proc Natl Acad Sci USA, 99(12): p. 8207-12, 2002.
von Budingen et al., Eur J Immunol, 34(8): p. 2072-83, 2004.
von Budingen et al., Eur J Immunol, 38(7): p. 2014-23, 2008.
von Budingen et al., J Neuroimmunol, 218(1-2): p. 134-9, 2010.
von Budingen et al., J Clin Invest, 122(12): p. 4533-43, 2012.
Waldman & Madaio, Lupus, 14(1): p. 19-24, 2005.
Wardemann et al., Science, 301(5638): p. 1374-7, 2003.
Winges et al., J Neuroimmunol, 192(1-2): p. 226-34, 2007.
Wood et al., *J. Clin. Lab. Immunol.,* 17(4):167-171, 1985.
Wu and Wu, *J. Biol. Chem.,* 262:4429-4432, 1987.
Wu and Wu, *Adv. Drug Delivery Rev.,* 12:159-167, 1993.
Wu et al., *Biochem. Biophys. Res. Commun.,* 233(1):221-226, 1997.
Wu et al., *Cancer Res.,* 58(8): 1605-8, 1998.
Yanase et al., J Clin Invest, 100(1): p. 25-31, 1997.
Zekeridou & Lennon, Neurol Neuroimmunol Neuroinflamm, 2(4): p. e110, 2015.
Zhang et al., *J Autoimmun.*, November-December; 33(3-4): 270-4, 2009.

What is claimed:

1. A composition comprising a recombinant human VH4 antibody or antigen-binding portion thereof and an acceptable carrier, wherein the antibody or antigen-binding portion has a set of heavy chain complementarity determining regions (CDRs) as set forth in SEQ ID NO: 19 and a set of light chain CDRs as set forth in SEQ ID NO: 20, and wherein the antibody or antigen-binding fragment binds to an antigen in human gray and/or white matter.

2. The composition of claim 1, wherein the antibody lacks an Fc domain or has a derivatized Fc domain to alter one or more effector functions.

3. The composition of claim 1, wherein the antibody is a single chain variable fragment.

4. The composition of claim 1, wherein the antibody comprises the VH chain of SEQ ID NO: 19 and the VL chain of SEQ ID NO: 20.

5. The composition of claim 1, wherein the composition comprises from 0.1 mg to 100 mg of the antibody or antigen-binding portion.

* * * * *

SEQUENCE LISTING

<160> NUMBER OF SEQ ID NOS: 128

<210> SEQ ID NO 1
<211> LENGTH: 130
<212> TYPE: PRT
<213> ORGANISM: Artificial
<220> FEATURE:
<223> OTHER INFORMATION: Synthetic polypeptide (AJL01 Heavy)

<400> SEQUENCE: 1

Thr Gly Val His Ser Gln Val Gln Leu Gln Gln Trp Gly Ala Gly Leu
1 5 10 15

Leu Lys Pro Ser Glu Thr Leu Ser Leu Thr Cys Ala Val Tyr Gly Gly
20 25 30

Ser Phe Asn Glu Phe Tyr Trp Ser Trp Ile Arg Gln Pro Ala Arg Lys
35 40 45

Gly Leu Glu Trp Ile Gly Glu Ile Ser His Ser Gly Arg Ala Asn Tyr
50 55 60

Asn Pro Ser Leu Lys Ser Arg Val Thr Leu Ser Val Asp Arg Ser Lys
65 70 75 80

Asn Gln Phe Ser Leu Asn Leu Ser Pro Val Ala Ala Ala Asp Thr Ala
85 90 95

Val Tyr Tyr Cys Ala Arg Arg Glu Ile Val Val Thr Val Arg Gly Arg
100 105 110

Arg Ala Phe Asp Ile Trp Gly Gln Gly Thr Met Val Thr Val Ser Ser
115 120 125

Ala Ser
130

<210> SEQ ID NO 2
<211> LENGTH: 115
<212> TYPE: PRT
<213> ORGANISM: Artificial
<220> FEATURE:
<223> OTHER INFORMATION: Synthetic polypeptide (AJL01 Light)

<400> SEQUENCE: 2

Thr Gly Val His Ser Glu Ile Val Leu Thr Gln Ser Pro Gly Thr Leu
1 5 10 15

Ser Leu Ser Pro Gly Glu Arg Ala Ala Leu Ser Cys Arg Ala Ser Gln
20 25 30

Ser Leu Ile Gly Ser Phe Leu Ala Trp Tyr Gln Gln Lys Pro Gly Gln
35 40 45

Ala Pro Arg Leu Leu Ile Tyr His Thr Ser Asn Arg Ala Ser Gly Ile
50 55 60

Pro Asp Arg Phe Ser Gly Gly Gly Phe Gly Thr Asp Phe Thr Leu Thr
65 70 75 80

Ile Ser Arg Leu Glu Pro Glu Asp Phe Ala Val Tyr Tyr Cys Gln Gln
85 90 95

Tyr Asp Ser Ser Pro Ile Thr Phe Gly Gln Gly Thr Arg Leu Glu Ile
100 105 110

Lys Arg Thr
115

<210> SEQ ID NO 3
<211> LENGTH: 127
<212> TYPE: PRT
<213> ORGANISM: Artificial
<220> FEATURE:

<223> OTHER INFORMATION: Synthetic polypeptide (AJL02 Heavy)

<400> SEQUENCE: 3

```
Thr Gly Val His Ser Gln Val Gln Leu Gln Glu Ser Gly Pro Gly Leu
1               5                   10                  15

Val Lys Pro Ser Gln Thr Leu Ser Leu Thr Cys Thr Val Ser Gly Gly
            20                  25                  30

Ser Ile Ser Ser Gly Gly His Tyr Trp Ser Trp Ile Arg Gln Ser Pro
        35                  40                  45

Gly Lys Gly Leu Glu Trp Ile Gly Asn Val Tyr Tyr Ser Gly Ser Thr
    50                  55                  60

Tyr Tyr Thr Pro Ser Leu Asp Ser Arg Leu Thr Ile Ser Leu Asp Thr
65                  70                  75                  80

Ser Lys Asn Gln Phe Ser Leu Arg Leu Ser Asn Val Thr Val Ala Asp
                85                  90                  95

Thr Ala Val Tyr Tyr Cys Ala Arg Gly Arg Asn Trp Glu Gly Glu Phe
            100                 105                 110

Asp Pro Trp Gly Gln Gly Thr Leu Val Thr Val Ser Ser Ala Ser
        115                 120                 125
```

<210> SEQ ID NO 4
<211> LENGTH: 114
<212> TYPE: PRT
<213> ORGANISM: Artificial
<220> FEATURE:
<223> OTHER INFORMATION: Synthetic polypeptide (AJL02 Light)

<400> SEQUENCE: 4

```
Thr Gly Val His Ser Asp Ile Gln Met Thr Gln Ser Pro Ser Ser Leu
1               5                   10                  15

Ser Ala Ser Leu Gly Asp Arg Val Thr Ile Thr Cys Arg Ala Ser Gln
            20                  25                  30

Gly Ile Ser Ser Ser Val Asn Trp Phe Gln Gln Lys Pro Gly Lys Ala
        35                  40                  45

Pro Glu Leu Leu Ile Tyr Ala Ala Ser Thr Leu Gln Ser Gly Val Pro
    50                  55                  60

Ser Arg Phe Ser Gly Ser Gly Ser Gly Thr Asp Phe Thr Leu Thr Val
65                  70                  75                  80

Ser Ser Leu Gln Pro Glu Asp Phe Ala Thr Tyr Tyr Cys Gln Gln Ser
                85                  90                  95

Tyr Ser Pro Pro Arg Thr Phe Gly Gln Gly Thr Lys Leu Glu Ile Lys
            100                 105                 110

Arg Thr
```

<210> SEQ ID NO 5
<211> LENGTH: 134
<212> TYPE: PRT
<213> ORGANISM: Artificial
<220> FEATURE:
<223> OTHER INFORMATION: Synthetic polypeptide (AJL03 Heavy)

<400> SEQUENCE: 5

```
Thr Gly Val His Ser Gln Leu Gln Leu Gln Glu Ser Gly Pro Gly Leu
1               5                   10                  15

Val Lys Pro Ser Glu Thr Leu Ser Leu Thr Cys Thr Val Ser Gly Ala
            20                  25                  30

Ser Ile Ser Ser Ser Arg Ser Tyr Trp Gly Trp Ile Arg Gln Pro Pro
        35                  40                  45
```

Gly Lys Gly Leu Glu Trp Ile Gly Ser Met Tyr Gln Ser Gly Ser Thr
    50                  55                  60

Tyr Tyr Ser Pro Ser Leu Lys Ser Arg Val Thr Ile Ser Met Asp Thr
65                  70                  75                  80

Ser Lys Asn Gln Phe Ser Leu Asn Leu Thr Ser Val Thr Ala Ala Asp
                85                  90                  95

Thr Ala Val Tyr Phe Cys Ala Arg His Ser Asn Pro Gly Thr Ala Asn
            100                 105                 110

Lys Leu Arg Leu Gly Glu Phe Ser Pro Trp Gly Gln Gly Thr Leu Val
        115                 120                 125

Thr Val Ser Ser Ala Ser
    130

<210> SEQ ID NO 6
<211> LENGTH: 114
<212> TYPE: PRT
<213> ORGANISM: Artificial
<220> FEATURE:
<223> OTHER INFORMATION: Synthetic polypeptide (AJL03 Light)

<400> SEQUENCE: 6

Thr Gly Val His Ser Asp Ile Gln Met Thr Gln Ser Pro Ser Ser Leu
1               5                   10                  15

Ser Ala Ser Val Gly Asp Arg Val Thr Ile Thr Cys Gln Ala Ser Gln
            20                  25                  30

Asp Ile Asn Asn Tyr Leu Asn Trp Phe Gln Gln Gln Pro Gly Lys Ala
        35                  40                  45

Pro Lys Leu Leu Ile Tyr Asp Ala Ser Lys Leu Gln Met Gly Val Pro
    50                  55                  60

Ser Arg Phe Ser Gly Ser Ala Ser Gly Thr Asp Phe Thr Phe Thr Ile
65                  70                  75                  80

Ser Ser Leu Gln Pro Glu Asp Ile Gly Thr Tyr Tyr Cys Gln Gln Tyr
                85                  90                  95

Tyr Asn Leu Pro Tyr Thr Phe Gly Gln Gly Thr Lys Leu Glu Ile Lys
            100                 105                 110

Arg Thr

<210> SEQ ID NO 7
<211> LENGTH: 125
<212> TYPE: PRT
<213> ORGANISM: Artificial
<220> FEATURE:
<223> OTHER INFORMATION: Synthetic polypeptide (AJL04 Heavy)

<400> SEQUENCE: 7

Thr Gly Val His Ser Gln Val Gln Leu Gln Glu Ser Gly Pro Gly Leu
1               5                   10                  15

Val Lys Pro Ser Glu Thr Leu Ser Leu Thr Cys Thr Val Ser Gly Asp
            20                  25                  30

Ser Ile Arg Ser Asn Phe Trp Thr Trp Ile Arg Gln Ser Pro Gly Arg
        35                  40                  45

Gly Leu Glu Trp Ile Gly Tyr Phe Ser Tyr Ser Gly Gly Ile Asn Tyr
    50                  55                  60

Ser Pro Ser Leu Lys Ser Arg Val Thr Ile Ser Val Asp Thr Ser Lys
65                  70                  75                  80

Asn Gln Phe Ser Leu Lys Leu Thr Ser Val Thr Ala Ala Asp Ala Ala
                85                  90                  95

Val Tyr Tyr Cys Ala Arg Asp Pro Asn Gly Asp Tyr Glu Val Asn Trp
100 105 110

Trp Gly Gln Gly Thr Leu Val Thr Val Ser Ser Ala Ser
115 120 125

<210> SEQ ID NO 8
<211> LENGTH: 114
<212> TYPE: PRT
<213> ORGANISM: Artificial
<220> FEATURE:
<223> OTHER INFORMATION: Synthetic polypeptide (AJL04 Light)

<400> SEQUENCE: 8

Thr Gly Val His Ser Asp Ile Gln Met Thr Gln Ser Pro Ser Ser Leu
1 5 10 15

Ser Ala Ser Val Gly Asp Arg Val Thr Ile Thr Cys Arg Ala Ser Gln
20 25 30

Asp Ile Ile Ile Tyr Leu Ala Trp Phe Gln Gln Arg Pro Gly Lys Ala
35 40 45

Pro Arg Ser Leu Ile Tyr Ser Ala Ser Thr Leu Gln Ser Gly Val Pro
50 55 60

Ser Lys Phe Ser Gly Ser Gly Ser Gly Thr Tyr Phe Thr Leu Thr Ile
65 70 75 80

Ser Ser Leu Gln Pro Glu Asp Ser Ala Thr Tyr Tyr Cys Gln Gln Tyr
85 90 95

Lys Ser Tyr Pro Ile Thr Phe Gly Gln Gly Thr Arg Leu Glu Ile Lys
100 105 110

Arg Thr

<210> SEQ ID NO 9
<211> LENGTH: 129
<212> TYPE: PRT
<213> ORGANISM: Artificial
<220> FEATURE:
<223> OTHER INFORMATION: Synthetic polypeptide (AJL05 Heavy)

<400> SEQUENCE: 9

Thr Gly Val His Ser Gln Leu Gln Leu Gln Glu Ser Gly Pro Gly Leu
1 5 10 15

Val Lys Pro Ser Glu Thr Leu Ser Leu Thr Cys Thr Val Ser Gly Gly
20 25 30

Ser Ile Arg Asn Ser Asn Tyr Tyr Trp Asp Trp Ile Arg Gln Pro Pro
35 40 45

Gly Lys Gly Leu Glu Trp Ile Gly Ser Gly Tyr Tyr Ser Gly Ser Ala
50 55 60

Tyr Tyr His Ser Ser Leu Lys Ser Arg Val Ser Ile Ser Val Asp Thr
65 70 75 80

Ser Lys Asn Gln Phe Ser Leu Asn Leu Thr Ser Val Thr Ala Ala Asp
85 90 95

Thr Ala Phe Tyr Tyr Cys Ala Arg Arg Ser Tyr Tyr Tyr Ala Ser Gly
100 105 110

Ser His Asp Tyr Trp Gly Gln Gly Thr Leu Val Thr Val Ser Ser Ala
115 120 125

Ser

<210> SEQ ID NO 10
<211> LENGTH: 114

<212> TYPE: PRT
<213> ORGANISM: Artificial
<220> FEATURE:
<223> OTHER INFORMATION: Synthetic polypeptide (AJL05 Light)

<400> SEQUENCE: 10

```
Thr Gly Val His Ser Asp Ile Gln Met Thr Gln Ser Pro Ser Ser Leu
1               5                   10                  15

Ser Ala Ser Val Gly Asp Arg Val Thr Ile Thr Cys Arg Ala Ser Gln
            20                  25                  30

Asp Ile Ser Ser Tyr Leu Ala Trp Phe Gln Gln Lys Pro Gly Lys Ala
        35                  40                  45

Pro Lys Ser Leu Ile Tyr Gly Ala Ser Ser Leu Gln Ser Gly Val Pro
    50                  55                  60

Ser Lys Phe Ser Gly Ser Gly Ser Gly Thr Asp Phe Thr Leu Thr Ile
65                  70                  75                  80

Ser Gly Leu Gln Pro Glu Asp Phe Ala Thr Tyr His Cys Gln Gln Tyr
                85                  90                  95

Arg Ser Phe Pro Ile Thr Phe Gly Gln Gly Thr Arg Leu Glu Ile Lys
            100                 105                 110

Arg Thr
```

<210> SEQ ID NO 11
<211> LENGTH: 131
<212> TYPE: PRT
<213> ORGANISM: Artificial
<220> FEATURE:
<223> OTHER INFORMATION: Synthetic polypeptide (AJL06 heavy)

<400> SEQUENCE: 11

```
Thr Gly Val His Ser Gln Leu Gln Leu Gln Glu Ser Gly Ser Gly Leu
1               5                   10                  15

Val Lys Pro Ser Gln Thr Leu Ser Leu Thr Cys Ala Val Ser Gly Gly
            20                  25                  30

Ser Ile Asn Thr Gly Asn Tyr Phe Trp Ser Trp Ile Arg Gln Pro Pro
        35                  40                  45

Gly Lys Gly Leu Glu Trp Ile Gly Tyr Met Phe Arg Ser Thr Ser Thr
    50                  55                  60

Tyr Tyr Asn Pro Ser Leu Lys Gly Arg Val Thr Ile Ser Gly Gly Thr
65                  70                  75                  80

Ser Leu Ser Gln Phe Ser Leu Arg Leu Asp Ser Val Thr Ala Ala Asp
                85                  90                  95

Thr Ala Ile Tyr Tyr Cys Ala Arg Gly Arg Tyr Tyr Cys Gly Val Asn
            100                 105                 110

Cys His Pro Phe Asp Ser Trp Gly Gln Gly Thr Leu Val Thr Val Ser
        115                 120                 125

Ser Ala Ser
    130
```

<210> SEQ ID NO 12
<211> LENGTH: 113
<212> TYPE: PRT
<213> ORGANISM: Artificial
<220> FEATURE:
<223> OTHER INFORMATION: Synthetic polypeptide (AJL06 light)

<400> SEQUENCE: 12

```
Thr Gly Val His Ser Asp Ile Gln Met Thr Gln Ser Pro Ser Ser Leu
1               5                   10                  15
```

Ser Ala Ser Val Gly Asp Arg Val Ile Ile Thr Cys Gln Ala Ser Gln
            20                  25                  30

Asp Ile Ser Ile Tyr Leu Asn Trp Tyr Gln Val Lys Pro Gly Lys Ala
        35                  40                  45

Pro Lys Leu Leu Ile Tyr Asp Ala Ser Asn Leu Gln Ala Gly Val Pro
    50                  55                  60

Ser Arg Phe Ser Gly Ser Gly Ser Gly Thr Asp Phe Ser Phe Thr Ile
65                  70                  75                  80

Ser Ser Leu Gln Pro Glu Asp Val Ala Ala Tyr Tyr Cys His Gln Tyr
                85                  90                  95

Asp Ser Leu Pro Ser Phe Gly Gln Gly Thr Lys Leu Glu Ile Lys Arg
            100                 105                 110

Thr

<210> SEQ ID NO 13
<211> LENGTH: 127
<212> TYPE: PRT
<213> ORGANISM: Artificial
<220> FEATURE:
<223> OTHER INFORMATION: Synthetic polypeptide (AJL07 heavy)

<400> SEQUENCE: 13

Thr Gly Val His Ser Gln Val Gln Leu Gln Glu Ser Gly Pro Gly Leu
1               5                   10                  15

Val Lys Pro Ser Glu Thr Leu Ser Leu Thr Cys Asn Val Ser Gly Gly
            20                  25                  30

Ser Ile Asn Asn Tyr Tyr Trp Ser Trp Ile Arg Gln Pro Pro Gly Lys
        35                  40                  45

Gly Leu Glu Trp Ile Gly Tyr Ile Tyr Tyr Asn Gly Asn Ile Asn Tyr
    50                  55                  60

Asn Pro Ser Leu Lys Ser Arg Val Thr Ile Ser Arg Asp Met Ser Lys
65                  70                  75                  80

Asn Gln Phe Ser Leu Asn Leu Arg Ser Val Thr Ala Ala Asp Thr Ala
                85                  90                  95

Val Tyr Tyr Cys Gly Ile Gly Tyr Ser Ala Val Ala Ala Gly Thr Val
            100                 105                 110

Asp Tyr Trp Gly His Gly Thr Leu Val Thr Val Ser Ser Ala Ser
        115                 120                 125

<210> SEQ ID NO 14
<211> LENGTH: 114
<212> TYPE: PRT
<213> ORGANISM: Artificial
<220> FEATURE:
<223> OTHER INFORMATION: Synthetic polypeptide (AJL07 light)

<400> SEQUENCE: 14

Thr Gly Val His Ser Ala Ile Gln Leu Thr Gln Ser Pro Ser Ser Leu
1               5                   10                  15

Ser Ala Ser Val Gly Asp Arg Val Thr Ile Thr Cys Arg Ala Ser Gln
            20                  25                  30

Gly Ile Ser Ser Gly Leu Ala Trp Tyr Gln Gln Glu Pro Gly Lys Ala
        35                  40                  45

Pro Lys Leu Leu Ile Tyr Asp Ala Ser Thr Leu Glu Ser Gly Val Pro
    50                  55                  60

Ser Arg Phe Ser Gly Ser Gly Ser Ala Ile Asp Phe Thr Leu Thr Ile
65                  70                  75                  80

```
Ser Ser Leu Gln Pro Glu Asp Phe Ala Thr Tyr Tyr Cys Gln Gln Phe
                85                  90                  95

Asn Thr Phe Pro Tyr Thr Phe Gly Gln Gly Thr Lys Leu Glu Ile Lys
            100                 105                 110

Arg Thr


<210> SEQ ID NO 15
<211> LENGTH: 131
<212> TYPE: PRT
<213> ORGANISM: Artificial
<220> FEATURE:
<223> OTHER INFORMATION: Synthetic polypeptide (AJL08 heavy)

<400> SEQUENCE: 15

Thr Gly Val His Ser Gln Val Gln Leu Gln Glu Ser Gly Pro Gly Leu
1               5                   10                  15

Val Lys Pro Ser Glu Thr Leu Ser Leu Thr Cys Ala Val Ser Gly Phe
            20                  25                  30

Ser Ile Thr Ser Gly Tyr Tyr Trp Gly Trp Ile Arg Gln Pro Pro Gly
        35                  40                  45

Lys Gly Leu Glu Trp Ile Gly Ser Ile Tyr His Thr Gly Thr Thr Tyr
    50                  55                  60

Tyr Asn Pro Ser Leu Lys Ser Arg Val Thr Ile Ser Val Asp Thr Ser
65                  70                  75                  80

Lys Asn Gln Phe Ser Leu Asn Leu Asn Ser Val Thr Ala Ala Asp Thr
                85                  90                  95

Ala Phe Tyr Tyr Cys Ala Arg Asp Pro Leu Phe Pro Gly Arg Asn Leu
            100                 105                 110

Leu Ser Val Phe Asp Asn Trp Gly Gln Gly Thr Leu Val Thr Val Ser
        115                 120                 125

Ser Ala Ser
    130


<210> SEQ ID NO 16
<211> LENGTH: 114
<212> TYPE: PRT
<213> ORGANISM: Artificial
<220> FEATURE:
<223> OTHER INFORMATION: Synthetic polypeptide (AJL08 light)

<400> SEQUENCE: 16

Thr Gly Val His Ser Asp Ile Gln Met Thr Gln Ser Pro Ser Thr Leu
1               5                   10                  15

Ser Ala Ser Val Gly Asp Arg Val Thr Ile Thr Cys Arg Ala Ser Gln
            20                  25                  30

Ser Ile Ser Thr Trp Leu Ala Trp Tyr Gln Gln Lys Pro Gly Lys Ala
        35                  40                  45

Pro Arg Leu Leu Ile Tyr Lys Ala Ser Ser Leu Glu Ser Gly Val Pro
    50                  55                  60

Ser Arg Phe Ser Gly Ser Gly Ser Gly Thr Glu Phe Thr Leu Thr Ile
65                  70                  75                  80

Ser Gly Leu Gln Pro Asp Asp Phe Ala Asn Tyr Ser Cys Gln Gln Tyr
                85                  90                  95

Asn Ile Tyr Pro Phe Thr Phe Gly Gln Gly Thr Lys Leu Glu Ile Lys
            100                 105                 110

Arg Thr
```

<210> SEQ ID NO 17
<211> LENGTH: 128
<212> TYPE: PRT
<213> ORGANISM: Artificial
<220> FEATURE:
<223> OTHER INFORMATION: Synthetic polypeptide (AJL09 heavy)

<400> SEQUENCE: 17

Thr Gly Val His Ser Gln Val Gln Leu Gln Glu Ser Gly Pro Gly Leu
1 5 10 15

Val Lys Pro Ser Glu Thr Leu Ser Leu Thr Cys Ser Val Ser Gly Gly
20 25 30

Ser Ile Ser Ser Tyr Tyr Trp Gly Trp Ile Arg Gln Ser Pro Gly Lys
35 40 45

Gly Leu Glu Cys Ile Gly Tyr Ile Tyr Phe Ser Gly Ser Thr Ser Tyr
50 55 60

Asn Pro Ser Leu Lys Ser Arg Val Thr Ile Ser Val Asp Thr Ala Lys
65 70 75 80

Asn Gln Ile Ser Leu Asn Leu Thr Ser Val Thr Ala Ala Asp Thr Ala
85 90 95

Val Tyr Phe Cys Ala Arg Val Trp Gly Ser Ser Trp Tyr Ala Asn Trp
100 105 110

Phe Asp Pro Trp Gly Gln Gly Thr Leu Val Thr Val Ser Ser Ala Ser
115 120 125

<210> SEQ ID NO 18
<211> LENGTH: 114
<212> TYPE: PRT
<213> ORGANISM: Artificial
<220> FEATURE:
<223> OTHER INFORMATION: Synthetic polypeptide (AJL09 light)

<400> SEQUENCE: 18

Thr Gly Val His Ser Ala Ile Gln Leu Thr Gln Ser Pro Ser Ser Leu
1 5 10 15

Ser Ala Ser Val Gly Asp Arg Val Thr Ile Thr Cys Arg Ala Ser Gln
20 25 30

Gly Ile Ser Ser Ala Leu Ala Trp Tyr Gln His Lys Pro Gly Lys Ala
35 40 45

Pro Lys Leu Leu Ile Phe Asp Ala Ser Thr Leu Ala Ala Gly Val Pro
50 55 60

Ser Arg Phe Ser Gly Ser Gly Ser Gly Thr Asp Phe Thr Leu Thr Ile
65 70 75 80

Ser Ser Leu Gln Pro Glu Asp Phe Ala Thr Tyr Tyr Cys Gln Gln Tyr
85 90 95

Asn Thr Tyr Val Leu Thr Phe Gly Gln Gly Thr Arg Leu Glu Ile Lys
100 105 110

Arg Thr

<210> SEQ ID NO 19
<211> LENGTH: 129
<212> TYPE: PRT
<213> ORGANISM: Artificial
<220> FEATURE:
<223> OTHER INFORMATION: Synthetic polypeptide (AJL10 heavy)

<400> SEQUENCE: 19

Thr Gly Val His Ser Gln Val Gln Leu Gln Glu Ser Gly Pro Gly Leu
1 5 10 15

-continued

```
Val Lys Pro Ser Glu Thr Leu Ser Leu Thr Cys Ser Val Ser Gly Gly
            20                  25                  30

Ala Val Ser Asn Tyr Tyr Trp Ser Trp Ile Arg Gln Ser Ala Gly Lys
        35                  40                  45

Gly Leu Glu Trp Leu Gly Arg Ile Tyr Ile Asn Gly Thr Thr Tyr Tyr
    50                  55                  60

Asn Pro Ser Leu Arg Ser Arg Val Ser Met Ser Val Asp Thr Ser Lys
65                  70                  75                  80

Gly Gln Phe Ser Leu Arg Leu Thr Ser Val Thr Ala Ala Asp Thr Ala
                85                  90                  95

Ile Tyr Tyr Cys Ala Arg Trp Gly Ala Leu Leu Gly Asp Tyr Tyr Tyr
            100                 105                 110

Gly Leu Asp Val Trp Gly Gln Gly Thr Thr Val Thr Val Ser Ser Ala
        115                 120                 125

Ser


<210> SEQ ID NO 20
<211> LENGTH: 119
<212> TYPE: PRT
<213> ORGANISM: Artificial
<220> FEATURE:
<223> OTHER INFORMATION: Synthetic polypeptide (AJL10 light)

<400> SEQUENCE: 20

Thr Gly Val His Gly Asp Ile Val Met Thr Gln Ser Pro Leu Ser Leu
1               5                   10                  15

Pro Val Thr Pro Gly Glu Pro Ala Ser Ile Ser Cys Arg Ser Thr Gln
            20                  25                  30

Ser Leu Leu His Ser Asn Glu Tyr Ile Tyr Leu Asp Trp Tyr Val Gln
        35                  40                  45

Lys Pro Gly Gln Ser Pro Gln Leu Leu Ile Phe Leu Ala Ser Asn Arg
    50                  55                  60

Ala Ser Gly Val Pro Asp Arg Phe Ser Gly Ser Ala Ser Gly Thr Asp
65                  70                  75                  80

Phe Thr Leu Lys Ile Ser Arg Val Glu Ala Glu Asp Val Gly Val Tyr
                85                  90                  95

Tyr Cys Met Gln Ala Leu Glu Ala Pro Trp Thr Phe Gly Gln Gly Thr
            100                 105                 110

Arg Leu Glu Ile Lys Arg Thr
        115


<210> SEQ ID NO 21
<211> LENGTH: 126
<212> TYPE: PRT
<213> ORGANISM: Artificial
<220> FEATURE:
<223> OTHER INFORMATION: Synthetic polypeptide (AJL11 heavy)

<400> SEQUENCE: 21

Thr Gly Val His Ser Gln Leu Gln Leu Gln Glu Ser Gly Pro Gly Leu
1               5                   10                  15

Val Lys Pro Ser Glu Thr Leu Ser Leu Thr Cys Ser Val Ser Gly Gly
            20                  25                  30

Ser Ile Thr Ser Thr Ser Tyr Tyr Trp Gly Trp Ile Arg Gln Ser Pro
        35                  40                  45

Gly Lys Gly Leu Glu Trp Ile Gly Ser Val Tyr Tyr Ser Gly Asn Thr
    50                  55                  60
```

-continued

```
Phe Tyr Asn Ala Ser Leu Lys Ser Arg Val Thr Ile Ser Ile Asp Thr
65                  70                  75                  80

Ser Lys Tyr Gln Phe Ser Leu Met Leu Arg Ser Val Thr Ala Ala Asp
                85                  90                  95

Thr Ala Val Tyr Tyr Cys Ala Arg Arg His Asp Trp Phe Trp Phe Asp
            100                 105                 110

Pro Trp Gly Gln Gly Thr Leu Val Thr Val Ser Ser Ala Ser
        115                 120                 125


<210> SEQ ID NO 22
<211> LENGTH: 115
<212> TYPE: PRT
<213> ORGANISM: Artificial
<220> FEATURE:
<223> OTHER INFORMATION: Synthetic polypeptide (AJL11 light)

<400> SEQUENCE: 22

Thr Gly Val His Ser Glu Ile Val Leu Thr Gln Ser Pro Gly Thr Leu
1               5                   10                  15

Ser Leu Ser Pro Gly Glu Arg Val Thr Leu Ser Cys Arg Ala Ser Gln
            20                  25                  30

Ser Val Ser Ser Ser Tyr Leu Ala Trp Tyr Gln Gln Lys Pro Gly Gln
        35                  40                  45

Ala Pro Arg Leu Leu Ile Tyr Asp Ser Ser Ser Arg Ala Thr Gly Ile
    50                  55                  60

Pro Asp Arg Phe Ser Gly Ser Gly Ser Gly Thr Asp Phe Thr Leu Thr
65                  70                  75                  80

Ile Ser Arg Leu Asp Pro Glu Asp Phe Ala Val Tyr Tyr Cys Gln Gln
                85                  90                  95

Tyr Gly Ser Ser Pro Ser Thr Phe Gly Gln Gly Thr Lys Leu Glu Ile
            100                 105                 110

Lys Arg Thr
        115


<210> SEQ ID NO 23
<211> LENGTH: 128
<212> TYPE: PRT
<213> ORGANISM: Artificial
<220> FEATURE:
<223> OTHER INFORMATION: Synthetic polypeptide (AJL12 heavy)

<400> SEQUENCE: 23

Thr Gly Val His Ser Gln Leu Gln Leu Gln Glu Ser Gly Pro Gly Leu
1               5                   10                  15

Val Lys Pro Ser Glu Thr Leu Ser Leu Thr Cys Thr Val Ser Gly Gly
            20                  25                  30

Ser Val Thr Ser Ser Asp Tyr Tyr Trp Ala Trp Ile Arg Gln Pro Pro
        35                  40                  45

Gly Lys Gly Pro Glu Trp Ile Gly Ser Ile Ser Asn Ser Gly Asn Thr
    50                  55                  60

Tyr Tyr Ser Pro Ser Leu Lys Ser Arg Val Ser Ile Ser Gly Asp Thr
65                  70                  75                  80

Ser Lys Lys Gln Phe Ser Leu Asn Leu Ser Ser Val Thr Asp Ala Asp
                85                  90                  95

Thr Ala Val Tyr Tyr Cys Thr Arg His Gly His Tyr Val Ser Gly Gly
            100                 105                 110

Leu Gly Pro Trp Gly Gln Gly Thr Leu Val Thr Val Ser Ser Ala Ser
```

```
        115                 120                 125


<210> SEQ ID NO 24
<211> LENGTH: 115
<212> TYPE: PRT
<213> ORGANISM: Artificial
<220> FEATURE:
<223> OTHER INFORMATION: Synthetic polypeptide (AJL12 light)

<400> SEQUENCE: 24

Thr Gly Val His Ser Glu Ile Val Leu Thr Gln Ser Pro Gly Thr Leu
1               5                   10                  15

Ser Leu Ser Pro Gly Glu Arg Ala Thr Leu Ser Cys Arg Ala Ser Gln
            20                  25                  30

Ser Val Gly Ser Tyr Tyr Leu Ala Trp Tyr Gln Gln Lys Pro Gly Gln
        35                  40                  45

Ala Pro Arg Leu Leu Ile His Gly Ala Ser Ser Arg Ala Thr Gly Thr
    50                  55                  60

Pro Asp Arg Phe Ser Gly Ser Gly Ser Gly Thr Asp Phe Thr Leu Thr
65                  70                  75                  80

Ile Ser Lys Leu Glu Pro Glu Asp Phe Ala Leu Tyr Tyr Cys Gln Gln
                85                  90                  95

Tyr Gly Pro Ser Pro Trp Thr Phe Gly Gln Gly Thr Lys Val Glu Ile
            100                 105                 110

Lys Arg Thr
        115


<210> SEQ ID NO 25
<211> LENGTH: 127
<212> TYPE: PRT
<213> ORGANISM: Artificial
<220> FEATURE:
<223> OTHER INFORMATION: Synthetic polypeptide (AJL13 heavy)

<400> SEQUENCE: 25

Thr Gly Val His Ser Gln Val Gln Leu Gln Glu Ser Gly Pro Gly Leu
1               5                   10                  15

Val Lys Pro Ser Glu Thr Leu Ser Leu Thr Cys Asn Val Ser Gly Gly
            20                  25                  30

Ser Ile Asn Asn Tyr Tyr Trp Ser Trp Ile Arg Gln Pro Pro Gly Lys
        35                  40                  45

Gly Leu Glu Trp Ile Gly Tyr Ile Tyr Tyr Asn Gly Asn Ile Asn Tyr
    50                  55                  60

Asn Pro Ser Leu Lys Ser Arg Val Thr Ile Ser Arg Asp Met Ser Lys
65                  70                  75                  80

Asn Gln Phe Ser Leu Asn Leu Arg Ser Val Thr Ala Ala Asp Thr Ala
                85                  90                  95

Val Tyr Tyr Cys Gly Ile Gly Tyr Ser Ala Val Ala Ala Gly Thr Val
            100                 105                 110

Asp Tyr Trp Gly Gln Gly Thr Leu Val Thr Val Ser Ser Ala Ser
        115                 120                 125


<210> SEQ ID NO 26
<211> LENGTH: 119
<212> TYPE: PRT
<213> ORGANISM: Artificial
<220> FEATURE:
<223> OTHER INFORMATION: Synthetic polypeptide (AJL13 light)

<400> SEQUENCE: 26
```

```
Thr Gly Val His Gly Asp Val Val Met Thr Gln Ser Pro Leu Ser Leu
1               5                   10                  15

Pro Val Thr Leu Gly Gln Pro Ala Ser Ile Ser Cys Arg Ser Ser Gln
            20                  25                  30

Ser Leu Val His Arg Asn Gly Asn Thr Tyr Leu Asn Trp Phe Gln Gln
        35                  40                  45

Arg Pro Gly Gln Ser Pro Arg Arg Leu Ile Tyr Thr Val Ser Lys Arg
    50                  55                  60

Gly Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Val Gly Asp Tyr
                85                  90                  95

Tyr Cys Met Gln Gly Thr His Trp Pro Trp Thr Ser Gly Gln Gly Thr
            100                 105                 110

Arg Leu Glu Ile Lys Arg Thr
        115


<210> SEQ ID NO 27
<211> LENGTH: 135
<212> TYPE: PRT
<213> ORGANISM: Artificial
<220> FEATURE:
<223> OTHER INFORMATION: Synthetic polypeptide (AJL14 heavy)

<400> SEQUENCE: 27

Thr Gly Val His Ser Gln Val Gln Leu Gln Glu Ser Gly Pro Gly Leu
1               5                   10                  15

Val Lys Pro Ser Gln Thr Leu Ser Leu Thr Cys Thr Val Ser Gly Gly
            20                  25                  30

Ser Leu Ser Ser Val Asn Tyr Tyr Trp Asn Trp Ile Arg Gln Pro Ala
        35                  40                  45

Gly Lys Gly Leu Glu Trp Met Gly Arg Ile Tyr Ala Ser Gly Tyr Thr
    50                  55                  60

Thr Tyr Asn Pro Ser Phe Gln Ser Arg Val Thr Ile Ser Leu Asp Pro
65                  70                  75                  80

Ser Lys Asn Gln Ile Ser Leu Lys Val Thr Ser Leu Thr Ala Ala Asp
                85                  90                  95

Thr Ala Ile Tyr Tyr Cys Ala Arg His Asp Leu Gly His Cys Ser Ser
            100                 105                 110

Thr Ser Cys Tyr Leu Ser Trp Phe Asp Ala Trp Gly Gln Gly Thr Thr
        115                 120                 125

Val Thr Val Ser Ser Ala Ser
    130                 135


<210> SEQ ID NO 28
<211> LENGTH: 120
<212> TYPE: PRT
<213> ORGANISM: Artificial
<220> FEATURE:
<223> OTHER INFORMATION: Synthetic polypeptide (AJL14 light)

<400> SEQUENCE: 28

Thr Gly Val His Ser Asp Ile Val Met Thr Gln Ser Pro Asp Ser Leu
1               5                   10                  15

Ala Val Ser Leu Gly Glu Arg Ala Thr Ile Asn Cys Arg Ser Ser Gln
            20                  25                  30

Thr Ile Phe Phe Ser Pro Asn Asn Asn Asn His Leu Ala Trp Tyr Gln
```

```
        35                  40                  45

Gln Lys Pro Gly Gln Pro Pro Arg Leu Leu Ile Tyr Trp Ala Ser Thr
    50                  55                  60

Arg Glu Ser Gly Val Pro Asp Arg Phe Ser Gly Ser Gly Ser Gly Thr
65                  70                  75                  80

Asp Phe Thr Leu Thr Ile Ser Gly Leu Gln Ala Glu Asp Val Ala Val
                85                  90                  95

Tyr Tyr Cys Gln Gln Tyr Tyr Ser Leu Pro Tyr Thr Phe Gly Gln Gly
            100                 105                 110

Thr Lys Leu Glu Ile Lys Arg Thr
        115                 120


<210> SEQ ID NO 29
<211> LENGTH: 134
<212> TYPE: PRT
<213> ORGANISM: Artificial
<220> FEATURE:
<223> OTHER INFORMATION: Synthetic polypeptide (AJL15 heavy)

<400> SEQUENCE: 29

Thr Gly Val His Ser Gln Leu Gln Leu Gln Glu Ser Gly Pro Gly Leu
1               5                   10                  15

Val Lys Pro Ser Glu Thr Leu Ser Leu Thr Cys Thr Val Ser Gly Gly
            20                  25                  30

Ser Ile Thr Ser Arg Asn Asn Tyr Trp Gly Trp Ile Arg Gln Ser Pro
        35                  40                  45

Gly Lys Gly Leu Glu Trp Ile Gly Ser Leu Tyr Tyr Thr Gly Ser Asp
    50                  55                  60

Tyr Tyr Asn Pro Ser Leu Lys Ser Arg Val Thr Ile Ser Val Asp Thr
65                  70                  75                  80

Ser Lys Asn Gln Phe Ser Leu Arg Leu Ser Ser Val Thr Ala Ala Asp
                85                  90                  95

Thr Ala Val Tyr Tyr Cys Val Arg Val Asn Val Asp Asp Phe Trp Ser
            100                 105                 110

Gly Leu Gly Gly Ala Trp Phe Asp Pro Trp Gly Gln Gly Thr Leu Val
        115                 120                 125

Thr Val Ser Ser Ala Ser
    130


<210> SEQ ID NO 30
<211> LENGTH: 119
<212> TYPE: PRT
<213> ORGANISM: Artificial
<220> FEATURE:
<223> OTHER INFORMATION: Synthetic polypeptide (AJL15 light)

<400> SEQUENCE: 30

Thr Gly Val His Gly Asp Ile Val Met Thr Gln Thr Pro Leu Ser Leu
1               5                   10                  15

Ser Val Thr Pro Gly Gln Pro Ala Ser Ile Ser Cys Lys Ser Ser Gln
            20                  25                  30

Ser Leu Leu Asp Ser Asp Gly Lys Thr His Leu Tyr Trp Tyr Leu Gln
        35                  40                  45

Lys Pro Gly Gln Ser Pro Gln Ser Leu Ile Tyr Glu Val Ser Lys Arg
    50                  55                  60

Phe Ser Gly Val Pro Asp Arg Phe Thr Gly Ser Gly Ser Gly Thr Asp
65                  70                  75                  80
```

```
Phe Thr Leu Lys Ile Ser Arg Val Glu Ala Glu Asp Val Gly Leu Tyr
                85                  90                  95

Tyr Cys Met Gln Ser Ala Gln Leu Pro Tyr Thr Phe Gly Gln Gly Thr
            100                 105                 110

Lys Leu Glu Ile Lys Arg Thr
        115


<210> SEQ ID NO 31
<211> LENGTH: 133
<212> TYPE: PRT
<213> ORGANISM: Artificial
<220> FEATURE:
<223> OTHER INFORMATION: Synthetic polypeptide (AJL16 heavy)

<400> SEQUENCE: 31

Thr Gly Val His Ser Gln Leu Gln Leu Gln Glu Ser Gly Pro Gly Leu
1               5                   10                  15

Val Lys Pro Ser Glu Thr Leu Ser Leu Thr Cys Thr Val Ser Gly Gly
            20                  25                  30

Ser Ile Ser Ser Ser Pro Tyr Tyr Trp Gly Trp Ile Arg Gln Pro Pro
        35                  40                  45

Gly Lys Gly Leu Glu Trp Ile Gly Ser Ile Tyr Tyr Ser Gly His Thr
    50                  55                  60

Tyr Tyr Asn Pro Ser Leu Lys Ser Arg Val Thr Ile Ser Val Asp Thr
65                  70                  75                  80

Ser Lys Asn Gln Phe Ser Leu Arg Leu Thr Ser Val Thr Ala Ala Asp
                85                  90                  95

Thr Ser Val Tyr Tyr Cys Ala Lys Gln Thr Asp Asp Tyr Gly Asp Tyr
            100                 105                 110

Ala Ser Arg Gly Trp Phe Asp Pro Trp Gly Gln Gly Thr Leu Val Thr
        115                 120                 125

Val Ser Ser Ala Ser
    130


<210> SEQ ID NO 32
<211> LENGTH: 114
<212> TYPE: PRT
<213> ORGANISM: Artificial
<220> FEATURE:
<223> OTHER INFORMATION: Synthetic polypeptide (AJL16 light)

<400> SEQUENCE: 32

Thr Gly Val His Ser Asp Ile Gln Met Thr Gln Ser Pro Ser Ser Leu
1               5                   10                  15

Ser Ala Ser Val Gly Asp Arg Val Thr Phe Thr Cys Gln Ala Ser His
            20                  25                  30

Asp Ile Ser Asn Tyr Leu Asn Trp Tyr Gln Gln Lys Pro Gly Lys Val
        35                  40                  45

Pro Glu Leu Leu Ile Tyr Asp Ala Ser Asn Leu Lys Thr Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Gln Gln Tyr
                85                  90                  95

Asp Asn Leu Pro Ile Thr Phe Gly Gln Gly Thr Arg Leu Glu Ile Lys
            100                 105                 110

Arg Thr
```

<210> SEQ ID NO 33
<211> LENGTH: 135
<212> TYPE: PRT
<213> ORGANISM: Artificial
<220> FEATURE:
<223> OTHER INFORMATION: Synthetic polypeptide (AJL18 heavy)

<400> SEQUENCE: 33

```
Thr Gly Val His Ser Gln Val Gln Leu Gln Glu Ser Gly Pro Gly Leu
1               5                   10                  15

Val Lys Pro Ser Gln Thr Leu Ser Leu Thr Cys Thr Val Ser Gly Asp
            20                  25                  30

Ser Ile Ser Ser Asp Lys Tyr Tyr Trp Thr Trp Ile Arg Gln Leu Pro
        35                  40                  45

Gly Lys Gly Leu Glu Trp Ile Gly Tyr Ile Ser Tyr Ser Gly Thr Thr
    50                  55                  60

Tyr Tyr Asn Pro Ser Leu Lys Ser Arg Val Ser Ile Ser Val Asp Thr
65                  70                  75                  80

Ser Gly Asn Gln Phe Ser Leu Arg Leu Ser Ser Val Thr Ala Ala Asp
                85                  90                  95

Thr Ala Arg Tyr Tyr Cys Ala Arg Val Tyr Tyr Asp Val Leu Ser Ala
            100                 105                 110

Tyr Tyr Asn Met Gly Ser Trp Val Asp Pro Trp Gly Gln Gly Thr Leu
        115                 120                 125

Val Thr Val Ser Ser Ala Ser
    130                 135
```

<210> SEQ ID NO 34
<211> LENGTH: 114
<212> TYPE: PRT
<213> ORGANISM: Artificial
<220> FEATURE:
<223> OTHER INFORMATION: Synthetic polypeptide (AJL18 light)

<400> SEQUENCE: 34

```
Thr Gly Val His Ser Asp Ile Gln Met Thr Gln Ser Pro Ser Ser Leu
1               5                   10                  15

Pro Ala Ser Val Gly Asp Arg Val Thr Ile Thr Cys Arg Ala Ser Gln
            20                  25                  30

Ser Ile Ser Ser Tyr Leu Asn Trp Tyr Gln Gln Lys Pro Gly Arg Ala
        35                  40                  45

Pro Lys Leu Leu Ile Tyr Ala Ala Ser Ser Leu Gln Ser Gly Val Ser
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Ser Ala Thr Tyr Tyr Cys Gln Gln Ser
                85                  90                  95

Tyr Ser Thr Pro Trp Thr Phe Gly Gln Gly Thr Lys Val Glu Ile Lys
            100                 105                 110

Arg Thr
```

<210> SEQ ID NO 35
<211> LENGTH: 127
<212> TYPE: PRT
<213> ORGANISM: Artificial
<220> FEATURE:
<223> OTHER INFORMATION: Synthetic polypeptide (AJL19 heavy)

<400> SEQUENCE: 35

```
Thr Gly Val His Ser Gln Val Gln Leu Gln Gln Trp Gly Ala Gly Leu
1               5                   10                  15

Leu Lys Pro Pro Glu Thr Leu Ser Leu Thr Cys Ala Val Phe Gly Gly
            20                  25                  30

Ser Leu Ser Gly Tyr Tyr Trp Ser Trp Ile Arg Gln Pro Pro Gly Lys
        35                  40                  45

Gly Pro Glu Trp Ile Ala Glu Ile Asn His Ser Gly Asp Ala Asn Tyr
    50                  55                  60

Asn Pro Ser Leu Lys Ser Arg Val Thr Ile Ser Val Asp Thr Ser Lys
65                  70                  75                  80

Asn Gln Phe Ser Leu Lys Met Ser Ser Val Thr Val Ala Asp Thr Ala
                85                  90                  95

Leu Tyr Tyr Cys Ala Thr Gln Gly Ser Arg Leu Thr Thr Phe Ala Phe
            100                 105                 110

Asp Val Trp Gly Gln Gly Thr Met Val Thr Val Ser Ser Ala Ser
        115                 120                 125


<210> SEQ ID NO 36
<211> LENGTH: 116
<212> TYPE: PRT
<213> ORGANISM: Artificial
<220> FEATURE:
<223> OTHER INFORMATION: Synthetic polypeptide (AJL19 light)

<400> SEQUENCE: 36

Thr Gly Val His Ser Glu Ile Val Leu Thr Gln Ser Pro Gly Thr Leu
1               5                   10                  15

Ser Leu Ser Pro Gly Glu Arg Val Thr Leu Ser Cys Arg Thr Ser Gln
            20                  25                  30

Ser Val Ser Ser Asp Ser Leu Ala Trp Tyr Gln Gln Lys Pro Gly Gln
        35                  40                  45

Thr Pro Arg Leu Leu Ile Tyr His Thr Ser Thr Arg Ala Ala Gly Ile
    50                  55                  60

Pro Asp Arg Phe Ser Gly Thr Gly Ser Gly Thr Asp Phe Thr Leu Thr
65                  70                  75                  80

Ile Ala Arg Leu Glu Pro Glu Asp Phe Ala Val Tyr Tyr Cys Gln His
                85                  90                  95

Tyr Gly Arg Ser Ser Leu Phe Thr Phe Gly Gln Gly Thr Lys Leu Glu
            100                 105                 110

Ile Lys Arg Thr
        115


<210> SEQ ID NO 37
<211> LENGTH: 132
<212> TYPE: PRT
<213> ORGANISM: Artificial
<220> FEATURE:
<223> OTHER INFORMATION: Synthetic polypeptide (AJL20 heavy)

<400> SEQUENCE: 37

Thr Gly Val His Ser Gln Leu Gln Leu Gln Glu Ser Gly Pro Gly Leu
1               5                   10                  15

Val Lys Pro Ser Glu Thr Leu Ser Leu Thr Cys Thr Val Ser Gly Gly
            20                  25                  30

Ser Ile Ser Gly Ser Ser Phe Tyr Trp Gly Trp Val Arg Gln Pro Pro
        35                  40                  45

Gly Arg Gly Leu Glu Trp Ile Gly Thr Ile Tyr Tyr Arg Gly Thr Thr
```

```
    50                  55                  60

Tyr Tyr Thr Pro Ser Leu Lys Ser Arg Val Thr Ile Ser Val Asp Thr
65                  70                  75                  80

Ser Lys Asn Gln Phe Ser Leu Arg Leu Asn Ser Val Thr Ala Ala Asp
                85                  90                  95

Thr Ala Ile Tyr Tyr Cys Ala Ser Leu Pro His Tyr Asp Phe Trp Ser
            100                 105                 110

Gly Ser Val Phe Phe Asp Tyr Trp Gly Gln Gly Thr Leu Val Thr Val
        115                 120                 125

Ser Ser Ala Ser
    130


<210> SEQ ID NO 38
<211> LENGTH: 114
<212> TYPE: PRT
<213> ORGANISM: Artificial
<220> FEATURE:
<223> OTHER INFORMATION: Synthetic polypeptide (AJL20 light)

<400> SEQUENCE: 38

Thr Gly Val His Ser Asp Ile Gln Met Thr Gln Ser Pro Ser Ser Leu
1               5                   10                  15

Ser Ala Ser Val Gly Asp Arg Val Thr Ile Thr Cys Arg Ala Ser Gln
            20                  25                  30

Gly Ile Ala Asn Tyr Leu Ala Trp Tyr Gln Gln Lys Pro Gly Asn Ile
        35                  40                  45

Pro Lys Leu Leu Ile Tyr Ala Ala Ser Thr Leu Gln Ser Gly Val Pro
    50                  55                  60

Ser Arg Phe Ser Gly Ser Gly Ser Gly Thr Asp Phe Ala Leu Thr Ile
65                  70                  75                  80

Ser Cys Leu Gln Pro Glu Asp Val Ala Thr Tyr Tyr Cys Gln Lys Tyr
                85                  90                  95

Asn Ser Ala Pro Leu Thr Phe Gly Gly Gly Thr Lys Val Glu Ile Lys
            100                 105                 110

Arg Thr


<210> SEQ ID NO 39
<211> LENGTH: 126
<212> TYPE: PRT
<213> ORGANISM: Artificial
<220> FEATURE:
<223> OTHER INFORMATION: Synthetic polypeptide (WR01 heavy)

<400> SEQUENCE: 39

Thr Gly Val His Ser Gln Val Gln Leu Gln Glu Ser Gly Pro Gly Leu
1               5                   10                  15

Val Lys Pro Ser Glu Thr Leu Ser Leu Thr Cys Thr Val Ser Gly Gly
            20                  25                  30

Ser Ile Asp Thr Tyr Tyr Trp Thr Trp Ile Arg Gln Pro Pro Gly Lys
        35                  40                  45

Gly Leu Glu Trp Ile Gly Tyr Ile Tyr Ser Thr Gly Ser Pro Lys Tyr
    50                  55                  60

Lys Pro Ser Leu Lys Ser Arg Val Val Met Ser Val Asp Thr Ser Thr
65                  70                  75                  80

Asn Glu Phe Ala Leu Arg Leu Ser Ser Val Thr Ala Ala Asp Thr Ala
                85                  90                  95

Val Tyr Tyr Cys Ala Arg Ser Ser Gly Phe Tyr Val Glu His Leu Glu
```

```
            100                 105                 110

Lys Trp Gly Gln Gly Thr Thr Val Thr Val Ser Ser Ala Ser
        115                 120                 125
```

<210> SEQ ID NO 40
<211> LENGTH: 115
<212> TYPE: PRT
<213> ORGANISM: Artificial
<220> FEATURE:
<223> OTHER INFORMATION: Synthetic polypeptide (WR01 light)

<400> SEQUENCE: 40

```
Thr Gly Val His Ser Glu Ile Val Leu Thr Gln Ser Pro Ala Thr Leu
1               5                   10                  15

Ser Leu Ser Pro Gly Glu Arg Ala Thr Leu Ser Cys Arg Ala Ser Gln
            20                  25                  30

Thr Val Ser Ser Ser Tyr Leu Asp Trp Phe Gln Gln Lys Pro Gly Gln
        35                  40                  45

Ala Pro Arg Leu Leu Ile Tyr Gly Ala Ser Ser Arg Ala Thr Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Phe Ala Thr Ser Pro Tyr Thr Phe Gly Gln Gly Thr Lys Leu Glu Ile
            100                 105                 110

Lys Arg Thr
        115
```

<210> SEQ ID NO 41
<211> LENGTH: 131
<212> TYPE: PRT
<213> ORGANISM: Artificial
<220> FEATURE:
<223> OTHER INFORMATION: Synthetic polypeptide (WR02 heavy)

<400> SEQUENCE: 41

```
Thr Gly Val His Ser Gln Val Gln Leu Gln Glu Ser Gly Pro Gly Leu
1               5                   10                  15

Val Lys Pro Ser Gln Thr Leu Ser Leu Thr Cys Thr Val Ser Gly Gly
            20                  25                  30

Ser Ile Ser Ser Gly Asp Tyr His Trp Ser Trp Ile Arg Gln Pro Pro
        35                  40                  45

Gly Lys Gly Leu Glu Trp Ile Gly Asn Ile Asn Tyr Asn Gly Gly Ala
    50                  55                  60

Tyr His Asn Pro Ser Leu Thr Asn Arg Val Ile Met Ser Val Asp Thr
65                  70                  75                  80

Ser Lys Asn His Phe Ser Leu Lys Leu Thr Ser Val Thr Ala Ala Asp
                85                  90                  95

Thr Ala Val Tyr Tyr Cys Ala Arg Glu Ser Gln Trp Leu Arg Tyr Gly
            100                 105                 110

Ala Phe Gly Met Asp Val Trp Gly Gln Gly Thr Thr Val Thr Val Ser
        115                 120                 125

Ser Ala Ser
    130
```

<210> SEQ ID NO 42
<211> LENGTH: 115

-continued

<212> TYPE: PRT
<213> ORGANISM: Artificial
<220> FEATURE:
<223> OTHER INFORMATION: Synthetic polypeptide (WR02 light)

<400> SEQUENCE: 42

```
Thr Gly Val His Ser Glu Ile Val Leu Thr Gln Ser Pro Gly Thr Leu
1               5                   10                  15

Ser Leu Ser Pro Gly Glu Arg Ala Thr Leu Ser Cys Arg Ala Ser Gln
            20                  25                  30

Ser Val Ser Ser Ser His Leu Val Trp Tyr Gln Gln Lys Ala Gly Gln
        35                  40                  45

Ala Pro Arg Leu Val Ile Tyr Gly Ala Asn Arg Arg Ala Ser Gly Thr
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Gly Ser Ser Pro Tyr Thr Phe Gly Gln Gly Thr Lys Leu Glu Ile
            100                 105                 110

Lys Arg Thr
        115
```

<210> SEQ ID NO 43
<211> LENGTH: 131
<212> TYPE: PRT
<213> ORGANISM: Artificial
<220> FEATURE:
<223> OTHER INFORMATION: Synthetic polypeptide (WR03 heavy)

<400> SEQUENCE: 43

```
Thr Gly Val His Ser Gln Val Gln Leu Gln Glu Ser Gly Pro Gly Leu
1               5                   10                  15

Val Lys Pro Ser Gly Thr Leu Ser Leu Thr Cys Ala Val Ser Gly Gly
            20                  25                  30

Ser Ile Ser Ser Ser Tyr Trp Trp Ser Trp Val Arg Gln Pro Pro Gly
        35                  40                  45

Lys Gly Leu Glu Trp Val Gly Glu Ile Tyr His Ser Gly Gly Ala Asn
    50                  55                  60

Tyr Ser Pro Ser Leu Lys Ser Arg Val Thr Ile Ser Val Asp Lys Ser
65                  70                  75                  80

Lys Asn Gln Phe Ser Leu Asn Leu Ile Ser Val Thr Ala Ala Asp Thr
                85                  90                  95

Ala Val Tyr Phe Cys Ala Arg Ser Arg Met Leu Val Gly Ala Asp Gly
            100                 105                 110

Gly Gly Ala Phe Asp Ile Trp Gly Gln Gly Thr Met Val Thr Val Ser
        115                 120                 125

Ser Ala Ser
    130
```

<210> SEQ ID NO 44
<211> LENGTH: 115
<212> TYPE: PRT
<213> ORGANISM: Artificial
<220> FEATURE:
<223> OTHER INFORMATION: Synthetic polypeptide (WR03 light)

<400> SEQUENCE: 44

```
Thr Gly Val His Ser Glu Ile Val Leu Thr Gln Ser Pro Gly Thr Leu
```

```
1               5                   10                  15

Ser Leu Ser Pro Gly Glu Arg Ala Thr Leu Ser Cys Gly Ala Ser Gln
            20                  25                  30

Ser Val Ser Ser Ser Tyr Leu Ala Trp Tyr Gln Gln Lys Pro Gly Leu
        35                  40                  45

Ala Pro Arg Leu Leu Ile Tyr Asp Ala Ser Ser Arg Ala Thr Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Gly Ser Ser Pro Gln Thr Phe Gly Gln Gly Thr Lys Val Glu Ile
            100                 105                 110

Lys Arg Thr
        115


<210> SEQ ID NO 45
<211> LENGTH: 126
<212> TYPE: PRT
<213> ORGANISM: Artificial
<220> FEATURE:
<223> OTHER INFORMATION: Synthetic polypeptide (WR04 heavy)

<400> SEQUENCE: 45

Thr Gly Val His Ser Gln Leu Gln Leu Gln Gln Ser Gly Pro Gly Leu
1               5                   10                  15

Val Lys Pro Ser Glu Thr Leu Ser Leu Thr Cys Thr Val Ser Gly Gly
            20                  25                  30

Ser Ile Ser Ser Gly Gly Ser Tyr Trp Gly Trp Ile Arg Gln Ala Pro
        35                  40                  45

Gly Lys Gly Leu Glu Trp Ile Gly Ser Met Tyr Tyr Ser Gly Ser Thr
    50                  55                  60

Phe Tyr Asn Pro Ser Val Lys Ser Arg Val Thr Ile Ser Val Asp Arg
65                  70                  75                  80

Ser Lys Glu Gln Phe Ser Leu Asn Leu Asn Ala Val Thr Ala Ala Asp
                85                  90                  95

Thr Ala Val Tyr Tyr Cys Val Arg His Arg Arg Ser Glu Pro Ser Asp
            100                 105                 110

Ser Trp Gly Gln Gly Thr Leu Val Thr Val Ser Ser Ala Ser
        115                 120                 125


<210> SEQ ID NO 46
<211> LENGTH: 115
<212> TYPE: PRT
<213> ORGANISM: Artificial
<220> FEATURE:
<223> OTHER INFORMATION: Synthetic polypeptide (WR04 light)

<400> SEQUENCE: 46

Thr Gly Val His Ser Glu Ile Val Met Thr Gln Ser Pro Ala Thr Leu
1               5                   10                  15

Ser Val Ser Pro Gly Glu Arg Ala Thr Leu Ser Cys Arg Ala Ser Gln
            20                  25                  30

Ser Val Ser Ser Asn Leu Ala Trp Tyr Gln Gln Lys Pro Gly Gln Ala
        35                  40                  45

Pro Arg Leu Leu Ile Tyr Gly Thr Ser Thr Arg Ala Thr Gly Ile Pro
    50                  55                  60
```

```
Ala Arg Phe Ser Gly Ser Gly Ser Gly Thr Glu Phe Thr Leu Thr Ile
65                  70                  75                  80

Ser Ser Leu Gln Ser Glu Asp Ser Ala Val Tyr Phe Cys Gln Gln Tyr
                85                  90                  95

Asn Asn Trp Pro Leu Tyr Thr Phe Gly Gln Gly Thr Lys Val Glu Ile
            100                 105                 110

Lys Arg Thr
        115


<210> SEQ ID NO 47
<211> LENGTH: 126
<212> TYPE: PRT
<213> ORGANISM: Artificial
<220> FEATURE:
<223> OTHER INFORMATION: Synthetic polypeptide (WR05 heavy)

<400> SEQUENCE: 47

Thr Gly Val His Ser Gln Val Gln Leu Gln Glu Ser Gly Pro Gly Leu
1               5                   10                  15

Val Lys Pro Ser Glu Thr Leu Ser Leu Thr Cys Ser Val Ser Gly Gly
            20                  25                  30

Ser Val Ser Ser Asn Gly His Phe Trp Ser Trp Ile Arg Leu Pro Pro
        35                  40                  45

Gly Lys Gly Leu Glu Trp Ile Gly Tyr Val Tyr Asn Thr Gly Thr Ser
    50                  55                  60

Gly Tyr Ser Pro Ser Leu Lys Ser Arg Val Thr Ile Ser Val Asp Thr
65                  70                  75                  80

Ser Lys Asn Gln Phe Ser Leu Thr Leu Arg Ser Val Thr Ala Ala Asp
                85                  90                  95

Thr Ala Ile Tyr Tyr Cys Ala Arg Gly Leu Thr Gly Asn Tyr Pro Ser
            100                 105                 110

His Trp Gly Gln Gly Thr Leu Val Thr Val Ser Ser Ala Ser
        115                 120                 125


<210> SEQ ID NO 48
<211> LENGTH: 114
<212> TYPE: PRT
<213> ORGANISM: Artificial
<220> FEATURE:
<223> OTHER INFORMATION: Synthetic polypeptide (WR05 light)

<400> SEQUENCE: 48

Thr Gly Val His Ser Asp Ile Gln Met Thr Gln Ser Pro Ser Ser Val
1               5                   10                  15

Ser Ala Ser Val Gly Asp Arg Val Thr Ile Thr Cys Arg Ala Ser Arg
            20                  25                  30

Gly Val Ser Thr Trp Leu Ala Trp Tyr Gln Gln Lys Pro Gly Glu Ala
        35                  40                  45

Pro Lys Leu Leu Ile Tyr Ala Ser Ser Arg Leu Glu Gly Gly Val Pro
    50                  55                  60

Ala Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Gly
                85                  90                  95

Asn Ser Phe Pro Leu Thr Phe Gly Gly Gly Thr Lys Val Glu Ile Lys
            100                 105                 110

Arg Thr
```

<210> SEQ ID NO 49
<211> LENGTH: 126
<212> TYPE: PRT
<213> ORGANISM: Artificial
<220> FEATURE:
<223> OTHER INFORMATION: Synthetic polypeptide (WR06 heavy)

<400> SEQUENCE: 49

```
Thr Gly Val His Ser Gln Leu Gln Leu Gln Glu Ser Gly Pro Gly Leu
1               5                   10                  15

Val Lys Pro Ser Glu Thr Leu Ser Leu Thr Cys Thr Val Ser Gly Gly
            20                  25                  30

Ser Val Ser Ser Ser Ala Tyr Trp Trp Ala Trp Ile Arg Gln Pro Pro
        35                  40                  45

Gly Gly Gly Leu Glu Trp Ile Gly His Ile Tyr Tyr Phe Gly Asn Lys
    50                  55                  60

Tyr Tyr Lys Ser Ser Leu Glu Ser Arg Val Thr Ile Ser Leu Asp Ala
65                  70                  75                  80

Ser Gln Asn Gln Phe Ser Leu Lys Leu Thr Ser Val Thr Ala Ala Asp
                85                  90                  95

Thr Ala Leu Tyr Tyr Cys Ala Arg Val Asp Thr Ala Leu Ala Phe Asp
            100                 105                 110

Phe Trp Gly Gln Gly Thr Met Val Thr Val Ser Ser Ala Ser
        115                 120                 125
```

<210> SEQ ID NO 50
<211> LENGTH: 114
<212> TYPE: PRT
<213> ORGANISM: Artificial
<220> FEATURE:
<223> OTHER INFORMATION: Synthetic polypeptide (WR06 light)

<400> SEQUENCE: 50

```
Thr Gly Val His Ser Asp Ile Gln Met Thr Gln Ser Pro Ser Ser Leu
1               5                   10                  15

Ser Ala Ser Val Gly Asp Arg Val Thr Ile Thr Cys Arg Ala Ser Gln
            20                  25                  30

Tyr Val Ser Ser Ser Leu Asn Trp Tyr Gln Gln Lys Pro Gly Lys Ala
        35                  40                  45

Pro Thr Leu Leu Ile Tyr Leu Ala Ser Asn Leu Arg Ser Gly Val Pro
    50                  55                  60

Ser Arg Phe Ser Gly Ser Glu Ser Gly Thr Asp Phe Thr Leu Thr Ile
65                  70                  75                  80

Asn Ser Leu Gln Pro Glu Asp Val Ala Thr Tyr Phe Cys Gln Gln Ser
                85                  90                  95

Tyr Ser Leu Pro Arg Thr Phe Gly Pro Gly Thr Lys Val Asp Ile Lys
            100                 105                 110

Arg Thr
```

<210> SEQ ID NO 51
<211> LENGTH: 135
<212> TYPE: PRT
<213> ORGANISM: Artificial
<220> FEATURE:
<223> OTHER INFORMATION: Synthetic polypeptide (WR07 heavy)

<400> SEQUENCE: 51

```
Thr Gly Val His Ser Gln Leu Gln Leu Gln Glu Ser Gly Pro Gly Leu
1               5                   10                  15
```

```
Val Lys Pro Ser Glu Thr Leu Ser Leu Thr Cys Ser Val Ser Gly Gly
            20                  25                  30

Ser Val Ser Ser Thr Thr Tyr Tyr Trp Gly Trp Ile Arg Gln Ser Pro
        35                  40                  45

Gly Lys Gly Leu Glu Trp Ile Gly Ser Ile Tyr His Ser Gly Lys Thr
    50                  55                  60

Tyr Tyr Asn Pro Ser Leu Lys Ser Arg Val Thr Ile Ser Val Asp Thr
65                  70                  75                  80

Ser Lys Asn Gln Phe Ser Leu Asn Leu Ser Ser Val Thr Ala Ala Asp
                85                  90                  95

Thr Ala Val Tyr Tyr Cys Ala Arg Glu Asn Ser His His Tyr Asp Ser
            100                 105                 110

Ser Gly Tyr Tyr Leu Gly Gly Phe Asp Tyr Trp Gly Gln Gly Thr Leu
        115                 120                 125

Val Thr Val Ser Ser Ala Ser
    130                 135


<210> SEQ ID NO 52
<211> LENGTH: 114
<212> TYPE: PRT
<213> ORGANISM: Artificial
<220> FEATURE:
<223> OTHER INFORMATION: Synthetic polypeptide (WR07 light)

<400> SEQUENCE: 52

Thr Gly Val His Ser Glu Ile Val Leu Thr Gln Ser Pro Gly Thr Leu
1               5                   10                  15

Ser Leu Ser Pro Gly Glu Arg Ala Thr Leu Ser Cys Arg Ala Ser Gln
            20                  25                  30

Ser Val Ser Ser Ser Tyr Leu Ala Trp Tyr Gln Gln Lys Pro Gly Gln
        35                  40                  45

Ala Pro Arg Leu Leu Ile Tyr Gly Ala Ser Ser Arg Ala Thr Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Phe Cys Gln His
                85                  90                  95

Tyr Gly Ser Pro Ser Thr Phe Gly Gln Gly Thr Lys Val Glu Ile Lys
            100                 105                 110

Arg Thr


<210> SEQ ID NO 53
<211> LENGTH: 126
<212> TYPE: PRT
<213> ORGANISM: Artificial
<220> FEATURE:
<223> OTHER INFORMATION: Synthetic polypeptide (WR08 heavy)

<400> SEQUENCE: 53

Thr Gly Val His Ser Gln Val Gln Leu Gln Glu Ser Gly Pro Gly Leu
1               5                   10                  15

Val Lys Pro Ser Gln Thr Leu Ser Leu Thr Cys Thr Val Ser Gly Gly
            20                  25                  30

Ser Ile Ser Ser Gly Tyr Tyr Trp Ser Trp Ile Arg Gln His Pro Gly
        35                  40                  45

Lys Gly Leu Asp Cys Ile Gly Tyr Ile His Tyr Thr Gly Thr Thr Tyr
    50                  55                  60
```

```
Tyr Asn Pro Ser Leu Lys Ser Arg Leu Thr Ile Ser Val Asp Thr Ser
65                  70                  75                  80

Lys Asn Gln Phe Ser Leu Asn Leu Thr Ser Val Thr Ala Ala Asp Thr
                85                  90                  95

Ala Val Tyr Tyr Cys Ala Arg Glu Glu Tyr Thr Thr Ser Ser Val Asp
            100                 105                 110

Tyr Trp Gly Arg Gly Thr Leu Val Thr Val Ser Ser Ala Ser
        115                 120                 125


<210> SEQ ID NO 54
<211> LENGTH: 119
<212> TYPE: PRT
<213> ORGANISM: Artificial
<220> FEATURE:
<223> OTHER INFORMATION: Synthetic polypeptide (WR08 light)

<400> SEQUENCE: 54

Thr Gly Val His Gly Asp Val Val Met Thr Gln Ser Pro Leu Ser Leu
1               5                   10                  15

Pro Val Thr Leu Gly Gln Pro Ala Ser Ile Ser Cys Arg Ser Ser Glu
            20                  25                  30

Ser Leu Val Ser Val Asp Gly Asn Thr Tyr Leu Asn Trp Phe His Gln
        35                  40                  45

Arg Pro Gly Gln Ser Pro Arg Arg Leu Ile Tyr Lys Val Ser Asn Arg
    50                  55                  60

Asp Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Val Gly Ile Tyr
                85                  90                  95

Tyr Cys Met Gln Ala Thr His Trp Leu Arg Thr Phe Gly Gln Gly Thr
            100                 105                 110

Arg Leu Glu Ile Lys Arg Thr
        115


<210> SEQ ID NO 55
<211> LENGTH: 126
<212> TYPE: PRT
<213> ORGANISM: Artificial
<220> FEATURE:
<223> OTHER INFORMATION: Synthetic polypeptide (WR09 heavy)

<400> SEQUENCE: 55

Thr Gly Val His Ser Gln Val Gln Leu Gln Glu Ser Gly Pro Gly Leu
1               5                   10                  15

Val Lys Pro Ser Gln Thr Leu Ser Leu Thr Cys Thr Val Ser Gly Gly
            20                  25                  30

Ser Ile Ser Ser Gly Tyr Tyr Trp Ser Trp Ile Arg Gln His Pro Gly
        35                  40                  45

Lys Gly Leu Glu Trp Ile Gly Tyr Ile His Tyr Thr Gly Thr Thr Tyr
    50                  55                  60

Tyr Asn Pro Ser Leu Lys Ser Arg Val Thr Ile Ser Val Asp Thr Ser
65                  70                  75                  80

Lys Asn Gln Phe Ser Leu Asn Leu Thr Ser Val Thr Ala Ala Asp Thr
                85                  90                  95

Ala Val Tyr Tyr Cys Ala Arg Glu Glu Tyr Thr Thr Ser Ser Val Asp
            100                 105                 110

Tyr Trp Gly Arg Gly Thr Leu Val Thr Val Ser Ser Ala Ser
```

115 120 125

<210> SEQ ID NO 56
<211> LENGTH: 117
<212> TYPE: PRT
<213> ORGANISM: Artificial
<220> FEATURE:
<223> OTHER INFORMATION: Synthetic polypeptide (WR09 light)

<400> SEQUENCE: 56

```
Thr Gly Val His Ser Glu Ile Val Leu Thr Gln Ser Pro Gly Thr Leu
1               5                   10                  15

Ser Leu Ser Pro Gly Glu Arg Ala Thr Leu Ser Cys Arg Ala Ser Gln
            20                  25                  30

Arg Val Ser Ser Gly Phe Leu Ala Trp Tyr Gln Gln Lys Pro Gly Gln
        35                  40                  45

Ala Pro Arg Leu Leu Ile Tyr Gly Ala Ser Ser Arg Ala Thr Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Glu Ser Ser Pro Ser Pro Tyr Asn Phe Gly Gln Gly Thr Lys Leu
            100                 105                 110

Glu Ile Lys Arg Thr
        115
```

<210> SEQ ID NO 57
<211> LENGTH: 133
<212> TYPE: PRT
<213> ORGANISM: Artificial
<220> FEATURE:
<223> OTHER INFORMATION: Synthetic polypeptide (WR10 heavy)

<400> SEQUENCE: 57

```
Thr Gly Val His Ser Gln Val Gln Leu Gln Glu Ser Gly Pro Gly Leu
1               5                   10                  15

Val Lys Pro Ser Gly Thr Leu Ser Leu Thr Cys Ala Val Ser Gly Gly
            20                  25                  30

Ser Ile Ser Asn Asn Lys Trp Trp Asn Trp Val Arg Gln Ser Pro Gly
        35                  40                  45

Lys Gly Leu Glu Trp Ile Gly Glu Ile Tyr His Ser Gly Gly Thr Asn
    50                  55                  60

Tyr Asn Pro Ser Leu Lys Ser Arg Val Thr Ile Ser Val Asp Lys Ser
65                  70                  75                  80

Lys Asn Leu Phe Ser Leu Lys Leu Ser Ser Val Thr Ala Ala Asp Thr
                85                  90                  95

Ala Val Tyr Tyr Cys Ala Ser Ala Thr Thr Met Val Arg Gly Leu Ser
            100                 105                 110

Leu Tyr Tyr Tyr Gly Leu Asp Val Trp Gly Pro Gly Thr Thr Val Thr
        115                 120                 125

Val Ser Ser Ala Ser
    130
```

<210> SEQ ID NO 58
<211> LENGTH: 115
<212> TYPE: PRT
<213> ORGANISM: Artificial
<220> FEATURE:

<223> OTHER INFORMATION: Synthetic polypeptide (WR10 light)

<400> SEQUENCE: 58

Thr Gly Val His Ser Glu Ile Val Leu Thr Gln Ser Pro Gly Thr Leu
1 5 10 15

Ser Leu Ser Pro Gly Glu Arg Ala Ala Leu Ser Cys Arg Ala Ser Gln
20 25 30

Ser Leu Ile Gly Ser Phe Leu Ala Trp Tyr Gln Gln Lys Pro Gly Gln
35 40 45

Ala Pro Arg Leu Leu Ile Tyr His Thr Ser Asn Arg Ala Ser Gly Ile
50 55 60

Pro Asp Arg Phe Ser Gly Gly Gly Phe Gly Thr Asp Phe Thr Leu Thr
65 70 75 80

Ile Ser Arg Leu Glu Pro Glu Asp Phe Ala Val Tyr Tyr Cys Gln Gln
85 90 95

Tyr Asp Ser Ser Pro Ile Thr Phe Gly Gln Gly Thr Arg Leu Glu Ile
100 105 110

Lys Arg Thr
115

<210> SEQ ID NO 59
<211> LENGTH: 133
<212> TYPE: PRT
<213> ORGANISM: Artificial
<220> FEATURE:
<223> OTHER INFORMATION: Synthetic polypeptide (WR11 heavy)

<400> SEQUENCE: 59

Thr Gly Val His Ser Gln Val Gln Leu Gln Glu Ser Gly Pro Gly Leu
1 5 10 15

Val Lys Pro Ser Gly Thr Leu Ser Leu Thr Cys Ala Val Ser Gly Gly
20 25 30

Ser Ile Ser Asn Asn Lys Trp Trp Asn Trp Val Arg Gln Ser Pro Gly
35 40 45

Lys Gly Leu Glu Trp Ile Gly Glu Ile Tyr His Ser Gly Gly Thr Asn
50 55 60

Tyr Asn Pro Ser Leu Lys Ser Arg Val Thr Ile Ser Val Asp Lys Ser
65 70 75 80

Lys Asn Leu Phe Ser Leu Lys Leu Ser Ser Val Thr Ala Ala Asp Thr
85 90 95

Ala Val Tyr Tyr Cys Ala Ser Ala Thr Thr Met Val Arg Gly Leu Ser
100 105 110

Leu Tyr Tyr Tyr Gly Leu Asp Val Trp Gly Gln Gly Thr Thr Val Thr
115 120 125

Val Ser Ser Ala Ser
130

<210> SEQ ID NO 60
<211> LENGTH: 116
<212> TYPE: PRT
<213> ORGANISM: Artificial
<220> FEATURE:
<223> OTHER INFORMATION: Synthetic polypeptide (WR11 light)

<400> SEQUENCE: 60

Thr Gly Val His Ser Glu Ile Val Leu Thr Gln Ser Pro Gly Thr Leu
1 5 10 15

Ser Leu Ser Pro Gly Glu Arg Ala Thr Leu Ser Cys Arg Ala Ser Gln

```
            20                  25                  30

Ser Val Ser Ser Phe Leu Ala Trp Tyr Gln Gln Lys Pro Gly Gln Ala
        35                  40                  45

Pro Arg Leu Leu Ile Tyr Asp Ala Ser Asn Arg Ala Thr Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Gln Gln Arg
                85                  90                  95

Thr Asn Trp Pro Pro Ser Leu Thr Phe Gly Gly Gly Thr Lys Val Glu
            100                 105                 110

Ile Lys Arg Thr
        115


<210> SEQ ID NO 61
<211> LENGTH: 136
<212> TYPE: PRT
<213> ORGANISM: Artificial
<220> FEATURE:
<223> OTHER INFORMATION: Synthetic polypeptide (WR12 heavy)

<400> SEQUENCE: 61

Thr Gly Val His Ser Gln Val Gln Leu Gln Glu Ser Gly Pro Gly Leu
1               5                   10                  15

Val Lys Pro Ser Gln Thr Leu Ser Leu Thr Cys Thr Val Ser Gly Asp
            20                  25                  30

Ser Val Ser Ser Asn Asp His Tyr Trp Ser Trp Ile Arg Gln Pro Pro
        35                  40                  45

Gly Gln Gly Leu Glu Trp Ile Gly Tyr Ile Ser His Gly Gly Thr Thr
    50                  55                  60

Tyr Tyr Asn Pro Ser Leu Lys Ser Arg Val Thr Met Ser Ile Asp Thr
65                  70                  75                  80

Ser Thr Asn Gln Phe Ser Leu Arg Val Thr Ser Val Arg Ala Ala Asp
                85                  90                  95

Met Ala Val Tyr Phe Cys Ala Arg Ala Pro Ala Pro Ile Thr Thr Phe
            100                 105                 110

Gly Met Val Thr Pro Val Pro Tyr Phe His Ser Trp Gly Gln Gly Thr
        115                 120                 125

Leu Val Thr Val Ser Ser Ala Ser
    130                 135


<210> SEQ ID NO 62
<211> LENGTH: 119
<212> TYPE: PRT
<213> ORGANISM: Artificial
<220> FEATURE:
<223> OTHER INFORMATION: Synthetic polypeptide (WR12 light)

<400> SEQUENCE: 62

Thr Gly Val His Gly Asp Ile Val Met Thr Gln Ser Pro Leu Ser Leu
1               5                   10                  15

Pro Val Ser Pro Gly Glu Pro Ala Ser Ile Ser Cys Arg Ser Ser Gln
            20                  25                  30

Ser Leu Leu His Ser Asn Gly Tyr Asn Tyr Leu Ser Trp Tyr Leu Gln
        35                  40                  45

Lys Pro Gly Gln Ser Pro Gln Leu Leu Ile Phe Ser Ser Ser Ile Arg
    50                  55                  60
```

Ala Ser Gly Val Pro Asp Arg Phe Ser Gly Ser Gly Ser Gly Thr Asp
65 70 75 80

Phe Thr Leu Thr Ile Asn Arg Val Glu Ala Glu Asp Val Gly Val Tyr
85 90 95

Tyr Cys Met Gln Ala Leu Gln Thr Pro Leu Thr Phe Gly Gly Gly Thr
100 105 110

Lys Leu Glu Ile Lys Arg Thr
115

<210> SEQ ID NO 63
<211> LENGTH: 136
<212> TYPE: PRT
<213> ORGANISM: Artificial
<220> FEATURE:
<223> OTHER INFORMATION: Synthetic polypeptide (WR13 heavy)

<400> SEQUENCE: 63

Thr Gly Val His Ser Gln Val Gln Leu Gln Glu Ser Gly Pro Gly Leu
1 5 10 15

Val Lys Pro Ser Gln Thr Leu Ser Leu Thr Cys Thr Val Ser Gly Asp
20 25 30

Ser Val Ser Ser Asn Asp His Tyr Trp Ser Trp Ile Arg Gln Pro Pro
35 40 45

Gly Gln Gly Leu Glu Trp Ile Gly Tyr Ile Ser His Gly Gly Thr Thr
50 55 60

Tyr Tyr Asn Pro Ser Leu Lys Ser Arg Val Thr Met Ser Ile Asp Thr
65 70 75 80

Ser Thr Asn Gln Phe Ser Leu Arg Val Thr Ser Val Arg Ala Ala Asp
85 90 95

Met Ala Val Tyr Phe Cys Ala Arg Ala Pro Ala Pro Ile Thr Thr Phe
100 105 110

Gly Met Val Thr Pro Val Pro Tyr Phe His Ser Trp Gly Gln Gly Thr
115 120 125

Leu Val Thr Val Ser Ser Ala Ser
130 135

<210> SEQ ID NO 64
<211> LENGTH: 119
<212> TYPE: PRT
<213> ORGANISM: Artificial
<220> FEATURE:
<223> OTHER INFORMATION: Synthetic polypeptide (WR13 light)

<400> SEQUENCE: 64

Thr Gly Val His Gly Asp Ile Val Met Thr Gln Ser Pro Leu Ser Leu
1 5 10 15

Pro Val Ser Pro Gly Glu Ser Ala Ser Ile Ser Cys Arg Ser Ser Gln
20 25 30

Ser Leu Leu His Ser Asn Gly Tyr Asn Tyr Leu Ser Trp Tyr Leu Gln
35 40 45

Lys Pro Gly Gln Ser Pro Gln Leu Leu Ile Phe Ser Ser Ser Ile Arg
50 55 60

Ala Ser Gly Val Pro Asp Arg Phe Ser Gly Ser Gly Ser Gly Thr Asp
65 70 75 80

Phe Thr Leu Thr Ile Asn Arg Val Glu Ala Glu Asp Val Gly Val Tyr
85 90 95

Tyr Cys Met Gln Ala Leu Gln Thr Pro Leu Thr Phe Gly Gln Gly Thr
100 105 110

Lys Leu Glu Ile Lys Arg Thr
        115

<210> SEQ ID NO 65
<211> LENGTH: 392
<212> TYPE: DNA
<213> ORGANISM: Artificial
<220> FEATURE:
<223> OTHER INFORMATION: Synthetic oligonucleotide (AJL01 heavy)

<400> SEQUENCE: 65
accggtgtac attcccaggt gcagctacag cagtggggcg caggactgtt gaagccttcg 60
gagaccctgt ccctcacctg cgctgtctat ggtgggtcct tcaatgaatt ctactggagc 120
tggatccgtc agcccgcacg gaagggcctg gagtggattg gagaaatcag tcatagcgga 180
agagccaact acaacccgtc cctcaagagt cgcgtcaccc tgtctgtaga caggtccaag 240
aaccagttct ccctgaacct gagccctgtg gccgccgcgg acacagctgt ctattactgt 300
gcgcgacggg agatagtcgt aactgttcgg gggcgtcgtg cttttgatat ctggggccaa 360
gggacaatgg tcaccgtctc ttcagcgtcg ac 392

<210> SEQ ID NO 66
<211> LENGTH: 345
<212> TYPE: DNA
<213> ORGANISM: Artificial
<220> FEATURE:
<223> OTHER INFORMATION: Synthetic oligonucleotide (AJL01 light)

<400> SEQUENCE: 66
accggtgtac attcagaaat tgtgttgacg cagtctccag gcaccctgtc tttgtctcca 60
ggggaaagag ccgccctctc ctgcagggcc agtcagagtc ttatcggcag cttcttagcc 120
tggtaccagc agaaacctgg ccaggctccc aggctcctca tctatcatac atccaacagg 180
gcctctggca tcccagacag gttcagtggc ggtgggtttg ggacagactt cactctcacc 240
atcagcagac tggagcctga agattttgca gtttattact gtcaacagta tgatagctca 300
ccgatcacct tcggccaagg gacacgactg gagattaaac gtacg 345

<210> SEQ ID NO 67
<211> LENGTH: 383
<212> TYPE: DNA
<213> ORGANISM: Artificial
<220> FEATURE:
<223> OTHER INFORMATION: Synthetic oligonucleotide (AJL02 heavy)

<400> SEQUENCE: 67
accggtgtac attcccaggt gcagctgcag gagtcgggcc caggactggt gaagccttca 60
cagaccctgt ccctcacctg tactgtctct ggtggctcca tcagcagtgg tggtcactac 120
tggagctgga tccgccagtc cccagggaag ggcctggagt ggattgggaa cgtctattat 180
agtggaagca cctactacac cccgtccctc gacagccgac ttaccatatc attagacacg 240
tctaagaacc agttctccct gaggctgagt aatgtgactg tcgcggacac ggccgtctat 300
tactgtgcga gaggtagaaa ttgggagggc gaattcgacc cctggggcca aggaaccctg 360
gtcaccgtct cctcagcgtc gac 383

<210> SEQ ID NO 68
<211> LENGTH: 342
<212> TYPE: DNA
<213> ORGANISM: Artificial

<220> FEATURE:
<223> OTHER INFORMATION: Synthetic oligonucleotide (AJL02 light)

<400> SEQUENCE: 68
accggtgtac attctgacat ccagatgacc cagtctccgt cctccctgtc tgcgtcttta 60
ggagacagag tcaccatcac ttgccgggca agtcagggca ttagcagctc tgtaaattgg 120
tttcagcaga aaccagggaa agcccctgaa ctcctgatct atgctgcatc cactttgcaa 180
agtggggtcc catcaagatt cagtggcagt ggatctggga cagatttcac tctcaccgtc 240
agcagtctgc aacctgaaga ttttgcaact tactactgtc agcagagtta cagtcccct 300 cgaacttttg gccaggggac caagctggaa atcaaacgta cg 342

<210> SEQ ID NO 69
<211> LENGTH: 404
<212> TYPE: DNA
<213> ORGANISM: Artificial
<220> FEATURE:
<223> OTHER INFORMATION: Synthetic oligonucleotide (AJL03 heavy)

<400> SEQUENCE: 69
accggtgtac attcccagct gcagctgcag gagtcgggcc caggactggt gaagccttcg 60
gagaccctgt ccctcacgtg cactgtctct ggtgcctcca tcagcagtag tcgttcctac 120
tggggctgga tccgccagcc cccagggaag gggctggagt ggattgggag tatgtatcaa 180
agtgggagca cttactacag tccgtccctc aagagtcgag tcaccatatc catggacacg 240
tccaagaacc agttctccct aaacctgacg tctgtgaccg ccgcggacac ggctgtgtat 300
ttctgtgcga gacattcgaa ccccggaacg gcgaacaaat tgcgtttggg ggagttttcg 360
ccctggggcc agggaaccct ggtcaccgtc tcctcagcgt cgac 404

<210> SEQ ID NO 70
<211> LENGTH: 342
<212> TYPE: DNA
<213> ORGANISM: Artificial
<220> FEATURE:
<223> OTHER INFORMATION: Synthetic oligonucleotide (AJL03 light)

<400> SEQUENCE: 70
accggtgtac attctgacat ccagatgacc cagtctccat cctccctgtc tgcatctgta 60
ggagacagag tcaccatcac ttgccaggcg agtcaggaca ttaacaacta tttaaattgg 120
tttcagcagc aaccagggaa agcccctaag ctgctgatct acgatgcatc caaattgcaa 180
atgggggtcc catcaaggtt cagtggaagt gcatctggga cagattttac ttttaccatc 240
agcagcctgc agcctgaaga tattggcaca tattactgtc aacagtatta taatctcccg 300
tacacttttg gccaggggac caagctggag atcaaacgta cg 342

<210> SEQ ID NO 71
<211> LENGTH: 377
<212> TYPE: DNA
<213> ORGANISM: Artificial
<220> FEATURE:
<223> OTHER INFORMATION: Synthetic oligonucleotide (AJL04 heavy)

<400> SEQUENCE: 71
accggtgtac attcccaggt gcagctgcag gagtcgggcc caggactggt gaagccttcg 60
gagaccctgt ccctcacctg cactgtctct ggtgactcca tcagaagtaa cttctggacc 120
tggatccggc agtccccagg gaggggactg gagtggattg ggtatttctc ttacagtggg 180
ggcatcaact acagcccctc cctcaagagt cgcgtcacca tttcagtgga cacatccaag 240
aaccagttct ccctaaaact gacctctgtg accgcggcgg acgcggccgt atattactgt 300
gcgagagatc ccaacggtga ctacgaagtt aactggtggg gccaaggaac cctggtcacc 360
gtctcctcag cgtcgac 377

<210> SEQ ID NO 72
<211> LENGTH: 342
<212> TYPE: DNA
<213> ORGANISM: Artificial
<220> FEATURE:
<223> OTHER INFORMATION: Synthetic oligonucleotide (AJL04 light)

<400> SEQUENCE: 72
accggtgtac attctgacat ccagatgacc cagtctccat cttcactgtc tgcatctgta 60
ggagacagag tcaccatcac ttgtcgggcg agtcaggaca ttattattta tttagcctgg 120
tttcagcaga gaccagggaa agcccctagg tccctgatct attctgcatc cactttgcag 180
agtggggtcc catcaaaatt cagcggcagt ggatctggga catatttcac tctcaccatc 240
agcagcctgc agcctgaaga ttctgcaact tattactgcc aacaatataa aagttatccc 300
atcaccttcg gccaagggac acgactggag attaaacgta cg 342

<210> SEQ ID NO 73
<211> LENGTH: 389
<212> TYPE: DNA
<213> ORGANISM: Artificial
<220> FEATURE:
<223> OTHER INFORMATION: Synthetic oligonucleotide (AJL05 heavy)

<400> SEQUENCE: 73
accggtgtac attcccagct gcagctgcag gagtcgggcc caggactggt gaagccttcg 60
gagaccctgt ccctcacctg cactgtctct ggtggctcca tcagaaatag taattactac 120
tgggactgga tccgccagcc cccaggaaag gggctggagt ggattgggag tggctattat 180
agtgggagcg cctactacca ttcgtccctc aagagtcgag tcagcatatc cgtagacacg 240
tccaagaacc agttttccct taatctgacc tctgtgaccg ccgcagacac ggctttttat 300
tactgtgcga gacgttccta ttattatgct tcggggagcc acgactactg gggccaggga 360
accctggtca ccgtctcctc agcgtcgac 389

<210> SEQ ID NO 74
<211> LENGTH: 342
<212> TYPE: DNA
<213> ORGANISM: Artificial
<220> FEATURE:
<223> OTHER INFORMATION: Synthetic oligonucleotide (AJL05 light)

<400> SEQUENCE: 74
accggtgtac attctgacat ccagatgacc cagtctccat cctcactgtc tgcatctgta 60
ggagacagag tcaccatcac ttgtcgggcg agtcaggaca ttagcagtta cttagcctgg 120
tttcagcaga aaccagggaa agcccctaag tccctgatct atggtgcttc cagtttgcag 180
agtggggtcc catcaaaatt cagcggcagt ggatctggga cagatttcac tctcaccatc 240
agcggcctgc agcctgaaga ttttgcaact tatcactgcc aacaatacag gagtttccct 300
atcactttcg gccaagggac acgactggag attaaacgta cg 342

<210> SEQ ID NO 75
<211> LENGTH: 395

-continued

<212> TYPE: DNA
<213> ORGANISM: Artificial
<220> FEATURE:
<223> OTHER INFORMATION: Synthetic oligonucleotide (AJL06 heavy)

<400> SEQUENCE: 75
accggtgtac attcccagct gcagctgcag gagtccggct caggactggt gaagccttca 60
cagaccctgt ccctcacctg cgctgtctct ggtggctcca tcaacactgg caattacttc 120
tggagctgga tccggcagcc accagggaag ggcctggagt ggattgggta catgtttcga 180
agtacgagta cctactacaa cccgtccctc aagggtcgag tcaccatttc aggaggcacg 240
tccctgagcc agttctccct gagactggac tctgtgactg ccgcggacac ggccatctac 300
tactgtgcga gaggacgtta ttattgtggt gttaattgcc atccctttga ctcctggggc 360
caaggaaccc tggtcaccgt ctcctcagcg tcgac 395

<210> SEQ ID NO 76
<211> LENGTH: 339
<212> TYPE: DNA
<213> ORGANISM: Artificial
<220> FEATURE:
<223> OTHER INFORMATION: Synthetic oligonucleotide (AJL06 light)

<400> SEQUENCE: 76
accggtgtac attctgacat ccagatgacc cagtctccat cctccctgtc tgcatctgta 60
ggagacagag tcatcatcac ttgccaggcg agccaagaca ttagcatcta tttaaattgg 120
tatcaggtga aaccagggaa agcccctaaa ctcctgatct acgatgcctc caatttgcaa 180
gcaggggtcc catcaaggtt cagtggaagt ggatcaggga cagattttag tttcaccatc 240
agcagcctgc agcctgaaga tgtggcagca tattactgtc atcagtatga ttctttaccg 300
agttttggcc aggggaccaa gctggaaatc aaacgtacg 339

<210> SEQ ID NO 77
<211> LENGTH: 383
<212> TYPE: DNA
<213> ORGANISM: Artificial
<220> FEATURE:
<223> OTHER INFORMATION: Synthetic oligonucleotide (AJL07 heavy)

<400> SEQUENCE: 77
accggtgtac attcccaggt gcagctgcag gagtcgggcc caggactggt gaagccttcg 60
gagaccctgt ccctcacctg caatgtctct ggtggctcca tcaacaacta ttactggagt 120
tggatccggc agcccccagg gaagggactg gagtggattg gttatatcta ttacaatggg 180
aatattaatt acaacccttc cctcaagagt cgagtcacca tatcaagaga catgtccaag 240
aaccagttct ccctgaacct gcggtctgtg accgctgcgg acacggccgt gtattactgt 300
ggaattggat atagtgcggt ggcagctggt acagttgact actggggcca tggcaccctg 360
gtcaccgtct cctcagcgtc gac 383

<210> SEQ ID NO 78
<211> LENGTH: 342
<212> TYPE: DNA
<213> ORGANISM: Artificial
<220> FEATURE:
<223> OTHER INFORMATION: Synthetic oligonucleotide (AJL07 light)

<400> SEQUENCE: 78
accggtgtac attcagccat ccagttgacc cagtctccat cctccctgtc tgcatctgtg 60

-continued

```
ggagacagag tcaccatcac ttgccgggca agtcagggca ttagcagtgg tttagcctgg    120

tatcagcagg aaccagggaa agctcctaaa ctcctgatct atgatgcctc cactttggaa    180

agtggggtcc catcaagatt cagcggcagt ggatctgcaa tagatttcac tctcaccatc    240

agcagtctgc agcctgaaga ttttgcaact tattactgtc aacagtttaa tactttcccg    300

tacacttttg gccaggggac caagctggag atcaaacgta cg                       342


<210> SEQ ID NO 79
<211> LENGTH: 395
<212> TYPE: DNA
<213> ORGANISM: Artificial
<220> FEATURE:
<223> OTHER INFORMATION: Synthetic oligonucleotide (AJL08 heavy)

<400> SEQUENCE: 79

accggtgtac attcccaggt gcagctgcag gagtcgggcc caggactggt gaagccttcg     60

gagaccctgt ccctcacctg cgctgtctct ggtttctcca tcaccagtgg ttactactgg    120

ggctggatcc ggcagccccc cgggaagggg ctggagtgga tagggagtat ctatcatact    180

gggactacct actacaaccc gtccctcaag agtcgagtca ccatatcagt agacacgtcc    240

aagaaccagt tctccctgaa cctaaactct gtgaccgccg cagacacggc cttttattac    300

tgtgcgagag atcctctatt cccggggcgg aacctactct ccgtttttga caactggggc    360

cagggcaccc tggtcaccgt ctcctcagcg tcgac                               395


<210> SEQ ID NO 80
<211> LENGTH: 342
<212> TYPE: DNA
<213> ORGANISM: Artificial
<220> FEATURE:
<223> OTHER INFORMATION: Synthetic oligonucleotide (AJL08 light)

<400> SEQUENCE: 80

accggtgtac attctgacat ccagatgacc cagtctcctt ccaccctgtc tgcatctgta     60

ggagacagag tcaccatcac ttgccgggcc agtcagagta ttagtacctg gttggcctgg    120

tatcagcaga aaccagggaa agcccctagg ctcctgatct ataaggcatc tagtttagaa    180

agtggggtcc catcacgttt cagcggcagt ggatctggga cagaattcac tctcaccatc    240

agcggcctgc agcctgatga ctttgcaaat tattcctgcc aacaatataa tatttacccg    300

ttcacttttg gccaggggac caagctggag atcaaacgta cg                       342


<210> SEQ ID NO 81
<211> LENGTH: 386
<212> TYPE: DNA
<213> ORGANISM: Artificial
<220> FEATURE:
<223> OTHER INFORMATION: Synthetic oligonucleotide (AJL09 heavy)

<400> SEQUENCE: 81

accggtgtac attcccaggt gcagctgcag gagtcgggcc caggactggt gaagccttcg     60

gagaccctgt ccctcacctg cagtgtctct ggtggctcca tcagtagtta ctactggggc    120

tggatccggc agtccccagg gaaaggactg gagtgcattg gatacatcta tttcagtggg    180

agcaccagct acaacccctc cctcaagagt cgagtcacca tatcagtaga cacggccaag    240

aaccagatct ccctgaacct gacctctgtg accgctgcgg acacggccgt gtatttttgt    300

gcgagagttt ggggcagcag ctggtacgct aactggttcg accccctgggg ccagggcacc    360

ctggtcaccg tctcctcagc gtcgac                                         386
```

<210> SEQ ID NO 82
<211> LENGTH: 342
<212> TYPE: DNA
<213> ORGANISM: Artificial
<220> FEATURE:
<223> OTHER INFORMATION: Synthetic oligonucleotide (AJL09 light)

<400> SEQUENCE: 82
accggtgtac attcagccat ccagttgacc cagtctccat cctccctgtc tgcgtctgtt 60
ggagacagag tcaccatcac ttgccgggca agtcagggca ttagcagtgc cttagcctgg 120
tatcagcaca aaccagggaa ggctcctaaa ctcctgatct ttgatgcctc cactttggca 180
gctggggtcc catccaggtt cagcggcagt ggatctggga cagatttcac tctcaccatc 240
agcagtctgc agcctgaaga ttttgctact tattactgtc agcagtataa tacttacgtt 300
ctcactttcg gccaagggac acgactggag attaaacgta cg 342

<210> SEQ ID NO 83
<211> LENGTH: 389
<212> TYPE: DNA
<213> ORGANISM: Artificial
<220> FEATURE:
<223> OTHER INFORMATION: Synthetic oligonucleotide (AJL10 heavy)

<400> SEQUENCE: 83
accggtgtac attcccaggt gcagctgcag gagtcgggcc caggactggt gaagccttcg 60
gagaccctgt ccctcacctg cagtgtctct ggtggcgccg tcagtaatta ctactggagt 120
tggatccggc agtccgccgg gaagggactg gagtggcttg ggcggatcta tatcaatgga 180
actacttact acaacccctc cctcaggagc cgggtctcca tgtcagttga cacgtccaag 240
ggccagttct ccctgaggtt gacctctgtg accgccgcgg acacggccat atattattgt 300
gcgagatggg gtgccctatt gggcgactac tattacggtt tggacgtctg gggccaaggg 360
accacggtca ccgtctcctc agcgtcgac 389

<210> SEQ ID NO 84
<211> LENGTH: 357
<212> TYPE: DNA
<213> ORGANISM: Artificial
<220> FEATURE:
<223> OTHER INFORMATION: Synthetic oligonucleotide (AJL10 light)

<400> SEQUENCE: 84
accggtgtac atggggatat tgtgatgact cagtctccac tctccctgcc cgtcacccct 60
ggagagccgg cctccatctc ctgcaggtct actcagagcc tcctacacag taatgaatac 120
atttatttgg attggtacgt gcagaagcca gggcagtctc cacaactcct gatctttttg 180
gcttctaatc gggcctccgg ggtccctgac aggttcagtg gcagtgcatc aggcacagat 240
tttacactga aaatcagcag agtggaggct gaggatgttg ggtttatta ctgcatgcaa 300 gctctagaag ctccgtggac gttcggccaa gggacacgac tggagattaa acgtacg 357

<210> SEQ ID NO 85
<211> LENGTH: 380
<212> TYPE: DNA
<213> ORGANISM: Artificial
<220> FEATURE:
<223> OTHER INFORMATION: Synthetic oligonucleotide (AJL11 heavy)

<400> SEQUENCE: 85

-continued accggtgtac attcccagct gcagctgcag gagtcgggcc caggactggt gaagccttcg 60
gagaccctgt ccctcacctg ctctgtctct ggtggctcca tcaccagtac ttcttattac 120
tgggggtgga tccgccagtc cccagggaag ggactggagt ggattggcag tgtctattac 180
agtgggaaca ccttctacaa cgcgtccctc aagagtcgag tcaccatatc catagacacg 240
tccaagtacc agttctccct gatgctgagg tctgtgaccg ccgcagacac ggctgtgtat 300
tactgtgcga gacgacatga ttggttctgg ttcgacccct ggggccaagg aaccctggtc 360
accgtctcct cagcgtcgac 380

<210> SEQ ID NO 86
<211> LENGTH: 345
<212> TYPE: DNA
<213> ORGANISM: Artificial
<220> FEATURE:
<223> OTHER INFORMATION: Synthetic oligonucleotide (AJL11 light)

<400> SEQUENCE: 86
accggtgtac attcagaaat tgtgttgacg cagtctccag gcaccctgtc tttgtctcca 60
ggggaaagag tcaccctctc ctgcagggcc agtcagagtg ttagcagcag ctacttagcc 120
tggtaccagc agaaacctgg ccaggctccc aggctcctca tctatgattc atccagcagg 180
gccactggca tcccagacag gttcagtggc agtgggtctg ggacagactt cactctcacc 240
atcagcagac tggaccctga agattttgcc gtgtattact gtcagcagta tggtagctca 300
ccaagcactt ttggccaggg gaccaagctg gagatcaaac gtacg 345

<210> SEQ ID NO 87
<211> LENGTH: 386
<212> TYPE: DNA
<213> ORGANISM: Artificial
<220> FEATURE:
<223> OTHER INFORMATION: Synthetic oligonucleotide (AJL12 heavy)

<400> SEQUENCE: 87
accggtgtac attcccagct gcagctgcag gagtcgggcc caggactggt gaagccttcg 60
gagaccctgt ccctcacctg cactgtctct ggtggctccg tcaccagtag tgattactac 120
tgggcctgga tccgccagcc cccagggaag ggccggagt ggattgggag tatctctaat 180
agtgggaaca cgtattacag tccgtccctc aagagtcgag tctccatatc gggagacacg 240
tccaagaagc agttctccct gaacctgagc tctgtgaccg acgcagacac ggctgtgtat 300
tactgtacga gacacggtca ctacgtttca ggggggctgg gcccctgggg ccaaggaacc 360
ctggtcaccg tctcctcagc gtcgac 386

<210> SEQ ID NO 88
<211> LENGTH: 345
<212> TYPE: DNA
<213> ORGANISM: Artificial
<220> FEATURE:
<223> OTHER INFORMATION: Synthetic oligonucleotide (AJL12 light)

<400> SEQUENCE: 88
accggtgtac attcagaaat tgtgttgacg cagtctccag gcaccctgtc tttgtctcca 60
ggggaaagag ccaccctctc ctgcagggcc agtcagagtg ttggcagtta ctacttagcc 120
tggtaccagc agaaacctgg ccaggctccc aggctcctca tccacggtgc atccagcagg 180
gccactggca ccccagacag gttcagtggc agtgggtctg ggacagactt cactctcacc 240
atcagcaaac tggagcctga agattttgca ctgtattact gtcagcagta tggtccctca 300
ccttggacgt tcggccaagg gaccaaggtg gaaatcaaac gtacg 345

<210> SEQ ID NO 89
<211> LENGTH: 383
<212> TYPE: DNA
<213> ORGANISM: Artificial
<220> FEATURE:
<223> OTHER INFORMATION: Synthetic oligonucleotide (AJL13 heavy)

<400> SEQUENCE: 89
accggtgtac attcccaggt gcagctgcag gagtcgggcc caggactggt gaagccttcg 60
gagaccctgt ccctcacctg caatgtctct ggtggctcca tcaacaacta ttactggagt 120
tggatccggc agcccccagg gaagggactg gagtggattg gttatatcta ttacaatggg 180
aatattaatt acaacccttc cctcaagagt cgagtcacca tatcaagaga catgtccaag 240
aaccagttct ccctgaacct gcggtctgtg accgctgcgg acacggccgt gtattactgt 300
ggaattggat atagtgcggt ggcagctggt acagttgact actggggcca gggaaccctg 360
gtcaccgtct cctcagcgtc gac 383

<210> SEQ ID NO 90
<211> LENGTH: 357
<212> TYPE: DNA
<213> ORGANISM: Artificial
<220> FEATURE:
<223> OTHER INFORMATION: Synthetic oligonucleotide (AJL13 light)

<400> SEQUENCE: 90
accggtgtac atggggatgt tgtgatgact cagtctccac tctccctgcc cgtcaccctt 60
ggacaaccgg cctccatctc ctgcaggtct agtcaaagcc tcgtacacag gaatggaaac 120
acctacttga attggtttca gcagaggcca ggccaatcgc caaggcgcct aatttataca 180
gtttctaagc ggggctctgg ggtcccagac agattcagcg gcagtgggtc aggcactgat 240
ttcacactga aaatcagcag ggtggaggct gaagatgttg gggactatta ctgcatgcaa 300
ggtacacact ggccttggac gtccggccaa gggacacgac tggagattaa acgtacg 357

<210> SEQ ID NO 91
<211> LENGTH: 407
<212> TYPE: DNA
<213> ORGANISM: Artificial
<220> FEATURE:
<223> OTHER INFORMATION: Synthetic oligonucleotide (AJL14 heavy)

<400> SEQUENCE: 91
accggtgtac attcccaggt gcagctgcag gagtcgggcc caggactggt gaagccttca 60
cagaccctgt ccctcacctg cactgtctct ggtggctccc tcagtagtgt taattactac 120
tggaactgga tccggcagcc cgccgggaag ggactggagt ggatggggcg tatctatgcc 180
agcgggtaca ccacctacaa cccgtccttc cagagtcgag tcaccatatc actggacccg 240
tccaagaacc agatctccct gaaggtgact tctctgaccg ccgcagacac ggccatctat 300
tactgtgcga gacacgacct tgggcattgt agtagtacga gctgttacct cagttggttc 360
gacgcctggg gccaagggac cacggtcacc gtctcctcag cgtcgac 407

<210> SEQ ID NO 92
<211> LENGTH: 360
<212> TYPE: DNA
<213> ORGANISM: Artificial
<220> FEATURE:

-continued

<223> OTHER INFORMATION: Synthetic oligonucleotide (AJL14 light)

<400> SEQUENCE: 92
accggtgtac attcggacat cgtgatgacc cagtctcccg actccctggc tgtgtctctg 60
ggcgagaggg ccaccatcaa ctgcaggtcc agccagacta ttttcttcag ccccaacaat 120
aacaaccact tagcttggta ccagcaaaaa ccagggcagc ctcctaggct gctcatttac 180
tgggcatcta cccgggaatc cggggtccct gaccgattca gtggcagcgg gtctgggaca 240
gatttcactc tcaccatcag cggcctgcag gctgaagatg tggcagttta ttactgtcag 300
caatattata gtcttcccta cacttttggc caggggacca agctggagat caaacgtacg 360

<210> SEQ ID NO 93
<211> LENGTH: 404
<212> TYPE: DNA
<213> ORGANISM: Artificial
<220> FEATURE:
<223> OTHER INFORMATION: Synthetic oligonucleotide (AJL15 heavy)

<400> SEQUENCE: 93
accggtgtac attcccagct gcagctgcag gagtcgggcc caggactggt gaagccttcg 60
gagaccctgt ccctcacctg cactgtctct ggtggctcca tcaccagtag gaataactac 120
tggggctgga tccgccagtc cccagggaag gggctggagt ggattgggag tctctattat 180
actgggagcg actactacaa cccgtccctc aagagtcgag tcaccatatc ggtagacaca 240
tcgaagaacc aattctccct gaggctgagt tctgtgaccg ccgcggacac ggccgtgtat 300
tattgtgtca gagttaacgt agacgacttt tggagtggtt taggggggc ctggttcgac 360 ccctggggcc aaggaaccct ggtcaccgtc tcctcagcgt cgac 404

<210> SEQ ID NO 94
<211> LENGTH: 357
<212> TYPE: DNA
<213> ORGANISM: Artificial
<220> FEATURE:
<223> OTHER INFORMATION: Synthetic oligonucleotide (AJL15 light)

<400> SEQUENCE: 94
accggtgtac atggggatat tgtgatgacc cagactccac tctctttgtc cgtcacccct 60
ggacagccgg cctccatctc ctgcaaatct agtcagagcc tcctggatag tgatggaaag 120
acccatttgt actggtacct gcagaagcca ggccagtctc cacagtccct gatctatgaa 180
gtttctaaac ggttctctgg agtgccagat aggttcactg gcagcgggtc agggacagat 240
ttcacactga aaatcagccg ggtggaggct gaggatgttg ggctttatta ctgcatgcaa 300
agtgcacagc ttccgtacac ttttggccag gggaccaagc tggaaatcaa acgtacg 357

<210> SEQ ID NO 95
<211> LENGTH: 401
<212> TYPE: DNA
<213> ORGANISM: Artificial
<220> FEATURE:
<223> OTHER INFORMATION: Synthetic oligonucleotide (AJL16 heavy)

<400> SEQUENCE: 95
accggtgtac attcccagct gcagctgcag gagtcgggcc caggactggt gaagccttcg 60
gagaccctgt ccctcacctg cactgtctct ggtggctcca tcagcagtag tccttactac 120
tggggctgga tccgccagcc cccagggaag gggctggagt ggattgggag tatctattat 180
agtgggcaca cctattataa cccctccctc aagagtcgag tcaccatatc cgttgacacg 240
tccaagaacc agttctccct gcggctgacc tctgtgaccg ccgcagacac gtctgtgtat 300
tactgtgcga aacagaccga tgactacggt gactacgcgt ccaggggctg gttcgacccc 360
tggggccaag gaaccctggt caccgtctcc tcagcgtcga c 401

<210> SEQ ID NO 96
<211> LENGTH: 342
<212> TYPE: DNA
<213> ORGANISM: Artificial
<220> FEATURE:
<223> OTHER INFORMATION: Synthetic oligonucleotide (AJL16 light)

<400> SEQUENCE: 96
accggtgtac attctgacat ccagatgacc cagtctccat cctccctgtc tgcatctgta 60
ggagacagag tcaccttcac ttgccaggcg agtcacgaca ttagcaacta tttaaattgg 120
tatcagcaga aaccagggaa agtccctgag ctcctgatct acgatgcatc caatttgaaa 180
acaggggtcc catcaaggtt cagtggaagt ggatctggga cagattttac tttcaccatc 240
agcagcctgc agcctgaaga tattgcaaca tattactgtc aacagtatga taatctccct 300
atcaccttcg gccaagggac acgactggag attaaacgta cg 342

<210> SEQ ID NO 97
<211> LENGTH: 407
<212> TYPE: DNA
<213> ORGANISM: Artificial
<220> FEATURE:
<223> OTHER INFORMATION: Synthetic oligonucleotide (AJL18 heavy)

<400> SEQUENCE: 97
accggtgtac attcccaggt gcagctgcag gagtcgggcc caggactggt gaagccttca 60
cagaccctgt ccctcacctg cactgtctct ggtgactcca tcagcagtga taaatactac 120
tggacctgga tccgccagct cccagggaag ggcctggagt ggattggcta catctcttac 180
agtgggacca cctactacaa tccgtccctc aagagtcgag tttccatttc agttgacacg 240
tctgggaacc agttctccct gaggctgagc tctgtgactg ccgcggacac ggcccgctat 300
tactgtgcgc gagtatatta cgatgttttg tctgcttatt ataatatggg gtcctgggta 360
gacccctggg gccaaggaac cctggtcacc gtctcctcag cgtcgac 407

<210> SEQ ID NO 98
<211> LENGTH: 342
<212> TYPE: DNA
<213> ORGANISM: Artificial
<220> FEATURE:
<223> OTHER INFORMATION: Synthetic oligonucleotide (AJL18 light)

<400> SEQUENCE: 98
accggtgtac attctgacat ccagatgacc cagtctccat cctccctgcc tgcatctgta 60
ggagacagag tcaccatcac ttgccgggca agtcagagca ttagcagcta tttaaattgg 120
tatcagcaga aaccagggag agcccctaag ctcctgatct atgctgcatc cagtttacaa 180
agtggggtct catcaaggtt cagtggcagt ggatctggga cagatttcac tctcaccatc 240
agcagtctgc aacctgaaga ttctgcaact tactactgtc aacagagtta cagtaccccg 300
tggacgttcg gccaagggac caaggtggag atcaaacgta cg 342

<210> SEQ ID NO 99
<211> LENGTH: 383
<212> TYPE: DNA

<213> ORGANISM: Artificial
<220> FEATURE:
<223> OTHER INFORMATION: Synthetic oligonucleotide (AJL19 heavy)

<400> SEQUENCE: 99
accggtgtac attcccaggt gcagctacag cagtggggcg caggactgtt gaagcctccg 60
gagaccctgt ccctcacctg cgctgtcttt ggtgggtccc tcagtggtta ctactggagt 120
tggatccgcc agcccccagg gaaggggccg gagtggattg cggaaatcaa tcatagtgga 180
gatgccaact acaacccgtc cctcaagagt cgagtcacta tctcagtaga cacgtccaag 240
aaccagtttt ccctgaagat gagttctgtg accgtcgcag acacggcttt atattactgt 300
gcgactcaag gctctaggtt gactacattc gcttttgatg tgtggggcca agggacaatg 360
gtcaccgtct cttcagcgtc gac 383

<210> SEQ ID NO 100
<211> LENGTH: 348
<212> TYPE: DNA
<213> ORGANISM: Artificial
<220> FEATURE:
<223> OTHER INFORMATION: Synthetic Oligonucleotide (AJL19 light)

<400> SEQUENCE: 100
accggtgtac attcagaaat tgtgttgacg cagtctccag gcaccctgtc tttgtctcca 60
ggggaaagag tcaccctctc ctgcaggacc agtcagagtg ttagcagcga ctccttagcc 120
tggtaccagc agaaacctgg ccagactccc aggctcctca tttatcatac atccaccagg 180
gccgctggca tcccagacag gttcagtggc actgggtctg ggacagactt cactctcacc 240
atcgccagac tggagcctga agattttgca gtctattact gtcagcacta tggtcggtca 300
tccctattca cctttggcca ggggaccaag ctggaaatca aacgtacg 348

<210> SEQ ID NO 101
<211> LENGTH: 398
<212> TYPE: DNA
<213> ORGANISM: Artificial
<220> FEATURE:
<223> OTHER INFORMATION: Synthetic oligonucleotide (AJL20 heavy)

<400> SEQUENCE: 101
accggtgtac attcccagct gcagctgcag gagtcgggcc caggactggt gaagccttcg 60
gagaccctgt ccctcacctg cactgtctct ggtggctcca tcagcggtag ttctttctac 120
tggggctggg tccgccagcc cccagggagg gggctggagt ggattggcac tatctattat 180
cgtgggacca cctattacac cccgtctctc aagagtcgag tcaccatatc cgtggacacc 240
tccaagaacc agttctccct gaggttgaac tctgtgaccg ccgcagacac ggctatatat 300
tactgtgcga gccttcccca ctacgatttt tggagtggtt ctgttttctt tgactactgg 360
ggccaaggaa ccctggtcac cgtctcctca gcgtcgac 398

<210> SEQ ID NO 102
<211> LENGTH: 342
<212> TYPE: DNA
<213> ORGANISM: Artificial
<220> FEATURE:
<223> OTHER INFORMATION: Synthetic oligonucleotide (AJL20 light)

<400> SEQUENCE: 102
accggtgtac attctgacat ccagatgacc cagtctccat cctccctgtc tgcatctgta 60
ggagacagag tcaccatcac ttgccgggcg agtcagggca ttgccaatta tttagcctgg 120

-continued

```
tatcagcaga aaccagggaa cattcctaag ctcctgatct atgctgcatc cactttgcaa    180

tcaggggtcc catctcggtt cagtggcagt ggatctggaa cagatttcgc tctcaccatc    240

agctgcctac agcctgagga tgttgcaact tattactgtc aaaagtataa cagtgcccct    300

ctcactttcg gcggagggac caaggtggag atcaaacgta cg                      342
```

<210> SEQ ID NO 103
<211> LENGTH: 380
<212> TYPE: DNA
<213> ORGANISM: Artificial
<220> FEATURE:
<223> OTHER INFORMATION: Synthetic oligonucleotide (WR01 heavy)

<400> SEQUENCE: 103

```
accggtgtac attcccaggt gcagctgcag gagtcgggcc caggactggt gaagccttcg     60

gagaccctgt ccctcacgtg cactgtttct ggtggctcca tcgatactta ctactggacc    120

tggatccggc agcccccggg gaagggactg gagtggattg ggtatattta ttccactggg    180

agccccaagt acaagccctc cctcaagagt cgggtcgtca tgtcagtgga cacgtccacg    240

aacgagttcg ccctgaggct gagctctgtg accgctgcgg acacggccgt gtattactgt    300

gcgagaagtt cgggatttta cgttgaacac ctggaaaagt ggggccaagg gaccacggtc    360

accgtctcct cagcgtcgac                                                380
```

<210> SEQ ID NO 104
<211> LENGTH: 345
<212> TYPE: DNA
<213> ORGANISM: Artificial
<220> FEATURE:
<223> OTHER INFORMATION: Synthetic oligonucleotide (WR01 light)

<400> SEQUENCE: 104

```
accggtgtac attcagaaat tgtgttgacg cagtctccag ccaccctgtc tttgtctcca     60

ggggaaagag ccactctctc ctgcagggcc agtcagactg tgagcagcag ctacttagac    120

tggttccagc agaaacctgg ccaggctccc aggctcctca tctatggtgc atccagcagg    180

gccactggca tcccagacag gttcagtggc agtgggtctg ggacagactt cactctaact    240

atcagcagac tggagcctga agattttgca gtgtattatt gtcagcagtt tgctacctca    300

ccgtacactt ttggccaggg gaccaagctg gagatcaaac gtacg                    345
```

<210> SEQ ID NO 105
<211> LENGTH: 395
<212> TYPE: DNA
<213> ORGANISM: Artificial
<220> FEATURE:
<223> OTHER INFORMATION: Synthetic oligonucleotide (WR02 heavy)

<400> SEQUENCE: 105

```
accggtgtac attcccaggt gcagctgcag gagtcgggcc caggactggt gaagccttca     60

cagaccctgt ccctcacctg cactgtctct ggtggctcca tcagcagtgg tgattaccac    120

tggagttgga tccgccagcc cccagggaag ggcctggagt ggattgggaa catcaattat    180

aatgggggcg cgtaccacaa tccgtccctc acgaatcgag ttatcatgtc agtagacacg    240

tccaagaatc acttctccct gaaactgacc tctgtgactg ccgcagacac ggccgtgtat    300

tactgtgcca gagagtctca gtggctgcga tacggcgcgt tcggtatgga cgtctggggc    360

caagggacca cggtcaccgt ctcctcagcg tcgac                               395
```

<210> SEQ ID NO 106
<211> LENGTH: 345
<212> TYPE: DNA
<213> ORGANISM: Artificial
<220> FEATURE:
<223> OTHER INFORMATION: Synthetic oligonucleotide (WR02 light)

<400> SEQUENCE: 106
accggtgtac attcagaaat tgtgttgacg cagtctccag gcaccctgtc tttgtctcca 60
ggggaaagag ccaccctctc ctgcagggcc agtcagagcg ttagcagcag ccacttagtc 120
tggtaccagc agaaagctgg ccaggctccc aggctcgtca tctatggtgc aaacaggagg 180
gcctctggca ccccagacag gttcagtggc agtgggtctg ggacagactt cactctcacc 240
atcagcagac tggagcctga agactttgca gtctattact gtcagcagta tggtagctcg 300
ccgtacactt ttggccaggg gaccaagctg gagatcaaac gtacg 345

<210> SEQ ID NO 107
<211> LENGTH: 395
<212> TYPE: DNA
<213> ORGANISM: Artificial
<220> FEATURE:
<223> OTHER INFORMATION: Synthetic oligonucleotide (WR03 heavy)

<400> SEQUENCE: 107
accggtgtac attcccaggt gcagctgcag gagtcgggcc caggactggt gaagccttcg 60
gggaccctgt ccctcacctg cgctgtctct ggtggctcca tcagcagtag ttactggtgg 120
agttgggtcc gccagccccc cgggaagggg ctggagtggg ttggagaaat ctatcatagt 180
gggggcgcca actacagccc gtccctcaag agtcgagtca ccatatcagt ggacaagtcc 240
aagaaccagt tctccctgaa cctgatctct gtgaccgccg cggacacggc cgtgtatttc 300
tgtgcgagat cacggatgct agtgggtgct gatggtggag gtgcttttga tatctggggc 360
caagggacaa tggtcaccgt ctcttcagcg tcgac 395

<210> SEQ ID NO 108
<211> LENGTH: 345
<212> TYPE: DNA
<213> ORGANISM: Artificial
<220> FEATURE:
<223> OTHER INFORMATION: Synthetic oligonucleotide (WR03 light)

<400> SEQUENCE: 108
accggtgtac attcagaaat tgtgttgacg cagtctccag gcaccctgtc tttgtctcca 60
ggggaaagag ccaccctctc ctgcggggcc agtcagagtg ttagcagcag ctacttagcc 120
tggtaccagc agaaacctgg cctggcgccc aggctcctca tctatgatgc atccagcagg 180
gccactggca tcccagacag gttcagtggc agtgggtctg ggacagactt cactctcacc 240
atcagcagac tggagcctga agattttgca gtgtattact gtcagcagta tggtagctca 300
cctcaaacgt tcggccaagg gaccaaggtg gaaatcaaac gtacg 345

<210> SEQ ID NO 109
<211> LENGTH: 380
<212> TYPE: DNA
<213> ORGANISM: Artificial
<220> FEATURE:
<223> OTHER INFORMATION: Synthetic oligonucleotide (WR04 heavy)

<400> SEQUENCE: 109
accggtgtac attcccagct gcagctgcag cagtcgggcc caggactggt gaagccttcg 60
gagaccctgt ccctcacctg cactgtctct ggtggctcca tcagcagtgg tggctcatac 120
tggggctgga tccgccaggc ccccgggaag ggcctggagt ggattgggag tatgtattat 180
agtgggagca ccttctacaa cccgtccgtc aagagtcgag tcaccatatc cgtagacagg 240
tccaaggagc agttctccct caatctgaac gctgtgaccg ccgcagacac ggctgtgtat 300
tactgtgtga gacataggag atcggaaccc agcgactcct ggggccaagg aaccctggtc 360
accgtctcct cagcgtcgac 380

<210> SEQ ID NO 110
<211> LENGTH: 345
<212> TYPE: DNA
<213> ORGANISM: Artificial
<220> FEATURE:
<223> OTHER INFORMATION: Synthetic oligonucleotide (WR04 light)

<400> SEQUENCE: 110
accggtgtac attcagaaat agtgatgacg cagtctccag ccaccctgtc tgtgtctcca 60
ggggaaagag ccaccctctc ctgcagggcc agtcagagtg ttagcagcaa cttagcctgg 120
taccagcaga aacctggcca ggctcccagg ctcctcatct atggtacatc caccagggcc 180
actggcattc cagccaggtt cagtggcagt gggtctggga cagaattcac tctcaccatc 240
agcagcctgc agtctgaaga ttctgcagtt tatttctgtc aacagtataa taactggccg 300
ctgtacactt ttggccaggg gaccaaggtg gagatcaaac gtacg 345

<210> SEQ ID NO 111
<211> LENGTH: 380
<212> TYPE: DNA
<213> ORGANISM: Artificial
<220> FEATURE:
<223> OTHER INFORMATION: Synthetic oligonucleotide (WR05 heavy)

<400> SEQUENCE: 111
accggtgtac attcccaggt gcagctgcag gagtcgggcc caggactggt gaagccttcg 60
gagaccctgt ctctcacctg cagtgtctct ggtggctccg tcagcagcaa tggtcacttc 120
tggagctgga tccggctgcc cccagggaag ggactggaat ggattggcta tgtctacaac 180
actgggacct ccggctacag cccctccctc aagagtcgag tcaccatatc agtagacacg 240
tccaagaacc agttctccct gacactgagg tctgtgaccg ctgcggacac ggccatttac 300
tactgcgcga gaggtctcac tgggaactac ccgtctcact ggggccaagg caccctggtc 360
accgtctcct cagcgtcgac 380

<210> SEQ ID NO 112
<211> LENGTH: 342
<212> TYPE: DNA
<213> ORGANISM: Artificial
<220> FEATURE:
<223> OTHER INFORMATION: Synthetic oligonucleotide (WR05 light)

<400> SEQUENCE: 112
accggtgtac attctgacat ccagatgacc cagtctccat cttccgtgtc tgcatctgta 60
ggagacagag tcaccatcac ttgtcgggcg agtcggggtg ttagtacctg gttagcctgg 120
tatcagcaga aaccagggga agcccctaag ctcctgatct atgcttcatc ccgtttagaa 180
ggtggggtcc cagcaaggtt cagcggcagt ggatctggga cagatttcac tctcaccatc 240
agcagcctgc agcctgaaga ttttgcaacc tactattgtc aacagggtaa cagcttcccc 300
ctcactttcg gcggagggac caaggtggag atcaaacgta cg 342

<210> SEQ ID NO 113
<211> LENGTH: 380
<212> TYPE: DNA
<213> ORGANISM: Artificial
<220> FEATURE:
<223> OTHER INFORMATION: Synthetic oligonucleotide (WR06 heavy)

<400> SEQUENCE: 113
accggtgtac attcccagct gcagctgcag gagtcgggcc caggactggt gaagccttcg 60
gagaccctgt ccctcacctg cactgtctct ggtggctccg tcagtagtag tgcttactgg 120
tgggcctgga tccgccagcc cccgggggga ggactggagt ggatcggcca tatctattac 180
tttgggaaca aatattacaa gtcgtccctc gagagtcgag tcaccatttc actagacgcg 240
tcccagaacc agttctccct gaagctgacc tccgtgaccg ccgcagacac ggctctgtat 300
tactgtgcga gagtggacac agctttggct tttgacttct ggggccaagg gacaatggtc 360
accgtctctt cagcgtcgac 380

<210> SEQ ID NO 114
<211> LENGTH: 342
<212> TYPE: DNA
<213> ORGANISM: Artificial
<220> FEATURE:
<223> OTHER INFORMATION: Synthetic oligonucleotide (WR06 light)

<400> SEQUENCE: 114
accggtgtac attctgacat ccagatgacc cagtctccat cctccctgtc tgcatctgta 60
ggagacagag tcaccatcac ttgccgggca agtcagtatg ttagtagttc tttgaattgg 120
tatcagcaga aaccagggaa agcccctaca ctcctgatct atcttgcgtc caatttgcga 180
agtggggtcc catcaaggtt cagtggcagt gaatctggga cagatttcac tctcaccatc 240
aacagtctgc agcctgaaga tgttgcaact tacttctgtc aacagagtta tagtctccct 300
cgcactttcg gccctgggac caaagtggat atcaaacgta cg 342

<210> SEQ ID NO 115
<211> LENGTH: 407
<212> TYPE: DNA
<213> ORGANISM: Artificial
<220> FEATURE:
<223> OTHER INFORMATION: Synthetic oligonucleotide (WR07 heavy)

<400> SEQUENCE: 115
accggtgtac attcccagct gcagctgcag gagtcgggcc caggactggt gaagccctcg 60
gagaccctgt ccctcacctg ctctgtctct ggtggctccg tcagtagtac aacttactac 120
tgggggtgga tccgccagtc cccagggaag gggctggagt ggattgggag catctatcat 180
agtgggaaaa cctactacaa cccgtccctc aagagtcgag tcaccatatc agtagacacg 240
tccaagaacc agttctccct gaacctgagc tctgtgaccg ccgcggacac ggccgtgtat 300
tattgtgcga gagagaattc ccatcactat gatagtagtg gttattactt aggtggattt 360
gactactggg gccagggaac cctggtcacc gtctcctcag cgtcgac 407

<210> SEQ ID NO 116
<211> LENGTH: 342
<212> TYPE: DNA
<213> ORGANISM: Artificial
<220> FEATURE:
<223> OTHER INFORMATION: Synthetic oligonucleotide (WR07 light)

-continued

<400> SEQUENCE: 116
accggtgtac attcagaaat tgtgttgacg cagtctccag gcaccctgtc tttgtctcca 60
ggggaaagag ccaccctctc ctgcagggcc agtcagagtg ttagcagcag ctacttagcc 120
tggtaccagc agaaacctgg ccaggctccc aggctcctca tctatggtgc atccagcagg 180
gccactggca tcccagacag gttcagtggc agtgggtctg ggacagactt cactctcacc 240
atcagcagac tggagcctga agatttcgca gtatatttct gccagcacta tggtagcccc 300
tccacgtttg gccaggggac caaggtggag atcaaacgta cg 342

<210> SEQ ID NO 117
<211> LENGTH: 380
<212> TYPE: DNA
<213> ORGANISM: Artificial
<220> FEATURE:
<223> OTHER INFORMATION: Synthetic oligonucleotide (WR08 heavy)

<400> SEQUENCE: 117
accggtgtac attcccaggt gcagctgcag gagtcgggcc caggactggt gaagccttca 60
cagaccctgt ccctcacctg cactgtctct ggtggctcca tcagcagtgg ttactactgg 120
agttggatcc gccagcaccc agggaagggc ctggattgta ttgggtacat ccattacacg 180
gggaccacct actacaaccc gtccctgaag agtcgactta ccatatcagt ggacacgtct 240
aagaaccagt tctccctgaa cctgacctct gtgactgccg cggacacggc cgtctattat 300
tgtgcgagag aagaatatac aacctcgtca gttgattact ggggccgggg caccctggtc 360
accgtctcct cagcgtcgac 380

<210> SEQ ID NO 118
<211> LENGTH: 357
<212> TYPE: DNA
<213> ORGANISM: Artificial
<220> FEATURE:
<223> OTHER INFORMATION: Synthetic oligonucleotide (WR08 light)

<400> SEQUENCE: 118
accggtgtac atggggatgt tgtgatgact cagtctccac tctccctgcc cgtcaccctt 60
ggacagccgg cctctatctc ctgcaggtct agtgaaagcc tcgtgtctgt tgatggaaat 120
acctacttga attggtttca ccagaggcca ggccaatctc caaggcgcct aatttataag 180
gtttctaacc gggactctgg ggtcccagac agattcagcg gcagtgggtc aggcactgat 240
ttcacactga aaatcagcag ggtggaggct gaggatgttg ggatttatta ctgcatgcaa 300
gccacacact ggcttcggac gttcggccaa gggacacgac tggagattaa acgtacg 357

<210> SEQ ID NO 119
<211> LENGTH: 380
<212> TYPE: DNA
<213> ORGANISM: Artificial
<220> FEATURE:
<223> OTHER INFORMATION: Synthetic oligonucleotide (WR09 heavy)

<400> SEQUENCE: 119
accggtgtac attcccaggt gcagctgcag gagtcgggcc caggactggt gaagccttca 60
cagaccctgt ccctcacctg cactgtctct ggtggctcca tcagcagtgg ttactactgg 120
agttggatcc gccagcaccc agggaagggc ctggagtgga ttgggtacat ccattacacg 180
gggaccacct actacaaccc gtccctgaag agtcgagtta ccatatcagt ggacacgtct 240

-continued

```
aagaaccagt tctccctgaa cctgacctct gtgactgccg cggacacggc cgtctattat    300

tgtgcgagag aagaatatac gacctcgtca gttgattact ggggccgtgg caccctggtc    360

accgtctcct cagcgtcgac                                                380
```

<210> SEQ ID NO 120
<211> LENGTH: 351
<212> TYPE: DNA
<213> ORGANISM: Artificial
<220> FEATURE:
<223> OTHER INFORMATION: Synthetic oligonucleotide (WR09 light)

<400> SEQUENCE: 120

```
accggtgtac attcagaaat tgtgttgacg cagtctccag gcaccctgtc tttgtctcca     60

ggggaaagag ccaccctctc ctgcagggcc agtcagaggg ttagcagcgg ctttttagcc    120

tggtaccagc agaaacctgg ccaggctccc aggctcctca tctatggtgc atccagcagg    180

gccactggca tcccagacag gttcagtggc agtggctctg ggacagactt cactctcacc    240

atcagcagac tggagcctga agattttgca gtgtattact gtcagcagta tgaaagttca    300

ccgtcaccgt acaactttgg ccaggggacc aagctggaga tcaaacgtac g             351
```

<210> SEQ ID NO 121
<211> LENGTH: 401
<212> TYPE: DNA
<213> ORGANISM: Artificial
<220> FEATURE:
<223> OTHER INFORMATION: Synthetic oligonucleotide (WR10 heavy)

<400> SEQUENCE: 121

```
accggtgtac attcccaggt gcagctgcag gagtcgggcc caggactggt gaagccttcg     60

gggaccctgt ccctcacctg cgctgtctct ggtggctcca tcagcaataa taagtggtgg    120

aattgggtcc gccagtcccc agggaagggg ctggagtgga ttggggaaat ctatcatagt    180

gggggcacca actacaaccc gtccctcaag agtcgagtca ccatatcggt agacaagtcc    240

aagaacctgt tctccctgaa gctgagctct gtgaccgccg cggacacggc cgtgtattac    300

tgtgcgagtg cgactactat ggttcgggga ctgagtcttt actactacgg tctggacgtc    360

tggggcccag ggaccacggt caccgtctcc tcagcgtcga c                        401
```

<210> SEQ ID NO 122
<211> LENGTH: 345
<212> TYPE: DNA
<213> ORGANISM: Artificial
<220> FEATURE:
<223> OTHER INFORMATION: Synthetic oligonucleotide (WR10 light)

<400> SEQUENCE: 122

```
accggtgtac attcagaaat tgtgttgacg cagtctccag gcaccctgtc tttgtctcca     60

ggggaaagag ccgccctctc ctgcagggcc agtcagagtc ttatcggcag cttcttagcc    120

tggtaccagc agaaacctgg ccaggctccc aggctcctca tctatcatac atccaacagg    180

gcctctggca tcccagacag gttcagtggc ggtgggtttg ggacagactt cactctcacc    240

atcagcagac tggagcctga agattttgca gtttattact gtcaacagta tgatagctca    300

ccgatcacct tcggccaagg gacacgactg gagattaaac gtacg                    345
```

<210> SEQ ID NO 123
<211> LENGTH: 401
<212> TYPE: DNA
<213> ORGANISM: Artificial -continued
<220> FEATURE:
<223> OTHER INFORMATION: Synthetic oligonucleotide (WR11 heavy)

<400> SEQUENCE: 123
accggtgtac attcccaggt gcagctgcag gagtcgggcc caggactggt gaagccttcg 60
gggaccctgt ccctcacctg cgctgtctct ggtggctcca tcagcaataa taagtggtgg 120
aattgggtcc gccagtcccc agggaagggg ctggagtgga ttggggaaat ctatcatagt 180
gggggcacca actacaaccc gtccctcaag agtcgagtca ccatatcggt agacaagtcc 240
aagaacctgt tctccctgaa gctgagctct gtgaccgccg cggacacggc cgtgtattac 300
tgtgcgagtg cgactactat ggttcgggga ctgagtcttt actactacgg tctggacgtc 360
tggggccaag ggaccacggt caccgtctcc tcagcgtcga c 401

<210> SEQ ID NO 124
<211> LENGTH: 348
<212> TYPE: DNA
<213> ORGANISM: Artificial
<220> FEATURE:
<223> OTHER INFORMATION: Synthetic oligonucleotide (WR11 light)

<400> SEQUENCE: 124
accggtgtac attcagaaat tgtgttgacg cagtctccag gcaccctgtc tttgtctcca 60
ggggaaagag ccaccctctc ctgcagggcc agtcagagtg ttagcagctt cttagcctgg 120
taccaacaga aacctggcca ggctcccaga ctcctcatct atgatgcatc caacagggcc 180
actggcatcc cagccaggtt cagtggcagt gggtctggga cagatttcac tctcaccatc 240
agcagcctag agcctgaaga ttttgcagtt tattactgtc agcagcgtac caactggcct 300
ccctcgctca ctttcggcgg agggaccaag gtggagatca aacgtacg 348

<210> SEQ ID NO 125
<211> LENGTH: 410
<212> TYPE: DNA
<213> ORGANISM: Artificial
<220> FEATURE:
<223> OTHER INFORMATION: Synthetic oligonucleotide (WR12 heavy)

<400> SEQUENCE: 125
accggtgtac attcccaggt gcagctgcag gagtcgggcc caggactggt gaagccttca 60
cagaccctgt ccctcacctg cactgtctct ggcgactccg tcagcagtaa tgatcactac 120
tggagttgga tccgccagcc cccagggcag ggcctggagt ggattgggta catctctcac 180
ggtgggacca cctactacaa cccgtccctc aagagtcgag ttaccatgtc gatcgacacg 240
tccacgaacc agttctccct gagggtgacc tccgtgcgag ccgcagacat ggccgtctac 300
ttctgtgcca gggccccggc ccctataacg acttttggaa tggtgacacc agtcccctac 360
tttcactcct ggggccaagg caccctggtc accgtctcct cagcgtcgac 410

<210> SEQ ID NO 126
<211> LENGTH: 357
<212> TYPE: DNA
<213> ORGANISM: Artificial
<220> FEATURE:
<223> OTHER INFORMATION: Synthetic oligonucleotide (WR12 light)

<400> SEQUENCE: 126
accggtgtac atggggatat tgtgatgact cagtctccac tgtccctgcc cgtcagccct 60
ggagagccgg cctccatctc ctgcaggtct agtcagagcc tcctccatag taatggatac 120

-continued

```
aactatttga gttggtacct gcagaagcca gggcagtctc cacaactcct gatcttttcg    180

agttctattc gggcctccgg ggtccctgac aggttcagtg gcagtggatc aggcacagat    240

tttacactga caatcaacag agtggaggct gaggatgttg gagtttatta ctgcatgcag    300

gctctacaaa ctccgctcac tttcggcgga gggaccaagc tggaaatcaa acgtacg       357


<210> SEQ ID NO 127
<211> LENGTH: 410
<212> TYPE: DNA
<213> ORGANISM: Artificial
<220> FEATURE:
<223> OTHER INFORMATION: Synthetic oligonucleotide (WR13 heavy)

<400> SEQUENCE: 127

accggtgtac attcccaggt gcagctgcag gagtcgggcc caggactggt gaagccttca     60

cagaccctgt ccctcacctg cactgtctct ggcgactccg tcagcagtaa tgatcactac    120

tggagttgga tccgccagcc cccagggcag ggcctggagt ggattgggta catctctcac    180

ggtgggacca cctactacaa cccgtccctc aagagtcgag ttaccatgtc gatcgacacg    240

tccacgaacc agttctccct gagggtgacc tccgtgcgag ccgcagacat ggccgtctac    300

ttctgtgcca gggccccggc ccctataacg acttttggaa tggtgacacc agtcccctac    360

tttcactcct ggggccaagg caccctggtc accgtctcct cagcgtcgac               410


<210> SEQ ID NO 128
<211> LENGTH: 357
<212> TYPE: DNA
<213> ORGANISM: Artificial
<220> FEATURE:
<223> OTHER INFORMATION: Synthetic oligonucleotide (WR13 light)

<400> SEQUENCE: 128

accggtgtac atggggatat tgtgatgact cagtctccac tgtccctgcc cgtcagccct     60

ggagagtcgg cctccatctc ctgcaggtct agtcagagcc tcctccatag taatggatac    120

aactatttga gttggtacct gcagaagcca gggcagtctc cacaactcct gatcttttcg    180

agttctattc gggcctccgg ggtccctgac aggttcagtg gcagtggatc aggcacagat    240

tttaccctga caatcaacag agtggaggct gaggatgttg gagtttatta ctgcatgcag    300

gctctacaaa ctccgctcac tttcggccag gggaccaagc tggaaatcaa acgtacg       357
```